(12) United States Patent
Hongo et al.

(10) Patent No.: US 7,858,330 B2
(45) Date of Patent: Dec. 28, 2010

(54) COMPOSITIONS AND METHODS FOR THE TREATMENT OF TUMOR OF HEMATOPOIETIC ORIGIN

(75) Inventors: Jo-Anne Hongo, Redwood City, CA (US); Wesley Chang, San Carlos, CA (US); Frederic J. de Sauvage, Foster City, CA (US); Dan L. Eaton, San Rafael, CA (US); Allen J. Ebens, Jr., San Carlos, CA (US); Gretchen D. Frantz, San Francisco, CA (US); Hartmut Koeppen, Berkeley, CA (US); Andrew Polson, San Francisco, CA (US); Victoria Smith, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 356 days.

(21) Appl. No.: 11/418,347

(22) Filed: May 4, 2006

(65) Prior Publication Data

US 2006/0251662 A1    Nov. 9, 2006

Related U.S. Application Data

(63) Continuation-in-part of application No. 11/315,529, filed on Dec. 21, 2005, which is a continuation-in-part of application No. 11/020,508, filed on Dec. 21, 2004, now abandoned, which is a continuation-in-part of application No. 10/989,826, filed on Nov. 16, 2004, now abandoned, and a continuation-in-part of application No. PCT/US2004/038262, filed on Nov. 16, 2004, said application No. 11/315,529 is a continuation-in-part of application No. PCT/US2004/043514, filed on Dec. 21, 2004, which is a continuation-in-part of application No. 10/989,826, which is a continuation-in-part of application No. 10/712,892, filed on Nov. 12, 2003, now abandoned, said application No. 10/989,826 is a continuation-in-part of application No. PCT/US03/36298, filed on Nov. 13, 2003, said application No. PCT/US2004/043514 is a continuation-in-part of application No. PCT/US2004/038262, which is a continuation-in-part of application No. 10/712,892, which is a continuation-in-part of application No. 10/643,795, filed on Aug. 19, 2003, now abandoned, which is a continuation-in-part of application No. 10/241,220, filed on Sep. 11, 2002, now abandoned, said application No. 10/712,892 is a continuation-in-part of application No. PCT/US03/25892, filed on Aug. 19, 2003, and a continuation-in-part of application No. 10/241,220, filed on Sep. 11, 2002, now abandoned, and a continuation-in-part of application No. PCT/US02/28859, said application No. PCT/US2004/038262 and a continuation-in-part of application No. PCT/US03/36298, filed on Nov. 13, 2003, and a continuation-in-part of application No. 10/643,795, filed on Aug. 19, 2003, now abandoned, and a continuation-in-part of application No. PCT/US03/25892, filed on Aug. 19, 2003.

(60) Provisional application No. 60/520,842, filed on Nov. 17, 2003, provisional application No. 60/532,426, filed on Dec. 24, 2003, provisional application No. 60/426,847, filed on Nov. 15, 2002, provisional application No. 60/520,842, filed on Nov. 17, 2003, provisional application No. 60/532,426, filed on Dec. 24, 2003, provisional application No. 60/426,847, filed on Nov. 15, 2002, provisional application No. 60/404,809, filed on Aug. 19, 2002, provisional application No. 60/339,227, filed on Oct. 19, 2001.

(51) Int. Cl.
    *G01N 33/574*    (2006.01)
(52) U.S. Cl. ..................................... 435/7.23; 435/7.1
(58) Field of Classification Search .................... None
    See application file for complete search history.

(56) References Cited

U.S. PATENT DOCUMENTS

| | | | |
|---|---|---|---|
| 5,208,020 | A | 5/1993 | Chari et al. |
| 6,503,510 | B2 | 1/2003 | Koishihara et al. |
| 2003/0148408 | A1 | 8/2003 | Frantz et al. |
| 2004/0180002 | A1 | 9/2004 | Young et al. |
| 2005/0226869 | A1 | 10/2005 | Chang et al. |
| 2005/0266008 | A1 | 12/2005 | Graziano et al. |
| 2008/0292632 | A1* | 11/2008 | Pastan et al. ............. 424/139.1 |

FOREIGN PATENT DOCUMENTS

| | | | |
|---|---|---|---|
| WO | WO 9963088 | | 12/1999 |
| WO | WO 01/38490 | * | 5/2001 |
| WO | WO 01/38490 A2 | | 5/2001 |
| WO | WO 0138490 | | 5/2001 |
| WO | WO 01/40466 A2 | | 6/2001 |
| WO | WO03/089624 A2 | | 10/2003 |
| WO | WO03/097803 A2 | | 11/2003 |

OTHER PUBLICATIONS

O'Connell et al. Am J Clin Pathol, 2004, 121:254-263.*
Rawstron et al. Br J Haematology, 1997, 97:46-55.*
Gussow et al. (1991, Methods in Enzymology 203:99-121).*
Blast Searches A1-A44.
Blast Searches B1-B18.
Blast Searches C1-C53.
Blast Searches D1-D35.
Blast Searches E1-E14.
Blast Searches F1-F28.
Blast Searches G1-G202.

(Continued)

*Primary Examiner*—Misook Yu
*Assistant Examiner*—Mark Halvorson
(74) *Attorney, Agent, or Firm*—Arnold & Porter LLP; Bonny Yeung; Jeffery P. Bernhardt

(57) ABSTRACT

The present invention is directed to compositions of matter useful for the treatment of hematopoietic tumor in mammals and to methods of using those compositions of matter for the same.

20 Claims, 45 Drawing Sheets

OTHER PUBLICATIONS

Blast Searches H1-H107.
Blast Searches I1-I39.
Blast Searches J1-J19.
Blast Searches K1-K4.
Blast Searches L1-L23.
Blast Searches M1-M63.
Blast Searches N1-N35.
Boring et al., "Cancer Statistics, 1993" *CA: A Cancer Journal for Clinicians* 43(1):7-26 (Jan.-Feb. 1993).
Bowie et al., "Deciphering the Message in Protein Sequences: Tolerance to Amino Acid Substitutions" *Science* 247:1306-1310 (1990)
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue" *Journal of Cell Biology* 111:2129-2138 (Nov. 1990).
Ellis et al., "Engineered Anti-CD38 Monoclonal Antibodies for Immunotherapy of Multiple Myeloma" *The Journal of Immunology* pp. 925-937 (1995).
Hatzivassiliou et al., "IRTA1 and IRTA2, novel immunoglobulin superfamily receptors expressed in B cells and involved in chromosome 1q21 abnormalities in B cell malignancy" *Immunity* 14(3):277-289 (Mar. 2001).
Herrera et al., "Treatment of SCID/human B cell precursor ALL with anti-CD19 and anti-CD22 immunotoxins" *Leukemia* 17(2):334-338 (Feb. 2003).
Lazar et al., "Transforming Growth Factor α: Mutation of Aspartic Acid 47 and Leucine 48 Results in Different Biological Activities" *Molecular & Cellular Biology* 8(3):1247-1252 (Mar. 1988).
Miller et al, "IRTAs: A new family of immunoglobulinlike receptors differentially expressed in B cells" *Blood* 99(8):2662-2669 (2002).
Szatrowski et al., "Lineage specific treatment of adult patients with acute lymphoblastic leukemia in first remission with anti-B4-blocked ricin or high-dose cytarabine: Cancer and Leukemia Group B Study 93" *Cancer* 97(6):1471-1480 (Mar. 15, 2003).
Tassone et al., "Cytotoxic activity of the maytansinoid immunoconjugate B-B4-DM1 against CD138+ multiple myeloma ce" *Blood* 104(12):3688-3696 (Dec. 1, 2004).
Tobinai kensai, "Rituximab and other emerging antibodies as molecular target-based therapy of lymphoma" *Int J Clin Oncol.* 8(4):212-223 (Aug. 2003).
Tur MK et al., "Recombinant CD64-specific single chain immunotoxin exhibits specific cytotoxicity against acute myeloid leukemia cells" *Cancer Research* 63(23):8414-8419 (Dec. 1, 2003).
von Mehren et al., "Monoclonal antibody therapy for cancer" *Annu Rev Med.* 54:343-369 (2003).
Conway, E.J., et al., "Phenotyping Studies of Clonotypic B Lymphocytes from Patients with Multiple Myeloma by Flow Cytometry", Arch Pathol Labe Med, vol. 133, pp. 1594-1599, (2009).
Office Action mailed Dec. 27, 2007—U.S. Appl. No. 11/315,529.
Office Action mailed Dec. 10, 2008—U.S. Appl. No. 11/315,529.
Final Office Action mailed Jun. 9, 2009—U.S. Appl. No. 11/315,529.
Boyd, The Basic science of oncology, p. 379, (1992).
Euhus, et al., Surgery, Gynecology and Obstetrics, vol. 175, Abstract, (1992).
Gao, et al., Aizheng, vol. 21, Abstract, (2002).
Green, et al., Immunological Reviews, vol. 193, pp. 70-81, (2003).
Gura, Science, 278: 1041-1042, (1997).
Gussow, et al., Methods in Enzymology, 203: 99-121, (1991).
Harlow and Lane, Antibodies: A laboratory manual, Cold Spring Harbor Laboratory, pp. 141-142, (1988).
Kaiser, Science, 313: 1370, (2006).
Morrison, et al., "Complement activation and Fc receptor binding by IgG", Protein engineering of antibody molecules for prophylactic and therapeutic applications, pp. 101-113, (1993).
Rihova, Advanced drug delivery reviews, vol. 29, pp. 273-289, (1998).
Rudikoff, et al., PNAS, vol. 79, pp. 1979-1983, (1982).
Schlom, "Monoclonal antibodies: They're more and less than you think", Molecular foundations of oncology, pp. 95-134, (1991).

* cited by examiner

FIGURE 1

DNA 182432

GTTGGTGACCAAGAGTACATCTCTTTTCAAATAGCTGGATTAGGTCCTC ATGCTGCTGTG
GTCATTGCTGGTCATCTTTGATGCAGTCACTGAACAGGCAGATTCGCTGACCCTTGTGGC
GCCCTCTTCTGTCTTCGAAGGAGACAGCATCGTTCTGAAATGCCAGGGAGAACAGAACTG
GAAAATTCAGAAGATGGCTTACCATAAGGATAACAAAGAGTTATCTGTTTTCAAAAAATT
CTCAGATTTCCTTATCCAAAGTGCAGTTTTAAGTGACAGTGGTAACTATTTCTGTAGTAC
CAAAGGACAACTCTTTCTCTGGGATAAAACTTCAAATATAGTAAAGATAAAAGTCCAAGA
GCTCTTTCAACGTCCTGTGCTGACTGCCAGCTCCTTCCAGCCCATCGAAGGGGGTCCAGT
GAGCCTGAAATGTGAGACCCGGCTCTCTCCACAGAGGTTGGATGTTCAACTCCAGTTCTG
CTTCTTCAGAGAAAACCAGGTCCTGGGGTCAGGCTGGAGCAGCTCTCCGGAGCTCCAGAT
TTCTGCCGTGTGGAGTGAAGACACAGGGTCTTACTGGTGCAAGGCAGAAACGGTGACTCA
CAGGATCAGAAACAGAGCCTCCAATCCCAGATTCACGTGCAGAGAATCCCCATCTCTAA
TGTAAGCTTGGAGATCCGGGCCCCGGGGGACAGGTGACTGAAGGACAAAAACTGATCCT
GCTCTGCTCAGTGGCTGGGGGTACAGGAAATGTCACATTCTCCTGGTACAGAGAGGCCAC
AGGAACCAGTATGGGAAAGAAAACCCAGCGTTCCCTGTCAGCAGAGCTGGAGATCCCAGC
TGTGAAAGAGAGTGATGCCGGCAAATATTACTGTAGAGCTGACAACGGCCATGTGCCTAT
CCAGAGCAAGGTGGTGAATATCCCTGTGAGAATTCCAGTGTCTCGCCCTGTCCTCACCCT
CAGGTCTCCTGGGGCCCAGGCTGCAGTGGGGGACCTGCTGGAGCTTCACTGTGAGGCCCT
GAGAGGCTCTCCCCCAATCTTGTACCAATTTTATCATGAGGATGTCACCCTTGGGAACAG
CTCGGCCCCCTCTGGAGGAGGGGCCTCCTTCAACCTCTCTTTGACTGCAGAACATTCTGG
AAACTACTCCTGTGAGGCCAACAACGGCCTGGGGGCCCAGTGCAGTGAGGCAGTGCCAGT
CTCCATCTCAGGACCTGATGGCTATAGAAGAGACCTCATGACAGCTGGAGTTCTCTGGGG
ACTGTTTGGTGTCCTTGGTTTCACTGGTGTTGCTTTGCTGTTGTATGCCTTGTTCCACAA
GATATCAGGAGAAAGTTCTGCCACTAATGAACCCAGAGGGGCTTCCAGGCCAAATCCTCA
AGAGTTCACCTATTCAAGCCCAACCCCAGACATGGAGGAGCTGCAGCCAGTGTATGTCAA
TGTGGGCTCTGTAGATGTGGATGTGGTTTATTCTCAGGTCTGGAGCATGCAGCAGCCAGA
AAGCTCAGCAAACATCAGGACACTTCTGGAGAACAAGGACTCCCAAGTCATCTACTCTTC
TGTGAAGAAATCATAACACTTGGAGGAATCAGAAGGGAAGATCAACAGCAAGGATGGGGC
ATCATTAAGACTTGCTATAAAACCTTATGAAAATGCTTGAGGCTTATCACCTGCCACAGC
CAGAACGTGCCTCAGGAGGCACCTCCTGTCATTTTGTCCTGATGATGTTTCTTCTCCAA
TATCTTCTTTTACCTATCAATATTCATTGAACTGCTGCTACATCCAGACACTGTGCAAAT
AAATTATTTCTGCTACCTTCAAAAAAAAAAAAAAAAAAAAAATGCAG

FIGURE 2A

DNA 182432

></usr/seqdb2/sst/DNA/Dnaseqs.min/ss.DNA182432
><subunit 1 of 1, 508 aa, 1 stop
><MW: 55542, pI: 6.30, NX(S/T): 5

MLLWSLLVIFDAVTEQADSLTLVAPSSVFEGDSIVLKCQGEQNWKIQKMAYHKDNKELSV
FKKFSDFLIQSAVLSDSGNYFCSTKGQLFLWDKTSNIVKIKVQELFQRPVLTASSFQPIE
GGPVSLKCETRLSPQRLDVQLQFCFFRENQVLGSGWSSSPELQISAVWSEDTGSYWCKAE
TVTHRIRKQSLQSQIHVQRIPISNVSLEIRAPGGQVTEGQKLILLCSVAGGTGNVTFSWY
REATGTSMGKKTQRSLSAELEIPAVKESDAGKYYCRADNGHVPIQSKVVNIPVRIPVSRP
VLTLRSPGAQAAVGDLLELHCEALRGSPPILYQFYHEDVTLGNSSAPSGGGASFNLSLTA
EHSGNYSCEANNGLGAQCSEAVPVSISGPDGYRRDLMTAGVLWGLFGVLGFTGVALLLYA
LFHKISGESSATNEPRGASRPNPQEFTYSSPTPDMEELQPVYVNVGSVDVDVVYSQVWSM
QQPESSANIRTLLENKDSQVIYSSVKKS

Signal sequence.
amino acids 1-14.

Transmembrane domain.
amino acids 400-420.

Immunoglobulin domain.
amino acids 17-84, 121-179, 219-277, 314-370.

N-glycosylation site.
amino acids 204-207, 234-237, 343-346, 355-358, 365-368

Glycosaminoglycan attachment site.
amino acids 348-351 cAMP- and cGMP-dependent protein kinase phosphorylation site.
amino acids 62-65, 187-190

Protein kinase C phosphorylation site.
amino acids 83-85, 125-127, 183-185, 252-254, 303-305, 504-506

Casein kinase II phosphorylation site.
amino acids 27-30, 158-161, 387-390, 491-494

Tyrosine kinase phosphorylation site.
amino acids 266-273

FIGURE 2B

N-myristoylation site.
amino acids 78-83, 121-126, 153-158, 173-178, 213-218, 230-235,
245-250, 308-313, 349-354, 351-356, 364-369, 375-360, 400-405

Amidation site.
amino acids 248-251

FIGURE 3

DNA340394

ATATATCGATATGCTGCCGAGGCTGTTGCTGTTGATCTGTGCTCCACTCTGTGAACCTGC
CGAGCTGTTTTTGATAGCCAGCCCCTCCCATCCCACAGAGGGGAGCCCAGTGACCCTGAC
GTGTAAGATGCCCTTTCTACAGAGTTCAGATGCCCAGTTCCAGTTCTGCTTTTTCAGAGA
CACCCGGGCCTTGGGCCCAGGCTGGAGCAGCTCCCCAAGCTCCAGATCGCTGCCATGTG
GAAAGAAGACACAGGGTCATACTGGTGCGAGGCACAGACAATGGCGTCCAAAGTCTTGAG
GAGCAGGAGATCCCAGATAAATGTGCACAGGGTCCCTGTCGCTGATGTGAGCTTGGAGAC
TCAGCCCCAGGAGGACAGGTGATGGAGGGAGACAGGCTGGTCCTCATCTGCTCAGTTGC
TATGGGCACAGGAGACATCACCTTCCTTTGGTACAAAGGGGCTGTAGGTTTAAACCTTCA
GTCAAAGACCCAGCGTTCACTGACAGCAGAGTATGAGATTCCTTCAGTGAGGGAGAGTGA
TGCTGAGCAATATTACTGTGTAGCTGAAAATGGCTATGGTCCCAGCCCCAGTGGGCTGGT
GAGCATCACTGTCAGAATCCCGGTGTCTCGCCCAATCCTCATGCTCAGGGCTCCCAGGGC
CCAGGCTGCAGTGGAGGATGTGCTGGAGCTTCACTGTGAGGCCCTGAGAGGCTCTCCTCC
GATCCTGTACTGGTTTTATCACGAGGATATCACCCTGGGGAGCAGGTCGGCCCCCTCTGG
AGGAGGAGCCTCCTTCAACCTTTCCCTGACTGAAGAACATTCTGGAAACTACTCCTGTGA
GGCCAACAATGGCCTGGGGGCCCAGCGCAGTGAGGCGGTGACACTCAACTTCACAGTGCC
TACTGGGGCCAGAAGCAATCATCTTACCTCAGGAGTCATTGAGGGCTGCTCAGCACCCT
TGGTCCAGCCACCGTGGCCTTATTATTTTGCTACGGCCTCAAAAGAAAAATAGGAAGACG
TTCAGCCAGGGATCCACTCAGGAGCCTTCCCAGCCCTCTACCCCAAGAGTTCACGTACCT
CAACTCACCTACCCCAGGGCAGCTACAGCCTATATATGAAAATGTGAATGTTGTAAGTGG
GGATGAGGTTTATTCACTGGCGTACTATAACCAGCCGGAGCAGGAATCAGTAGCAGCAGA
AACCCTGGGGACACATATGGAGGACAAGGTTTCCTTAGACATCTATTCCAGGCTGAGGAA
AGCAAACATTACAGATGTGGACTATGAAGATGCTATGTAAGGTTATGGAAGATTCTGCTC
TT

FIGURE 4

DNA340394

```
><subunit 1 of 1, 429 aa, 1 stop
><MW: 46936, pI: 5.42, NX(S/T): 4
MLPRLLLLICAPLCEPAELFLIASPSHPTEGSPVTLTCKMPFLQSSDAQFQFCFFRDTRA
LGPGWSSSPKLQIAAMWKEDTGSYWCEAQTMASKVLRSRRSQINVHRVPVADVSLETQPP
GGQVMEGDRLVLICSVAMGTGDITFLWYKGAVGLNLQSKTQRSLTAEYEIPSVRESDAEQ
YYCVAENGYGPSPSGLVSITVRIPVSRPILMLRAPRAQAAVEDVLELHCEALRGSPPILY
WFYHEDITLGSRSAPSGGGASFNLSLTEEHSGNYSCEANNGLGAQRSEAVTLNFTVPTGA
RSNHLTSGVIEGLLSTLGPATVALLFCYGLKRKIGRRSARDPLRSLPSPLPQEFTYLNSP
TPGQLQPIYENVNVVSGDEVYSLAYYNQPEQESVAAETLGTHMEDKVSLDIYSRLRKANI
TDVDYEDAM
```

Signal sequence.
amino acids 1-16.

N-glycosylation site.
amino acids 263-266, 273-276, 293-296, 419-422.

Glycosaminoglycan attachment site.
amino acids 256-259.

Protein kinase C phosphorylation site.
amino acids 37-39, 68-70, 98-100, 160-162, 172-174, 200-202, 338-340.

Casein kinase II phosphorylation site.
amino acids 172-175, 176-179, 265-268, 338-341, 376-379, 401-404, 421-424.

Tyrosine kinase phosphorylation site.
amino acids 174-181.

N-myristoylation site.
amino acids 31-36, 82-87, 257-262, 259-264, 272-277, 283-288, 299-304, 308-313, 312-317.

Amidation site.
amino acids 334-337.

Immunoglobulin.
amino acids 31-88, 127-185, 222-278.

FIGURE 5

DNA56041

GATGTGCTCCTTGGAGCTGGTGTGCAGTGTCCTGACTGTAAGATCAAGTCCAAACCTGTT
TTGGAATTGAGGAAACTTCTCTTTTGATCTCAGCCCTTGGTGGTCCAGGTCTTCATGCTG
CTGTGGGTGATATTACTGGTCCTGGCTCCTGTCAGTGGACAGTTTGCAAGGACACCCAGG
CCCATTATTTTCCTCCAGCCTCCATGGACCACAGTCTTCCAAGGAGAGAGAGTGACCCTC
ACTTGCAAGGGATTTCGCTTCTACTCACCACAGAAAACAAAATGGTACCATCGGTACCTT
GGGAAAGAAATACTAAGAGAAACCCCAGACAATATCCTTGAGGTTCAGGAATCTGGAGAG
TACAGATGCCAGGCCCAGGGCTCCCCTCTCAGTAGCCCTGTGCACTTGGATTTTTCTTCA
GAGATGGGATTTCCTCATGCTGCCCAGGCTAATGTTGAACTCCTGGGCTCAAGTGATCTG
CTCACCTAGGCCTCTCAAAGCGCTGGGATTACAGCTTCGCTGATCCTGCAAGCTCCACTT
TCTGTGTTTGAAGGAGACTCTGTGGTTCTGAGGTGCCGGGCAAAGGCGGAAGTAACACTG
AATAATACTATTTACAAGAATGATAATGTCCTGGCATTCCTTAATAAAGAACTGACTTC
CAAAAAAAAAAAAAAAAAAAAAAA

FIGURE 6

DNA56041

><subunit 1 of 1, 124 aa, 1 stop
><MW: 14080, pI: 7.48, NX(S/T): 0
MLLWVILLVLAPVSGQFARTPRPIIFLQPPWTTVFQGERVTLTCKGFRFYSPQKTKWYHR
YLGKEILRETPDNILEVQESGEYRCQAQGSPLSSPVHLDFSSEMGFPHAAQANVELLGSS
DLLT

Signal sequence.
amino acids 1-15.

Protein kinase C phosphorylation site.
amino acids 20-22, 43-45.

N-myristoylation site.
amino acids 89-94.

FIGURE 7A

DNA257955

AGTGAAGGGGTTTCCCATATGAAAAATACAGAAGAATTATTTGAATACTAGCAAATACA
CAACTTGATATTTCTAGAGAACCCAGGCACAGTCTTGGAGACATTACTCCTGAGAGACTG
CAGCTGATGGAAGATGAGCCCCAACTTCTAAAAATGTATCACTACCGGGATTGAGATACA
AACAGCATTTAGGAAGGTCTCATCTGAGTAGCAGCTTCCTGCCCTCCTTCTTGGAGATAA
GTCGGGCTTTTGGTGAGACAGACTTTCCCAACCCTCTGCCCGGCCGGTGCCC ATGCTTCT
GTGGCTGCTGCTGCTGATCCTGACTCCTGGAAGAGAACAATCAGGGGTGGCCCCAAAAGC
TGTACTTCTCCTCAATCCTCCATGGTCCACAGCCTTCAAAGGAGAAAAGTGGCTCTCAT
ATGCAGCAGCATATCACATTCCCTAGCCCAGGGAGACACATATTGGTATCACGATGAGAA
GTTGTTGAAAATAAAACATGACAAGATCCAAATTACAGAGCCTGGAAATTACCAATGTAA
GACCCGAGGATCCTCCCTCAGTGATGCCGTGCATGTGGAATTTTCACCTGACTGGCTGAT
CCTGCAGGCTTTACATCCTGTCTTTGAAGGAGACAATGTCATTCTGAGATGTCAGGGGAA
AGACAACAAAAACACTCATCAAAAGGTTTACTACAAGGATGGAAAACAGCTTCCTAATAG
TTATAATTTAGAGAAGATCACAGTGAATTCAGTCTCCAGGGATAATAGCAAATATCATTG
TACTGCTTATAGGAAGTTTTACATACTTGACATTGAAGTAACTTCAAAACCCCTAAATAT
CCAAGTTCAAGAGCTGTTTCTACATCCTGTGCTGAGAGCCAGCTCTTCCACGCCCATAGA
GGGGAGTCCCATGACCCTGACCTGTGAGACCCAGCTCTCTCCACAGAGGCCAGATGTCCA
GCTGCAATTCTCCCTCTTCAGAGATAGCCAGACCCTCGGATTGGGCTGGAGCAGGTCCCC
CAGACTCCAGATCCCTGCCATGTGGACTGAAGACTCAGGGTCTTACTGGTGTGAGGTGGA
GACAGTGACTCACAGCATCAAAAAAAGGAGCCTGAGATCTCAGATACGTGTACAGAGAGT
CCCTGTGTCTAATGTGAATCTAGAGATCCGGCCCACCGGAGGGCAGCTGATTGAAGGAGA
AAATATGGTCCTTATTTGCTCAGTAGCCCAGGGTTCAGGGACTGTCACATTCTCCTGGCA
CAAAGAAGGAAGAGTAAGAAGCCTGGGTAGAAAGACCCAGCGTTCCCTGTTGGCAGAGCT
GCATGTTCTCACCGTGAAGGAGAGTGATGCAGGGAGATACTACTGTGCAGCTGATAACGT
TCACAGCCCCATCCTCAGCACGTGGATTCGAGTCACCGTGAGAATTCCGGTATCTCACCC
TGTCCTCACCTTCAGGGCTCCCAGGGCCCACACTGTGGTGGGGACCTGCTGGAGCTTCA
CTGTGAGTCCCTGAGAGGCTCTCCCCCGATCCTGTACCGATTTTATCATGAGGATGTCAC
CCTGGGGAACAGCTCAGCCCCCTCTGGAGGAGGAGCCTCCTTCAACCTCTCTCTGACTGC
AGAACATTCTGGAAACTACTCCTGTGATGCAGACAATGGCCTGGGGGCCCAGCACAGTCA
TGGAGTGAGTCTCAGGGTCACAGTTCCGGTGTCTCGCCCCGTCCTCACCCTCAGGGCTCC
CGGGGCCCAGGCTGTGGTGGGGACCTGCTGGAGCTTCACTGTGAGTCCCTGAGAGGCTC
CTTCCCGATCCTGTACTGGTTTTATCACGAGGATGACACCTTGGGGAACATCTCGGCCCA
CTCTGGAGGAGGGGCATCCTTCAACCTCTCTCTGACTACAGAACATTCTGGAAACTACTC
ATGTGAGGCTGACAATGGCCTGGGGGCCCAGCACAGTAAAGTGGTGACACTCAATGTTAC
AGGAACTTCCAGGAACAGAACAGGCCTTACCGCTGCGGGAATCACGGGGCTGGTGCTCAG
CATCCTCGTCCTTGCTGCTGCTGCTGCTCTGCTGCATTACGCCAGGGCCCGAAGGAAACC
AGGAGGACTTTCTGCCACTGGAACATCAGTCACAGTCCTAGTGAGTGTCAGGAGCCTTC
CTCGTCCAGGCCTTCCAGGATAGACCCTCAAGAGCCCACTCACTCTAAACCACTAGCCCC
AATGGAGCTGGAGCCAATGTACAGCAATGTAAATCCTGGAGATAGCAACCCGATTTATTC
CCAGATCTGGAGCATCCAGCATACAAAAGAAACTCAGCTAATTGTCCAATGATGCATCA
AGAGCATGAGGAACTTACAGTCCTCTATTCAGAACTGAAGAAGACACACCCAGACGACTC
TGCAGGGGAGGCTAGCAGCAGAGGCAGGGCCATGAAGAAGATGATGAAGAAACTATGA
GAATGTACCACGTGTATTACTGGCCTCAGACCAC TAGCCCCTTACCCAGAGTGGCCCACA
GGAAACAGCCTGCACCATTTTTTTTCTGTTCTCTCCAACCACACATCATCCATCTCTCC

FIGURE 7B

AGACTCTGCCTCCTACGAGGCTGGGCTGCAGGGTATGTGAGGCTGAGCAAAAGGTCTGCA
AATCTCCCCTGTGCCTGATCTGTGTGTTCCCCAGGAAGAGAGCAGGCAGCCTCTGAGCAA
GCACTGTGTTATTTTCACAGTGGAGACACGTGGCAAGGCAGGAGGGCCCTCAGCTCCTAG
GGCTGTCGAATAGAGGAGGAGAGAGAAATGGTCTAGCCAGGGTTACAAGGGCACAATCAT
GACCATTTGATCCAAGTGTGATCGAAAGCTGTTAATGTGCTCTCTGTATAAACAATTTGC
TCCAAATATTTTGTTTCCCTTTTTTGTGTGGCTGGTAGTGGCATTGCTGATGTTTTGGTG
TATATGCTGTATCCTTGCTACCATATTGGG

FIGURE 8A

DNA257955

><subunit 1 of 1, 734 aa, 1 stop
><MW: 80856, pI: 6.97, NX(S/T): 8
MLLWLLLLILTPGREQSGVAPKAVLLLNPPWSTAFKGEKVALICSSISHSLAQGDTYWYH
DEKLLKIKHDKIQITEPGNYQCKTRGSSLSDAVHVEFSPDWLILQALHPVFEGDNVILRC
QGKDNKNTHQKVYYKDGKQLPNSYNLEKITVNSVSRDNSKYHCTAYRKFYILDIEVTSKP
LNIQVQELFLHPVLRASSSTPIEGSPMTLTCETQLSPQRPDVQLQFSLFRDSQTLGLGWS
RSPRLQIPAMWTEDSGSYWCEVETVTHSIKKRSLRSQIRVQRVPVSNVNLEIRPTGGQLI
EGENMVLICSVAQGSGTVTFSWHKEGRVRSLGRKTQRSLLAELHVLTVKESDAGRYYCAA
DNVHSPILSTWIRVTVRIPVSHPVLTFRAPRAHTVVGDLLELHCESLRGSPPILYRFYHE
DVTLGNSSAPSGGGASFNLSLTAEHSGNYSCDADNGLGAQHSHGVSLRVTVPVSRPVLTL
RAPGAQAVVGDLLELHCESLRGSFPILYWFYHEDDTLGNISAHSGGGASFNLSLTTEHSG
NYSCEADNGLGAQHSKVVTLNVTGTSRNRTGLTAAGITGLVLSILVLAAAAALLHYARAR
RKPGGLSATGTSSHSPSECQEPSSSRPSRIDPQEPTHSKPLAPMELEPMYSNVNPGDSNP
IYSQIWSIQHTKENSANCPMMQEHEELTVLYSELKKTHPDDSAGEASSRGRAHEEDDEE
NYENVPRVLLASDH Signal sequence.
amino acids 1-13.

Transmembrane domain.
amino acids 574-594.

N-glycosylation site.
amino acids 426-429, 438-441, 448-451, 519-522, 531-534, 541-544, 561-564, 568-571.

Glycosaminoglycan attachment site.
amino acids 431-434, 524-527.

cAMP- and cGMP-dependent protein kinase phosphorylation site.
amino acids 270-273.

Protein kinase C phosphorylation site.
amino acids 177-179, 242-244, 268-270, 273-275, 335-337, 347-349, 375-377, 386-388, 406-408, 466-468, 479-481, 499-501, 565-567, 624-626, 708-710.

Casein kinase II phosphorylation site.
amino acids 88-91, 200-203, 347-350, 615-618, 628-631, 698-701, 703-706.

Tyrosine kinase phosphorylation site.
amino acids 349-356.

FIGURE 8B

N-myristoylation site.
amino acids 78-83, 86-91, 204-209, 236-241, 256-261, 432-437, 434-439, 447-452, 458-463, 518-523, 525-530, 527-532, 540-545, 551-556, 564-569, 571-576, 579-584, 604-609, 605-610.

Amidation site.
amino acids 331-334.

N-6 Adenine-specific DNA methylases signature.
amino acids 25-31.

Immunoglobulin domain.
amino acids 37-84, 113-165, 204-262, 302-360, 397-453, 490-546.

FIGURE 9A

DNA329863

CTCAATCAGCTTTATGCAGAGAAGAAGCTTACTGAGCTCACTGCTGGTGCTGGTGTAGGC
AAGTGCTGCTTTGGCAATCTGGGCTGACCTGGCTTGTCTCCTCAGAACTCCTTCTCCAAC
CCTGGAGCAGGCTTCCATGCTGCTGTGGGCGTCCTTGCTGGCCTTTGCTCCAGTCTGTGG
ACAATCTGCAGCTGCACACAAACCTGTGATTTCCGTCCATCCTCCATGGACCACATTCTT
CAAAGGAGAGAGAGTGACTCTGACTTGCAATGGATTTCAGTTCTATGCAACAGAGAAAAC
AACATGGTATCATCGGCACTACTGGGGAGAAAAGTTGACCCTGACCCCAGGAAACACCCT
CGAGGTTCGGGAATCTGGACTGTACAGATGCCAGGCCCGGGGCTCCCCACGAAGTAACCC
TGTGCGCTTGCTCTTTTCTTCAGACTCCTTAATCCTGCAGGCACCATATTCTGTGTTTGA
AGGTGACACATTGGTTCTGAGATGCCACAGAAGAAGGAAAGAGAAATTGACTGCTGTGAA
ATATACTTGGAATGGAAACATTCTTTCCATTTCTAATAAAAGCTGGGATCTTCTTATCCC
ACAAGCAAGTTCAAATAACAATGGCAATTATCGATGCATTGGATATGGAGATGAGAATGA
TGTATTTAGATCAAATTTCAAAATAATTAAAATTCAAGAACTATTTCCACATCCAGAGCT
GAAAGCTACAGACTCTCAGCCTACAGAGGGGAATTCTGTAAACCTGAGCTGTGAAACACA
GCTTCCTCCAGAGCGGTCAGACACCCCACTTCACTTCAACTTCTTCAGAGATGGCGAGGT
CATCCTGTCAGACTGGAGCACGTACCCGGAACTCCAGCTCCCAACCGTCTGGAGAGAAAA
CTCAGGATCCTATTGGTGTGGTGCTGAAACAGTGAGGGGTAACATCCACAAGCACAGTCC
CTCGCTACAGATCCATGTGCAGCGGATCCCTGTGTCTGGGGTGCTCCTGGAGACCCAGCC
CTCAGGGGCCAGGCTGTTGAAGGGGAGATGCTGGTCCTTGTCTGCTCCGTGGCTGAAGG
CACAGGGGATACCACATTCTCCTGGCACCGAGAGGACATGCAGGAGAGTCTGGGGAGGAA
AACTCAGCGTTCCCTGAGAGCAGAGCTGGAGCTCCCTGCCATCAGACAGAGCCATGCAGG
GGGATACTACTGTACAGCAGACAACAGCTACGGCCCTGTCCAGAGCATGGTGCTGAATGT
CACTGTGAGAGAGACCCCAGGCAACAGAGATGGCCTTGTCGCCGCGGGAGCCACTGGAGG
GCTGCTCAGTGCTCTTCTCCTGGCTGTGGCCCTGCTGTTTCACTGCTGGCGTCGGAGGAA
GTCAGGAGTTGGTTTCTTGGGAGACGAAACCAGGCTCCCTCCCGCTCCAGGCCCAGGAGA
GTCCTCCCATTCCATCTGCCCTGCCCAGGTGGAGCTTCAGTCGTTGTATGTTGATGTACA
CCCCAAAAAGGGAGATTTGGTATACTCTGAGATCCAGACTACTCAGCTGGGAGAAGAAGA
GGAAGCTAATACCTCCAGGACACTTCTAGAGGATAAGGATGTCTCAGTTGTCTACTCTGA
GGTAAAGACACAACACCCAGATAACTCAGCTGGAAAGATCAGCTCTAAGGATGAAGAAAG
TTAAGAGAATGAAAAGTTACGGGAACGTCCTACTCATGTGATTTCTCCCTTGTCCAAAGT
CCCAGGCCCAGTGCAGTCCTTGCGGCACCTGGAATGATCAACTCATTCCAGCTTTCTAAT
TCTTCTCATGCATATGCATTCACTCCCAGGAATACTCATTCGTCTACTCTGATGTTGGGA
TGGAATGGCCTCTGAAAGACTTCACTAAAATGACCAGGATCCACAGTTAAGAGAAGACCC
TGTAGTATTTGCTGTGGGCCTGACCTAATGCATTCCCTAGGGTCTGCTTTAGAGAAGGGG
GATAAAGAGAGAGAAGGACTGTTATGAAAACAGAAGCACAAATTTTGGTGAATTGGGAT
TTGCAGAGATGAAAAGACTGGGTGACCTGGATCTCTGCTTAATACATCTACAACCATTG
TCTCACTGGAGACTCACTTGCATCAGTTTGTTTAACTGTGAGTGGCTGCACAGGCACTGT
GCAAACAATGAAAAGCCCCTTCACTTCTGCCTGCACAGCTTACACTGTCAGGATTCAGTT
GCAGATTAAAGAACCCATCTGGAATGGTTTACAGAGAGAGGAATTTAAAAGAGGACATCA
GAAGAGCTGGAGATGCAAGCTCTAGGCTGCGCTTCCAAAAGCAAATGATAATTATGTTAA
TGTCATTAGTGACAAAGATTTGCAACATTAGAGAAAAGAGACACAAATATAAAATTAAAA
ACTTAAGTACCAACTCTCCAAAACTAAATTTGAACTTAAAATATTAGTATAAACTCATAA
TAAACTCTGCCTTTAAAAAAGATAAATATTTCCTACGTCTGTTCACTGAAATAATTACC

FIGURE 9B

AACCCCTTAGCAATAAGCACTCCTTGCAGAGAGGTTTTATTCTCTAAATACCATTCCCTT
CTCAAAGGAAATAAGGTTGCTTTTCTTGTAGGAACTGTGTCTTTGAGTTACTAATTAGTT
TATATGAGAATAATTCTTGCAATAAATGAAGAAGGAATAAAAGAAATAGGAAGCCACAAA
TTTGTATGGATATTTCATGATACACCTACTGGTTAAATAATTGACAAAAACCAGCAGCCA
AATATTAGAGGTCTCCTGATGGAAGTGTACAATACCACCTACAAATTATCCATGCCCCAA
GTGTTAAAACTGAATCCATTCAAGTCTTTCTAACTGAATACTTGTTTTATAGAAAATGCA
TGGAGAAAAGGAATTTGTTTAAATAACATTATGGGATTGCAACCAGCAAAACATAAACTG
AGAAAAAGTTCTATAGGGCAAATCACCTGGCTTCTATAACAAATAAATGGGAAAAAAATG
AAATAAAAGAAGAGAGGGAGGAAGAAAGGGAGAGAGAAGAAAAGAAAAATGAAGAAAAG
TAATTAGAATATTTTCAACATAAAGAAAGACGAATATTTAAGGTGACAGATATCCCAAC
TACGCTGATTTGATCTTTACAAATTATATGAGTGTATGAATTTGTCACATGTATCACCCC
CAAAAAAGAGAAAAGAAAAATAGAAGACATATAAATTAAATGAGACGAGACATGTCGA
CCAAAAGGAATGTGTGGGTCTTGTTTGGATCCTGACTCAAATTAAGAAAAAATAAAACTA
CCTACGAAATACTAAGAAAAATTTGTATACTAATATTAAGAAATTGTTGTGTTTTGGA
TATAAGTGATAGTTTATTGTAGTGATGTTTTTATAAAAGCAAAAGGATATTCACTTTCAG
CGCTTATACTGAAGTATTAGATTAAAGCTTATTAACGTA

FIGURE 10A

DNA329863

><subunit 1 of 1, 515 aa, 1 stop
><MW: 57224, pI: 6.45, NX(S/T): 4
MLLWASLLAFAPVCGQSAAAHKPVISVHPPWTTFFKGERVTLTCNGFQFYATEKTTWYHR
HYWGEKLTLTPGNTLEVRESGLYRCQARGSPRSNPVRLLFSSDSLILQAPYSVFEGDTLV
LRCHRRRKEKLTAVKYTWNGNILSISNKSWDLLIPQASSNNNGNYRCIGYGDENDVFRSN
FKIIKIQELFPHPELKATDSQPTEGNSVNLSCETQLPPERSDTPLHFNFFRDGEVILSDW
STYPELQLPTVWRENSGSYWCGAETVRGNIHKHSPSLQIHVQRIPVSGVLLETQPSGGQA
VEGEMLVLVCSVAEGTGDTTFSWHREDMQESLGRKTQRSLRAELELPAIRQSHAGGYYCT
ADNSYGPVQSMVLNVTVRETPGNRDGLVAAGATGGLLSALLLAVALLFHCWRRRKSGVGF
LGDETRLPPAPGPGESSHSICPAQVELQSLYVDVHPKKGDLVYSEIQTTQLGEEEEANTS
RTLLEDKDVSVVYSEVKTQHPDNSAGKISSKDEES Signal Sequence.
amino acids 1-16.

Transmembrane domain.
amino acids 387-407.

N-glycosylation site.
amino acids 147-150, 209-212, 374-377, 478-481.

Glycosaminoglycan attachment site.
amino acids 416-419.

cAMP- and cGMP-dependent protein kinase phosphorylation site.
amino acids 413-416.

Protein kinase C phosphorylation site.
amino acids 52-54, 90-92, 146-148, 265-267, 336-338, 339-341,
376-378, 479-481, 509-511.

Casein kinase II phosphorylation site.
amino acids 112-115, 242-245, 311-314, 376-379, 482-485, 509-
512, 510-513.

Tyrosine kinase phosphorylation site.
amino acids 457-463.

N-myristoylation site.
amino acids 15-20, 81-86, 89-94, 140-145, 163-168, 205-210, 257-
262, 315-320, 355-360, 382-387, 386-391, 391-396, 394-399, 395-
400.

FIGURE 10B

Amidation site.
amino acids 332-335.

Immunoglobulin domain.
amino acids 37-87, 116-169, 205-263, 303-361.

FIGURE 11

DNA346528

ACACACCCACAGGACCTGCAGCTGAACGAAGTTGAAGACAACTCAGGAGATCTGTTGGAA
AGAGAACGATAGAGGAAAATATATGAATGTTGCCATCTTTAGTTCCCTGTGTTGGGAAAA
CTGTCTGGCTGTACCTCCAAGCCTGGCCAAACCCTGTGTTTGAAGGAGATGCCCTGACTC
TGCGATGTCAGGGATGGAAGAATACACCACTGTCTCAGGTGAAGTTCTACAGAGATGGAA
AATTCCTTCATTTCTCTAAGGAAAACCAGACTCTGTCCATGGGAGCAGCAACAGTGCAGA
GCCGTGGCCAGTACAGCTGCTCTGGGCAGGTGATGTATATTCCACAGACATTCACACAAA
CTTCAGAGACTGCCATGGTTCAAGTCCAAGAGCTGTTTCCACCTCCTGTGCTGAGTGCCA
TCCCCTCTCCTGAGCCCCGAGAGGGTAGCCTGGTGACCCTGAGATGTCAGACAAAGCTGC
ACCCCCTGAGGTCAGCCTTGAGGCTCCTTTTCTCCTTCCACAAGGACGGCCACACCTTGC
AGGACAGGGGCCCTCACCCAGAACTCTGCATCCCGGGAGCCAAGGAGGGAGACTCTGGGC
TTTACTGGTGTGAGGTGGCCCCTGAGGGTGGCCAGGTCCAGAAGCAGAGCCCCCAGCTGG
AGGTCAGAGTGCAGGCTCCTGTATCCCGTCCTGTGCTCACTCTGCACCACGGGCCTGCTG
ACCCTGCTGTGGGGACATGGTGCAGCTCCTCTGTGAGGCACAGAGGGGCTCCCCTCCGA
TCCTGTATTCCTTCTACCTTGATGAGAAGATTGTGGGGAACCACTCAGCTCCCTGTGGTG
GAACCACCTCCCTCCTCTTCCCAGTGAAGTCAGAACAGGATGCTGGGAACTACTCCTGCG
AGGCTGAGAACAGTGTCTCCAGAGAGGAGTGAGCCCAAGAAGCTGTCTCTGAAGGGTT
CTCAAGTCTTGTTCACTCCCGCCAGCAACTGGCTGGTTCCTTGGCTTCCTGCGAGCCTGC
TTGGCCTGATGGTTATTGCTGCTGCACTTCTGGTTTATGTGAGATCCTGGAGAAAAGCTG
GGCCCCTTCCATCCCAGATACCACCCACAGCTCCAGGTGGAGAGCAGTGCCCACTATATG
CCAACGTGCATCACCAGAAAGGGAAAGATGAAGGTGTTGTCTACTCTGTGGTGCATAGAA
CCTCAAAGAGGAGTGAAGGACAGTTCTATCATCTGTGCGGAGGTGAGATGCCTGCAGCCC
AGTGAGGTTTCATCCACGGAGGTGAATATGAGAAGCAGGACTCTCCAAGAACCCCTTAGC
GACTGTGAGGAGGTTCTCTGCTAGTGATGGTGTTCTCCTATCAACACACGCCCACCCCCA
GTCTCCAGTGCTCCTCAGGAAGACAGTGGGGTCCTCAACTCTTTCTGTGGGTCCTTCAGT
TCCCAAGCCCAGCATCACAGAGCCCCCTGAGCCCTTGTCCTGGTCAGGAGCACCTGAACC
CTGGGTTCTTTTCTTAGCAGAAGACCAACCAATGGAATGGGAAGGGAGATGCTCCCACCA
ACACACACACTTAGGTTCAATCAGTGACACTGGACACATAAGCCACAGATGTCTTCTTTC
CATACAAGCATGTTAGTTCGCCCCAATATACATATATATATGAAATAGTCATGTGCCGCA
TAACAACATTTCAGTCAGTGATAGACTGCATACACAACAGTGGTCCCATAAGACTGTAAT
GGAGTTTAAAAATTCCTACTGCCTAGTGATATCATAGTTGCCTTAACATCATAACACAAC
ACATTTCTCACGCGTTTGTGGTGATGCTGGTACAAACAAGCTACAGCGCCGCTAGTCATA
TACAAATATAGCACATACAATTATGTACAGTACACTATACTTGATAATGATAATAAACAA
CTATGTTACTGGT

FIGURE 12

DNA346528

><subunit 1 of 1, 392 aa, 1 stop
><MW: 42948, pI: 8.37, NX(S/T): 3
MLPSLVPCVGKTVWLYLQAWPNPVFEGDALTLRCQGWKNTPLSQVKFYRDGKFLHFSKEN
QTLSMGAATVQSRGQYSCSGQVMYIPQTFTQTSETAMVQVQELFPPPVLSAIPSPEPREG
SLVTLRCQTKLHPLRSALRLLFSFHKDGHTLQDRGPHPELCIPGAKEGDSGLYWCEVAPE
GGQVQKQSPQLEVRVQAPVSRPVLTLHHGPADPAVGDMVQLLCEAQRGSPPILYSFYLDE
KIVGNHSAPCGGTTSLLFPVKSEQDAGNYSCEAENSVSRERSEPKKLSLKGSQVLFTPAS
NWLVPWLPASLLGLMVIAAALLVYVRSWRKAGPLPSQIPPTAPGGEQCPLYANVHHQKGK
DEGVVYSVVHRTSKRSEGQFYHLCGGEMPAAQ

Transmembrane domain.
amino acids 302-322.

N-glycosylation site.
amino acids 60-63, 245-248, 268-271.

cAMP- and cGMP-dependent protein kinase phosphorylation site.
amino acids 285-288.

Protein kinase C phosphorylation site.
amino acids 31-33, 124-126, 288-290, 327-329, 372-374, 373-375.

Casein kinase II phosphorylation site.
amino acids 150-153, 262-265.

Tyrosine kinase phosphorylation site.
amino acids 166-173, 261-269, 358-366, 374-381.

N-myristoylation site.
amino acids 74-79, 120-125, 164-169, 171-176, 251-256, 267-272, 363-368.

Immunoglobulin domain.
amino acids 27-80, 120-177, 216-273.

FIGURE 13

```
ATGGGATGGTCATGTATCATCCTTTTTCTAGTAGCAACTGCAACTGGAGCGTACGCTCAGG
TACAGTTGAAGCAATCTGGACCTAGCCTAGTGCAGCCCTCACAGAGCCTGTCCATAACCTG
CACAGTCTCTGGTTTCTCATTAACTAACTATGGTGTACACTGGGTTCGCCAGTCTCCAGGA
AAGGGTCTGGAGTGGCTGGGACTGATATGGATAGGTGGAAACACAGACTACAATGCAGCTT
TCATGTCCCGACTGAGCATCACCAAGGACAACTCCAAGAGCCAAGTTTTCTTTAAAATGAA
CAGTCTGCAAGCTGATGACACTGCCATATACTACTGTGTCAAAGGCTATGGTGACTTCTAC
TATGCTATGGACTACTGGGGTCAAGGAACCACGGTCACTGTCTCTGCAGCCTCCACCAAGG
GCCCATCGGTCTTCCCCCTGGCACCCTCCTCCAAGAGCACCTCTGGGGGCACAGCGGCCCT
GGGCTGCCTGGTCAAGGACTACTTCCCCGAACCGGTGACGGTGTCGTGGAACTCAGGCGCC
CTGACCAGCGGCGTGCACACCTTCCCGGCTGTCCTACAGTCCTCAGGACTCTACTCCCTCA
GCAGCGTGGTGACTGTGCCCTCTAGCAGCTTGGGCACCCAGACCTACATCTGCAACGTGAA
TCACAAGCCCAGCAACACCAAGGTGGACAAGAAAGTTGAGCCCAAATCTTGTGACAAAACT
CACACATGCCCACCGTGCCCAGCACCTGAACTCCTGGGGGGACCGTCAGTCTTCCTCTTCC
CCCCAAAACCCAAGGACACCCTCATGATCTCCCGGACCCCTGAGGTCACATGCGTGGTGGT
GGACGTGAGCCACGAAGACCCTGAGGTCAAGTTCAACTGGTACGTGGACGGCGTGGAGGTG
CATAATGCCAAGACAAAGCCGCGGGAGGAGCAGTACAACAGCACGTACCGGGTGGTCAGCG
TCCTCACCGTCCTGCACCAGGACTGGCTGAATGGCAAGGAGTACAAGTGCAAGGTCTCCAA
CAAAGCCCTCCCAGCCCCCATCGAGAAAACCATCTCCAAAGCCAAAGGGCAGCCCCGAGAA
CCACAGGTGTACACCCTGCCCCCATCCCGGGAAGAGATGACCAAGAACCAGGTCAGCCTGA
CCTGCCTGGTCAAAGGCTTCTATCCCAGCGACATCGCCGTGGAGTGGGAGAGCAATGGGCA
GCCGGAGAACAACTACAAGACCACGCCTCCCGTGCTGGACTCCGACGGCTCCTTCTTCCTC
TACAGCAAGCTCACCGTGGACAAGAGCAGGTGGCAGCAGGGGAACGTCTTCTCATGCTCCG
TGATGCATGAGGCTCTGCACAACCACTACACGCAGAAGAGCCTCTCCCTGTCTCCGGGTAA
ATGA
```

FIGURE 14

ATGGGATGGTCATGTATCATCCTTTTTCTAGTAGCAACTGCAACTGGAGTACATTCAGATA
TCGTGATGACCCAGTCTCATAAATTCATGTCCACATCAGTAGGAGACAGGGTCAGCATCTC
CTGCAAGGCCAGTCAGGATGTGAGTTCTGCTGTAGCCTGGTATCAACAGAAGCCAGGACAT
TCTCCTAAACTACTGATTTACTCGGGATACCGGTACACTAGAGTCCCTGATCGCTTCACTG
GCAGTGGATCTGGGACGGATTTCACTTTCACCATCAGCAGTGTGCAGGCTGAAGACCTGGC
ATTTTATTTCTGTCAGCAACATTATAGTACTCCATTCACGTTCGGCTCGGGTACCAAGGTG
GAGATCAAACGAACTGTGGCTGCACCATCTGTCTTCATCTTCCCGCCATCTGATGAGCAGT
TGAAATCTGGAACTGCTTCTGTTGTGTGCCTGCTGAATAACTTCTATCCCAGAGAGGCCAA
AGTACAGTGGAAGGTGGATAACGCCCTCCAATCGGGTAACTCCCAGGAGAGTGTCACAGAG
CAGGACAGCAAGGACAGCACCTACAGCCTCAGCAGCACCCTGACGCTGAGCAAAGCAGACT
ACGAGAAACACAAAGTCTACGCCTGCGAAGTCACCCATCAGGGCCTGAGCTCGCCCGTCAC
AAAGAGCTTCAACAGGGGAGAGTGTTAA

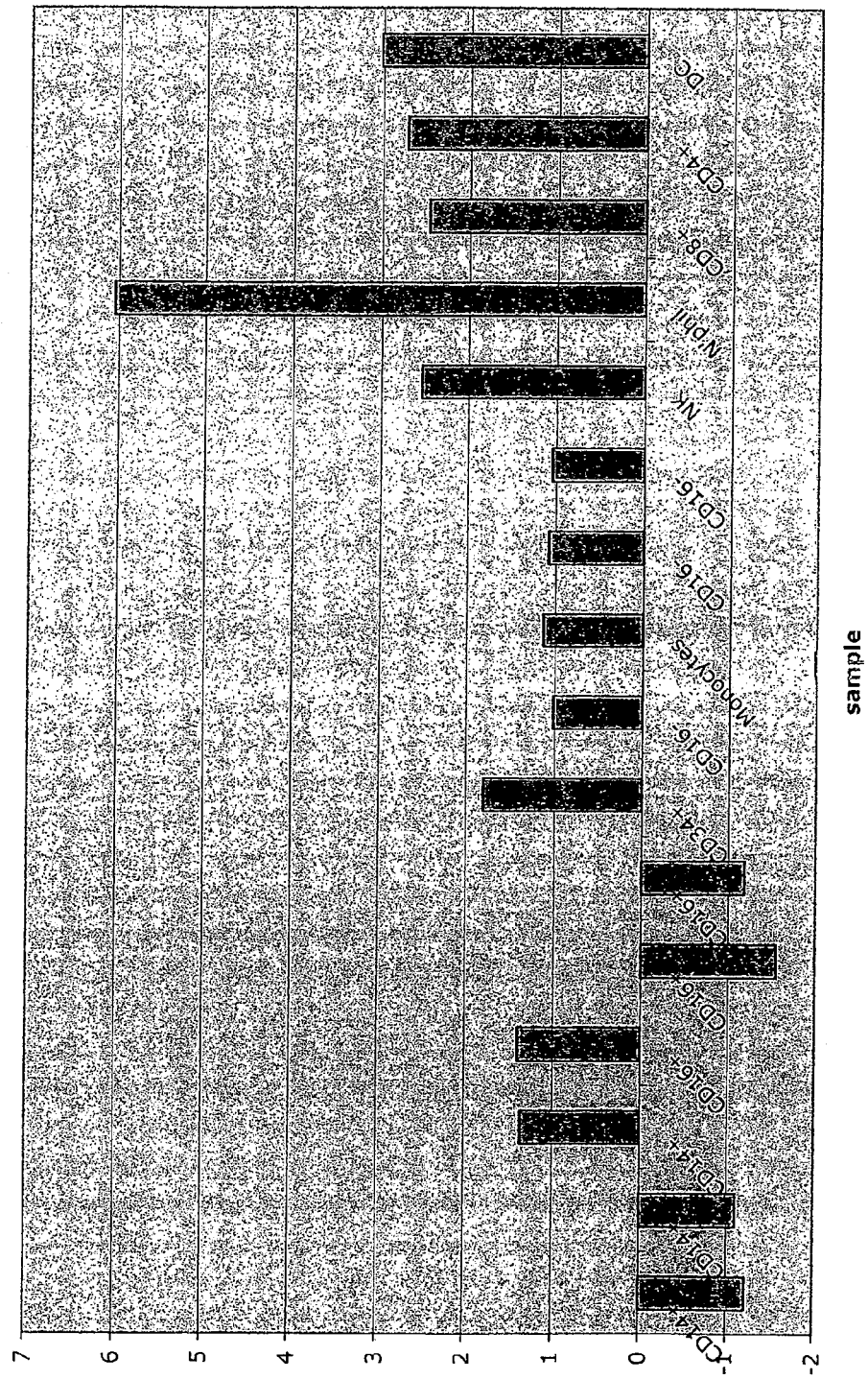

SPAP1

IRTA2

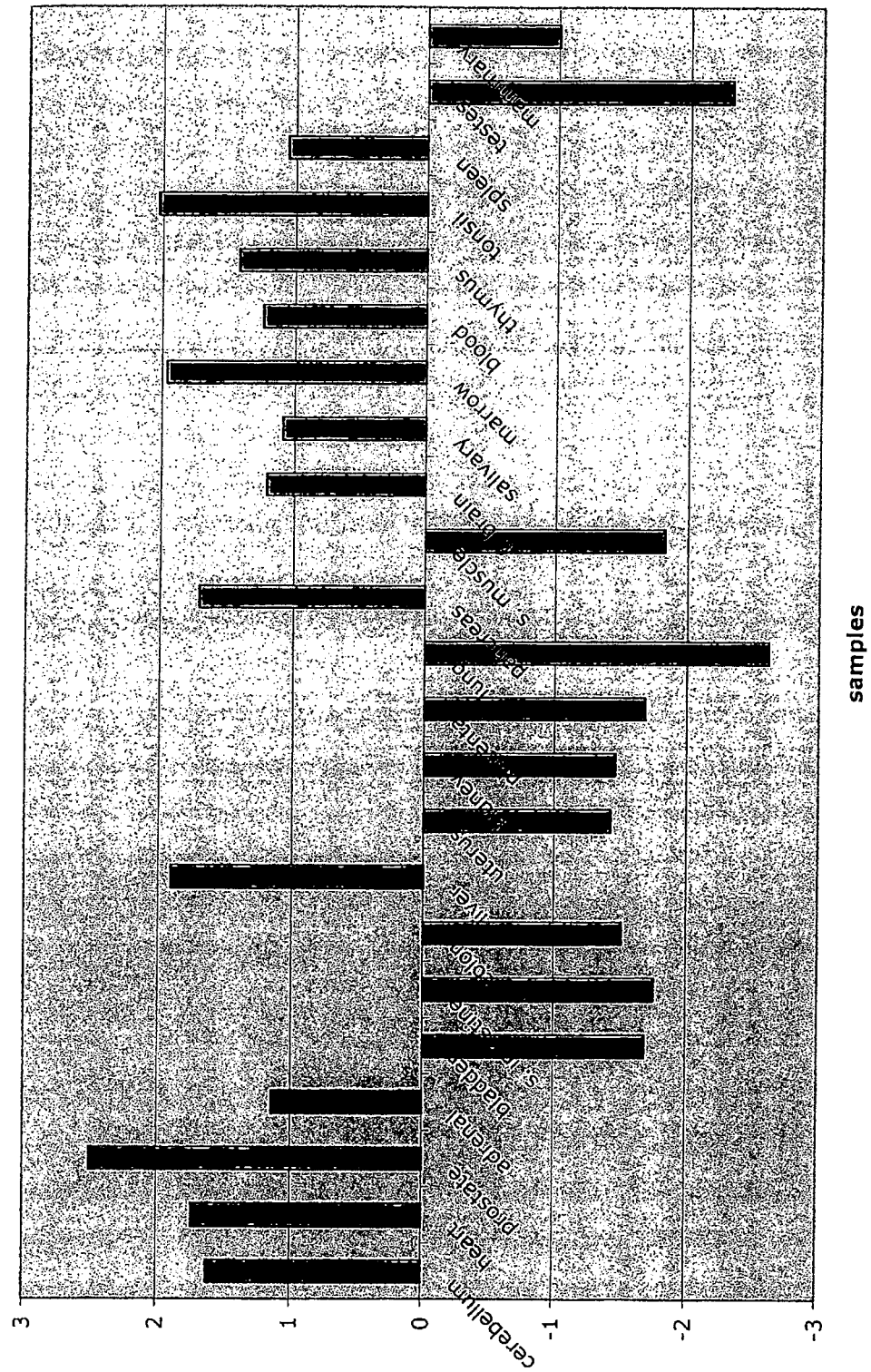

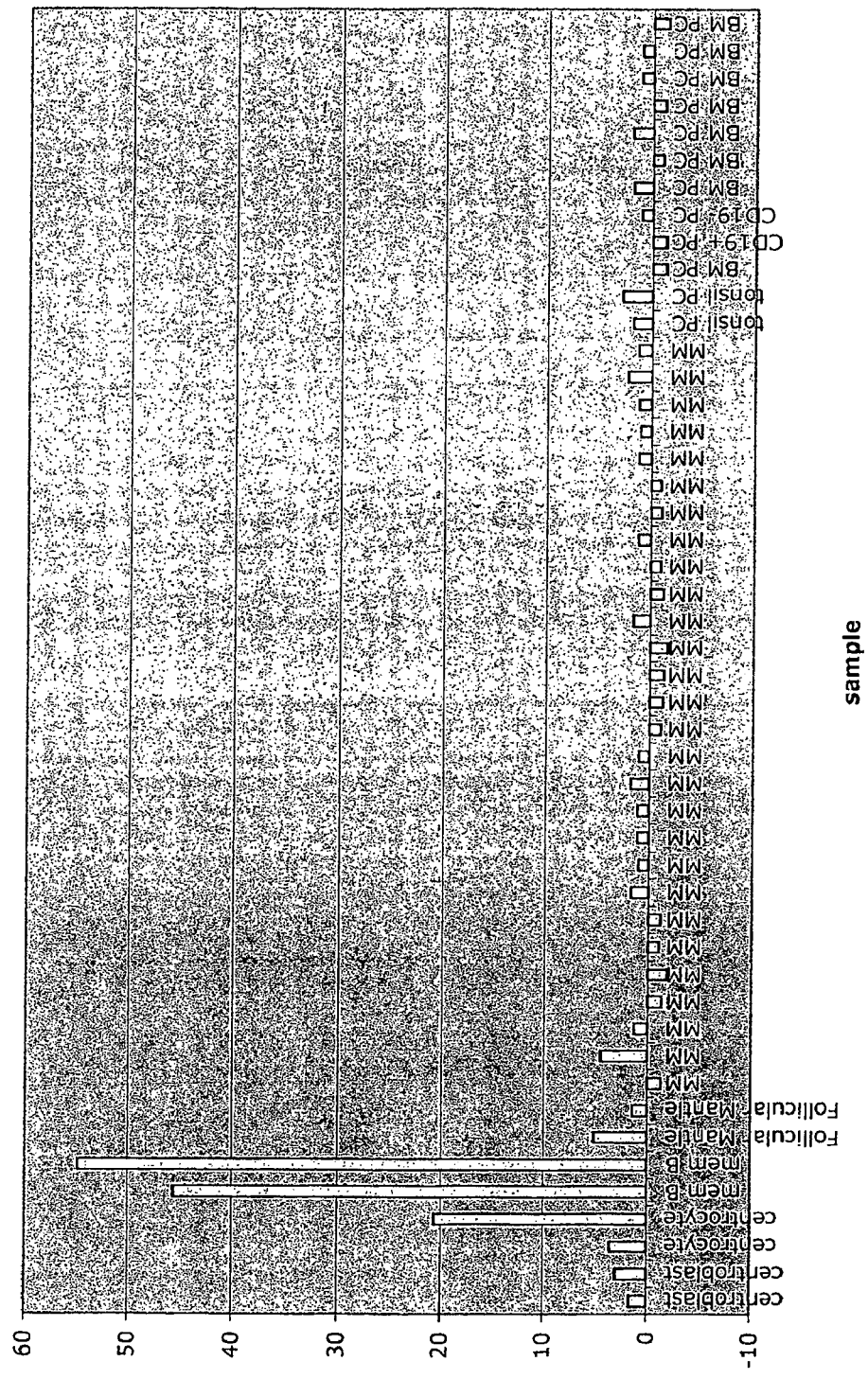

FIGURE 21A

DNA257845

AATTCACTAATGCATTCTGCTCTTTTTGAGAGCACAGCTTCTCAGATGTGCTCCTTGGAG
CTGGTGTGCAGTGTCCTGACTGTAAGATCAAGTCCAAACCTGTTTTGGAATTGAGGAAAC
TTCTCTTTTGATCTCAGCCCTTGGTGGTCCAGGTCTTATGCTGCTGTGGGTGATATTAC
TGGTCCTGGCTCCTGTCAGTGGACAGTTTGCAAGGACACCCAGGCCCATTATTTTCCTCC
AGCCTCCATGGACCACAGTCTTCCAAGGAGAGAGAGTGACCCTCACTTGCAAGGGATTTC
GCTTCTACTCACCACAGAAAACAAAATGGTACCATCGGTACCTCGGGAAAGAAATACTAA
GAGAAACCCCAGACAATATCCTTGAGGTTCAGGAATCTGGAGAGTACAGATGCCAGGCCC
AGGGCTCCCCTCTCAGTAGCCCTGTGCACTTGGATTTTTCTTCAGCTTCGCTGATCCTGC
AAGCTCCACTTTCTGTGTTTGAAGGAGACTCTGTGGTTCTGAGGTGCCGGGCAAAGGCGG
AAGTAACACTGAATAATACTATTTACAAGAATGATAATGTCCTGGCATTCCTTAATAAAA
GAACTGACTTCCATATTCCTCATGCATGTCTCAAGGACAATGGTGCATATCGCTGTACTG
GATATAAGGAAAGTTGTTGCCCTGTTTCTTCCAATACAGTCAAAATCCAAGTCCAAGAGC
CATTTACACGTCCAGTGCTGAGAGCCAGCTCCTTCCAGCCCATCAGCGGGAACCCAGTGA
CCCTGACCTGTGAGACCCAGCTCTCTCTAGAGAGGTCAGATGTCCCGCTCCGGTTCCGCT
TCTTCAGAGATGACCAGACCCTGGGATTAGGCTGGAGTCTCTCCCCGAATTTCCAGATTA
CTGCCATGTGGAGTAAAGATTCAGGGTTCTACTGGTGTAAGGCAGCAACAATGCCTCACA
GCGTCATATCTGACAGCCCGAGATCCTGGATACAGGTGCAGATCCCTGCATCTCATCCTG
TCCTCACTCTCAGCCCTGAAAAGGCTCTGAATTTTGAGGGAACCAAGGTGACACTTCACT
GTGAAACCCAGGAAGATTCTCTGCGCACTTTGTACAGGTTTTATCATGAGGGTGTCCCCC
TGAGGCACAAGTCAGTCCGCTGTGAAAGGGGAGCATCCATCAGCTTCTCACTGACTACAG
AGAATTCAGGGAACTACTACTGCACAGCTGACAATGGCCTTGGCGCCAAGCCCAGTAAGG
CTGTGAGCCTCTCAGTCACTGTTCCCGTGTCTCATCCTGTCCTCAACCTCAGCTCTCCTG
AGGACCTGATTTTTGAGGGAGCCAAGGTGACACTTCACTGTGAAGCCCAGAGAGGTTCAC
TCCCCATCCTGTACCAGTTTCATCATGAGGATGCTGCCCTGGAGCGTAGGTCGGCCAACT
CTGCAGGAGGAGTGGCCATCAGCTTCTCTCTGACTGCAGAGCATTCAGGGAACTACTACT
GCACAGCTGACAATGGCTTTGGCCCCAGCGCAGTAAGGCGGTGAGCCTCTCCATCACTG
TCCCTGTGTCTCATCCTGTCCTCACCCTCAGCTCTGCTGAGGCCCTGACTTTTGAAGGAG
CCACTGTGACACTTCACTGTGAAGTCCAGAGAGGTTCCCCACAAATCCTATACCAGTTTT
ATCATGAGGACATGCCCCTGTGGAGCAGCTCAACACCCTCTGTGGGAAGAGTGTCCTTCA
GCTTCTCTCTGACTGAAGGACATTCAGGGAATTACTACTGCACAGCTGACAATGGCTTTG
GTCCCCAGCGCAGTGAAGTGGTGAGCCTTTTGTCACTGTTCCAGTGTCTCGCCCCATCC
TCACCCTCAGGGTTCCCAGGGCCAGGCTGTGGTGGGGACCTGCTGGAGCTTCACTGTG
AGGCCCCGAGAGGCTCTCCCCAATCCTGTACTGGTTTTATCATGAGGATGTCACCCTGG
GGAGCAGCTCAGCCCCCTCTGGAGGAGAAGCTTCTTTCAACCTCTCTCTGACTGCAGAAC
ATTCTGGAAACTACTCATGTGAGGCCAACAATGGCCTAGTGCCCAGCACAGTGACACAA
TATCACTCAGTGTTATAGTTCCAGTATCTCGTCCCATCCTCACCTTCAGGGCTCCCAGGG
CCCAGGCTGTGGTGGGGACCTGCTGGAGCTTCACTGTGAGGCCCTGAGAGGCTCCTCCC
CAATCCTGTACTGGTTTTATCATGAAGATGTCACCCTGGGTAAGATCTCAGCCCCCTCTG
GAGGAGGGGCCTCCTTCAACCTCTCTCTGACTACAGAACATTCTGGAATCTACTCCTGTG
AGGCAGACAATGGTCCGGAGGCCCAGCGCAGTGAGATGGTGACACTGAAAGTTGCAGTTC

FIGURE 21B

```
CGGTGTCTCGCCCGGTCCTCACCCTCAGGGCTCCCGGGACCCATGCTGCGGTGGGGGACC
TGCTGGAGCTTCACTGTGAGGCCCTGAGAGGCTCTCCCCTGATCCTGTACCGGTTTTTC
ATGAGGATGTCACCCTAGGAAATAGGTCGTCCCCCTCTGGAGGAGCGTCCTTAAACCTCT
CTCTGACTGCAGAGCACTCTGGAAACTACTCCTGTGAGGCCGACAATGGCCTCGGGGCCC
AGCGCAGTGAGACAGTGACACTTTATATCACAGGGCTGACCGCGAACAGAAGTGGCCCTT
TTGCCACAGGAGTCGCCGGGGGCCTGCTCAGCATAGCAGGCCTTGCTGCGGGGCACTGC
TGCTCTACTGCTGGCTCTCGAGAAAGCAGGGAGAAAGCCTGCCTCTGACCCCGCCAGGA
GCCCTCCAGACTCGGACTCCCAAGAGCCCACCTATCACAATGTACCAGCCTGGGAAGAGC
TGCAACCAGTGTACACTAATGCAAATCCTAGAGGAGAAAATGTGGTTTACTCAGAAGTAC
GGATCATCCAAGAGAAAAAGAAACATGCAGTGGCCTCTGACCCCAGGCATCTCAGGAACA
AGGGTTCCCCTATCATCTACTCTGAAGTTAAGGTGGCGTCAACCCCGGTTTCCGGATCCC
TGTTCTTGGCTTCCTCAGCTCCTCACAGATGAGTCCACACGTCTCTCCAACTGCTGTTTC
AGCCTCTGCACCCCAAAGTTCCCCTTGGGGGAGAAGCAGCATTGAAGTGGGAAGATTTAG
GCTGCCCCAGACCATATCTACTGGCCTTTGTTTCACATGTCCTCATTCTCAGTCTGACCA
GAATGCAGGGCCCTGCTGGACTGTCACCTGTTTCCCAGTTAAAGCCCTGACTGGCAGGTT
TTTTAATCCAGTGGCAAGGTGCTCCCACTCCAGGGCCCAGCACATCTCCTGGATTCCTTA
GTGGGCTTCAGCTGTGATTGCTGTTCTGAGTACTGCTCTCATCACACCCCCACAGAGGGG
GTCTTACCACACAAAGGGAGAGTGGGCCTTCAGGAGATGCCGGGCTGGCCTAACAGCTCA
GGTGCTCCTAAACTCCGACACAGAGTTCCTGCTTTGGGTGGATGCATTTCTCAATTGTCA
TCAGCCTGGTGGGGCTACTGCAGTGTGCTGCCAAATGGGACAGCACACAGCCTGTGCACA
TGGGACATGTGATGGGTCTCCCCACGGGGCTGCATTTCACACTCCTCCACCTGTCTCAA
ACTCTAAGGTCGGCACTTGACACCAAGGTAACTTCTCTCCTGCTCATGTGTCAGTGTCTA
CCTGCCCAAGTAAGTGGCTTTCATACACCAAGTCCCAAGTTCTTCCCATCCTAACAGAAG
TAACCCAGCAAGTCAAGGCCAGGAGGACCAGGGGTGCAGACAGAACACATACTGGAACAC
AGGAGGTGCTCAATTACTATTTGACTGACTGACTGAATGAATGAATGAATGAGGAAGAAA
ACTGTGGGTAATCAAACTGGCATAAAATCCAGTGCACTCCCTAGGAAATCCGGGAGGTAT
TCTGGCTTCCCTAAGAAACAACGGAAGAGAAGGAGCTTGGATGAGGAAACTGTTCAGCAA
GAGGAAGGGCTTCTCACACTTTCATGTGCTTGTGGATCACCTGAGGATCCTGTGAAAATA
CAGATACTGATTCAGTGGGTCTGTGTAGAGCCTGAGACTGCCATTCTAACATGTTCCCAG
GGGATGCTGATGCTGCTGGCCCTGGGACTGCACTGCATGCATGTGAAGCCCTATAGGTCT
CAGCAGAGGCCCATGGAGAGGGAATGTGTGGCTCTGGCTGCCCAGGGCCCAACTCGGTTC
ACACGGATCGTGCTGCTCCCTGGCCAGCCTTTGGCCACAGCACCACCAGCTGCTGTTGCT
GAGAGAGCTTCTTCTCTGTGACATGTTGGCTTTCATCAGCCACCCTGGGAAGCGGAAAGT
AGCTGCCACTATCTTTGTTTCCCCACCTCAGGCCTCACACTTTCCATGAAAAGGGTGAA
TGTATATAACCTGAGCCCTCTCCATTCAGAGTTGTTCTCCATCTCTGAGCAATGGGATG
TTCTGTTCCGCTTTTATGATATCCATCACATCTTATCTTGATCTTTGCTCCCAGTGGATT
GTACAGTGATGACTTTTAAGCCCCACGGCCCTGAAATAAAATCCTTCCAAGGGCATTGGA
AGCTCTCCACCTGAACCATGGCTTTTCATGCTTCCAAGTGTCAGGGCCTTGCCCAGAT
AGACAGGGCTGACTCTGCTGCCCCAACCTTTCAAGGAGGAAACCAGACACCTGAGACAGG
AGCCTGTATGCAGCCCAGTGCAGCCTTGCAGAGGACAAGGCTGGAGGCATTTGTCATCAC
TACAGATATGCAACTAAATAGACGTGGAGCAAGAGAAATGCATTCCCACCGAGGCCGCT
TTTTTAGGCCTAGTTGAAAGTCAAGAAGGACAGCAGCAAGCATAGGCTCAGGATTAAAGA
AAAAAATCTGCTCACAGTTTGTTCTGGAGGTCACATCACCAACAAAGCTCACGCCCTATG
```

FIGURE 21C

```
CAGTTCTGAGAAGGTGGAGGCACCAGGCTCAAAAGAGGAAATTTAGAATTTCTCATTGGG
AGAGTAAGGTACCCCCATCCCAGAATGATAACTGCACAGTGGCAGAACAAACTCCACCCT
AATGTGGGTGGACCCCATCCAGTCTGTTGAAGGCCTGAGTGTAACAAAAGGGCTTATTCT
TCCTCAAGTAAGGGGGAACTCCTGCTTTGGGCTGGGACATAAGTTTTTCTGCTTTCAGAC
GCAAACTGAAAAATGGCTCTTCTTGGGTCTTGAGCTTGCTGGCATATGGACTGAAAGAAA
CTATGCTATTGGATCTCCTGGATCTCCAGCTTGCTGACTGCAGATCTTGAGATATGTCAG
CCTCTACAGTCACAAGAGCTAATTCATTCTAATAAACCAATCTTTCTGTAAA
```

FIGURE 22A

```
DNA257845
></usr/seqdb2/sst/DNA/Dnaseqs.min/ss.DNA257845
><subunit 1 of 1, 977 aa, 1 stop
><MW: 106477, pI: 7.04, NX(S/T): 9
```

MLLWVILLVLAPVSGQFARTPRPIIFLQPPWTTVFQGERVTLTCKGFRFYSPQKTKWYHR
YLGKEILRETPDNILEVQESGEYRCQAQGSPLSSPVHLDFSSASLILQAPLSVFEGDSVV
LRCRAKAEVTLNNTIYKNDNVLAFLNKRTDFHIPHACLKDNGAYRCTGYKESCCPVSSNT
VKIQVQEPFTRPVLRASSFQPISGNPVTLTCETQLSLERSDVPLRFRFFRDDQTLGLGWS
LSPNFQITAMWSKDSGFYWCKAATMPHSVISDSPRSWIQVQIPASHPVLTLSPEKALNFE
GTKVTLHCETQEDSLRTLYRFYHEGVPLRHKSVRCERGASISFSLTTENSGNYYCTADNG
LGAKPSKAVSLSVTVPVSHPVLNLSSPEDLIFEGAKVTLHCEAQRGSLPILYQFHHEDAA
LERRSANSAGGVAISFSLTAEHSGNYYCTADNGFGPQRSKAVSLSITVPVSHPVLTLSSA
EALTFEGATVTLHCEVQRGSPQILYQFYHEDMPLWSSSTPSVGRVSFSFSLTEGHSGNYY
CTADNGFGPQRSEVVSLFVTVPVSRPILTLRVPRAQAVVGDLLELHCEAPRGSPPILYWF
YHEDVTLGSSSAPSGGEASFNLSLTAEHSGNYSCEANNGLVAQHSDTISLSVIVPVSRPI
LTFRAPRAQAVVGDLLELHCEALRGSSPILYWFYHEDVTLGKISAPSGGGASFNLSLTTE
HSGIYSCEADNGPEAQRSEMVTLKVAVPVSRPVLTLRAPGTHAAVGDLLELHCEALRGSP
LILYRFFHEDVTLGNRSSPSGGASLNLSLTAEHSGNYSCEADNGLGAQRSETVTLYITGL
TANRSGPFATGVAGGLLSIAGLAAGALLLYCWLSRKAGRKPASDPARSPPDSDSQEPTYH
NVPAWEELQPVYTNANPRGENVVYSEVRIIQEKKKHAVASDPRHLRNKGSPIIYSEVKVA
STPVSGSLFLASSAPHR

Signal sequence.
amino acids 1-15

Transmembrane domain.
amino acids 851-871

N-glycosylation sites.
amino acids 132-135, 383-386, 621-624, 631-634, 714-717, 795-798, 806-809, 816-819, 843-846

Glycosaminoglycan attachment site.
amino acids 707-710

N-myristoylation sites.
amino acids 89-94, 162-167, 204-209, 236-241, 301-306, 338-343, 351-356, 362-367, 394-399, 431-436, 444-449, 487-492, 537-542, 615-620, 630-635, 708-703, 710-715, 723-728, 760-765, 802-807, 815-820, 826-831, 839-844, 851-856, 854-859, 861-866

FIGURE 22B

Amidation site.
amino acids 877-880

Immunoglobulin domains.
amino acids 37-87, 116-168, 204-262, 301-357, 394-450, 487-543, 580-636, 673-729, 766-821

SEQUENCE LISTING

<160> NUMBER OF SEQ ID NOS: 19

<210> SEQ ID NO 1
<211> LENGTH: 1846
<212> TYPE: DNA
<213> ORGANISM: Homo sapiens

<400> SEQUENCE: 1

| | | | | | |
|---|---|---|---|---|---|
| gttggtgacc | aagagtacat | ctcttttcaa | atagctggat | taggtcctca | 50 |
| tgctgctgtg | gtcattgctg | gtcatctttg | atgcagtcac | tgaacaggca | 100 |
| gattcgctga | cccttgtggc | gccctcttct | gtcttcgaag | gagacagcat | 150 |
| cgttctgaaa | tgccagggag | aacagaactg | gaaaattcag | aagatggctt | 200 |
| accataagga | taacaaagag | ttatctgttt | tcaaaaaatt | ctcagatttc | 250 |
| cttatccaaa | gtgcagtttt | aagtgacagt | ggtaactatt | tctgtagtac | 300 |
| caaaggacaa | ctctttctct | gggataaaac | ttcaaatata | gtaaagataa | 350 |
| aagtccaaga | gctcttttcaa | cgtcctgtgc | tgactgccag | ctccttccag | 400 |
| cccatcgaag | ggggtccagt | gagcctgaaa | tgtgagaccc | ggctctctcc | 450 |
| acagaggttg | gatgttcaac | tccagttctg | cttcttcaga | gaaaaccagg | 500 |
| tcctggggtc | aggctggagc | agctctccgg | agctccagat | ttctgccgtg | 550 |
| tggagtgaag | acacagggtc | ttactggtgc | aaggcagaaa | cggtgactca | 600 |
| caggatcaga | aaacagagcc | tccaatccca | gattcacgtg | cagagaatcc | 650 |
| ccatctctaa | tgtaagcttg | gagatccggg | cccccgggg | acaggtgact | 700 |
| gaaggacaaa | aactgatcct | gctctgctca | gtggctgggg | gtacaggaaa | 750 |
| tgtcacattc | tcctggtaca | gagaggccac | aggaaccagt | atgggaaaga | 800 |
| aaacccagcg | ttccctgtca | gcagagctgg | agatcccagc | tgtgaaagag | 850 |
| agtgatgccg | gcaaatatta | ctgtagagct | gacaacggcc | atgtgcctat | 900 |
| ccagagcaag | gtggtgaata | tccctgtgag | aattccagtg | tctcgccctg | 950 |
| tcctcaccct | caggtctcct | ggggcccagg | ctgcagtggg | ggacctgctg | 1000 |
| gagcttcact | gtgaggccct | gagaggctct | cccccaatct | tgtaccaatt | 1050 |
| ttatcatgag | gatgtcaccc | ttgggaacag | ctcggccccc | tctggaggag | 1100 |
| gggcctcctt | caacctctct | tgactgcag | aacattctgg | aaactactcc | 1150 |
| tgtgaggcca | acaacggcct | gggggcccag | tgcagtgagg | cagtgccagt | 1200 |
| ctccatctca | ggacctgatg | gctatagaag | agacctcatg | acagctggag | 1250 |
| ttctctgggg | actgtttggt | gtccttggtt | tcactggtgt | tgctttgctg | 1300 |
| ttgtatgcct | tgttccacaa | gatatcagga | gaaagttctg | ccactaatga | 1350 |
| acccagaggg | gcttccaggc | caaatcctca | agagttcacc | tattcaagcc | 1400 |
| caaccccaga | catggaggag | ctgcagccag | tgtatgtcaa | tgtgggctct | 1450 |
| gtagatgtgg | atgtggttta | ttctcaggtc | tggagcatgc | agcagccaga | 1500 |
| aagctcagca | acatcagga | cacttctgga | gaacaaggac | tcccaagtca | 1550 |
| tctactcttc | tgtgaagaaa | tcataacact | tggaggaatc | agaagggaag | 1600 |
| atcaacagca | aggatgggc | atcattaaga | cttgctataa | aaccttatga | 1650 |
| aaatgcttga | ggcttatcac | ctgccacagc | cagaacgtgc | ctcaggaggc | 1700 |

```
acctcctgtc attttttgtcc tgatgatgtt tcttctccaa tatcttctttt         1750 tacctatcaa tattcattga actgctgcta catccagaca ctgtgcaaat         1800
aaattatttc tgctaccttc aaaaaaaaaa aaaaaaaaaa atgcag            1846
```

<210> SEQ ID NO 2
<211> LENGTH: 508
<212> TYPE: PRT
<213> ORGANISM: Homo sapiens

<400> SEQUENCE: 2

```
Met Leu Leu Trp Ser Leu Leu Val Ile Phe Asp Ala Val Thr Glu
 1               5                  10                  15

Gln Ala Asp Ser Leu Thr Leu Val Ala Pro Ser Ser Val Phe Glu
            20                  25                  30

Gly Asp Ser Ile Val Leu Lys Cys Gln Gly Glu Gln Asn Trp Lys
            35                  40                  45

Ile Gln Lys Met Ala Tyr His Lys Asp Asn Lys Glu Leu Ser Val
            50                  55                  60

Phe Lys Lys Phe Ser Asp Phe Leu Ile Gln Ser Ala Val Leu Ser
            65                  70                  75

Asp Ser Gly Asn Tyr Phe Cys Ser Thr Lys Gly Gln Leu Phe Leu
            80                  85                  90

Trp Asp Lys Thr Ser Asn Ile Val Lys Ile Lys Val Gln Glu Leu
            95                 100                 105

Phe Gln Arg Pro Val Leu Thr Ala Ser Ser Phe Gln Pro Ile Glu
           110                 115                 120

Gly Gly Pro Val Ser Leu Lys Cys Glu Thr Arg Leu Ser Pro Gln
           125                 130                 135

Arg Leu Asp Val Gln Leu Gln Phe Cys Phe Phe Arg Glu Asn Gln
           140                 145                 150

Val Leu Gly Ser Gly Trp Ser Ser Ser Pro Glu Leu Gln Ile Ser
           155                 160                 165

Ala Val Trp Ser Glu Asp Thr Gly Ser Tyr Trp Cys Lys Ala Glu
           170                 175                 180

Thr Val Thr His Arg Ile Arg Lys Gln Ser Leu Gln Ser Gln Ile
           185                 190                 195

His Val Gln Arg Ile Pro Ile Ser Asn Val Ser Leu Glu Ile Arg
           200                 205                 210

Ala Pro Gly Gly Gln Val Thr Glu Gly Gln Lys Leu Ile Leu Leu
           215                 220                 225

Cys Ser Val Ala Gly Gly Thr Gly Asn Val Thr Phe Ser Trp Tyr
           230                 235                 240

Arg Glu Ala Thr Gly Thr Ser Met Gly Lys Lys Thr Gln Arg Ser
           245                 250                 255

Leu Ser Ala Glu Leu Glu Ile Pro Ala Val Lys Glu Ser Asp Ala
           260                 265                 270

Gly Lys Tyr Tyr Cys Arg Ala Asp Asn Gly His Val Pro Ile Gln
           275                 280                 285

Ser Lys Val Val Asn Ile Pro Val Arg Ile Pro Val Ser Arg Pro
           290                 295                 300

Val Leu Thr Leu Arg Ser Pro Gly Ala Gln Ala Ala Val Gly Asp
           305                 310                 315

Leu Leu Glu Leu His Cys Glu Ala Leu Arg Gly Ser Pro Pro Ile
```

```
                320                 325                 330
Leu Tyr Gln Phe Tyr His Glu Asp Val Thr Leu Gly Asn Ser Ser
            335                 340                 345
Ala Pro Ser Gly Gly Gly Ala Ser Phe Asn Leu Ser Leu Thr Ala
        350                 355                 360
Glu His Ser Gly Asn Tyr Ser Cys Glu Ala Asn Asn Gly Leu Gly
    365                 370                 375
Ala Gln Cys Ser Glu Ala Val Pro Val Ser Ile Ser Gly Pro Asp
380                 385                 390
Gly Tyr Arg Arg Asp Leu Met Thr Ala Gly Val Leu Trp Gly Leu
            395                 400                 405
Phe Gly Val Leu Gly Phe Thr Gly Val Ala Leu Leu Leu Tyr Ala
        410                 415                 420
Leu Phe His Lys Ile Ser Gly Glu Ser Ser Ala Thr Asn Glu Pro
    425                 430                 435
Arg Gly Ala Ser Arg Pro Asn Pro Gln Glu Phe Thr Tyr Ser Ser
440                 445                 450
Pro Thr Pro Asp Met Glu Glu Leu Gln Pro Val Tyr Val Asn Val
            455                 460                 465
Gly Ser Val Asp Val Asp Val Val Tyr Ser Gln Val Trp Ser Met
        470                 475                 480
Gln Gln Pro Glu Ser Ser Ala Asn Ile Arg Thr Leu Leu Glu Asn
    485                 490                 495
Lys Asp Ser Gln Val Ile Tyr Ser Ser Val Lys Lys Ser
500                 505

<210> SEQ ID NO 3
<211> LENGTH: 1322
<212> TYPE: DNA
<213> ORGANISM: Homo sapiens

<400> SEQUENCE: 3
atatatcgat atgctgccga ggctgttgct gttgatctgt gctccactct        50
gtgaacctgc cgagctgttt ttgatagcca gcccctccca tcccacagag       100
gggagcccag tgaccctgac gtgtaagatg ccctttctac agagttcaga       150
tgcccagttc cagttctgct ttttcagaga cacccgggcc ttgggcccag       200
gctggagcag ctcccccaag ctccagatcg ctgccatgtg aaagaagac        250 acagggtcat actggtgcga ggcacagaca atggcgtcca aagtcttgag       300
gagcaggaga tcccagataa atgtgcacag ggtccctgtc gctgatgtga       350
gcttggagac tcagccccca ggaggacagg tgatggaggg agacaggctg       400
gtcctcatct gctcagttgc tatgggcaca ggagacatca ccttcctttg       450
gtacaaaggg gctgtaggtt taaaccttca gtcaaagacc cagcgttcac       500
tgacagcaga gtatgagatt ccttcagtga gggagagtga tgctgagcaa       550
tattactgtg tagctgaaaa tggctatggt cccagcccca gtgggctggt       600
gagcatcact gtcagaatcc cggtgtctcg cccaatcctc atgctcaggg       650
ctcccagggc ccaggctgca gtggaggatg tgctggagct tcactgtgag       700
gccctgagag gctctcctcc gatcctgtac tggttttatc acgaggatat       750
caccctgggg agcaggtcgg cccccctctgg aggaggagcc tccttcaacc       800
tttccctgac tgaagaacat tctggaaact actcctgtga ggccaacaat       850
```

-continued

| | |
|---|---|
| ggcctggggg cccagcgcag tgaggcggtg acactcaact tcacagtgcc | 900 |
| tactggggcc agaagcaatc atcttacctc aggagtcatt gaggggctgc | 950 |
| tcagcaccct tggtccagcc accgtggcct tattattttg ctacggcctc | 1000 |
| aaaagaaaaa taggaagacg ttcagccagg gatccactca ggagccttcc | 1050 |
| cagccctcta ccccaagagt tcacgtacct caactcacct accccagggc | 1100 |
| agctacagcc tatatatgaa aatgtgaatg ttgtaagtgg ggatgaggtt | 1150 |
| tattcactgg cgtactataa ccagccggag caggaatcag tagcagcaga | 1200 |
| aaccctgggg acacatatgg aggacaaggt ttccttagac atctattcca | 1250 |
| ggctgaggaa agcaaacatt acagatgtgg actatgaaga tgctatgtaa | 1300 |
| ggttatggaa gattctgctc tt | 1322 |

<210> SEQ ID NO 4
<211> LENGTH: 429
<212> TYPE: PRT
<213> ORGANISM: Homo sapiens

<400> SEQUENCE: 4

```
Met Leu Pro Arg Leu Leu Leu Ile Cys Ala Pro Leu Cys Glu
  1               5                  10                  15

Pro Ala Glu Leu Phe Leu Ile Ala Ser Pro Ser His Pro Thr Glu
             20                  25                  30

Gly Ser Pro Val Thr Leu Thr Cys Lys Met Pro Phe Leu Gln Ser
             35                  40                  45

Ser Asp Ala Gln Phe Gln Phe Cys Phe Phe Arg Asp Thr Arg Ala
             50                  55                  60

Leu Gly Pro Gly Trp Ser Ser Pro Lys Leu Gln Ile Ala Ala
             65                  70                  75

Met Trp Lys Glu Asp Thr Gly Ser Tyr Trp Cys Glu Ala Gln Thr
             80                  85                  90

Met Ala Ser Lys Val Leu Arg Ser Arg Arg Ser Gln Ile Asn Val
             95                 100                 105

His Arg Val Pro Val Ala Asp Val Ser Leu Glu Thr Gln Pro Pro
            110                 115                 120

Gly Gly Gln Val Met Glu Gly Asp Arg Leu Val Leu Ile Cys Ser
            125                 130                 135

Val Ala Met Gly Thr Gly Asp Ile Thr Phe Leu Trp Tyr Lys Gly
            140                 145                 150

Ala Val Gly Leu Asn Leu Gln Ser Lys Thr Gln Arg Ser Leu Thr
            155                 160                 165

Ala Glu Tyr Glu Ile Pro Ser Val Arg Glu Ser Asp Ala Glu Gln
            170                 175                 180

Tyr Tyr Cys Val Ala Glu Asn Gly Tyr Gly Pro Ser Pro Ser Gly
            185                 190                 195

Leu Val Ser Ile Thr Val Arg Ile Pro Val Ser Arg Pro Ile Leu
            200                 205                 210

Met Leu Arg Ala Pro Arg Ala Gln Ala Ala Val Glu Asp Val Leu
            215                 220                 225

Glu Leu His Cys Glu Ala Leu Arg Gly Ser Pro Pro Ile Leu Tyr
            230                 235                 240

Trp Phe Tyr His Glu Asp Ile Thr Leu Gly Ser Arg Ser Ala Pro
            245                 250                 255
```

```
Ser Gly Gly Gly Ala Ser Phe Asn Leu Ser Leu Thr Glu Glu His
            260                 265                 270

Ser Gly Asn Tyr Ser Cys Glu Ala Asn Gly Leu Gly Ala Gln
            275                 280                 285

Arg Ser Glu Ala Val Thr Leu Asn Phe Thr Val Pro Thr Gly Ala
            290                 295                 300

Arg Ser Asn His Leu Thr Ser Gly Val Ile Glu Gly Leu Leu Ser
            305                 310                 315

Thr Leu Gly Pro Ala Thr Val Ala Leu Leu Phe Cys Tyr Gly Leu
            320                 325                 330

Lys Arg Lys Ile Gly Arg Arg Ser Ala Arg Asp Pro Leu Arg Ser
            335                 340                 345

Leu Pro Ser Pro Leu Pro Gln Glu Phe Thr Tyr Leu Asn Ser Pro
            350                 355                 360

Thr Pro Gly Gln Leu Gln Pro Ile Tyr Glu Asn Val Asn Val Val
            365                 370                 375

Ser Gly Asp Glu Val Tyr Ser Leu Ala Tyr Tyr Asn Gln Pro Glu
            380                 385                 390

Gln Glu Ser Val Ala Ala Glu Thr Leu Gly Thr His Met Glu Asp
            395                 400                 405

Lys Val Ser Leu Asp Ile Tyr Ser Arg Leu Arg Lys Ala Asn Ile
            410                 415                 420

Thr Asp Val Asp Tyr Glu Asp Ala Met
            425

<210> SEQ ID NO 5
<211> LENGTH: 685
<212> TYPE: DNA
<213> ORGANISM: Homo sapiens

<400> SEQUENCE: 5
gatgtgctcc ttggagctgg tgtgcagtgt cctgactgta agatcaagtc           50
caaacctgtt ttggaattga ggaaacttct cttttgatct cagcccttgg          100
tggtccaggt cttcatgctg ctgtgggtga tattactggt cctggctcct          150
gtcagtggac agtttgcaag gacacccagg cccattattt tcctccagcc          200
tccatggacc acagtcttcc aaggagagag agtgaccctc acttgcaagg          250
gatttcgctt ctactcacca cagaaaacaa aatggtacca tcggtacctt          300
gggaaagaaa tactaagaga aaccccagac aatatccttg aggttcagga          350
atctggagag tacagatgcc aggcccaggg ctcccctctc agtagccctg          400
tgcacttgga tttttcttca gagatgggat ttcctcatgc tgcccaggct          450
aatgttgaac tcctgggctc aagtgatctc ctcacctagg cctctcaaag          500
cgctgggatt acagcttcgc tgatcctgca agctccactt tctgtgtttg          550
aaggagactc tgtggttctg aggtgccggg caaaggcgga agtaacactg          600
aataatacta tttacaagaa tgataatgtc ctggcattcc ttaataaaag          650
aactgacttc caaaaaaaaa aaaaaaaaaa aaaaa                          685

<210> SEQ ID NO 6
<211> LENGTH: 124
<212> TYPE: PRT
<213> ORGANISM: Homo sapiens
```

```
<400> SEQUENCE: 6

Met Leu Leu Trp Val Ile Leu Leu Val Leu Ala Pro Val Ser Gly
 1               5                  10                  15

Gln Phe Ala Arg Thr Pro Arg Pro Ile Ile Phe Leu Gln Pro Pro
                20                  25                  30

Trp Thr Thr Val Phe Gln Gly Glu Arg Val Thr Leu Thr Cys Lys
                35                  40                  45

Gly Phe Arg Phe Tyr Ser Pro Gln Lys Thr Lys Trp Tyr His Arg
                50                  55                  60

Tyr Leu Gly Lys Glu Ile Leu Arg Glu Thr Pro Asp Asn Ile Leu
                65                  70                  75

Glu Val Gln Glu Ser Gly Glu Tyr Arg Cys Gln Ala Gln Gly Ser
                80                  85                  90

Pro Leu Ser Ser Pro Val His Leu Asp Phe Ser Ser Glu Met Gly
                95                 100                 105

Phe Pro His Ala Ala Gln Ala Asn Val Glu Leu Leu Gly Ser Ser
               110                 115                 120

Asp Leu Leu Thr

<210> SEQ ID NO 7
<211> LENGTH: 2970
<212> TYPE: DNA
<213> ORGANISM: Homo sapiens

<400> SEQUENCE: 7
agtgaagggg tttcccatat gaaaaataca gaaagaatta tttgaatact         50
agcaaataca caacttgata tttctagaga acccaggcac agtcttggag        100
acattactcc tgagagactg cagctgatgg aagatgagcc ccaacttcta        150
aaaatgtatc actaccggga ttgagataca aacagcattt aggaaggtct        200
catctgagta gcagcttcct gccctccttc ttggagataa gtcgggcttt        250
tggtgagaca gactttccca accctctgcc cggccggtgc ccatgcttct        300
gtggctgctg ctgctgatcc tgactcctgg aagagaacaa tcaggggtgg        350
ccccaaaagc tgtacttctc ctcaatcctc catggtccac agccttcaaa        400
ggagaaaaag tggctctcat atgcagcagc atatcacatt ccctagccca        450
gggagacaca tattggtatc acgatgagaa gttgttgaaa ataaaacatg        500
acaagatcca aattacagag cctggaaatt accaatgtaa gacccgagga        550
tcctccctca gtgatgccgt gcatgtggaa ttttcacctg actggctgat        600
cctgcaggct ttacatcctg tctttgaagg agacaatgtc attctgagat        650 gtcagggaa  agacaacaaa aacactcatc aaaggttta  ctacaaggat        700 ggaaaacagc ttcctaatag ttataattta gagaagatca cagtgaattc        750
agtctccagg gataatagca aatatcattg tactgcttat aggaagtttt        800
acatacttga cattgaagta acttcaaaac ccctaaatat ccaagttcaa        850
gagctgtttc tacatcctgt gctgagagcc agctcttcca cgcccataga        900
ggggagtccc atgaccctga cctgtgagac cagctctctc cacagaggc         950 cagatgtcca gctgcaattc tccctcttca gagatagcca gaccctcgga       1000
ttgggctgga gcaggtcccc cagactccag atccctgcca tgtggactga       1050
agactcaggg tcttactggt gtgaggtgga gacagtgact cacagcatca       1100
```

-continued

| | |
|---|---|
| aaaaaaggag cctgagatct cagatacgtg tacagagagt ccctgtgtct | 1150 |
| aatgtgaatc tagagatccg gcccaccgga gggcagctga ttgaaggaga | 1200 |
| aaatatggtc cttatttgct cagtagccca gggttcaggg actgtcacat | 1250 |
| tctcctggca caaagaagga agagtaagaa gcctgggtag aaagacccag | 1300 |
| cgttccctgt tggcagagct gcatgttctc accgtgaagg agagtgatgc | 1350 |
| agggagatac tactgtgcag ctgataacgt tcacagcccc atcctcagca | 1400 |
| cgtggattcg agtcaccgtg agaattccgg tatctcaccc tgtcctcacc | 1450 |
| ttcagggctc ccagggccca cactgtggtg ggggacctgc tggagcttca | 1500 |
| ctgtgagtcc ctgagaggct ctcccccgat cctgtaccga ttttatcatg | 1550 |
| aggatgtcac cctggggaac agctcagccc cctctggagg aggagcctcc | 1600 |
| ttcaacctct ctctgactgc agaacattct ggaaactact cctgtgatgc | 1650 |
| agacaatggc ctgggggccc agcacagtca tggagtgagt ctcagggtca | 1700 |
| cagttccggt gtctcgcccc gtcctcaccc tcagggctcc cggggcccag | 1750 |
| gctgtggtgg gggacctgct ggagcttcac tgtgagtccc tgagaggctc | 1800 |
| cttcccgatc ctgtactggt tttatcacga ggatgacacc ttggggaaca | 1850 |
| tctcggccca ctctggagga ggggcatcct tcaacctctc tctgactaca | 1900 |
| gaacattctg gaaactactc atgtgaggct gacaatggcc tgggggccca | 1950 |
| gcacagtaaa gtggtgacac tcaatgttac aggaacttcc aggaacagaa | 2000 |
| caggccttac cgctgcggga atcacggggc tggtgctcag catcctcgtc | 2050 |
| cttgctgctg ctgctgctct gctgcattac gccagggccc gaaggaaacc | 2100 |
| aggaggactt tctgccactg gaacatctag tcacagtcct agtgagtgtc | 2150 |
| aggagccttc ctcgtccagg ccttccagga tagaccctca agagcccact | 2200 |
| cactctaaac cactagcccc aatggagctg gagccaatgt acagcaatgt | 2250 |
| aaatcctgga gatagcaacc cgatttattc ccagatctgg agcatccagc | 2300 |
| atacaaaaga aaactcagct aattgtccaa tgatgcatca agagcatgag | 2350 |
| gaacttacag tcctctattc agaactgaag aagacacacc cagacgactc | 2400 |
| tgcaggggag gctagcagca gaggcagggc ccatgaagaa gatgatgaag | 2450 |
| aaaactatga gaatgtacca cgtgtattac tggcctcaga ccactagccc | 2500 |
| cttacccaga gtggcccaca ggaaacagcc tgcaccattt ttttttctgt | 2550 |
| tctctccaac cacacatcat ccatctctcc agactctgcc tcctacgagg | 2600 |
| ctgggctgca gggtatgtga ggctgagcaa aaggtctgca aatctcccct | 2650 |
| gtgcctgatc tgtgtgttcc ccaggaagag agcaggcagc ctctgagcaa | 2700 |
| gcactgtgtt attttcacag tggagacacg tggcaaggca ggagggccct | 2750 |
| cagctcctag ggctgtcgaa tagaggagga gagagaaatg gtctagccag | 2800 |
| ggttacaagg gcacaatcat gaccatttga tccaagtgtg atcgaaagct | 2850 |
| gttaatgtgc tctctgtata aacaatttgc tccaaatatt ttgtttccct | 2900 |
| tttttgtgtg gctggtagtg gcattgctga tgttttggtg tatatgctgt | 2950 |
| atccttgcta ccatattggg | 2970 |

<210> SEQ ID NO 8

<211> LENGTH: 734
<212> TYPE: PRT
<213> ORGANISM: Homo sapiens

<400> SEQUENCE: 8

| Met | Leu | Leu | Trp | Leu | Leu | Leu | Ile | Leu | Thr | Pro | Gly | Arg | Glu |
| 1 | | | | 5 | | | | | 10 | | | | 15 |

Gln Ser Gly Val Ala Pro Lys Ala Val Leu Leu Asn Pro Pro
           20                  25                  30

Trp Ser Thr Ala Phe Lys Gly Glu Lys Val Ala Leu Ile Cys Ser
                35                  40                  45

Ser Ile Ser His Ser Leu Ala Gln Gly Asp Thr Tyr Trp Tyr His
                50                  55                  60

Asp Glu Lys Leu Leu Lys Ile Lys His Asp Lys Ile Gln Ile Thr
            65                  70                  75

Glu Pro Gly Asn Tyr Gln Cys Lys Thr Arg Gly Ser Ser Leu Ser
            80                  85                  90

Asp Ala Val His Val Glu Phe Ser Pro Asp Trp Leu Ile Leu Gln
            95                  100                 105

Ala Leu His Pro Val Phe Glu Gly Asp Asn Val Ile Leu Arg Cys
            110                 115                 120

Gln Gly Lys Asp Asn Lys Asn Thr His Gln Lys Val Tyr Tyr Lys
            125                 130                 135

Asp Gly Lys Gln Leu Pro Asn Ser Tyr Asn Leu Glu Lys Ile Thr
            140                 145                 150

Val Asn Ser Val Ser Arg Asp Asn Ser Lys Tyr His Cys Thr Ala
            155                 160                 165

Tyr Arg Lys Phe Tyr Ile Leu Asp Ile Glu Val Thr Ser Lys Pro
            170                 175                 180

Leu Asn Ile Gln Val Gln Glu Leu Phe Leu His Pro Val Leu Arg
            185                 190                 195

Ala Ser Ser Ser Thr Pro Ile Glu Gly Ser Pro Met Thr Leu Thr
            200                 205                 210

Cys Glu Thr Gln Leu Ser Pro Gln Arg Pro Asp Val Gln Leu Gln
            215                 220                 225

Phe Ser Leu Phe Arg Asp Ser Gln Thr Leu Gly Leu Gly Trp Ser
            230                 235                 240

Arg Ser Pro Arg Leu Gln Ile Pro Ala Met Trp Thr Glu Asp Ser
            245                 250                 255

Gly Ser Tyr Trp Cys Glu Val Glu Thr Val Thr His Ser Ile Lys
            260                 265                 270

Lys Arg Ser Leu Arg Ser Gln Ile Arg Val Gln Arg Val Pro Val
            275                 280                 285

Ser Asn Val Asn Leu Glu Ile Arg Pro Thr Gly Gly Gln Leu Ile
            290                 295                 300

Glu Gly Glu Asn Met Val Leu Ile Cys Ser Val Ala Gln Gly Ser
            305                 310                 315

Gly Thr Val Thr Phe Ser Trp His Lys Glu Gly Arg Val Arg Ser
            320                 325                 330

Leu Gly Arg Lys Thr Gln Arg Ser Leu Leu Ala Glu Leu His Val
            335                 340                 345

Leu Thr Val Lys Glu Ser Asp Ala Gly Arg Tyr Tyr Cys Ala Ala
            350                 355                 360

Asp Asn Val His Ser Pro Ile Leu Ser Thr Trp Ile Arg Val Thr

```
                365                 370                 375
Val Arg Ile Pro Val Ser His Pro Val Leu Thr Phe Arg Ala Pro
            380                 385                 390
Arg Ala His Thr Val Val Gly Asp Leu Leu Glu Leu His Cys Glu
            395                 400                 405
Ser Leu Arg Gly Ser Pro Pro Ile Leu Tyr Arg Phe Tyr His Glu
            410                 415                 420
Asp Val Thr Leu Gly Asn Ser Ser Ala Pro Ser Gly Gly Gly Ala
            425                 430                 435
Ser Phe Asn Leu Ser Leu Thr Ala Glu His Ser Gly Asn Tyr Ser
            440                 445                 450
Cys Asp Ala Asp Asn Gly Leu Gly Ala Gln His Ser His Gly Val
            455                 460                 465
Ser Leu Arg Val Thr Val Pro Val Ser Arg Pro Val Leu Thr Leu
            470                 475                 480
Arg Ala Pro Gly Ala Gln Ala Val Val Gly Asp Leu Leu Glu Leu
            485                 490                 495
His Cys Glu Ser Leu Arg Gly Ser Phe Pro Ile Leu Tyr Trp Phe
            500                 505                 510
Tyr His Glu Asp Asp Thr Leu Gly Asn Ile Ser Ala His Ser Gly
            515                 520                 525
Gly Gly Ala Ser Phe Asn Leu Ser Leu Thr Thr Glu His Ser Gly
            530                 535                 540
Asn Tyr Ser Cys Glu Ala Asp Asn Gly Leu Gly Ala Gln His Ser
            545                 550                 555
Lys Val Val Thr Leu Asn Val Thr Gly Thr Ser Arg Asn Arg Thr
            560                 565                 570
Gly Leu Thr Ala Ala Gly Ile Thr Gly Leu Val Leu Ser Ile Leu
            575                 580                 585
Val Leu Ala Ala Ala Ala Leu Leu His Tyr Ala Arg Ala Arg
            590                 595                 600
Arg Lys Pro Gly Gly Leu Ser Ala Thr Gly Thr Ser Ser His Ser
            605                 610                 615
Pro Ser Glu Cys Gln Glu Pro Ser Ser Arg Pro Ser Arg Ile
            620                 625                 630
Asp Pro Gln Glu Pro Thr His Ser Lys Pro Leu Ala Pro Met Glu
            635                 640                 645
Leu Glu Pro Met Tyr Ser Asn Val Asn Pro Gly Asp Ser Asn Pro
            650                 655                 660
Ile Tyr Ser Gln Ile Trp Ser Ile Gln His Thr Lys Glu Asn Ser
            665                 670                 675
Ala Asn Cys Pro Met Met His Gln Glu His Glu Glu Leu Thr Val
            680                 685                 690
Leu Tyr Ser Glu Leu Lys Lys Thr His Pro Asp Asp Ser Ala Gly
            695                 700                 705
Glu Ala Ser Ser Arg Gly Arg Ala His Glu Glu Asp Glu Glu
            710                 715                 720
Asn Tyr Glu Asn Val Pro Arg Val Leu Leu Ala Ser Asp His
            725                 730

<210> SEQ ID NO 9
<211> LENGTH: 3459
<212> TYPE: DNA
<213> ORGANISM: Homo sapiens
```

<400> SEQUENCE: 9

```
ctcaatcagc tttatgcaga gaagaagctt actgagctca ctgctggtgc          50
tggtgtaggc aagtgctgct ttggcaatct gggctgacct ggcttgtctc         100
ctcagaactc cttctccaac cctggagcag gcttccatgc tgctgtgggc         150
gtccttgctg gcctttgctc cagtctgtgg acaatctgca gctgcacaca         200
aacctgtgat ttccgtccat cctccatgga ccacattctt caaaggagag         250
agagtgactc tgacttgcaa tggatttcag ttctatgcaa cagagaaaac         300
aacatggtat catcggcact actggggaga aaagttgacc ctgaccccag         350
gaaacaccct cgaggttcgg gaatctggac tgtacagatg ccaggcccgg         400
ggctccccac gaagtaaccc tgtgcgcttg ctcttttctt cagactcctt         450
aatcctgcag gcaccatatt ctgtgtttga aggtgacaca ttggttctga         500
gatgccacag aagaaggaaa gagaaattga ctgctgtgaa atatacttgg         550
aatggaaaca ttcttttccat ttctaataaa agctgggatc ttcttatccc         600
acaagcaagt tcaaataaca atggcaatta tcgatgcatt ggatatggag         650
atgagaatga tgtatttaga tcaaatttca aaataattaa aattcaagaa         700
ctatttccac atccagagct gaaagctaca gactctcagc ctacagaggg         750
gaattctgta aacctgagct gtgaaacaca gcttcctcca gagcggtcag         800
acacccccact tcacttcaac ttcttcagag atggcgaggt catcctgtca         850
gactggagca cgtacccgga actccagctc ccaaccgtct ggagagaaaa         900
ctcaggatcc tattggtgtg gtgctgaaac agtgaggggg aacatccaca         950
agcacagtcc ctcgctacag atccatgtgc agcggatccc tgtgtctggg        1000
gtgctcctgg agacccagcc ctcagggggc caggctgttg aaggggagat        1050
gctggtcctt gtctgctccg tggctgaagg cacagggat accacattct         1100
cctggcaccg agaggacatg caggagagtc tggggaggaa aactcagcgt        1150
tccctgagag cagagctgga gctccctgcc atcagacaga gccatgcagg        1200
gggatactac tgtacagcag acaacagcta cggccctgtc cagagcatgg        1250
tgctgaatgt cactgtgaga gagaccccag gcaacagaga tggccttgtc        1300
gccgcgggag ccactggagg gctgctcagt gctcttctcc tggctgtggc        1350
cctgctgttt cactgctggc gtcggaggaa gtcaggagtt ggtttcttgg        1400
gagacgaaac caggctccct cccgctccag gcccaggaga gtcctcccat        1450
tccatctgcc ctgcccaggt ggagcttcag tcgttgtatg ttgatgtaca        1500
ccccaaaaag ggagatttgg tatactctga gatccagact actcagctgg        1550
gagaagaaga ggaagctaat acctccagga cacttctaga ggataaggat        1600
gtctcagttg tctactctga ggtaaagaca caacacccag ataactcagc        1650
tggaaagatc agctctaagg atgaagaaag ttaagagaat gaaaagttac        1700
gggaacgtcc tactcatgtg atttctccct tgtccaaagt cccaggccca        1750
gtgcagtcct tgcggcacct ggaatgatca actcattcca gctttctaat        1800
tcttctcatg catatgcatt cactcccagg aatactcatt cgtctactct        1850
gatgttggga tggaatggcc tctgaaagac ttcactaaaa tgaccaggat        1900
```

-continued

```
ccacagttaa gagaagaccc tgtagtattt gctgtgggcc tgacctaatg         1950
cattccctag ggtctgcttt agagaagggg gataaagaga gagaaggact         2000
gttatgaaaa acagaagcac aaattttggt gaattgggat ttgcagagat         2050
gaaaaagact gggtgacctg gatctctgct taatacatct acaaccattg         2100
tctcactgga gactcacttg catcagtttg tttaactgtg agtggctgca         2150
caggcactgt gcaaacaatg aaaagcccct tcacttctgc ctgcacagct         2200
tacactgtca ggattcagtt gcagattaaa gaacccatct ggaatggttt         2250
acagagagag gaatttaaaa gaggacatca gaagagctgg agatgcaagc         2300
tctaggctgc gcttccaaaa gcaaatgata attatgttaa tgtcattagt         2350
gacaaagatt tgcaacatta gagaaaagag acacaaatat aaaattaaaa         2400
acttaagtac caactctcca aaactaaatt tgaacttaaa atattagtat         2450
aaactcataa taaactctgc ctttaaaaaa agataaatat ttcctacgtc         2500
tgttcactga ataattacc aacccttag caataagcac tccttgcaga          2550
gaggttttat tctctaaata ccattccctt ctcaaaggaa ataaggttgc         2600
ttttcttgta ggaactgtgt ctttgagtta ctaattagtt tatatgagaa         2650
taattcttgc aataaatgaa gaaggaataa aagaaatagg aagccacaaa         2700
tttgtatgga tatttcatga tacacctact ggttaaataa ttgacaaaaa         2750
ccagcagcca aatattagag gtctcctgat ggaagtgtac aataccacct         2800
acaaattatc catgccccaa gtgttaaaac tgaatccatt caagtctttc         2850
taactgaata cttgttttat agaaaatgca tggagaaaag gaatttgttt         2900
aaataacatt atgggattgc aaccagcaaa acataaactg agaaaaagtt         2950
ctatagggca aatcacctgg cttctataac aaataaatgg gaaaaaaatg         3000
aaataaaaag aagagaggga ggaagaaagg gagagagaag aaaagaaaaa         3050
tgaagaaaag taattagaat attttcaaca taaagaaaag acgaatattt         3100
aaggtgacag atatcccaac tacgctgatt tgatctttac aaattatatg         3150
agtgtatgaa tttgtcacat gtatcacccc caaaaaaaga gaaaaagaaa         3200
aatagaagac atataaatta aatgagacga gacatgtcga ccaaaaggaa         3250
tgtgtgggtc ttgtttggat cctgactcaa attaagaaaa aataaaacta         3300
cctacgaaat actaagaaaa atttgtatac taatattaag aaattgttgt         3350
gtgttttgga tataagtgat agtttattgt agtgatgttt ttataaaagc         3400
aaaaggatat tcactttcag cgcttatact gaagtattag attaaagctt         3450
attaacgta                                                      3459
```

<210> SEQ ID NO 10
<211> LENGTH: 515
<212> TYPE: PRT
<213> ORGANISM: Homo sapiens

<400> SEQUENCE: 10

```
Met Leu Leu Trp Ala Ser Leu Leu Ala Phe Ala Pro Val Cys Gly
 1               5                  10                  15

Gln Ser Ala Ala Ala His Lys Pro Val Ile Ser Val His Pro Pro
                20                  25                  30

Trp Thr Thr Phe Phe Lys Gly Glu Arg Val Thr Leu Thr Cys Asn
```

-continued

```
                35                  40                  45
Gly Phe Gln Phe Tyr Ala Thr Glu Lys Thr Thr Trp Tyr His Arg
                50                  55                  60
His Tyr Trp Gly Glu Lys Leu Thr Leu Thr Pro Gly Asn Thr Leu
            65                  70                  75
Glu Val Arg Glu Ser Gly Leu Tyr Arg Cys Gln Ala Arg Gly Ser
                80                  85                  90
Pro Arg Ser Asn Pro Val Arg Leu Leu Phe Ser Ser Asp Ser Leu
                95                 100                 105
Ile Leu Gln Ala Pro Tyr Ser Val Phe Glu Gly Asp Thr Leu Val
            110                 115                 120
Leu Arg Cys His Arg Arg Lys Glu Lys Leu Thr Ala Val Lys
            125                 130                 135
Tyr Thr Trp Asn Gly Asn Ile Leu Ser Ile Ser Asn Lys Ser Trp
            140                 145                 150
Asp Leu Leu Ile Pro Gln Ala Ser Ser Asn Asn Gly Asn Tyr
            155                 160                 165
Arg Cys Ile Gly Tyr Gly Asp Glu Asn Asp Val Phe Arg Ser Asn
            170                 175                 180
Phe Lys Ile Ile Lys Ile Gln Glu Leu Phe Pro His Pro Glu Leu
            185                 190                 195
Lys Ala Thr Asp Ser Gln Pro Thr Glu Gly Asn Ser Val Asn Leu
            200                 205                 210
Ser Cys Glu Thr Gln Leu Pro Pro Glu Arg Ser Asp Thr Pro Leu
            215                 220                 225
His Phe Asn Phe Phe Arg Asp Gly Glu Val Ile Leu Ser Asp Trp
            230                 235                 240
Ser Thr Tyr Pro Glu Leu Gln Leu Pro Thr Val Trp Arg Glu Asn
            245                 250                 255
Ser Gly Ser Tyr Trp Cys Gly Ala Glu Thr Val Arg Gly Asn Ile
            260                 265                 270
His Lys His Ser Pro Ser Leu Gln Ile His Val Gln Arg Ile Pro
            275                 280                 285
Val Ser Gly Val Leu Leu Glu Thr Gln Pro Ser Gly Gly Gln Ala
            290                 295                 300
Val Glu Gly Glu Met Leu Val Leu Val Cys Ser Val Ala Glu Gly
            305                 310                 315
Thr Gly Asp Thr Thr Phe Ser Trp His Arg Glu Asp Met Gln Glu
            320                 325                 330
Ser Leu Gly Arg Lys Thr Gln Arg Ser Leu Arg Ala Glu Leu Glu
            335                 340                 345
Leu Pro Ala Ile Arg Gln Ser His Ala Gly Gly Tyr Tyr Cys Thr
            350                 355                 360
Ala Asp Asn Ser Tyr Gly Pro Val Gln Ser Met Val Leu Asn Val
            365                 370                 375
Thr Val Arg Glu Thr Pro Gly Asn Arg Asp Gly Leu Val Ala Ala
            380                 385                 390
Gly Ala Thr Gly Gly Leu Leu Ser Ala Leu Leu Leu Ala Val Ala
            395                 400                 405
Leu Leu Phe His Cys Trp Arg Arg Arg Lys Ser Gly Val Gly Phe
            410                 415                 420
Leu Gly Asp Glu Thr Arg Leu Pro Pro Ala Pro Gly Pro Gly Glu
            425                 430                 435
```

```
Ser Ser His Ser Ile Cys Pro Ala Gln Val Glu Leu Gln Ser Leu
            440                 445                 450

Tyr Val Asp Val His Pro Lys Lys Gly Asp Leu Val Tyr Ser Glu
            455                 460                 465

Ile Gln Thr Thr Gln Leu Gly Glu Glu Glu Ala Asn Thr Ser
            470                 475                 480

Arg Thr Leu Leu Glu Asp Lys Asp Val Ser Val Val Tyr Ser Glu
            485                 490                 495

Val Lys Thr Gln His Pro Asp Asn Ser Ala Gly Lys Ile Ser Ser
            500                 505                 510

Lys Asp Glu Glu Ser
            515

<210> SEQ ID NO 11
<211> LENGTH: 1933
<212> TYPE: DNA
<213> ORGANISM: Homo sapiens

<400> SEQUENCE: 11
```

| | | | | |
|---|---|---|---|---|
| acacacccac | aggacctgca | gctgaacgaa | gttgaagaca | actcaggaga | 50 |
| tctgttggaa | agagaacgat | agaggaaaat | atatgaatgt | tgccatcttt | 100 |
| agttccctgt | gttgggaaaa | ctgtctggct | gtacctccaa | gcctggccaa | 150 |
| accctgtgtt | tgaaggagat | gccctgactc | tgcgatgtca | gggatggaag | 200 |
| aatacaccac | tgtctcaggt | gaagttctac | agagatggaa | aattccttca | 250 |
| tttctctaag | gaaaaccaga | ctctgtccat | gggagcagca | acagtgcaga | 300 |
| gccgtggcca | gtacagctgc | tctgggcagg | tgatgtatat | tccacagaca | 350 |
| ttcacacaaa | cttcagagac | tgccatggtt | caagtccaag | agctgtttcc | 400 |
| acctcctgtg | ctgagtgcca | tccctctcc | tgagccccga | gagggtagcc | 450 |
| tggtgaccct | gagatgtcag | acaaagctgc | accccctgag | gtcagccttg | 500 |
| aggctccttt | tctccttcca | caaggacggc | cacaccttgc | aggacagggg | 550 |
| ccctcaccca | gaactctgca | tcccgggagc | caaggaggga | gactctgggc | 600 |
| tttactggtg | tgaggtggcc | cctgagggtg | gccaggtcca | gaagcagagc | 650 |
| ccccagctgg | aggtcagagt | gcaggctcct | gtatcccgtc | ctgtgctcac | 700 |
| tctgcaccac | gggcctgctg | accctgctgt | ggggacatg | gtgcagctcc | 750 |
| tctgtgaggc | acagaggggc | tcccctccga | tcctgtattc | cttctacctt | 800 |
| gatgagaaga | ttgtggggaa | ccactcagct | ccctgtggtg | gaaccacctc | 850 |
| cctcctcttc | ccagtgaagt | cagaacagga | tgctgggaac | tactcctgcg | 900 |
| aggctgagaa | cagtgtctcc | agagagagga | gtgagcccaa | gaagctgtct | 950 |
| ctgaagggtt | ctcaagtctt | gttcactccc | gccagcaact | ggctggttcc | 1000 |
| ttggcttcct | gcgagcctgc | ttggcctgat | ggttattgct | gctgcacttc | 1050 |
| tggtttatgt | gagatcctgg | agaaaagctg | gccccttcc | atcccagata | 1100 |
| ccacccacag | ctccaggtgg | agagcagtgc | ccactatatg | ccaacgtgca | 1150 |
| tcaccagaaa | gggaaagatg | aaggtgttgt | ctactctgtg | gtgcatagaa | 1200 |
| cctcaaagag | gagtgaagga | cagttctatc | atctgtgcgg | aggtgagatg | 1250 |
| cctgcagccc | agtgaggttt | catccacgga | ggtgaatatg | agaagcagga | 1300 |

| | |
|---|---|
| ctctccaaga accccttagc gactgtgagg aggttctctg ctagtgatgg | 1350 |
| tgttctccta tcaacacacg cccaccccca gtctccagtg ctcctcagga | 1400 |
| agacagtggg gtcctcaact ctttctgtgg gtccttcagt tcccaagccc | 1450 |
| agcatcacag agcccctga gcccttgtcc tggtcaggag cacctgaacc | 1500 |
| ctgggttctt ttcttagcag aagaccaacc aatggaatgg gaagggagat | 1550 |
| gctcccacca acacacacac ttaggttcaa tcagtgacac tggacacata | 1600 |
| agccacagat gtcttctttc catacaagca tgttagttcg ccccaatata | 1650 |
| catatatata tgaaatagtc atgtgccgca taacaacatt tcagtcagtg | 1700 |
| atagactgca tacacaacag tggtcccata agactgtaat ggagtttaaa | 1750 |
| aattcctact gcctagtgat atcatagttg ccttaacatc ataacacaac | 1800 |
| acatttctca cgcgtttgtg gtgatgctgg tacaaacaag ctacagcgcc | 1850 |
| gctagtcata tacaaatata gcacatacaa ttatgtacag tacactatac | 1900 |
| ttgataatga taataaacaa ctatgttact ggt | 1933 |

```
<210> SEQ ID NO 12
<211> LENGTH: 392
<212> TYPE: PRT
<213> ORGANISM: Homo sapiens

<400> SEQUENCE: 12

Met Leu Pro Ser Leu Val Pro Cys Val Gly Lys Thr Val Trp Leu
 1               5                  10                  15

Tyr Leu Gln Ala Trp Pro Asn Pro Val Phe Glu Gly Asp Ala Leu
                20                  25                  30

Thr Leu Arg Cys Gln Gly Trp Lys Asn Thr Pro Leu Ser Gln Val
                35                  40                  45

Lys Phe Tyr Arg Asp Gly Lys Phe Leu His Phe Ser Lys Glu Asn
                50                  55                  60

Gln Thr Leu Ser Met Gly Ala Ala Thr Val Gln Ser Arg Gly Gln
                65                  70                  75

Tyr Ser Cys Ser Gly Gln Val Met Tyr Ile Pro Gln Thr Phe Thr
                80                  85                  90

Gln Thr Ser Glu Thr Ala Met Val Gln Val Glu Leu Phe Pro
                95                 100                 105

Pro Pro Val Leu Ser Ala Ile Pro Ser Pro Glu Pro Arg Glu Gly
               110                 115                 120

Ser Leu Val Thr Leu Arg Cys Gln Thr Lys Leu His Pro Leu Arg
               125                 130                 135

Ser Ala Leu Arg Leu Leu Phe Ser Phe His Lys Asp Gly His Thr
               140                 145                 150

Leu Gln Asp Arg Gly Pro His Pro Glu Leu Cys Ile Pro Gly Ala
               155                 160                 165

Lys Glu Gly Asp Ser Gly Leu Tyr Trp Cys Glu Val Ala Pro Glu
               170                 175                 180

Gly Gly Gln Val Gln Lys Gln Ser Pro Gln Leu Glu Val Arg Val
               185                 190                 195

Gln Ala Pro Val Ser Arg Pro Val Leu Thr Leu His His Gly Pro
               200                 205                 210

Ala Asp Pro Ala Val Gly Asp Met Val Gln Leu Leu Cys Glu Ala
               215                 220                 225
```

```
Gln Arg Gly Ser Pro Pro Ile Leu Tyr Ser Phe Tyr Leu Asp Glu
                230                 235                 240

Lys Ile Val Gly Asn His Ser Ala Pro Cys Gly Gly Thr Thr Ser
            245                 250                 255

Leu Leu Phe Pro Val Lys Ser Glu Gln Asp Ala Gly Asn Tyr Ser
        260                 265                 270

Cys Glu Ala Glu Asn Ser Val Ser Arg Glu Arg Ser Glu Pro Lys
    275                 280                 285

Lys Leu Ser Leu Lys Gly Ser Gln Val Leu Phe Thr Pro Ala Ser
290                 295                 300

Asn Trp Leu Val Pro Trp Leu Pro Ala Ser Leu Leu Gly Leu Met
                305                 310                 315

Val Ile Ala Ala Ala Leu Leu Val Tyr Val Arg Ser Trp Arg Lys
            320                 325                 330

Ala Gly Pro Leu Pro Ser Gln Ile Pro Pro Thr Ala Pro Gly Gly
        335                 340                 345

Glu Gln Cys Pro Leu Tyr Ala Asn Val His His Gln Lys Gly Lys
    350                 355                 360

Asp Glu Gly Val Val Tyr Ser Val His Arg Thr Ser Lys Arg
365                 370                 375

Ser Glu Gly Gln Phe Tyr His Leu Cys Gly Gly Glu Met Pro Ala
                380                 385                 390

Ala Gln

<210> SEQ ID NO 13
<211> LENGTH: 1407
<212> TYPE: DNA
<213> ORGANISM: Homo sapiens

<400> SEQUENCE: 13
atgggatggt catgtatcat ccttttttcta gtagcaactg caactggagc         50
gtacgctcag gtacagttga agcaatctgg acctagccta gtgcagccct          100
cacagagcct gtccataacc tgcacagtct ctggtttctc attaactaac          150
tatggtgtac actgggttcg ccagtctcca ggaaagggtc tggagtggct          200
gggactgata tggataggtg aaacacaga ctacaatgca gctttcatgt           250
cccgactgag catcaccaag acaactccaa gagccaagt tttctttaaa           300 atgaacagtc tgcaagctga tgacactgcc atatactact gtgtcaaagg          350
ctatggtgac ttctactatg ctatggacta ctggggtcaa ggaaccacgg          400
tcactgtctc tgcagcctcc accaagggcc catcggtctt ccccctggca          450
ccctcctcca agagcacctc tgggggcaca gcggccctgg gctgcctggt          500
caaggactac ttccccgaac cggtgacggt gtcgtggaac tcaggcgccc          550
tgaccagcgg cgtgcacacc ttcccggctg tcctacagtc ctcaggactc          600
tactccctca gcagcgtggt gactgtgccc tctagcagct tgggcaccca          650
gacctacatc tgcaacgtga atcacaagcc cagcaacacc aaggtggaca          700
agaaagttga gcccaaatct tgtgacaaaa ctcacacatg cccaccgtgc          750
ccagcacctg aactcctggg gggaccgtca gtcttcctct tccccccaaa          800
acccaaggac accctcatga tctcccggac ccctgaggtc acatgcgtgg          850
tggtggacgt gagccacgaa gaccctgagg tcaagttcaa ctggtacgtg          900
```

| | | |
|---|---|---|
| gacggcgtgg aggtgcataa tgccaagaca aagccgcggg aggagcagta | 950 | |
| caacagcacg taccgggtgg tcagcgtcct caccgtcctg caccaggact | 1000 | |
| ggctgaatgg caaggagtac aagtgcaagg tctccaacaa agccctccca | 1050 | |
| gcccccatcg agaaaccat ctccaaagcc aaagggcagc cccgagaacc | 1100 | |
| acaggtgtac accctgcccc catcccggga agagatgacc aagaaccagg | 1150 | |
| tcagcctgac ctgcctggtc aaaggcttct atcccagcga catcgccgtg | 1200 | |
| gagtgggaga gcaatgggca gccggagaac aactacaaga ccacgcctcc | 1250 | |
| cgtgctggac tccgacggct ccttcttcct ctacagcaag ctcaccgtgg | 1300 | |
| acaagagcag gtggcagcag gggaacgtct tctcatgctc cgtgatgcat | 1350 | |
| gaggctctgc acaaccacta cacgcagaag agcctctccc tgtctccggg | 1400 | |
| taaatga | 1407 | |

<210> SEQ ID NO 14
<211> LENGTH: 699
<212> TYPE: DNA
<213> ORGANISM: Artificial sequence
<220> FEATURE:
<223> OTHER INFORMATION: Murine monoclonal antibody 1D6.3.8

<400> SEQUENCE: 14

| | | |
|---|---|---|
| atgggatggt catgtatcat ccttttttcta gtagcaactg caactggagt | 50 | |
| acattcagat atcgtgatga cccagtctca taaattcatg tccacatcag | 100 | |
| taggagacag ggtcagcatc tcctgcaagg ccagtcagga tgtgagttct | 150 | |
| gctgtagcct ggtatcaaca gaagccagga cattctccta aactactgat | 200 | |
| ttactcggga taccggtaca ctagagtccc tgatcgcttc actggcagtg | 250 | |
| gatctgggac ggatttcact ttcaccatca gcagtgtgca ggctgaagac | 300 | |
| ctggcatttt atttctgtca gcaacattat agtactccat tcacgttcgg | 350 | |
| ctcgggtacc aaggtggaga tcaaacgaac tgtggctgca ccatctgtct | 400 | |
| tcatcttccc gccatctgat gagcagttga aatctggaac tgcttctgtt | 450 | |
| gtgtgcctgc tgaataactt ctatcccaga gaggccaaag tacagtggaa | 500 | |
| ggtggataac gccctccaat cgggtaactc ccaggagagt gtcacagagc | 550 | |
| aggacagcaa ggacagcacc tacagcctca gcagcaccct gacgctgagc | 600 | |
| aaagcagact acgagaaaca caaagtctac gcctgcgaag tcacccatca | 650 | |
| gggcctgagc tcgcccgtca caaagagctt caacagggga gagtgttaa | 699 | |

<210> SEQ ID NO 15
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 15

| | | |
|---|---|---|
| tcagcacgtg gattcgagtc a | 21 | |

<210> SEQ ID NO 16
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 16
gtgaggacgg ggcgagac                                                    18

<210> SEQ ID NO 17
<211> LENGTH: 53
<212> TYPE: PRT
<213> ORGANISM: Artificial sequence
<220> FEATURE:
<223> OTHER INFORMATION: Synthetic gD tag and signal sequence

<400> SEQUENCE: 17

Met Gly Gly Thr Ala Ala Arg Leu Gly Ala Val Ile Leu Phe Val
 1               5                  10                  15

Val Ile Val Gly His Gly Val Arg Gly Lys Tyr Ala Leu Ala Asp
                20                  25                  30

Ala Ser Leu Lys Met Ala Asp Pro Asn Arg Phe Arg Gly Lys Asp
            35                  40                  45

Leu Pro Val Leu Asp Gln Leu Leu
            50

<210> SEQ ID NO 18
<211> LENGTH: 5392
<212> TYPE: DNA
<213> ORGANISM: Homo sapiens

<400> SEQUENCE: 18
aattcactaa tgcattctgc tcttttgag agcacagctt ctcagatgtg              50
ctccttggag ctggtgtgca gtgtcctgac tgtaagatca agtccaaacc            100 tgttttgaa ttgaggaaac ttctcttttg atctcagccc ttggtggtcc             150
aggtcttcat gctgctgtgg gtgatattac tggtcctggc tcctgtcagt            200
ggacagtttg caaggacacc caggcccatt attttcctcc agcctccatg            250
gaccacagtc ttccaaggag agagagtgac cctcacttgc aagggatttc            300
gcttctactc accacagaaa acaaaatggt accatcggta cctcgggaaa            350
gaaatactaa gagaaacccc agacaatatc cttgaggttc aggaatctgg            400
agagtacaga tgccaggccc agggctcccc tctcagtagc cctgtgcact            450 tggattttc ttcagcttcg ctgatcctgc aagctccact ttctgtgttt             500
gaaggagact ctgtggttct gaggtgccgg gcaaaggcgg aagtaacact            550
gaataatact atttacaaga atgataatgt cctggcattc cttaataaaa            600
gaactgactt ccatattcct catgcatgtc tcaaggacaa tggtgcatat            650
cgctgtactg gatataagga agttgttgc cctgtttctt ccaatacagt             700
caaaatccaa gtccaagagc catttacacg tccagtgctg agagccagct            750
ccttccagcc catcagcggg aacccagtga ccctgacctg tgagacccag            800
ctctctctag agaggtcaga tgtcccgctc cggttccgct tcttcagaga            850
tgaccagacc ctgggattag ctggagtct ctccccgaat tccagatta              900 ctgccatgtg gagtaaagat tcagggttct actggtgtaa ggcagcaaca            950
atgcctcaca gcgtcatatc tgacagcccg agatcctgga tacaggtgca           1000
gatccctgca tctcatcctg tcctcactct cagccctgaa aaggctctga           1050
attttgaggg aaccaaggtg cacttcact gtgaaaccca ggaagattct            1100

-continued

| | |
|---|---|
| ctgcgcactt tgtacaggtt ttatcatgag ggtgtccccc tgaggcacaa | 1150 |
| gtcagtccgc tgtgaaaggg gagcatccat cagcttctca ctgactacag | 1200 |
| agaattcagg gaactactac tgcacagctg acaatggcct tggcgccaag | 1250 |
| cccagtaagg ctgtgagcct ctcagtcact gttcccgtgt ctcatcctgt | 1300 |
| cctcaacctc agctctcctg aggacctgat ttttgaggga gccaaggtga | 1350 |
| cacttcactg tgaagcccag agaggttcac tccccatcct gtaccagttt | 1400 |
| catcatgagg atgctgccct ggagcgtagg tcggccaact ctgcaggagg | 1450 |
| agtggccatc agcttctctc tgactgcaga gcattcaggg aactactact | 1500 |
| gcacagctga caatggcttt ggcccccagc gcagtaaggc ggtgagcctc | 1550 |
| tccatcactg tccctgtgtc tcatcctgtc ctcaccctca gctctgctga | 1600 |
| ggccctgact tttgaaggag ccactgtgac acttcactgt gaagtccaga | 1650 |
| gaggttcccc acaaatccta taccagtttt atcatgagga catgcccctg | 1700 |
| tggagcagct caacaccctc tgtgggaaga gtgtccttca gcttctctct | 1750 |
| gactgaagga cattcaggga attactactg cacagctgac aatggctttg | 1800 |
| gtccccagcg cagtgaagtg gtgagccttt tgtcactgt tccagtgtct | 1850 |
| cgccccatcc tcaccctcag ggttcccagg gccaggctg tggtgggga | 1900 |
| cctgctggag cttcactgtg aggccccgag aggctctccc ccaatcctgt | 1950 |
| actggttta tcatgaggat gtcaccctgg ggagcagctc agcccctct | 2000 |
| ggaggagaag cttctttcaa cctctctctg actgcagaac attctggaaa | 2050 |
| ctactcatgt gaggccaaca atggcctagt ggcccagcac agtgacacaa | 2100 |
| tatcactcag tgttatagtt ccagtatctc gtcccatcct caccttcagg | 2150 |
| gctcccaggg cccaggctgt ggtgggggac ctgctggagc ttcactgtga | 2200 |
| ggccctgaga ggctcctccc caatcctgta ctggttttat catgaagatg | 2250 |
| tcaccctggg taagatctca gcccctctg gaggagggc ctccttcaac | 2300 |
| ctctctctga ctacagaaca ttctggaatc tactcctgtg aggcagacaa | 2350 |
| tggtccggag gcccagcgca gtgagatggt gacactgaaa gttgcagttc | 2400 |
| cggtgtctcg cccggtcctc accctcaggg ctcccgggac ccatgctgcg | 2450 |
| gtgggggacc tgctggagct tcactgtgag gccctgagag gctctcccct | 2500 |
| gatcctgtac cggttttttc atgaggatgt caccctagga aataggtcgt | 2550 |
| ccccctctgg aggagcgtcc ttaaacctct ctctgactgc agagcactct | 2600 |
| ggaaactact cctgtgaggc cgacaatggc ctcggggccc agcgcagtga | 2650 |
| gacagtgaca ctttatatca cagggctgac cgcgaacaga agtggcccctt | 2700 |
| ttgccacagg agtcgccggg ggcctgctca gcatagcagg ccttgctgcg | 2750 |
| ggggcactgc tgctctactg ctggctctcg agaaaagcag ggagaaagcc | 2800 |
| tgcctctgac cccgccagga gccctccaga ctcggactcc caagagccca | 2850 |
| cctatcacaa tgtaccagcc tgggaagagc tgcaaccagt gtacactaat | 2900 |
| gcaaatccta gaggagaaaa tgtggtttac tcagaagtac ggatcatcca | 2950 |
| agagaaaaag aaacatgcag tggcctctga ccccaggcat ctcaggaaca | 3000 |
| agggttcccc tatcatctac tctgaagtta aggtggcgtc aaccccggtt | 3050 |
| tccggatccc tgttcttggc ttcctcagct cctcacagat gagtccacac | 3100 |

| | |
|---|---|
| gtctctccaa ctgctgtttc agcctctgca ccccaaagtt ccccttgggg | 3150 |
| gagaagcagc attgaagtgg aagatttag gctgccccag accatatcta | 3200 |
| ctggcctttg tttcacatgt cctcattctc agtctgacca gaatgcaggg | 3250 |
| ccctgctgga ctgtcacctg tttcccagtt aaagccctga ctggcaggtt | 3300 |
| ttttaatcca gtggcaaggt gctcccactc cagggcccag cacatctcct | 3350 |
| ggattcctta gtgggcttca gctgtgattg ctgttctgag tactgctctc | 3400 |
| atcacacccc cacagagggg gtcttaccac acaaagggag agtgggcctt | 3450 |
| caggagatgc cgggctggcc taacagctca ggtgctccta aactccgaca | 3500 |
| cagagttcct gctttgggtg gatgcatttc tcaattgtca tcagcctggt | 3550 |
| ggggctactg cagtgtgctg ccaaatggga cagcacacag cctgtgcaca | 3600 |
| tgggacatgt gatgggtctc cccacggggg ctgcatttca cactcctcca | 3650 |
| cctgtctcaa actctaaggt cggcacttga caccaaggta acttctctcc | 3700 |
| tgctcatgtg tcagtgtcta cctgcccaag taagtggctt tcatacacca | 3750 |
| agtcccaagt tcttcccatc ctaacagaag taacccagca agtcaaggcc | 3800 |
| aggaggacca ggggtgcaga cagaaacacat actggaacac aggaggtgct | 3850 |
| caattactat ttgactgact gactgaatga atgaatgaat gaggaagaaa | 3900 |
| actgtgggta atcaaactgg cataaaatcc agtgcactcc ctaggaaatc | 3950 |
| cgggaggtat tctggcttcc ctaagaaaca acggaagaga aggagcttgg | 4000 |
| atgaggaaac tgttcagcaa gaggaagggc ttctcacact ttcatgtgct | 4050 |
| tgtggatcac ctgaggatcc tgtgaaaata cagatactga ttcagtgggt | 4100 |
| ctgtgtagag cctgagactg ccattctaac atgttcccag gggatgctga | 4150 |
| tgctgctggc cctgggactg cactgcatgc atgtgaagcc ctataggtct | 4200 |
| cagcagaggc ccatggagag ggaatgtgtg gctctggctg cccagggccc | 4250 |
| aactcggttc acacggatcg tgctgctccc tggccagcct ttggccacag | 4300 |
| caccaccagc tgctgttgct gagagagctt cttctctgtg acatgttggc | 4350 |
| tttcatcagc caccctggga agcggaaagt agctgccact atctttgttt | 4400 |
| ccccacctca ggcctcacac tttcccatga aaagggtgaa tgtatataac | 4450 |
| ctgagccctc tccattcaga gttgttctcc catctctgag caatgggatg | 4500 |
| ttctgttccg cttttatgat atccatcaca tcttatcttg atctttgctc | 4550 |
| ccagtggatt gtacagtgat gacttttaag ccccacggcc ctgaaataaa | 4600 |
| atccttccaa gggcattgga agctctctcc acctgaacca tggcttttca | 4650 |
| tgcttccaag tgtcagggcc ttgcccagat agacagggct gactctgctg | 4700 |
| ccccaacctt tcaaggagga aaccagacac ctgagacagg agcctgtatg | 4750 |
| cagcccagtg cagccttgca gaggacaagg ctggaggcat tgtcatcac | 4800 |
| tacagatatg caactaaaat agacgtggag caagagaaat gcattcccac | 4850 |
| cgaggccgct tttttaggcc tagttgaaag tcaagaagga cagcagcaag | 4900 |
| cataggctca ggattaaaga aaaaaatctg ctcacagttt gttctggagg | 4950 |
| tcacatcacc aacaaagctc acgccctatg cagttctgag aaggtggagg | 5000 |
| caccaggctc aaaagaggaa atttagaatt tctcattggg agagtaaggt | 5050 |

```
accccccatcc cagaatgata actgcacagt ggcagaacaa actccaccct          5100
aatgtgggtg accccatcc agtctgttga aggcctgagt gtaacaaaag           5150
ggcttattct tcctcaagta agggggaact cctgctttgg gctgggacat           5200 aagttttct gctttcagac gcaaactgaa aaatggctct tcttgggtct            5250
tgagcttgct ggcatatgga ctgaaagaaa ctatgctatt ggatctcctg           5300
gatctccagc ttgctgactg cagatcttga gatatgtcag cctctacagt           5350
cacaagagct aattcattct aataaaccaa tctttctgta aa                   5392
```

<210> SEQ ID NO 19
<211> LENGTH: 977
<212> TYPE: PRT
<213> ORGANISM: Homo sapiens

<400> SEQUENCE: 19

```
Met Leu Leu Trp Val Ile Leu Val Leu Ala Pro Val Ser Gly
  1               5                  10                  15

Gln Phe Ala Arg Thr Pro Arg Pro Ile Ile Phe Leu Gln Pro Pro
                 20                  25                  30

Trp Thr Thr Val Phe Gln Gly Glu Arg Val Thr Leu Thr Cys Lys
                 35                  40                  45

Gly Phe Arg Phe Tyr Ser Pro Gln Lys Thr Lys Trp Tyr His Arg
                 50                  55                  60

Tyr Leu Gly Lys Glu Ile Leu Arg Glu Thr Pro Asp Asn Ile Leu
                 65                  70                  75

Glu Val Gln Glu Ser Gly Glu Tyr Arg Cys Gln Ala Gln Gly Ser
                 80                  85                  90

Pro Leu Ser Ser Pro Val His Leu Asp Phe Ser Ser Ala Ser Leu
                 95                 100                 105

Ile Leu Gln Ala Pro Leu Ser Val Phe Glu Gly Asp Ser Val Val
                110                 115                 120

Leu Arg Cys Arg Ala Lys Ala Glu Val Thr Leu Asn Asn Thr Ile
                125                 130                 135

Tyr Lys Asn Asp Asn Val Leu Ala Phe Leu Asn Lys Arg Thr Asp
                140                 145                 150

Phe His Ile Pro His Ala Cys Leu Lys Asp Asn Gly Ala Tyr Arg
                155                 160                 165

Cys Thr Gly Tyr Lys Glu Ser Cys Cys Pro Val Ser Ser Asn Thr
                170                 175                 180

Val Lys Ile Gln Val Gln Glu Pro Phe Thr Arg Pro Val Leu Arg
                185                 190                 195

Ala Ser Ser Phe Gln Pro Ile Ser Gly Asn Pro Val Thr Leu Thr
                200                 205                 210

Cys Glu Thr Gln Leu Ser Leu Glu Arg Ser Asp Val Pro Leu Arg
                215                 220                 225

Phe Arg Phe Phe Arg Asp Asp Gln Thr Leu Gly Leu Gly Trp Ser
                230                 235                 240

Leu Ser Pro Asn Phe Gln Ile Thr Ala Met Trp Ser Lys Asp Ser
                245                 250                 255

Gly Phe Tyr Trp Cys Lys Ala Ala Thr Met Pro His Ser Val Ile
                260                 265                 270

Ser Asp Ser Pro Arg Ser Trp Ile Gln Val Gln Ile Pro Ala Ser
                275                 280                 285
```

-continued

```
His Pro Val Leu Thr Leu Ser Pro Glu Lys Ala Leu Asn Phe Glu
            290                 295                 300

Gly Thr Lys Val Thr Leu His Cys Glu Thr Gln Glu Asp Ser Leu
            305                 310                 315

Arg Thr Leu Tyr Arg Phe Tyr His Glu Gly Val Pro Leu Arg His
            320                 325                 330

Lys Ser Val Arg Cys Glu Arg Gly Ala Ser Ile Ser Phe Ser Leu
            335                 340                 345

Thr Thr Glu Asn Ser Gly Asn Tyr Tyr Cys Thr Ala Asp Asn Gly
            350                 355                 360

Leu Gly Ala Lys Pro Ser Lys Ala Val Ser Leu Ser Val Thr Val
            365                 370                 375

Pro Val Ser His Pro Val Leu Asn Leu Ser Ser Pro Glu Asp Leu
            380                 385                 390

Ile Phe Glu Gly Ala Lys Val Thr Leu His Cys Glu Ala Gln Arg
            395                 400                 405

Gly Ser Leu Pro Ile Leu Tyr Gln Phe His His Glu Asp Ala Ala
            410                 415                 420

Leu Glu Arg Arg Ser Ala Asn Ser Ala Gly Gly Val Ala Ile Ser
            425                 430                 435

Phe Ser Leu Thr Ala Glu His Ser Gly Asn Tyr Tyr Cys Thr Ala
            440                 445                 450

Asp Asn Gly Phe Gly Pro Gln Arg Ser Lys Ala Val Ser Leu Ser
            455                 460                 465

Ile Thr Val Pro Val Ser His Pro Val Leu Thr Leu Ser Ser Ala
            470                 475                 480

Glu Ala Leu Thr Phe Glu Gly Ala Thr Val Thr Leu His Cys Glu
            485                 490                 495

Val Gln Arg Gly Ser Pro Gln Ile Leu Tyr Gln Phe Tyr His Glu
            500                 505                 510

Asp Met Pro Leu Trp Ser Ser Thr Pro Ser Val Gly Arg Val
            515                 520                 525

Ser Phe Ser Phe Ser Leu Thr Glu Gly His Ser Gly Asn Tyr Tyr
            530                 535                 540

Cys Thr Ala Asp Asn Gly Phe Gly Pro Gln Arg Ser Glu Val Val
            545                 550                 555

Ser Leu Phe Val Thr Val Pro Val Ser Arg Pro Ile Leu Thr Leu
            560                 565                 570

Arg Val Pro Arg Ala Gln Ala Val Val Gly Asp Leu Leu Glu Leu
            575                 580                 585

His Cys Glu Ala Pro Arg Gly Ser Pro Pro Ile Leu Tyr Trp Phe
            590                 595                 600

Tyr His Glu Asp Val Thr Leu Gly Ser Ser Ala Pro Ser Gly
            605                 610                 615

Gly Glu Ala Ser Phe Asn Leu Ser Leu Thr Ala Glu His Ser Gly
            620                 625                 630

Asn Tyr Ser Cys Glu Ala Asn Asn Gly Leu Val Ala Gln His Ser
            635                 640                 645

Asp Thr Ile Ser Leu Ser Val Ile Val Pro Val Ser Arg Pro Ile
            650                 655                 660

Leu Thr Phe Arg Ala Pro Arg Ala Gln Ala Val Val Gly Asp Leu
            665                 670                 675

Leu Glu Leu His Cys Glu Ala Leu Arg Gly Ser Ser Pro Ile Leu
```

-continued

```
              680                 685                 690
Tyr Trp Phe Tyr His Glu Asp Val Thr Leu Gly Lys Ile Ser Ala
              695                 700                 705
Pro Ser Gly Gly Gly Ala Ser Phe Asn Leu Ser Leu Thr Thr Glu
              710                 715                 720
His Ser Gly Ile Tyr Ser Cys Glu Ala Asp Asn Gly Pro Glu Ala
              725                 730                 735
Gln Arg Ser Glu Met Val Thr Leu Lys Val Ala Val Pro Val Ser
              740                 745                 750
Arg Pro Val Leu Thr Leu Arg Ala Pro Gly Thr His Ala Ala Val
              755                 760                 765
Gly Asp Leu Leu Glu Leu His Cys Glu Ala Leu Arg Gly Ser Pro
              770                 775                 780
Leu Ile Leu Tyr Arg Phe Phe His Glu Asp Val Thr Leu Gly Asn
              785                 790                 795
Arg Ser Ser Pro Ser Gly Gly Ala Ser Leu Asn Leu Ser Leu Thr
              800                 805                 810
Ala Glu His Ser Gly Asn Tyr Ser Cys Glu Ala Asp Asn Gly Leu
              815                 820                 825
Gly Ala Gln Arg Ser Glu Thr Val Thr Leu Tyr Ile Thr Gly Leu
              830                 835                 840
Thr Ala Asn Arg Ser Gly Pro Phe Ala Thr Gly Val Ala Gly Gly
              845                 850                 855
Leu Leu Ser Ile Ala Gly Leu Ala Ala Gly Ala Leu Leu Leu Tyr
              860                 865                 870
Cys Trp Leu Ser Arg Lys Ala Gly Arg Lys Pro Ala Ser Asp Pro
              875                 880                 885
Ala Arg Ser Pro Pro Asp Ser Asp Ser Gln Glu Pro Thr Tyr His
              890                 895                 900
Asn Val Pro Ala Trp Glu Glu Leu Gln Pro Val Tyr Thr Asn Ala
              905                 910                 915
Asn Pro Arg Gly Glu Asn Val Val Tyr Ser Glu Val Arg Ile Ile
              920                 925                 930
Gln Glu Lys Lys Lys His Ala Val Ala Ser Asp Pro Arg His Leu
              935                 940                 945
Arg Asn Lys Gly Ser Pro Ile Ile Tyr Ser Glu Val Lys Val Ala
              950                 955                 960
Ser Thr Pro Val Ser Gly Ser Leu Phe Leu Ala Ser Ser Ala Pro
              965                 970                 975
His Arg
```

COMPOSITIONS AND METHODS FOR THE TREATMENT OF TUMOR OF HEMATOPOIETIC ORIGIN

RELATED APPLICATIONS

This application is a continuation-in-part of, and claims priority under 35 USC §120 to, U.S. application Ser. No. 11/315,529, filed Dec. 21, 2005, wherein U.S. application Ser. No. 11/315,529, filed Dec. 21, 2005 is a continuation-in-part of, and claims priority under 35 USC §120 to both, PCT Application No. PCT/US2004/043514, filed Dec. 21, 2004 and also to U.S. application Ser. No. 11/020,508, filed Dec. 21, 2004, and wherein PCT Application No. PCT/US2004/043514, filed Dec. 21, 2004, and U.S. application Ser. No. 11/020,508, filed Dec. 21, 2004, both of which are also continuation-in-parts of and claim priority under 35 USC §120 to both, PCT Application PCT/US2004/038262, filed Nov. 16, 2004, and also to U.S. application Ser. No. 10/989,826, filed Nov. 16, 2004, both of which claim priority to US Provisional Applications, 60/520,842, filed Nov. 17, 2003 and also to 60/532,426, filed Dec. 24, 2003, and wherein PCT Application PCT/US2004/038262, filed Nov. 16, 2004, and U.S. application Ser. No. 10/989,826, filed Nov. 16, 2004, both of which are also continuations-in-part of, and claim priority under USC §120 to both, PCT Application PCT/US03/36298, filed Nov. 13, 2003 and also to U.S. application Ser. No. 10/712,892, filed Nov. 13, 2003, both of which claim priority to U.S. Provisional Application 60/426,847, filed Nov. 15, 2002, and wherein PCT Application PCT/US03/36298, filed Nov. 13, 2003 and U.S. application Ser. No. 10/712,892, filed Nov. 13, 2003, both of which are also continuations-in-part of, and claim priority under USC §120 to both, PCT Application PCT/US03/25892, filed Aug. 19, 2003 and also to U.S. application Ser. No. 10/643,795, filed Aug. 19, 2003, both of which claim priority to U.S. Provisional Application 60/404,809, filed Aug. 19, 2002, and wherein PCT Application PCT/US03/25892, filed Aug. 19, 2003 and U.S. application Ser. No. 10/643,795, filed Aug. 19, 2003 both of which are continuations-in-part of, and claim priority under USC §120 to PCT/US02/28859, filed Sep. 11, 2002 and also to U.S. application Ser. No. 10/241,220, filed Sep. 11, 2002, both of which claim priority under 35 USC §119 to U.S. Provisional Application 60/339,227, filed Oct. 19, 2001.

FIELD OF THE INVENTION

The present invention is directed to compositions of matter useful for the treatment of hematopoietic tumor in mammals and to methods of using those compositions of matter for the same.

BACKGROUND OF THE INVENTION

Malignant tumors (cancers) are the second leading cause of death in the United States, after heart disease (Boring et al., *CA Cancel J. Clin.* 43:7 (1993)). Cancer is characterized by the increase in the number of abnormal, or neoplastic, cells derived from a normal tissue which proliferate to form a tumor mass, the invasion of adjacent tissues by these neoplastic tumor cells, and the generation of malignant cells which eventually spread via the blood or lymphatic system to regional lymph nodes and to distant sites via a process called metastasis. In a cancerous state, a cell proliferates under conditions in which normal cells would not grow. Cancer manifests itself in a wide variety of forms, characterized by different degrees of invasiveness and aggressiveness.

Cancers which involve cells generated during hematopoiesis, a process by which cellular elements of blood, such as lymphocytes, leukocytes, platelets, erythrocytes and natural killer cells are generated are referred to as hematopoietic cancers. Lymphocytes which can be found in blood and lymphatic tissue and are critical for immune response are categorized into two main classes of lymphocytes: B lymphocytes (B cells) and T lymphocytes (T cells), which mediate humoral and cell mediated immunity, respectively.

B cells mature within the bone marrow and leave the marrow expressing an antigen-binding antibody on their cell surface. When a naive B cell first encounters the antigen for which its membrane-bound antibody is specific, the cell begins to divide rapidly and its progeny differentiate into memory B cells and effector cells called "plasma cells". Memory B cells have a longer life span and continue to express membrane-bound antibody with the same specificity as the original parent cell. Plasma cells do not produce membrane-bound antibody but instead produce the antibody in a form that can be secreted. Secreted antibodies are the major effector molecule of humoral immunity.

T cells mature within the thymus which provides an environment for the proliferation and differentiation of immature T cells. During T cell maturation, the T cells undergo the gene rearrangements that produce the T-cell receptor and the positive and negative selection which helps determine the cell-surface phenotype of the mature T cell. Characteristic cell surface markers of mature T cells are the CD3:T-cell receptor complex and one of the coreceptors, CD4 or CD8.

In attempts to discover effective cellular targets for cancer therapy, researchers have sought to identify transmembrane or otherwise membrane-associated polypeptides that are specifically expressed on the surface of one or more particular type(s) of cancer cell as compared to on one or more normal non-cancerous cell(s). Often, such membrane-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies. In this regard, it is noted that antibody-based therapy has proved very effective in the treatment of certain cancers. For example, HERCEPTIN® and RITUXAN® (both from Genentech Inc., South San Francisco, Calif.) are antibodies that have been used successfully to treat breast cancer and non-Hodgkin's lymphoma, respectively. More specifically, HERCEPTIN® is a recombinant DNA-derived humanized monoclonal antibody that selectively binds to the extracellular domain of the human epidermal growth factor receptor 2 (HER2) proto-oncogene. HER2 protein overexpression is observed in 25-30% of primary breast cancers. RITUXAN® is a genetically engineered chimeric murine/human monoclonal antibody directed against the CD20 antigen found on the surface of normal and malignant B lymphocytes. Both these antibodies are recombinantly produced in CHO cells.

In other attempts to discover effective cellular targets for cancer therapy, researchers have sought to identify (1) non-membrane-associated polypeptides that are specifically produced by one or more particular type(s) of cancer cell(s) as compared to by one or more particular type(s) of non-cancerous normal cell(s), (2) polypeptides that are produced by cancer cells at an expression level that is significantly higher than that of one or more normal non-cancerous cell(s), or (3) polypeptides whose expression is specifically limited to only a single (or very limited number of different) tissue type(s) in both the cancerous and non-cancerous state (e.g., normal prostate and prostate tumor tissue). Such polypeptides may remain intracellularly located or may be secreted by the cancer cell. Moreover, such polypeptides may be expressed not by the cancer cell itself, but rather by cells which produce and/or secrete polypeptides-having a potentiating or growth-enhancing effect on cancer cells. Such secreted polypeptides are often proteins that provide cancer cells with a growth advantage over normal cells and include such things as, for example, angiogenic factors, cellular adhesion factors, growth factors, and the like. Identification of antagonists of such non-membrane associated polypeptides would be expected to serve as effective therapeutic agents for the treatment of such cancers. Furthermore, identification of the expression pattern of such polypeptides would be useful for the diagnosis of particular cancers in mammals.

Despite the above identified advances in mammalian cancer therapy, there is a great need for additional therapeutic agents capable of detecting the presence of tumor in a mammal and for effectively inhibiting neoplastic cell growth, respectively. Accordingly, it is an objective of the present invention to identify polypeptides, cell membrane-associated, secreted or intracellular polypeptides whose expression is specifically limited to only a single (or very limited number of different) tissue type(s), hematopoietic tissues, in both a cancerous and non-cancerous state, and to use those polypeptides, and their encoding nucleic acids, to produce compositions of matter useful in the therapeutic treatment detection of hematopoietic cancer in mammals.

SUMMARY OF THE INVENTION

A. Embodiments

In the present specification, Applicants describe for the first time the identification of various cellular polypeptides (and their encoding nucleic acids or fragments thereof) which are specifically expressed by both tumor and normal cells of a specific cell type, for example cells generated during hematopoiesis, i.e. lymphocytes, leukocytes, erythrocytes and platelets. All of the above polypeptides are herein referred to as Tumor Antigens of Hematopoietic Origin polypeptides ("TAHO" polypeptides) and are expected to serve as effective targets for cancer therapy in mammals.

Accordingly, in one embodiment of the present invention, the invention provides an isolated nucleic acid molecule having a nucleotide sequence that encodes a tumor antigen of hematopoietic origin polypeptide (a "TAHO" polypeptide) or fragment thereof.

In certain aspects, the isolated nucleic acid molecule comprises a nucleotide sequence having at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% nucleic acid sequence identity, to (a) a DNA molecule encoding a full-length TAHO polypeptide having an amino acid sequence as disclosed herein, a TAHO polypeptide amino acid sequence lacking the signal peptide as disclosed herein, an extracellular domain of a transmembrane TAHO polypeptide, with or without the signal peptide, as disclosed herein or any other specifically defined fragment of a full-length TAHO polypeptide amino acid sequence as disclosed herein, or (b) the complement of the DNA molecule of (a).

In other aspects, the isolated nucleic acid molecule comprises a nucleotide sequence having at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% nucleic acid sequence identity, to (a) a DNA molecule comprising the coding sequence of a full-length TAHO polypeptide cDNA as disclosed herein, the coding sequence of a TAHO polypeptide lacking the signal peptide as disclosed herein, the coding sequence of an extracellular domain of a transmembrane TAHO polypeptide, with or without the signal peptide, as disclosed herein or the coding sequence of any other specifically defined fragment of the full-length TAHO polypeptide amino acid sequence as disclosed herein, or (b) the complement of the DNA molecule of (a).

In further aspects, the invention concerns an isolated nucleic acid molecule comprising a nucleotide sequence having at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% nucleic acid sequence identity, to (a) a DNA molecule that encodes the same mature polypeptide encoded by the full-length coding region of any of the human protein cDNAs deposited with the ATCC as disclosed herein, or (b) the complement of the DNA molecule of (a).

Another aspect of the invention provides an isolated nucleic acid molecule comprising a nucleotide sequence encoding a TAHO polypeptide which is either transmembrane domain-deleted or transmembrane domain-inactivated, or is complementary to such encoding nucleotide sequence, wherein the transmembrane domain(s) of such polypeptide(s) are disclosed herein. Therefore, soluble extracellular domains of the herein described TAHO polypeptides are contemplated.

In other aspects, the present invention is directed to isolated nucleic acid molecules which hybridize to (a) a nucleotide sequence encoding a TAHO polypeptide having a full-length amino acid sequence as disclosed herein, a TAHO polypeptide amino acid sequence lacking the signal peptide as disclosed herein, an extracellular domain of a transmembrane TAHO polypeptide, with or without the signal peptide, as disclosed herein or any other specifically defined fragment of a full-length TAHO polypeptide amino acid sequence as disclosed herein, or (b) the complement of the nucleotide sequence of (a). In this regard, an embodiment of the present invention is directed to fragments of a full-length TAHO polypeptide coding sequence, or the complement thereof, as disclosed herein, that may find use as, for example, hybridization probes useful as, for example, detection probes, anti-sense oligonucleotide probes, or for encoding fragments of a full-length TAHO polypeptide that may optionally encode a polypeptide comprising a binding site for an anti-TAHO polypeptide antibody, a TAHO binding oligopeptide or other small organic molecule that binds to a TAHO polypeptide. Such nucleic acid fragments are usually at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length. It is noted that novel fragments of a TAHO polypeptide-encoding nucleotide sequence may be determined in a routine manner by aligning the TAHO polypeptide-encoding nucleotide sequence with other known nucleotide sequences using any of a number of well known sequence alignment programs and determining which TAHO polypeptide-encoding nucleotide sequence fragment(s) are novel. All of such novel fragments of TAHO polypeptide-encoding nucleotide sequences are contemplated herein. Also contemplated are the TAHO polypeptide fragments encoded by these nucleotide molecule fragments, preferably those TAHO polypeptide fragments that comprise a binding site for an anti-TAHO antibody, a TAHO binding oligopeptide or other small organic molecule that binds to a TAHO polypeptide.

In another embodiment, the invention provides isolated TAHO polypeptides encoded by any of the isolated nucleic acid sequences hereinabove identified.

In a certain aspect, the invention concerns an isolated TAHO polypeptide, comprising an amino acid sequence having at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% amino acid sequence identity, to a TAHO polypeptide having a full-length amino acid sequence as disclosed herein, a TAHO polypeptide amino acid sequence lacking the signal peptide as disclosed herein, an extracellular domain of a transmembrane TAHO polypeptide protein, with or without the signal peptide, as disclosed herein, an amino acid sequence encoded by any of the nucleic acid sequences disclosed herein or any other specifically defined fragment of a full-length TAHO polypeptide amino acid sequence as disclosed herein.

In a further aspect, the invention concerns an isolated TAHO polypeptide comprising an amino acid sequence having at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to an amino acid sequence encoded by any of the human protein cDNAs deposited with the ATCC as disclosed herein.

In a specific aspect, the invention provides an isolated TAHO polypeptide without the N-terminal signal sequence and/or without the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the TAHO polypeptide and recovering the TAHO polypeptide from the cell culture.

Another aspect of the invention provides an isolated TAHO polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the TAHO polypeptide and recovering the TAHO polypeptide from the cell culture.

In other embodiments of the present invention, the invention provides vectors comprising DNA encoding any of the herein described polypeptides. Host cells comprising any such vector are also provided. By way of example, the host cells may be CHO cells, E. coli cells, or yeast cells. A process for producing any of the herein described polypeptides is further provided and comprises culturing host cells under conditions suitable for expression of the desired polypeptide and recovering the desired polypeptide from the cell culture.

In other embodiments, the invention provides isolated chimeric polypeptides comprising any of the herein described TAHO polypeptides fused to a heterologous (non-TAHO) polypeptide. Example of such chimeric molecules comprise any of the herein described TAHO polypeptides fused to a heterologous polypeptide such as, for example, an epitope tag sequence or a Fc region of an immunoglobulin.

In another embodiment, the invention provides an antibody which binds, preferably specifically, to any of the above or below described polypeptides. Optionally, the antibody is a monoclonal antibody, antibody fragment, chimeric antibody, humanized antibody, single-chain antibody or antibody that competitively inhibits the binding of an anti-TAHO polypeptide antibody to its respective antigenic epitope. Antibodies of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies of the present invention may optionally be produced in CHO cells or bacterial cells and preferably induce death of a cell to which they bind. For detection purposes, the antibodies of the present invention may be detectably labeled, attached to a solid support, or the like.

In other embodiments of the present invention, the invention provides vectors comprising DNA encoding any of the herein described antibodies. Host cell comprising any such vector are also provided. By way of example, the host cells may be CHO cells, E. coli cells, or yeast cells. A process for producing any of the herein described antibodies is further provided and comprises culturing host cells under conditions suitable for expression of the desired antibody and recovering the desired antibody from the cell culture.

In another embodiment, the invention provides oligopeptides ("TAHO binding oligopeptides") which bind, preferably specifically, to any of the above or below described TAHO polypeptides. Optionally, the TAHO binding oligopeptides of the present invention may be conjugated to a growth inhibitory agent or cytotoxic agent such as a toxin, including, for example, a maytansinoid or calicheamicin, an antibiotic, a radioactive isotope, a nucleolytic enzyme, or the like. The TAHO binding oligopeptides of the present invention may optionally be produced in CHO cells or bacterial cells and preferably induce death of a cell to which they bind. For detection purposes, the TAHO binding oligopeptides of the present invention may be detectably labeled, attached to a solid support, or the like.

In other embodiments of the present invention, the invention provides vectors comprising DNA encoding any of the herein described TAHO binding oligopeptides. Host cell comprising any such vector are also provided. By way of example, the host cells may be CHO cells, E. coli cells, or yeast cells. A process for producing any of the herein described TAHO binding oligopeptides is further provided and comprises culturing host cells under conditions suitable for expression of the desired oligopeptide and recovering the desired oligopeptide from the cell culture.

In another embodiment, the invention provides small organic molecules ("TAHO binding organic molecules") which bind, preferably specifically, to any of the above or below described TAHO polypeptides. Optionally, the TAHO binding organic molecules of the present invention may be conjugated to a growth inhibitory agent or cytotoxic agent such as a toxin, including, for example, a maytansinoid or calicheamicin, an antibiotic, a radioactive isotope, a nucleolytic enzyme, or the like. The TAHO binding organic molecules of the present invention preferably induce death of a cell to which they bind. For detection purposes, the TAHO binding organic molecules of the present invention may be detectably labeled, attached to a solid support, or the like.

In a still further embodiment, the invention concerns a composition of matter comprising a TAHO polypeptide as described herein, a chimeric TAHO polypeptide as described herein, an anti-TAHO antibody as described herein, a TAHO binding oligopeptide as described herein, or a TAHO binding organic molecule as described herein, in combination with a carrier. Optionally, the carrier is a pharmaceutically acceptable carrier.

In yet another embodiment, the invention concerns an article of manufacture comprising a container and a composition of matter contained within the container, wherein the composition of matter may comprise a TAHO polypeptide as described herein, a chimeric TAHO polypeptide as described herein, an anti-TAHO antibody as described herein, a TAHO binding oligopeptide as described herein, or a TAHO binding organic molecule as described herein. The article may further optionally comprise a label affixed to the container, or a package insert included with the container, that refers to the use of the composition of matter for the therapeutic treatment.

Another embodiment of the present invention is directed to the use of a TAHO polypeptide as described herein, a chimeric TAHO polypeptide as described herein, an anti-TAHO polypeptide antibody as described herein, a TAHO binding oligopeptide as described herein, or a TAHO binding organic molecule as described herein, for the preparation of a medicament useful in the treatment of a condition which is responsive to the TAHO polypeptide, chimeric TAHO polypeptide, anti-TAHO polypeptide antibody, TAHO binding oligopeptide, or TAHO binding organic molecule.

B. Further Additional Embodiments

In one aspect, the present invention provides a method of diagnosing the presence of a multiple myeloma tumor in a mammal. In one embodiment, the method concerns detecting the presence of cells expressing a polypeptide with an amino acid sequence having at least 95% amino acid sequence identity to: (a) the polypeptide having the amino acid sequence shown in FIG. 22 (SEQ ID NO: 19); (b) the polypeptide having the amino acid sequence shown in FIG. 22 (SEQ ID NO: 19), lacking its associated signal peptide; (c) an extracellular domain of the polypeptide having the amino acid sequence shown in FIG. 22 (SEQ ID NO: 19), with its associated signal peptide; (d) an extracellular domain of the polypeptide having the amino acid sequence shown in FIG. 22 (SEQ ID NO: 19), lacking its associated signal peptide; (e) a polypeptide encoded by the nucleotide sequence shown in FIG. 21 (SEQ ID NO: 18); or (f) a polypeptide encoded by the full-length coding region of the nucleotide sequence shown in FIG. 21 (SEQ ID NO: 18). In another embodiment, the polypeptide has: (a) the amino acid sequence shown in FIG. 22 (SEQ ID NO: 19); (b) the amino acid sequence shown in FIG. 22 (SEQ ID NO: 19), lacking its associated signal peptide sequence; (c) an amino acid sequence of an extracellular domain of the polypeptide shown in FIG. 22 (SEQ ID NO: 19), with its associated signal peptide sequence; (d) an amino acid sequence of an extracellular domain of the polypeptide shown in FIG. 22 (SEQ ID NO: 19), lacking its associated signal peptide sequence; (e) an amino acid sequence encoded by the nucleotide sequence shown in FIG. 21 (SEQ ID NO: 18); or (f) an amino acid sequence encoded by the full-length coding region of the nucleotide sequence shown in FIG. 21 (SEQ ID NO: 18). In one embodiment, the method includes the step of contacting a test sample of tissue cells obtained from the mammal with an antibody that binds to the polypeptide of (a)-(b) or (e)-(f); or the extracellular domain of (c)-(d) in combination with an antibody that binds to CD38. The method may further include the step of detecting the formation of a complex between the antibody that binds the polypeptide or extracellular domain, and the polypeptide or extracellular domain, and a complex between an antibody that binds to CD38 and CD38, wherein an increased number of cells demonstrating the complex formations, as compared to a control sample, is indicative of the presence of a multiple myeloma tumor in the mammal. In another embodiment, the method further includes the step of contacting the test sample with an antibody that binds to CD138, and detecting the formation of a complex between the antibody that binds CD138 and CD138.

In another aspect, the present invention provides a method of detecting the presence of multiple myeloma tumor cells in a sample suspected of containing the cells. In one embodiment, the method concerns detecting the tumor cells by detecting cells expressing a polypeptide with an amino acid sequence having at least 95% amino acid sequence identity to: (a) the polypeptide having the amino acid sequence shown in FIG. 22 (SEQ ID NO: 19); (b) the polypeptide having the amino acid sequence shown in FIG. 22 (SEQ ID NO: 19), lacking its associated signal peptide; (c) an extracellular domain of the polypeptide having the amino acid sequence shown in FIG. 22 (SEQ ID NO: 19), with its associated signal peptide; (d) an extracellular domain of the polypeptide having the amino acid sequence shown in FIG. 22 (SEQ ID NO: 19), lacking its associated signal peptide; (e) a polypeptide encoded by the nucleotide sequence shown in FIG. 21 (SEQ ID NO: 18); or (f) a polypeptide encoded by the full-length coding region of the nucleotide sequence shown in FIG. 21 (SEQ ID NO: 18). In another embodiment, the polypeptide has: (a) the amino acid sequence shown in FIG. 22 (SEQ ID NO: 19); (b) the amino acid sequence shown in FIG. 22 (SEQ ID NO: 19), lacking its associated signal peptide sequence; (c) an amino acid sequence of an extracellular domain of the polypeptide shown in FIG. 22 (SEQ ID NO: 19), with its associated signal peptide sequence; (d) an amino acid sequence of an extracellular domain of the polypeptide shown in FIG. 22 (SEQ ID NO: 19), lacking its associated signal peptide sequence; (e) an amino acid sequence encoded by the nucleotide sequence shown in FIG. 21 (SEQ ID NO: 18); or (f) an amino acid sequence encoded by the full-length coding region of the nucleotide sequence shown in FIG. 21 (SEQ ID NO: 18). In one other embodiment, the method includes the step of contacting the sample with an antibody that binds to the polypeptide or extracellular domain in combination with an antibody that binds to CD38. In another embodiment, the method further includes the step of detecting the formation of a complex between the antibody that binds the polypeptide or extracellular domain and the polypeptide or extracellular domain, and a complex between an antibody that binds to CD38 and CD38, wherein the formation of the complexes indicates the presence of the multiple myeloma tumor cells. In another embodiment, the method further includes the step of contacting the test sample with an antibody that binds to CD138, and detecting the formation of a complex between the antibody that binds CD138 and CD138.

In all embodiments, at least one of the antibodies is a monoclonal antibody.

In all embodiments, at least one of said antibodies is an antibody fragment.

In all embodiments, at least one of said antibodies is a chimeric or a humanized antibody.

In all embodiments, a least one of said antibodies is detectably labeled. In all embodiments, the test sample of tissue cells is obtained from an individual suspected of having said tumor.

In all embodiments, at least one of said antibodies is produced in bacteria. In all embodiments, at least one of said antibodies is produced in CHO cells.

BRIEF DESCRIPTION OF THE DRAWINGS

FIG. 1 shows a nucleotide sequence (SEQ ID NO: 1) of a TAHO3 (PRO31998) cDNA, wherein SEQ ID NO: 1 is a clone designated herein as "DNA182432" (also referred here in as "FcRH2" or "SPAP1").

FIG. 2 shows the amino acid sequence (SEQ ID NO:2) derived from the coding sequence of SEQ ID NO:1 shown in FIG. 1.

FIG. 3 shows a nucleotide sequence (SEQ ID NO:3) of a TAHO17 (PRO85143) cDNA, wherein SEQ ID NO:3 is a clone designated herein as "DNA340394" (also referred herein as "FcRH1" or "IRTA5").

FIG. 4 shows the amino acid sequence (SEQ ID NO:4) derived from the coding sequence of SEQ ID NO:3 shown in FIG. 3.

FIG. 5 shows a nucleotide sequence (SEQ ID NO:5) of a TAHO18 (PRO820) cDNA, wherein SEQ ID NO:35 is a clone designated herein as "DNA56041" (also referred herein as "FcRH5" or "IRTA2" which is a portion of the extracellular region of TAHO38).

FIG. 6 shows the amino acid sequence (SEQ ID NO:6) derived from the coding sequence of SEQ ID NO:5 shown in FIG. 5.

FIG. 7 shows a nucleotide sequence (SEQ ID NO:7) of a TAHO20 (PRO52483) cDNA, wherein SEQ ID NO:7 is a clone designated herein as "DNA257955" (also referred herein as "FcRH3" or "IRTA3").

FIG. 8 shows the amino acid sequence (SEQ ID NO:8) derived from the coding sequence of SEQ ID NO:7 shown in FIG. 7.

FIG. 9 shows a nucleotide sequence (SEQ ID NO:9) of a TAHO21 (PRO85193) cDNA, wherein SEQ ID NO:9 is a clone designated herein as "DNA329863" (also referred herein as "FcRH4" or "IRTA1").

FIG. 10 shows the amino acid sequence (SEQ ID NO: 10) derived from the coding sequence of SEQ ID NO:9 shown in FIG. 9.

FIG. 11 shows a nucleotide sequence (SEQ ID NO: 11) of a TAHO22 (PRO96849) cDNA, wherein SEQ ID NO: 11 is a clone designated herein as "DNA346528" (also referred herein as "FcRH6" or "FAIL").

FIG. 12 shows the amino acid sequence (SEQ ID NO: 12) derived from the coding sequence of SEQ ID NO: 11 shown in FIG. 11.

FIG. 13 shows a nucleotide sequence (SEQ ID NO: 13) which encodes for the heavy chain of anti-FcRH2-1D6, designated herein as 1D6 (also referred herein as 1D6.3.8).

FIG. 14 shows a nucleotide sequence (SEQ ID NO: 14) which encodes for the light chain of anti-FcRH2-1D6, designated herein as 1D6 (also referred herein as 1D6.3.8).

FIGS. 15A-15D show microarry data showing the expression of TAHO3 in normal samples and in diseased samples, such as significant expression in NHL samples, follicular lymphoma (FL) and memory B cells (mem B). Abbreviations used in the Figures are designated as follows: Non-Hodgkin's Lymphoma (NHL), follicular lymphoma (FL), normal lymph node (NLN), normal B cells (NB), multiple myeloma cells (MM), small intestine (s. intestine), fetal liver (f. liver), smooth muscle (s. muscle), fetal brain (f. brain), natural killer cells (NK), neutrophils (N'phil), dendrocytes (DC), memory B cells (mem B), plasma cells (PC), bone marrow plasma cells (BM PC).

FIGS. 19A-19D show microarray data showing the expression of TAHO21 in normal samples and in diseased samples, such as significant expression in NHL samples, centrocytes and memory B cells. Abbreviations used in the Figures are designated as follows: Non-Hodgkin's Lymphoma (NHL), follicular lymphoma (FL), normal lymph node (NLN), normal B cells (NB), multiple myeloma cells (MM), small intestine (s. intestine), fetal liver (f. liver), smooth muscle (s. muscle), fetal brain (f. brain), natural killer cells (NK), neutrophils (N'phil), dendrocytes (DC), memory B cells (mem B), plasma cells (PC), bone marrow plasma cells (BM PC).

FIG. 21A-C shows a nucleotide sequence (SEQ ID NO: 18) of a TAHO38 (PRO52387) cDNA, wherein SEQ ID NO: 18 is a clone designated herein as "DNA257845" (also referred herein as "FcRH5c" or "IRTA2c" which is the full-length polypeptide, including the intracellular, transmembrane and extracellular regions).

FIG. 22A-B shows the amino acid sequence (SEQ ID NO: 19) derived from the coding sequence of SEQ ID NO: 18 shown in FIG. 21A-C.

DETAILED DESCRIPTION OF THE PREFERRED EMBODIMENTS

I. Definitions

Figure 15A:
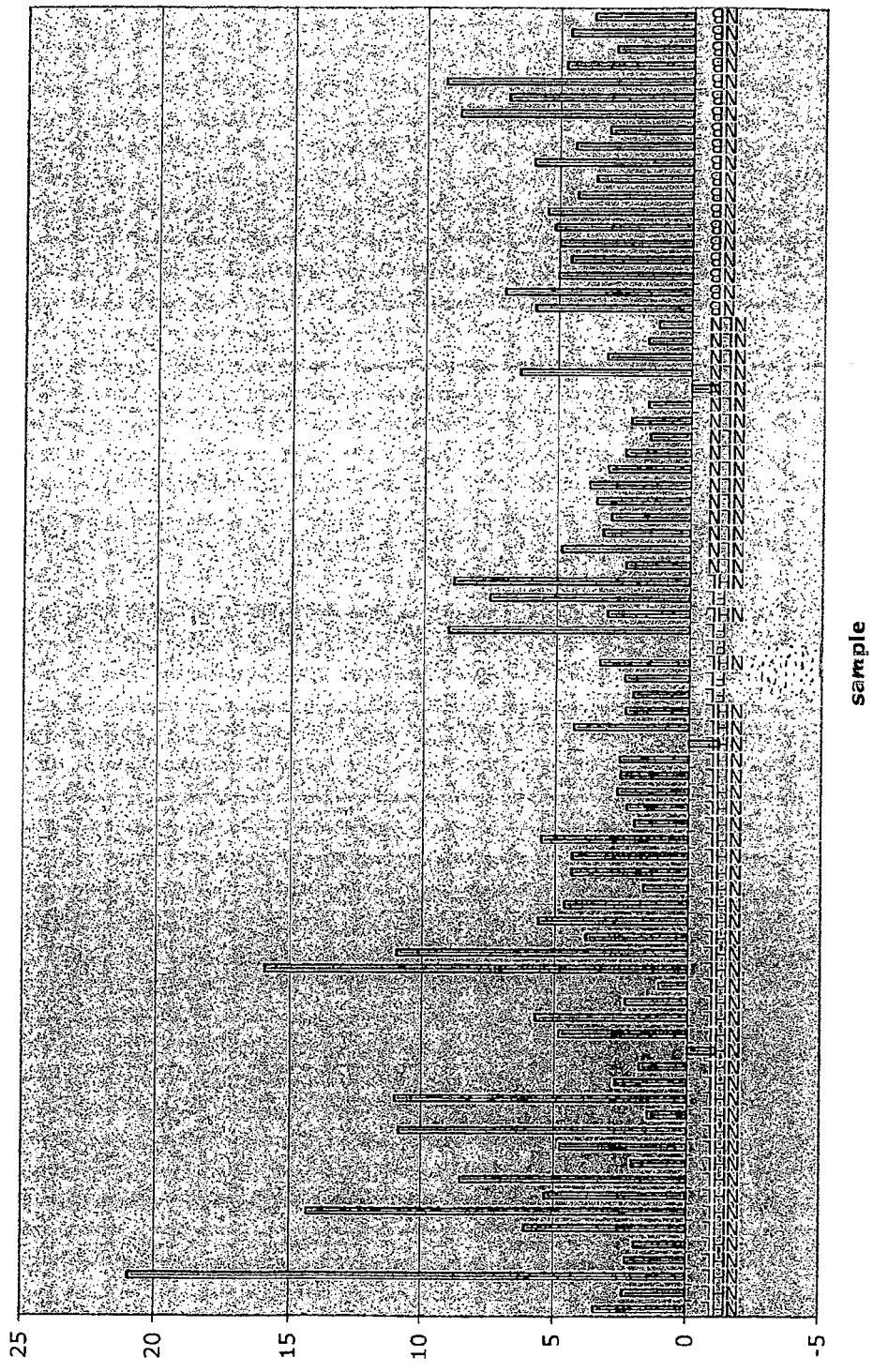

The terms "TAHO polypeptide" and "TAHO" as used herein and when immediately followed by a numerical designation, refer to various polypeptides, wherein the complete designation (i.e., TAHO/number) refers to specific polypeptide sequences as described herein. The terms "TAHO/number polypeptide" and "TAHO/number" wherein the term "number" is provided as an actual numerical designation as used herein encompass native sequence polypeptides, polypeptide variants and fragments of native sequence polypeptides and polypeptide variants (which are further defined herein). The TAHO polypeptides described herein may be isolated from a variety of sources, such as from human tissue types or from another source, or prepared by recombinant or synthetic methods. The term "TAHO polypeptide" refers to each individual TAHO/number polypeptide disclosed herein. All disclosures in this specification which refer to the "TAHO polypeptide" refer to each of the polypeptides individually as well as jointly. For example, descriptions of the preparation of, purification of, derivation of, formation of antibodies to or against, formation of TAHO binding oligopeptides to or against, formation of TAHO binding organic molecules to or against, administration of, compositions containing, treatment of a disease with, etc., pertain to each polypeptide of the invention individually. The term "TAHO polypeptide" also includes variants of the TAHO/number polypeptides disclosed herein.

"TAHO3" is also herein referred to as "FcRH2" or "SPAP1". "TAHO17" is also herein referred to as "FcRH1" or "IRTA5". "TAHO18" is also herein referred to as "IRTA2" or "FcRH5", a portion of the extracellular region. TAHO18 is a portion of the extracellular region of TAHO38. "TAHO20" is also herein referred to as "FcRH3" or "IRTA3". "TAHO21" is also herein referred to as "IRTA1" or "FcRH4". "TAHO22" is also herein referred to as "FcRH6" or "FAIL". "TAHO38" is also herein referred to as "IRTA2c" or "FcRH5c", the full-length polypeptide including the intracellular, transmembrane and extracellular regions.

A "native sequence TAHO polypeptide" comprises a polypeptide having the same amino acid sequence as the corresponding TAHO polypeptide derived from nature. Such native sequence TAHO polypeptides can be isolated from nature or can be produced by recombinant or synthetic means. The term "native sequence TAHO polypeptide" specifically encompasses naturally-occurring truncated or secreted forms of the specific TAHO polypeptide (e.g., an extracellular domain sequence), naturally-occurring variant forms (e.g., alternatively spliced forms) and naturally-occurring allelic variants of the polypeptide. In certain embodiments of the invention, the native sequence TAHO polypeptides disclosed herein are mature or full-length native sequence polypeptides comprising the full-length amino acids sequences shown in the accompanying figures. Start and stop codons (if indicated) are shown in bold font and underlined in the figures. Nucleic acid residues indicated as "N" in the accompanying figures are any nucleic acid residue. However, while the TAHO polypeptides disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the TAHO polypeptides.

The TAHO polypeptide "extracellular domain" or "ECD" refers to a form of the TAHO polypeptide which is essentially free of the transmembrane and cytoplasmic domains. Ordinarily, a TAHO polypeptide ECD will have less than 1% of such transmembrane and/or cytoplasmic domains and preferably, will have less than 0.5% of such domains. It will be understood that any transmembrane domains identified for the TAHO polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a TAHO polypeptide may contain from about 5 or fewer amino acids on either side of the transmembrane domain/extracellular domain boundary as identified in the Examples or specification and such polypeptides, with or without the associated signal peptide, and nucleic acid encoding them, are contemplated by the present invention.

The approximate location of the "signal peptides" of the various TAHO polypeptides disclosed herein may be shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., *Prot. Eng.* 10:1-6 (1997) and von Heinje et al., *Nucl. Acids. Res.* 14:4683-4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"TAHO polypeptide variant" means a TAHO polypeptide, preferably an active TAHO polypeptide, as defined herein having at least about 80% amino acid sequence identity with a full-length native sequence TAHO polypeptide sequence as disclosed herein, a TAHO polypeptide sequence lacking the signal peptide as disclosed herein, an extracellular domain of a TAHO polypeptide, with or without the signal peptide, as disclosed herein or any other fragment of a full-length TAHO polypeptide sequence as disclosed herein (such as those encoded by a nucleic acid that represents only a portion of the complete coding sequence for a full-length TAHO polypeptide). Such TAHO polypeptide variants include, for instance, TAHO polypeptides wherein one or more amino acid residues are added, or deleted, at the N- or C-terminus of the full-length native amino acid sequence. Ordinarily, a TAHO polypeptide variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a full-length native sequence TAHO polypeptide sequence as disclosed herein, a TAHO polypeptide sequence lacking the signal peptide as disclosed herein, an extracellular domain of a TAHO polypeptide, with or without the signal peptide, as disclosed herein or any other specifically defined fragment of a full-length TAHO polypeptide sequence as disclosed herein. Ordinarily, TAHO variant polypeptides are at least about 10 amino acids in length, alternatively at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, TAHO variant polypeptides will have no more than one conservative amino acid substitution as compared to the native TAHO polypeptide sequence, alternatively no more than 2, 3, 4, 5, 6, 7, 8, 9, or 10 conservative amino acid substitution as compared to the native TAHO polypeptide sequence.

"Percent (%) amino acid sequence identity" with respect to the TAHO polypeptide sequences identified herein is defined as the percentage of amino acid residues in a candidate sequence that are identical with the amino acid residues in the specific TAHO polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "TAHO", wherein "TAHO" represents the amino acid sequence of a hypothetical TAHO polypeptide of interest, "Comparison Protein" represents the amino acid sequence of a polypeptide against which the "TAHO" polypeptide of interest is being compared, and "X," "Y" and "Z" each represent different hypothetical amino acid residues. Unless specifically stated otherwise, all % amino acid sequence identity values used herein are obtained as described in the immediately preceding paragraph using the ALIGN-2 computer program.

"TAHO variant polynucleotide" or "TAHO variant nucleic acid sequence" means a nucleic acid molecule which encodes a TAHO polypeptide, preferably an active TAHO polypeptide, as defined herein and which has at least about 80% nucleic acid sequence identity with a nucleotide acid sequence encoding a full-length native sequence TAHO polypeptide sequence as disclosed herein, a full-length native sequence TAHO polypeptide sequence lacking the signal peptide as disclosed herein, an extracellular domain of a TAHO polypeptide, with or without the signal peptide, as disclosed herein or any other fragment of a full-length TAHO polypeptide sequence as disclosed herein (such as those encoded by a nucleic acid that represents only a portion of the complete coding sequence for a full-length TAHO polypeptide). Ordinarily, a TAHO variant polynucleotide will have at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% nucleic acid sequence identity with a nucleic acid sequence encoding a full-length native sequence TAHO polypeptide sequence as disclosed herein, a full-length native sequence TAHO polypeptide sequence lacking the signal peptide as disclosed herein, an extracellular domain of a TAHO polypeptide, with or without the signal sequence, as disclosed herein or any other fragment of a full-length TAHO polypeptide sequence as disclosed herein. Variants do not encompass the native nucleotide sequence.

Ordinarily, TAHO variant polynucleotides are at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

"Percent (%) nucleic acid sequence identity" with respect to TAHO-encoding nucleic acid sequences identified herein is defined as the percentage of nucleotides in a candidate sequence that are identical with the nucleotides in the TAHO nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein; however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "TAHO-DNA", wherein "TAHO-DNA" represents a hypothetical TAHO-encoding nucleic acid sequence of interest, "Comparison DNA" represents the nucleotide sequence of a nucleic acid molecule against which the "TAHO-DNA" nucleic acid molecule of interest is being compared, and "N", "L" and "V" each represent different hypothetical nucleotides. Unless specifically stated otherwise, all % nucleic acid sequence identity values used herein are obtained as described in the immediately preceding paragraph using the ALIGN-2 computer program.

In other embodiments, TAHO variant polynucleotides are nucleic acid molecules that encode a TAHO polypeptide and which are capable of hybridizing, preferably under stringent hybridization and wash conditions, to nucleotide sequences encoding a full-length TAHO polypeptide as disclosed herein. TAHO variant polypeptides may be those that are encoded by a TAHO variant polynucleotide.

The term "full-length coding region" when used in reference to a nucleic acid encoding a TAHO polypeptide refers to the sequence of nucleotides which encode the full-length TAHO polypeptide of the invention (which is often shown between start and stop codons, inclusive thereof, in the accompanying figures). The term "full-length coding region" when used in reference to an ATCC deposited nucleic acid refers to the TAHO polypeptide-encoding portion of the cDNA that is inserted into the vector deposited with the ATCC (which is often shown between start and stop codons, inclusive thereof, in the accompanying figures (start and stop codons are bolded and underlined in the figures)).

"Isolated," when used to describe the various TAHO polypeptides disclosed herein, means polypeptide that has been identified and separated and/or recovered from a component of its natural environment. Contaminant components of its natural environment are materials that would typically interfere with therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the TAHO polypeptide natural environment will not be present. Ordinarily, however, isolated polypeptide will be prepared by at least one purification step.

An "isolated" TAHO polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with a 10 minute wash at 42° C. in 0.2×SSC (sodium chloride/sodium citrate) followed by a 10 minute high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a TAHO polypeptide or anti-TAHO antibody fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" for the purposes herein refers to form(s) of a TAHO polypeptide which retain a biological and/or an immunological activity of native or naturally-occurring TAHO, wherein "biological" activity refers to a biological function (either inhibitory or stimulatory) caused by a native or naturally-occurring TAHO other than the ability to induce the production of an antibody against an antigenic epitope possessed by a native or naturally-occurring TAHO and an "immunological" activity refers to the ability to induce the production of an antibody against an antigenic epitope possessed by a native or naturally-occurring TAHO.

The term "antagonist" is used in the broadest sense, and includes any molecule that partially or fully blocks, inhibits, or neutralizes a biological activity of a native TAHO polypeptide disclosed herein. In a similar manner, the term "agonist" is used in the broadest sense and includes any molecule that mimics a biological activity of a native TAHO polypeptide disclosed herein. Suitable agonist or antagonist molecules specifically include agonist or antagonist antibodies or antibody fragments, fragments or amino acid sequence variants of native TAHO polypeptides, peptides, antisense oligonucleotides, small organic molecules, etc. Methods for identifying agonists or antagonists of a TAHO polypeptide may comprise contacting a TAHO polypeptide with a candidate agonist or antagonist molecule and measuring a detectable change in one or more biological activities normally associated with the TAHO polypeptide.

"Treating" or "treatment" or "alleviation" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for a TAHO polypeptide-expressing cancer if, after receiving a therapeutic amount of an anti-TAHO antibody, TAHO binding oligopeptide or TAHO binding organic molecule according to the methods of the present invention, the patient shows observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues. To the extent the anti-TAHO antibody or TAHO binding oligopeptide may prevent growth and/or kill existing cancer cells, it may be cytostatic and/or cytotoxic. Reduction of these signs or symptoms may also be felt by the patient.

The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR). Metastasis can be determined by staging tests and by bone scan and tests for calcium level and other enzymes to determine spread to the bone. CT scans can also be done to look for spread to the pelvis and lymph nodes in the area. Chest X-rays and measurement of liver enzyme levels by known methods are used to look for metastasis to the lungs and liver, respectively. Other routine methods for monitoring the disease include transrectal ultrasonography (TRUS) and transrectal needle biopsy (TRNB).

For bladder cancer, which is a more localized cancer, methods to determine progress of disease include urinary cytologic evaluation by cystoscopy, monitoring for presence of blood in the urine, visualization of the urothelial tract by sonography or an intravenous pyelogram, computed tomography (CT) and magnetic resonance imaging (MRI). The presence of distant metastases can be assessed by CT of the abdomen, chest x-rays, or radionuclide imaging of the skeleton.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of the treatment of, alleviating the symptoms of a cancer refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

By "solid phase" or "solid support" is meant a non-aqueous matrix to which an antibody, TAHO binding oligopeptide or TAHO binding organic molecule of the present invention can adhere or attach. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a TAHO polypeptide, an antibody thereto or a TAHO binding oligopeptide) to a mammal. The components of the liposome are commonly arranged in a bilayer formation, similar to the lipid arrangement of biological membranes.

A "small" molecule or "small" organic molecule is defined herein to have a molecular weight below about 500 Daltons.

An "effective amount" of a polypeptide, antibody, TAHO binding oligopeptide, TAHO binding organic molecule or an agonist or antagonist thereof as disclosed herein is an amount sufficient to carry out a specifically stated purpose. An "effective amount" may be determined empirically and in a routine manner, in relation to the stated purpose.

The term "therapeutically effective amount" refers to an amount of an antibody, polypeptide, TAHO binding oligopeptide, TAHO binding organic molecule or other drug effective to "treat" a disease or disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See the definition herein of "treating". To the extent the drug may prevent growth and/or kill existing cancer cells, it may be cytostatic and/or cytotoxic.

A "growth inhibitory amount" of an anti-TAHO antibody, TAHO polypeptide, TAHO binding oligopeptide or TAHO binding organic molecule is an amount capable of inhibiting the growth of a cell, especially tumor, e.g., cancer cell, either in vitro or in vivo. A "growth inhibitory amount" of an anti-TAHO antibody, TAHO polypeptide, TAHO binding oligopeptide or TAHO binding organic molecule for purposes of inhibiting neoplastic cell growth may be determined empirically and in a routine manner.

A "cytotoxic amount" of an anti-TAHO antibody, TAHO polypeptide, TAHO binding oligopeptide or TAHO binding organic molecule is an amount capable of causing the destruction of a cell, especially tumor, e.g., cancer cell, either in vitro or in vivo. A "cytotoxic amount" of an anti-TAHO antibody, TAHO polypeptide, TAHO binding oligopeptide or TAHO binding organic molecule for purposes of inhibiting neoplastic cell growth may be determined empirically and in a routine manner.

The term "antibody" is used in the broadest sense and specifically covers, for example, single anti-TAHO monoclonal antibodies (including agonist, antagonist, and neutralizing antibodies), anti-TAHO antibody compositions with polyepitopic specificity, polyclonal antibodies, single chain anti-TAHO antibodies, and fragments of anti-TAHO antibodies (see below) as long as they exhibit the desired biological or immunological activity. The term "immunoglobulin" (Ig) is used interchangeable with antibody herein.

An "isolated antibody" is one which has been identified and separated and/or recovered from a component of its natural environment. Contaminant components of its natural environment are materials which would interfere with therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., *Basic and Clinical Immunology*, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and define specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (L1), 50-56 (L2) and 89-97 (L3) in the $V_L$, and around about 1-35 (H1), 50-65 (H2) and 95-102 (H3) in the $V_H$; Kabat et al., *Sequences of Proteins of Immunological Interest,* 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 53-55 (H2) and 96-101 (H3) in the $V_H$; Chothia and Lesk *J. Mol. Biol.* 196:901-917 (1987)).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., *Nature,* 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., *Nature,* 352:624-628 (1991) and Marks et al., *J. Mol. Biol.,* 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., *Proc. Natl. Acad. Sci. USA,* 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "intact" antibody is one which comprises an antigen-binding site as well as a $C_L$ and at least heavy chain constant domains, $C_H1$, $C_H2$ and $C_H3$. The constant domains may be native sequence constant domains (e.g. human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al., *Protein Eng.* 8(10): 1057-1062 [1995]); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332: 323-329 (1988); and Presta, *Curr. Op. Struct. Biol.* 2:593-596 (1992).

A "species-dependent antibody," e.g., a mammalian anti-human IgE antibody, is an antibody which has a stronger binding affinity for an antigen from a first mammalian species than it has for a homologue of that antigen from a second mammalian species. Normally, the species-dependent antibody "bind specifically" to a human antigen (i.e., has a binding affinity (Kd) value of no more than about $1 \times 10^{-7}$ M, preferably no more than about $1 \times 10^{-8}$ and most preferably no more than about $1 \times 10^{-9}$ M) but has a binding affinity for a homologue of the antigen from a second non-human mammalian species which is at least about 50 fold, or at least about 500 fold, or at least about 1000 fold, weaker than its binding affinity for the human antigen. The species-dependent antibody can be of any of the various types of antibodies as defined above, but preferably is a humanized or human antibody.

A "TAHO binding oligopeptide" is an oligopeptide that binds, preferably specifically, to a TAHO polypeptide as described herein. TAHO binding oligopeptides may be chemically synthesized using known oligopeptide synthesis methodology or may be prepared and purified using recombinant technology. TAHO binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a TAHO polypeptide as described herein. TAHO binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708, 871, 4,833,092, 5,223,409, 5,403,484, 5,571,689, 5,663,143; PCT Publication Nos. WO 84/03506 and WO84/03564; Geysen et al., Proc. Natl. Acad. Sci. U.S.A., 81:3998-4002 (1984); Geysen et al., Proc. Natl. Acad. Sci. U.S.A., 82:178-182 (1985); Geysen et al., in Synthetic Peptides as Antigens, 130-149 (1986); Geysen et al., J. Immunol. Meth., 102:259-274 (1987); Schoofs et al., J. Immunol., 140:611-616 (1988), Cwirla, S. E. et al. (1990) Proc. Natl. Acad. Sci. USA, 87:6378; Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363, and Smith, G. P. (1991) Current Opin. Biotechnol., 2:668).

A "TAHO binding organic molecule" is an organic molecule other than an oligopeptide or antibody as defined herein that binds, preferably specifically, to a TAHO polypeptide as described herein. TAHO binding organic molecules may be identified and chemically synthesized using known methodology (see, e.g., PCT Publication Nos. WO00/00823 and WO00/39585). TAHO binding organic molecules are usually less than about 2000 daltons in size, alternatively less than about 1500, 750, 500, 250 or 200 daltons in size, wherein such organic molecules that are capable of binding, preferably specifically, to a TAHO polypeptide as described herein may be identified without undue experimentation using well known techniques. In this regard, it is noted that techniques for screening organic molecule libraries for molecules that are capable of binding to a polypeptide target are well known in the art (see, e.g., PCT Publication Nos. WO00/00823 and WO00/39585).

An antibody, oligopeptide or other organic molecule "which binds" an antigen of interest, e.g. a tumor-associated polypeptide antigen target, is one that binds the antigen with sufficient affinity such that the antibody, oligopeptide or other organic molecule is useful as a therapeutic agent in targeting a cell or tissue expressing the antigen, and does not significantly cross-react with other proteins. In such embodiments, the extent of binding of the antibody, oligopeptide or other organic molecule to a "non-target" protein will be less than about 10% of the binding of the antibody, oligopeptide or other organic molecule to its particular target protein as determined by fluorescence activated cell sorting (FACS) analysis or radioimmunoprecipitation (RIA). With regard to the binding of an antibody, oligopeptide or other organic molecule to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

An antibody, oligopeptide or other organic molecule that "inhibits the growth of tumor cells expressing a TAHO polypeptide" or a "growth inhibitory" antibody, oligopeptide or other organic molecule is one which results in measurable growth inhibition of cancer cells expressing or overexpressing the appropriate TAHO polypeptide. The TAHO polypeptide may be a transmembrane polypeptide expressed on the surface of a cancer cell or may be a polypeptide that is produced and secreted by a cancer cell. Preferred growth inhibitory anti-TAHO antibodies, oligopeptides or organic molecules inhibit growth of TAHO-expressing tumor cells by greater than 20%, preferably from about 20% to about 50%, and even more preferably, by greater than 50% (e.g., from about 50% to about 100%) as compared to the appropriate control, the control typically being tumor cells not treated with the antibody, oligopeptide or other organic molecule being tested. In one embodiment, growth inhibition can be measured at an antibody concentration of about 0.1 to 30 μg/ml or about 0.5 nM to 200 nM in cell culture, where the growth inhibition is determined 1-10 days after exposure of the tumor cells to the antibody. Growth inhibition of tumor cells in vivo can be determined in various ways such as is described in the Experimental Examples section below. The antibody is growth inhibitory in vivo if administration of the anti-TAHO antibody at about 1 μg/kg to about 100 mg/kg body weight results in reduction in tumor size or tumor cell proliferation within about 5 days to 3 months from the first administration of the antibody, preferably within about 5 to 30 days.

An antibody, oligopeptide or other organic molecule which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses a TAHO polypeptide. Preferably the cell is a tumor cell, e.g., a hematopoietic cell, such as a B cell, T cell, basophil, eosinophil, neutrophil, monocyte, platelet or erythrocyte. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody, oligopeptide or other organic molecule which induces apoptosis is one which results in about 2 to 50 fold, preferably about 5 to 50 fold, and most preferably about 10 to 50 fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. (USA) 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol.* 9:457-492 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202:163 (1996), may be performed.

The terms "cancer" and "cancerous" refer to or describe the physiological condition in mammals that is typically characterized by unregulated cell growth. Examples of cancer include, but are not limited to, hematopoietic cancers or blood-related cancers, such as lymphoma, leukemia, myeloma or lymphoid malignancies, but also cancers of the spleen and cancers of the lymph nodes. More particular examples of such B-cell associated cancers, including for example, high, intermediate and low grade lymphomas (including B cell lymphomas such as, for example, mucosa-associated-lymphoid tissue B cell lymphoma and non-Hodgkin's lymphoma, mantle cell lymphoma, Burkitt's lymphoma, small lymphocytic lymphoma, marginal zone lymphoma, diffuse large cell lymphoma, follicular lymphoma, and Hodgkin's lymphoma and T cell lymphomas) and leukemias (including secondary leukemia, chronic lymphocytic leukemia, such as B cell leukemia (CD5+ B lymphocytes), myeloid leukemia, such as acute myeloid leukemia, chronic myeloid leukemia, lymphoid leukemia, such as acute lymphoblastic leukemia and myelodysplasia), multiple myeloma, such as plasma cell malignancy, and other hematological and/or B cell- or T-cell-associated cancers. Also included are cancers of additional hematopoietic cells, including polymorphonuclear leukocytes, such as basophils, eosinophils, neutrophils and monocytes, dendritic cells, platelets, erythrocytes and natural killer cells. The origins of B-cell cancers are as follows: marginal zone B-cell lymphoma origins in memory B-cells in marginal zone, follicular lymphoma and diffuse large B-cell lymphoma originates in centrocytes in the light zone of germinal centers, multiple myeloma originates in plasma cells, chronic lymphocytic leukemia and small lymphocytic leukemia originates in B1 cells (CD5+), mantle cell lymphoma originates in naive B-cells in the mantle zone and Burkitt's lymphoma originates in centroblasts in the dark zone of germinal centers. Tissues which include hematopoietic cells referred herein to as "hematopoietic cell tissues" include thymus and bone marrow and peripheral lymphoid tissues, such as spleen, lymph nodes, lymphoid tissues associated with mucosa, such as the gut-associated lymphoid tissues, tonsils, Peyer's patches and appendix and lymphoid tissues associated with other mucosa, for example, the bronchial linings.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all pre-cancerous and cancerous cells and tissues.

An antibody, oligopeptide or other organic molecule which "induces cell death" is one which causes a viable cell to become nonviable. The cell is one which expresses a TAHO polypeptide and is of a cell type which specifically expresses or overexpresses a TAHO polypeptide. The cell may be cancerous or normal cells of the particular cell type. The TAHO polypeptide may be a transmembrane polypeptide expressed on the surface of a cancer cell or may be a polypeptide that is produced and secreted by a cancer cell. The cell may be a cancer cell, e.g., a B cell or T cell. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the antibody, oligopeptide or other organic molecule is able to induce cell death, loss of membrane integrity as evaluated by uptake of propidium iodide (PI), trypan blue (see Moore et al. *Cytotechnology* 17:1-11 (1995)) or 7AAD can be assessed relative to untreated cells. Preferred cell death-inducing antibodies, oligopeptides or other organic molecules are those which induce PI uptake in the PI uptake assay in BT474 cells.

A "TAHO-expressing cell" is a cell which expresses an endogenous or transfected TAHO polypeptide either on the cell surface or in a secreted form. A "TAHO-expressing cancer" is a cancer comprising cells that have a TAHO polypeptide present on the cell surface or that produce and secrete a TAHO polypeptide. A "TAHO-expressing cancer" optionally produces sufficient levels of TAHO polypeptide on the surface of cells thereof, such that an anti-TAHO antibody, oligopeptide to other organic molecule can bind thereto and have a therapeutic effect with respect to the cancer. In another embodiment, a "TAHO-expressing cancer" optionally produces and secretes sufficient levels of TAHO polypeptide, such that an anti-TAHO antibody, oligopeptide to other organic molecule antagonist can bind thereto and have a therapeutic effect with respect to the cancer. With regard to the latter, the antagonist may be an antisense oligonucleotide which reduces, inhibits or prevents production and secretion of the secreted TAHO polypeptide by tumor cells. A cancer which "overexpresses" a TAHO polypeptide is one which has significantly higher levels of TAHO polypeptide at the cell surface thereof, or produces and secretes, compared to a noncancerous cell of the same tissue type. Such overexpression may be caused by gene amplification or by increased transcription or translation. TAHO polypeptide overexpression may be determined in a detection or prognostic assay by evaluating increased levels of the TAHO protein present on the surface of a cell, or secreted by the cell (e.g., via an immunohistochemistry assay using anti-TAHO antibodies prepared against an isolated TAHO polypeptide which may be prepared using recombinant DNA technology from an isolated nucleic acid encoding the TAHO polypeptide; FACS analysis, etc.). Alternatively, or additionally, one may measure levels of TAHO polypeptide-encoding nucleic acid or mRNA in the cell, e.g., via fluorescent in situ hybridization using a nucleic acid based probe corresponding to a TAHO-encoding nucleic acid or the complement thereof; (FISH; see WO98/45479 published October, 1998), Southern blotting, Northern blotting, or polymerase chain reaction (PCR) techniques, such as real time quantitative PCR (RT-PCR). One may also study TAHO polypeptide overexpression by measuring shed antigen in a biological fluid such as serum, e.g., using antibody-based assays (see also, e.g., U.S. Pat. No.

4,933,294 issued Jun. 12, 1990; WO91/05264 published Apr. 18, 1991; U.S. Pat. No. 5,401,638 issued Mar. 28, 1995; and Sias et al., *J. Immunol. Methods* 132:73-80 (1990)). Aside from the above assays, various in vivo assays are available to the skilled practitioner. For example, one may expose cells within the body of the patient to an antibody which is optionally labeled with a detectable label, e.g., a radioactive isotope, and binding of the antibody to cells in the patient can be evaluated, e.g., by external scanning for radioactivity or by analyzing a biopsy taken from a patient previously exposed to the antibody.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

The word "label" when used herein refers to a detectable compound or composition which is conjugated directly or indirectly to the antibody, oligopeptide or other organic molecule so as to generate a "labeled" antibody, oligopeptide or other organic molecule. The label may be detectable by itself (e.g. radioisotope labels or fluorescent labels) or, in the case of an enzymatic label, may catalyze chemical alteration of a substrate compound or composition which is detectable.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "growth inhibitory agent" when used herein refers to a compound or composition which inhibits growth of a cell, especially a TAHO-expressing cancer cell, either in vitro or in vivo. Thus, the growth inhibitory agent may be one which significantly reduces the percentage of TAHO-expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3,6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "package insert" is used to refer to instructions customarily included in commercial packages of therapeutic products, that contain information about the indications, usage, dosage, administration, contraindications and/or warnings concerning the use of such therapeutic products.

Table 1

```
/*
 *
 * C-C increased from 12 to 15
 * Z is average of EQ
 * B is average of ND
 * match with stop is _M; stop-stop = 0; J (joker) match = 0
 */
define  _M   -8    /* value of a match with a stop */ int      _day[26][26] = {
/*      A  B  C  D  E  F  G  H  I  J  K  L  M  N  O  P  Q  R  S  T  U  V  W  X  Y  Z */
/* A */ { 2, 0,-2, 0, 0,-4, 1,-1,-1, 0,-1,-2,-1, 0,_M, 1, 0,-2, 1, 1, 0, 0,-6, 0,-3, 0},
/* B */ { 0, 3,-4, 3, 2,-5, 0, 1,-2, 0, 0,-3,-2, 2,_M,-1, 1, 0, 0, 0, 0,-2,-5, 0,-3, 1},
/* C */ {-2,-4,15,-5,-5,-4,-3,-3,-2, 0,-5,-6,-5,-4,_M,-3,-5,-4, 0,-2, 0,-2,-8, 0, 0,-5},
/* D */ { 0, 3,-5, 4, 3,-6, 1, 1,-2, 0, 0,-4,-3, 2,_M,-1, 2,-1, 0, 0, 0, 0,-2,-7, 0,-4, 2},
/* E */ { 0, 2,-5, 3, 4,-5, 0, 1,-2, 0, 0,-3,-2, 1,_M,-1, 2,-1, 0, 0, 0, 0,-2,-7, 0,-4, 3},
/* F */ {-4,-5,-4,-6,-5, 9,-5,-2, 1, 0,-5, 2, 0,-4,_M,-5,-5,-4,-3,-3, 0,-1, 0, 0, 7,-5},
/* G */ { 1, 0,-3, 1, 0,-5, 5,-2,-3, 0,-2,-4,-3, 0,_M,-1,-1,-3, 1, 0, 0,-1,-7, 0,-5, 0},
/* H */ {-1, 1,-3, 1, 1,-2,-2, 6,-2, 0, 0,-2,-2, 2,_M, 0, 3, 2,-1,-1, 0,-2,-3, 0, 0, 2},
/* I */ {-1,-2,-2,-2, 1,-3,-2, 5, 0,-2, 2, 2,-2,_M,-2,-2,-2,-1, 0, 0, 4,-5, 0,-1,-2},
/* J */ { 0, 0, 0, 0, 0, 0, 0, 0, 0, 0, 0, 0, 0, 0,_M, 0, 0, 0, 0, 0, 0, 0, 0, 0, 0, 0},
/* K */ {-1, 0,-5, 0, 0,-5,-2, 0,-2, 0, 5,-3, 0, 1,_M,-1, 1, 3, 0, 0, 0,-2,-3, 0,-4, 0},
/* L */ {-2,-3,-6,-4,-3, 2,-4,-2, 2, 0,-3, 6, 4,-3,_M,-3,-2,-3,-3,-1, 0, 2,-2, 0,-1,-2},
/* M */ {-1,-2,-5,-3,-2, 0,-3,-2, 2, 0, 0, 4, 6,-2,_M,-2,-1, 0,-2,-1, 0, 2,-4, 0,-2,-1},
/* N */ { 0, 2,-4, 2, 1,-4, 0, 2,-2, 0, 1,-3,-2, 2,_M,-1, 1, 0, 1, 0, 0,-2,-4, 0,-2, 1},
/* O */ {_M,_M,_M,_M,_M,_M,_M,_M,_M,_M,_M,_M,_M,_M, 0,_M,_M,_M,_M,_M,_M,_M,_M,_M,_M,_M},
/* P */ { 1,-1,-3,-1,-1,-5,-1, 0,-2, 0,-1,-3,-2,-1,_M, 6, 0, 0, 1, 0, 0,-1,-6, 0,-5, 0},
/* Q */ { 0, 1,-5, 2, 2,-5,-1, 3,-2, 0, 1,-2,-1, 1,_M, 0, 4,-1,-1,-1, 0,-2,-5, 0,-4, 3},
/* R */ {-2, 0,-4,-1,-1,-4,-3, 2,-2, 0, 3,-3, 0,_M, 0, 1, 6, 0,-1, 0,-2, 2, 0,-4, 0},
/* S */ { 1, 0, 0, 0, 0,-3, 1,-1,-1, 0, 0,-3,-2, 1,_M, 1,-1, 0, 2, 1, 0,-1,-2, 0,-3, 0},
/* T */ { 1, 0,-2, 0, 0,-3, 0,-1, 0, 0, 0,-1,-1, 0,_M, 0,-1,-1, 1, 3, 0, 0,-5, 0,-3, 0},
/* U */ { 0, 0, 0, 0, 0, 0, 0, 0, 0, 0, 0, 0, 0, 0,_M, 0, 0, 0, 0, 0, 0, 0, 0, 0, 0, 0},
/* V */ { 0,-2,-2,-2,-2,-1,-1,-2, 4, 0,-2, 2, 2,-2,_M,-1,-2,-2,-1, 0, 0, 4,-6, 0,-2,-2},
/* W */ {-6,-5,-8,-7,-7, 0,-7,-3,-5, 0,-3,-2,-4,-4,_M,-6,-5, 2,-2,-5, 0,-6,17, 0, 0,-6},
/* X */ { 0, 0, 0, 0, 0, 0, 0, 0, 0, 0, 0, 0, 0, 0,_M, 0, 0, 0, 0, 0, 0, 0, 0, 0, 0, 0},
/* Y */ {-3,-3, 0,-4,-4, 7,-5, 0,-1, 0,-4,-1,-2,-2,_M,-5,-4,-4,-3,-3, 0,-2, 0, 0,10,-4},
/* Z */ { 0, 1,-5, 2, 3,-5, 0, 2,-2, 0, 0,-2,-1, 1,_M, 0, 3, 0, 0, 0, 0,-2,-6, 0,-4, 4}
};
```

Table 1 (cont')

```
/*
*/
#include <stdio.h>
include <ctype.h> define  MAXJMP   16     /* max jumps in a diag */
define  MAXGAP   24     /* don't continue to penalize gaps larger than this */
#define  JMPS     1024   /* max jmps in an path */
define  MX       4      /* save if there's at least MX-1 bases since last jmp */ define  DMAT     3      /* value of matching bases */
define  DMIS     0      /* penalty for mismatched bases */
#define  DINS0    8      /* penalty for a gap */
#define  DINS1    1      /* penalty per base */
#define  PINS0    8      /* penalty for a gap */
define  PINS1    4      /* penalty per residue */ struct jmp {
        short           n[MAXJMP];      /* size of jmp (neg for dely) */
        unsigned short  x[MAXJMP];      /* base no. of jmp in seq x */
};                                      /* limits seq to 2^16 -1 */ struct diag {
        int             score;          /* score at last jmp */
        long            offset;         /* offset of prev block */
        short           ijmp;           /* current jmp index */
        struct jmp      jp;             /* list of jmps */
};

struct path {
        int             spc;            /* number of leading spaces */
        short           n[JMPS];        /* size of jmp (gap) */
        int             x[JMPS];        /* loc of jmp (last elem before gap) */
};

char            *ofile;                 /* output file name */
char            *namex[2];              /* seq names: getseqs() */
char            *prog;                  /* prog name for err msgs */
char            *seqx[2];               /* seqs: getseqs() */
int             dmax;                   /* best diag: nw() */
int             dmax0;                  /* final diag */
int             dna;                    /* set if dna: main() */
int             endgaps;                /* set if penalizing end gaps */
int             gapx, gapy;             /* total gaps in seqs */
int             len0, len1;             /* seq lens */
int             ngapx, ngapy;           /* total size of gaps */
int             smax;                   /* max score: nw() */
int             *xbm;                   /* bitmap for matching */
long            offset;                 /* current offset in jmp file */
struct  diag    *dx;                    /* holds diagonals */
struct  path    pp[2];                  /* holds path for seqs */ char            *calloc(), *malloc(), *index(), *strcpy();
char            *getseq(), *g_calloc();
```

Table 1 (cont')

```
/* Needleman-Wunsch alignment program
 *
 * usage: progs file1 file2
 *    where file1 and file2 are two dna or two protein sequences.
 *    The sequences can be in upper- or lower-case an may contain ambiguity
 *    Any lines beginning with ';', '>' or '<' are ignored
 *    Max file length is 65535 (limited by unsigned short x in the jmp struct)
 *    A sequence with 1/3 or more of its elements ACGTU is assumed to be DNA
 *    Output is in the file "align.out"
 *
 * The program may create a tmp file in /tmp to hold info about traceback.
 * Original version developed under BSD 4.3 on a vax 8650
 */
include "nw.h"
#include "day.h"

static  _dbval[26] = {
        1,14,2,13,0,0,4,11,0,0,12,0,3,15,0,0,0,5,6,8,8,7,9,0,10,0
};

static  _pbval[26] = {
        1, 2|(1<<('D'-'A'))|(1<<('N'-'A')), 4, 8, 16, 32, 64,
        128, 256, 0xFFFFFFFF, 1<<10, 1<<11, 1<<12, 1<<13, 1<<14,
        1<<15, 1<<16, 1<<17, 1<<18, 1<<19, 1<<20, 1<<21, 1<<22,
        1<<23, 1<<24, 1<<25|(1<<('E'-'A'))|(1<<('Q'-'A'))
};

main(ac, av)                                                                    main
        int     ac;
        char    *av[];
{
        prog = av[0];
        if (ac != 3) {
                fprintf(stderr,"usage: %s file1 file2\n", prog);
                fprintf(stderr,"where file1 and file2 are two dna or two protein sequences.\n");
                fprintf(stderr,"The sequences can be in upper- or lower-case\n");
                fprintf(stderr,"Any lines beginning with ';' or '<' are ignored\n");
                fprintf(stderr,"Output is in the file \"align.out\"\n");
                exit(1);
        }
        namex[0] = av[1];
        namex[1] = av[2];
        seqx[0] = getseq(namex[0], &len0);
        seqx[1] = getseq(namex[1], &len1);
        xbm = (dna)? _dbval : _pbval;

endgaps = 0;            /* 1 to penalize endgaps */
        ofile = "align.out";    /* output file */ nw();           /* fill in the matrix, get the possible jmps */
        readjmps();     /* get the actual jmps */
        print();        /* print stats, alignment */ cleanup(0);     /* unlink any tmp files */}
```

Table 1 (cont')

```
/* do the alignment, return best score: main()
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw()
{
        char        *px, *py;        /* seqs and ptrs */
        int         *ndely, *dely;   /* keep track of dely */
        int         ndelx, delx;     /* keep track of delx */
        int         *tmp;            /* for swapping row0, row1 */
        int         mis;             /* score for each type */
        int         ins0, ins1;      /* insertion penalties */
        register    id;              /* diagonal index */
        register    ij;              /* jmp index */
        register    *col0, *col1;    /* score for curr, last row */
        register    xx, yy;          /* index into seqs */ dx = (struct diag *)g_calloc("to get diags", len0+len1+1, sizeof(struct diag));
        ndely = (int *)g_calloc("to get ndely", len1+1, sizeof(int));
        dely = (int *)g_calloc("to get dely", len1+1, sizeof(int));
        col0 = (int *)g_calloc("to get col0", len1+1, sizeof(int));
        col1 = (int *)g_calloc("to get col1", len1+1, sizeof(int));
        ins0 = (dna)? DINS0 : PINS0;
        ins1 = (dna)? DINS1 : PINS1;
        smax = -10000;
        if (endgaps) {
                for (col0[0] = dely[0] = -ins0, yy = 1; yy <= len1; yy++) {
                        col0[yy] = dely[yy] = col0[yy-1] - ins1;
                        ndely[yy] = yy;
                }
                col0[0] = 0;         /* Waterman Bull Math Biol 84 */
        }
        else
                for (yy = 1; yy <= len1; yy++)
                        dely[yy] = -ins0;
        /* fill in match matrix
         */
        for (px = seqx[0], xx = 1; xx <= len0; px++, xx++) {
                /* initialize first entry in col
                 */
                if (endgaps) {
                        if (xx == 1)
                                col1[0] = delx = -(ins0+ins1);
                        else
                                col1[0] = delx = col0[0] - ins1;
                        ndelx = xx;
                }
                else {
                        col1[0] = 0;
                        delx = -ins0;
                        ndelx = 0;
                }
```

Table 1 (cont')

```
                                                                                    ...nw
for (py = seqx[1], yy = 1; yy <= len1; py++, yy++) {
    mis = col0[yy-1];
    if (dna)
            mis += (xbm[*px-'A']&xbm[*py-'A'])? DMAT : DMIS;
    else
            mis += _day[*px-'A'][*py-'A'];

/* update penalty for del in x seq;
     * favor new del over ongong del
     * ignore MAXGAP if weighting endgaps
     */
    if (endgaps || ndely[yy] < MAXGAP) {
            if (col0[yy] - ins0 >= dely[yy]) {
                    dely[yy] = col0[yy] - (ins0+ins1);
                    ndely[yy] = 1;
            } else {
                    dely[yy] -= ins1;
                    ndely[yy]++;
            }
    } else {
            if (col0[yy] - (ins0+ins1) >= dely[yy]) {
                    dely[yy] = col0[yy] - (ins0+ins1);
                    ndely[yy] = 1;
            } else
                    ndely[yy]++;
    }

/* update penalty for del in y seq;
     * favor new del over ongong del
     */
    if (endgaps || ndelx < MAXGAP) {
            if (col1[yy-1] - ins0 >= delx) {
                    delx = col1[yy-1] - (ins0+ins1);
                    ndelx = 1;
            } else {
                    delx -= ins1;
                    ndelx++;
            }
    } else {
            if (col1[yy-1] - (ins0+ins1) >= delx) {
                    delx = col1[yy-1] - (ins0+ins1);
                    ndelx = 1;
            } else
                    ndelx++;
    }

/* pick the maximum score; we're favoring
     * mis over any del and delx over dely
     */
                                                                                    ...nw
    id = xx - yy + len1 - 1;
    if (mis >= delx && mis >= dely[yy])
            col1[yy] = mis;
```

Table 1 (cont')

```
        else if (delx > = dely[yy]) {
                    col1[yy] = delx;
                    ij = dx[id].ijmp;
                    if (dx[id].jp.n[0] && (!dna || (ndelx > = MAXJMP
                        && xx > dx[id].jp.x[ij]+MX) || mis > dx[id].score+DINS0)) {
                            dx[id].ijmp++;
                            if (++ij > = MAXJMP) {
                                writejmps(id);
                                ij = dx[id].ijmp = 0;
                                dx[id].offset = offset;
                                offset += sizeof(struct jmp) + sizeof(offset);
                            }
                    }
                    dx[id].jp.n[ij] = ndelx;
                    dx[id].jp.x[ij] = xx;
                    dx[id].score = delx;
        }
        else {
                    col1[yy] = dely[yy];
                    ij = dx[id].ijmp;
if (dx[id].jp.n[0] && (!dna || (ndely[yy] > = MAXJMP
                        && xx > dx[id].jp.x[ij]+MX) || mis > dx[id].score+DINS0)) {
                            dx[id].ijmp++;
                            if (++ij > = MAXJMP) {
                                writejmps(id);
                                ij = dx[id].ijmp = 0;
                                dx[id].offset = offset;
                                offset += sizeof(struct jmp) + sizeof(offset);
                            }
                    }
                    dx[id].jp.n[ij] = -ndely[yy];
                    dx[id].jp.x[ij] = xx;
                    dx[id].score = dely[yy];
        }
        if (xx == len0 && yy < len1) {
                /* last col
                */
                if (endgaps)
                        col1[yy] -= ins0+ins1*(len1-yy);
                if (col1[yy] > smax) {
                        smax = col1[yy];
                        dmax = id;
                }
        }
    }
    if (endgaps && xx < len0)
            col1[yy-1] -= ins0+ins1*(len0-xx);
    if (col1[yy-1] > smax) {
            smax = col1[yy-1];
            dmax = id;
    }
        tmp = col0; col0 = col1; col1 = tmp;          }
(void) free((char *)ndely);
(void) free((char *)dely);
(void) free((char *)col0);
(void) free((char *)col1);                           }
```

Table 1 (cont')

```
/*
*
* print() -- only routine visible outside this module
*
* static:
* getmat() -- trace back best path, count matches: print()
* pr_align() -- print alignment of described in array p[]: print()
* dumpblock() -- dump a block of lines with numbers, stars: pr_align()
* nums() -- put out a number line: dumpblock()
* putline() -- put out a line (name, [num], seq, [num]): dumpblock()
* stars() - -put a line of stars: dumpblock()
* stripname() -- strip any path and prefix from a seqname
*/ include "nw.h"

define SPC     3
#define P_LINE  256     /* maximum output line */
define P_SPC   3       /* space between name or num and seq */ extern  _day[26][26];
int     olen;           /* set output line length */
FILE    *fx;            /* output file */ print()
{
        int     lx, ly, firstgap, lastgap;      /* overlap */ if ((fx = fopen(ofile, "w")) == 0) {
                fprintf(stderr,"%s: can't write %s\n", prog, ofile);
                cleanup(1);
        }
        fprintf(fx, "<first sequence: %s (length = %d)\n", namex[0], len0);
        fprintf(fx, "<second sequence: %s (length = %d)\n", namex[1], len1);
        olen = 60;
        lx = len0;
        ly = len1;
        firstgap = lastgap = 0;
        if (dmax < len1 - 1) {          /* leading gap in x */
                pp[0].spc = firstgap = len1 - dmax - 1;
                ly -= pp[0].spc;
        }
        else if (dmax > len1 - 1) {     /* leading gap in y */
                pp[1].spc = firstgap = dmax - (len1 - 1);
                lx -= pp[1].spc;
        }
        if (dmax0 < len0 - 1) {         /* trailing gap in x */
                lastgap = len0 - dmax0 -1;
                lx -= lastgap;
        }
        else if (dmax0 > len0 - 1) {    /* trailing gap in y */
                lastgap = dmax0 - (len0 - 1);
                ly -= lastgap;
        }
        getmat(lx, ly, firstgap, lastgap);
        pr_align();             }
``` print

Table 1 (cont')

```
/*
 * trace back the best path, count matches
 */
static
getmat(lx, ly, firstgap, lastgap)                                                    getmat
        int     lx, ly;                 /* "core" (minus endgaps) */
        int     firstgap, lastgap;      /* leading trailing overlap */
{
        int             nm, i0, i1, siz0, siz1;
        char            outx[32];
        double          pct;
        register        n0, n1;
        register char   *p0, *p1;
        /* get total matches, score
         */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;
        nm = 0;
        while ( *p0 && *p1 ) {
                if (siz0) {
                        p1++;
                        n1++;
                        siz0--;
                }
                else if (siz1) {
                        p0++;
                        n0++;
                        siz1--;
                }
                else {
                        if (xbm[*p0-'A']&xbm[*p1-'A'])
                                nm++;
                        if (n0++ == pp[0].x[i0])
                                siz0 = pp[0].n[i0++];
                        if (n1++ == pp[1].x[i1])
                                siz1 = pp[1].n[i1++];
                        p0++;
                        p1++;
                }
        }

/* pct homology:
         * if penalizing endgaps, base is the shorter seq
         * else, knock off overhangs and take shorter core
         */
        if (endgaps)
                lx = (len0 < len1)? len0 : len1;
        else
                lx = (lx < ly)? lx : ly;
        pct = 100.*(double)nm/(double)lx;
        fprintf(fx, "\n");
        fprintf(fx, " < %d match%s in an overlap of %d: %.2f percent similarity\n",
                nm, (nm == 1)? "" : "es", lx, pct);
```

Table 1 (cont')

...getmat

```
fprintf(fx, " <gaps in first sequence: %d", gapx);
if (gapx) {
        (void) sprintf(outx, " (%d %s%s)",
                ngapx, (dna)? "base":"residue", (ngapx = = 1)? "":"s");
        fprintf(fx,"%s", outx);
fprintf(fx, ", gaps in second sequence: %d", gapy);
if (gapy) {
        (void) sprintf(outx, " (%d %s%s)",
                ngapy, (dna)? "base":"residue", (ngapy = = 1)? "":"s");
        fprintf(fx,"%s", outx);
}
if (dna)
        fprintf(fx,
        "\n<score: %d (match  =  %d, mismatch  =  %d, gap penalty  =  %d  +  %d per base)\n",
        smax, DMAT, DMIS, DINS0, DINS1);
else
        fprintf(fx,
        "\n<score: %d (Dayhoff PAM 250 matrix, gap penalty  =  %d  +  %d per residue)\n",
        smax, PINS0, PINS1);
if (endgaps)
        fprintf(fx,
        " <endgaps penalized. left endgap: %d %s%s, right endgap: %d %s%s\n",
        firstgap, (dna)? "base" : "residue", (firstgap = = 1)? "" : "s",
        lastgap, (dna)? "base" : "residue", (lastgap = = 1)? "" : "s");
else
        fprintf(fx, " <endgaps not penalized\n");
}
static       nm;           /* matches in core -- for checking */
static       lmax;         /* lengths of stripped file names */
static       ij[2];        /* jmp index for a path */
static       nc[2];        /* number at start of current line */
static       ni[2];        /* current elem number -- for gapping */
static       siz[2];
static char  *ps[2];       /* ptr to current element */
static char  *po[2];       /* ptr to next output char slot */
static char  out[2][P_LINE]; /* output line */
static char  star[P_LINE]; /* set by stars() */
/*
* print alignment of described in struct path pp[]
*/
static
``` pr_align

```
pr_align()
{
        int       nn;    /* char count */
        int       more;
        register  i;

for (i =  0, lmax  = 0; i < 2; i++) {
                nn  = stripname(namex[i]);
                if (nn > lmax)
                        lmax  = nn;
                nc[i]  = 1;
                ni[i]  = 1;
                siz[i]  = ij[i]  = 0;
                ps[i]  = seqx[i];
                po[i]  = out[i];                  }
```

Table 1 (cont')

```
for (nn = nm = 0, more = 1; more; ) {                                           ...pr_align
        for (i = more = 0; i < 2; i++) {
                /*
                 * do we have more of this sequence?
                 */
                if (!*ps[i])
                        continue;
                more++;
                if (pp[i].spc) {        /* leading space */
                        *po[i]++ = ' ';
                        pp[i].spc--;
                }
                else if (siz[i]) {      /* in a gap */
                        *po[i]++ = '-';
                        siz[i]--;
                }
                else {                  /* we're putting a seq element
                                         */
                        *po[i] = *ps[i];
                        if (islower(*ps[i]))
                                *ps[i] = toupper(*ps[i]);
                        po[i]++;
                        ps[i]++;
                        /*
                         * are we at next gap for this seq?
                         */
                        if (ni[i] == pp[i].x[ij[i]]) {
                                /*
                                 * we need to merge all gaps
                                 * at this location
                                 */
                                siz[i] = pp[i].n[ij[i]++];
                                while (ni[i] == pp[i].x[ij[i]])
                                        siz[i] += pp[i].n[ij[i]++];
                        }
                        ni[i]++;
                }
        }
        if (++nn == olen || !more && nn) {
                dumpblock();
                for (i = 0; i < 2; i++)
                        po[i] = out[i];
                nn = 0;
        }
    }
}
/*
 * dump a block of lines, including numbers, stars: pr_align()
 */
static
dumpblock()                                                                     dumpblock
{
        register i;
        for (i = 0; i < 2; i++)
                *po[i]-- = '\0';
```

Table 1 (cont')

...dumpblock

```
                (void) putc('\n', fx);
                for (i = 0; i < 2; i++) {
                        if (*out[i] && (*out[i] != ' ' || *(po[i]) != ' ')) {
                                if (i == 0)
                                        nums(i);
                                if (i == 0 && *out[1])
                                        stars();
                                putline(i);
                                if (i == 0 && *out[1])
                                        fprintf(fx, star);
                                if (i == 1)
                                        nums(i);
                        }
                }
        }
}
/*
 * put out a number line: dumpblock()
 */
static
nums(ix)                                                                        nums
        int     ix;     /* index in out[] holding seq line */
{
        char            nline[P_LINE];
        register        i, j;
        register char   *pn, *px, *py;
        for (pn = nline, i = 0; i < lmax+P_SPC; i++, pn++)
                *pn = ' ';
        for (i = nc[ix], py = out[ix]; *py; py++, pn++) {
                if (*py == ' ' || *py == '-')
                        *pn = ' ';
                else {
                        if (i%10 == 0 || (i == 1 && nc[ix] != 1)) {
                                j = (i < 0)? -i : i;
                                for (px = pn; j; j /= 10, px--)
                                        *px = j%10 + '0';
                                if (i < 0)
                                        *px = '-';
                        }
                        else
                                *pn = ' ';
                        i++;
                }
        }
        *pn = '\0';
        nc[ix] = i;
        for (pn = nline; *pn; pn++)
                (void) putc(*pn, fx);
        (void) putc('\n', fx);
}
/*
 * put out a line (name, [num], seq, [num]): dumpblock()
 */
static
putline(ix)                                                                     putline
        int     ix;                             {
```

Table 1 (cont')

...putline

```
        int         i;
        register char   *px;

for (px = namex[ix], i = 0; *px && *px != ':'; px++, i++)
                (void) putc(*px, fx);
        for (; i < lmax+P_SPC; i++)
                (void) putc(' ', fx);

/* these count from 1:
         * ni[] is current element (from 1)
         * nc[] is number at start of current line
         */
        for (px = out[ix]; *px; px++)
                (void) putc(*px&0x7F, fx);
        (void) putc('\n', fx);
}

/*
 * put a line of stars (seqs always in out[0], out[1]): dumpblock()
 */
static
stars()                                                                 stars
{
        int         i;
        register char   *p0, *p1, cx, *px;

if (!*out[0] || (*out[0] == ' ' && *(po[0]) == ' ') ||
            !*out[1] || (*out[1] == ' ' && *(po[1]) == ' '))
                return;
        px = star;
        for (i = lmax+P_SPC; i; i--)
                *px++ = ' ';

for (p0 = out[0], p1 = out[1]; *p0 && *p1; p0++, p1++) {
                if (isalpha(*p0) && isalpha(*p1)) { if (xbm[*p0-'A']&xbm[*p1-'A']) {
                                cx = '*';
                                nm++;
                        }
                        else if (!dna && _day[*p0-'A'][*p1-'A'] > 0)
                                cx = '.';
                        else
                                cx = ' ';
                }
                else
                        cx = ' ';
                *px++ = cx;
        }
        *px++ = '\n';
        *px = '\0';
}
```

Table 1 (cont')

```
/*
 * strip path or prefix from pn, return len: pr_align()
 */
static
stripname(pn)                                                              stripname
        char    *pn;    /* file name (may be path) */
{
        register char   *px, *py;

py = 0;
        for (px = pn; *px; px++)
                if (*px == '/')
                        py = px + 1;
        if (py)
                (void) strcpy(pn, py);
        return(strlen(pn));

}
```

Table 1 (cont')

```
/*
 * cleanup() -- cleanup any tmp file
 * getseq() -- read in seq, set dna, len, maxlen
 * g_calloc() -- calloc() with error checkin
 * readjmps() -- get the good jmps, from tmp file if necessary
 * writejmps() -- write a filled array of jmps to a tmp file: nw()
 */
include "nw.h"
include <sys/file.h> char    *jname = "/tmp/homgXXXXXX";        /* tmp file for jmps */
FILE    *fj;
int     cleanup();                          /* cleanup tmp file */
long    lseek();
/*
 * remove any tmp file if we blow
 */
cleanup(i)                                                                      cleanup
        int     i;
{
        if (fj)
                (void) unlink(jname);
        exit(i);
}
/*
 * read, return ptr to seq, set dna, len, maxlen
 * skip lines starting with ';', '<', or '>'
 * seq in upper or lower case
 */
char    *
getseq(file, len)                                                               getseq
        char    *file;  /* file name */
        int     *len;   /* seq len */
{
        char            line[1024], *pseq;
        register char   *px, *py;
        int             natgc, tlen;
        FILE            *fp;
        if ((fp = fopen(file,"r")) == 0) {
                fprintf(stderr,"%s: can't read %s\n", prog, file);
                exit(1);
        }
        tlen = natgc = 0;
        while (fgets(line, 1024, fp)) {
                if (*line == ';' || *line == '<' || *line == '>')
                        continue;
                for (px = line; *px != '\n'; px++)
                        if (isupper(*px) || islower(*px))
                                tlen++;
        }
        if ((pseq = malloc((unsigned)(tlen+6))) == 0) {
                fprintf(stderr,"%s: malloc() failed to get %d bytes for %s\n", prog, tlen+6, file);
                exit(1);
        }
        pseq[0] = pseq[1] = pseq[2] = pseq[3] = '\0';
```

Table 1 (cont')

...getseq

```
            py = pseq + 4;
        *len = tlen;
        rewind(fp);
        while (fgets(line, 1024, fp)) {
                if (*line == ';' || *line == '<' || *line == '>')
                        continue;
                for (px = line; *px != '\n'; px++) {
                        if (isupper(*px))
                                *py++ = *px;
                        else if (islower(*px))
                                *py++ = toupper(*px);
                        if (index("ATGCU",*(py-1)))
                                natgc++;
                }
        }
        *py++ = '\0';
        *py = '\0';
        (void) fclose(fp);
        dna = natgc > (tlen/3);
        return(pseq+4);
}
char    *
g_calloc(msg, nx, sz)
        char    *msg;           /* program, calling routine */
        int     nx, sz;         /* number and size of elements */
{
        char            *px, *calloc();
        if ((px = calloc((unsigned)nx, (unsigned)sz)) == 0) {
                if (*msg) {
                        fprintf(stderr, "%s: g_calloc() failed %s (n=%d, sz=%d)\n", prog, msg, nx, sz);
                        exit(1);
                }
        }
        return(px);
}

/*
* get final jmps from dx[] or tmp file, set pp[], reset dmax: main()
*/
readjmps()
{
        int             fd = -1;
        int             siz, i0, i1;
        register i, j, xx;
        if (fj) {
                (void) fclose(fj);
                if ((fd = open(jname, O_RDONLY, 0)) < 0) {
                        fprintf(stderr, "%s: can't open() %s\n", prog, jname);
                        cleanup(1);
                }
        }
        for (i = i0 = i1 = 0, dmax0 = dmax, xx = len0; ; i++) {
                while (1) {
                        for (j = dx[dmax].ijmp; j >= 0 && dx[dmax].jp.x[j] >= xx; j--)
                                ;
``` g_calloc readjmps

Table 1 (cont')

...readjmps

```
                    if (j < 0 && dx[dmax].offset && fj) {
                            (void) lseek(fd, dx[dmax].offset, 0);
                            (void) read(fd, (char *)&dx[dmax].jp, sizeof(struct jmp));
                            (void) read(fd, (char *)&dx[dmax].offset, sizeof(dx[dmax].offset));
                            dx[dmax].ijmp = MAXJMP-1;                                        }
                    else
                            break;          }
            if (i > = JMPS) {
                    fprintf(stderr, "%s: too many gaps in alignment\n", prog);
                    cleanup(1);
            }
            if (j > = 0) {
                    siz = dx[dmax].jp.n[j];
                    xx = dx[dmax].jp.x[j];
                    dmax += siz;
                    if (siz < 0) {                 /* gap in second seq.*/
                            pp[1].n[i1] = -siz;
                            xx += siz;
                            /* id = xx - yy + len1 - 1                                 */
                            pp[1].x[i1] = xx - dmax + len1 - 1;
                            gapy++;
                            ngapy -= siz;
/* ignore MAXGAP when doing endgaps */
                            siz = (-siz < MAXGAP || endgaps)? -siz : MAXGAP;
                            i1++;
                    }
                    else if (siz > 0) {   /* gap in first seq */
                            pp[0].n[i0] = siz;
                            pp[0].x[i0] = xx;
                            gapx++;
                            ngapx += siz;
/* ignore MAXGAP when doing endgaps */
                            siz = (siz < MAXGAP || endgaps)? siz : MAXGAP;
                            i0++;
                    }
            }
            else
                    break;
    }
/* reverse the order of jmps  */
    for (j = 0, i0--; j < i0; j++, i0--) {
            i = pp[0].n[j]; pp[0].n[j] = pp[0].n[i0]; pp[0].n[i0] = i;
            i = pp[0].x[j]; pp[0].x[j] = pp[0].x[i0]; pp[0].x[i0] = i;
    }
    for (j = 0, i1--; j < i1; j++, i1--) {
            i = pp[1].n[j]; pp[1].n[j] = pp[1].n[i1]; pp[1].n[i1] = i;
            i = pp[1].x[j]; pp[1].x[j] = pp[1].x[i1]; pp[1].x[i1] = i;
    }
    if (fd > = 0)
            (void) close(fd);
    if (fj) {
            (void) unlink(jname);
            fj = 0;
            offset = 0;
    }                                       }
```

Table 1 (cont')

```
/*
 * write a filled jmp struct offset of the prev one (if any): nw()
 */
writejmps(ix)                                                           writejmps
        int     ix;
{
        char    *mktemp();

if (!fj) {
                if (mktemp(jname) < 0) {
                        fprintf(stderr, "%s: can't mktemp() %s\n", prog, jname);
                        cleanup(1);
                }
                if ((fj = fopen(jname, "w")) = = 0) {
                        fprintf(stderr, "%s: can't write %s\n", prog, jname);
                        exit(1);
                }
        }
        (void) fwrite((char *)&dx[ix].jp, sizeof(struct jmp), 1, fj);
        (void) fwrite((char *)&dx[ix].offset, sizeof(dx[ix].offset), 1, fj);
}
```

TABLE 2

| TAHO | XXXXXXXXXXXXXXX | (Length = 15 amino acids) |
|---|---|---|
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the TAHO polypeptide) = 5 divided by 15 = 33.3%

TABLE 3

| TAHO | XXXXXXXXXX | (Length = 10 amino acids) |
|---|---|---|
| Comparison Protein | XXXXXYYYYYZZYZ | (Length = 15 amino acids) |

% amino acid sequence identity = (the number of identically matching amino acid residues between the two polypeptide sequences as determined by ALIGN-2) divided by (the total number of amino acid residues of the TAHO polypeptide) = 5 divided by 10 = 50%

TABLE 4

| TAHO-DNA | NNNNNNNNNNNNNN | (Length = 14 nucleotides) |
|---|---|---|
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the TAHO-DNA nucleic acid sequence) = 6 divided by 14 = 42.9%

TABLE 5

| TAHO-DNA | NNNNNNNNNNNN | (Length = 12 nucleotides) |
|---|---|---|
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the TAHO-DNA nucleic acid sequence) = 4 divided by 12 = 33.3%

II. Compositions and Methods of the Invention

A. Anti-TAHO Antibodies

In one embodiment, the present invention provides anti-TAHO antibodies which may find use herein as therapeutic agents. Exemplary antibodies include polyclonal, monoclonal, humanized, bispecific, and heteroconjugate antibodies.

1. Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

2. Monoclonal Antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va., USA. Human myeloma and mouse-human heteromyeloma cell lines also have been described for the production of human monoclonal antibodies (Kozbor, *J. Immunol.*, 133:3001 (1984); and Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., *Anal. Biochem.*, 107:220 (1980).

Once hybridoma cells that produce antibodies of the desired specificity, affinity, and/or activity are identified, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.* 130: 151-188 (1992).

In a further embodiment, monoclonal antibodies or antibody fragments can be isolated from antibody phage libraries generated using the techniques described in McCafferty et al., *Nature*, 348:552-554 (1990). Clackson et al., *Nature*, 352: 624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain ($C_H$ and $C_L$) sequences for the homologous murine sequences (U.S. Pat. No. 4,816,567; and Morrison, et al., *Proc. Natl. Acad. Sci. USA*, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

3. Human and Humanized Antibodies

The anti-TAHO antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522-525 (1986); Riechmann et al., *Nature*, 332:323-329 (1988); and Presta, *Curr. Op. Struct. Biol.*, 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., *J. Immunol.* 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.* 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved.

In general, the hypervariable region residues are directly and most substantially involved in influencing antigen binding.

Various forms of a humanized anti-TAHO antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggemann et al., *Year in Immuno.* 7:33 (1993); U.S. Pat. Nos. 5,545,806, 5,569,825, 5,591,669 (all of GenPharm); U.S. Pat. No. 5,545,807; and WO 97/17852.

Alternatively, phage display technology (McCafferty et al., *Nature* 348:552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., *Current Opinion in Structural Biology* 3:564-571 (1993). Several sources of V-gene segments can be used for phage display. Clackson et al., *Nature,* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

4. Antibody Fragments

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science,* 229:81 (1985)). However, these fragments can now be produced directly by recombinant host cells. Fab, Fv and ScFv antibody fragments can all be expressed in and secreted from *E. coli,* thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carteret al., *Bio/Technology* 10: 163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See *Antibody Engineering,* ed. Borrebaeck, supra. The antibody fragment may also be a "linear antibody", e.g., as described in U.S. Pat. No. 5,641,870 for example. Such linear antibody fragments may be monospecific or bispecific.

5. Bispecific Antibodies

Bispecific antibodies are antibodies that have binding specificities for at least two different epitopes. Exemplary bispecific antibodies may bind to two different epitopes of a TAHO protein as described herein. Other such antibodies may combine a TAHO binding site with a binding site for another protein. Alternatively, an anti-TAHO arm may be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRIII (CD16), so as to focus and localize cellular defense mechanisms to the TAHO-expressing cell. Bispecific antibodies may also be used to localize cytotoxic agents to cells which express TAHO. These antibodies possess a TAHO-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')$_2$ bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., *Nature* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.* 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology* 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.* 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.* 148(5): 1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a $V_H$ connected to a $V_L$ by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al., *J. Immunol.* 147:60 (1991).

6. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

7. Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

8. Effector Function Engineering

It may be desirable to modify the antibody of the invention with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement lysis and ADCC capabilities. See Stevenson et al., *Anti-Cancer Drug Design* 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG$_1$, IgG$_2$, IgG$_3$, or IgG$_4$) that is responsible for increasing the in vivo serum half-life of the IgG molecule.

9. Immunoconjugates

The invention also pertains to immunoconjugates comprising an antibody conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, auristatin peptides, such as monomethylauristatin (MMAE) (synthetic analog of dolastatin), maytansinoids, such as DM1, a trichothene, and CC1065, and the derivatives of these toxins that have toxin activity, are also contemplated herein.

Maytansine and Maytansinoids

In one preferred embodiment, an anti-TAHO antibody (full length or fragments) of the invention is conjugated to one or more maytansinoid molecules.

Maytansinoids, such as DM1, are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansinoid-Antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *Proc. Natl. Acad. Sci. USA* 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., *Cancer Research* 52:127-

131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansonid drug, which could be increased by increasing the number of maytansinoid molecules per antibody molecule. The A7-maytansinoid conjugate showed low systemic cytotoxicity in mice.

Anti-TAHO Polypeptide Antibody-Maytansinoid Conjugates (Immunoconjugates)

Anti-TAHO antibody-maytansinoid conjugates are prepared by chemically linking an anti-TAHO antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al., *Cancer Research* 52:127-131 (1992). The linking groups include disulfide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., *Biochem. J.* 173:723-737 [1978]), sulfosuccinimidyl maleimidomethyl cyclohexane carboxylate (SMCC) and N-succinimidyl-4-(2-pyridylthio)pentanoate (SPP) to provide for a disulfide linkage. Other useful linkers include cys-MC-vc-PAB (a valine-citrulline (vc) dipeptide linker reagent having a maleimide component and a para-aminobenzylcarbamoyl (PAB) self-immolative component.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hyrdoxymethyl, the C-15 position modified with a hydroxyl group, and the C-20 position having a hydroxyl group. In a preferred embodiment, the linkage is formed at the C-3 position of maytansinol or a maytansinol analogue.

Calicheamicin

Another immunoconjugate of interest comprises an anti-TAHO antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta^I_1$ (Hinman et al., *Cancer Research* 53:3336-3342 (1993), Lode et al., *Cancer Research* 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the anti-TAHO antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated anti-TAHO antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., *Cancer Research* 52:127-131 (1992); U.S. Pat. No. 5,208,020) may be used.

Alternatively, a fusion protein comprising the anti-TAHO antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

10. Immunoliposomes

The anti-TAHO antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., *Proc. Natl. Acad. Sci. USA* 82:3688 (1985); Hwang et al., *Proc. Natl. Acad. Sci. USA* 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257: 286-288 (1982) via a disulfide interchange reaction. A chemotherapeutic agent is optionally contained within the liposome. See Gabizon et al., *J. National Cancer Inst.* 81(19): 1484 (1989).

B. TAHO Binding Oligopeptides

TAHO binding oligopeptides of the present invention are oligopeptides that bind, preferably specifically, to a TAHO polypeptide as described herein. TAHO binding oligopeptides may be chemically synthesized using known oligopeptide synthesis methodology or may be prepared and purified using recombinant technology. TAHO binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a TAHO polypeptide as described herein. TAHO binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., *Proc. Natl. Acad. Sci. U.S.A.*, 81:3998-4002 (1984); Geysen et al., *Proc. Natl. Acad. Sci. U.S.A.*, 82:178-182 (1985); Geysen et al., in Synthetic Peptides as Antigens, 130-149 (1986); Geysen et al., *J. Immunol. Meth.*, 102:259-274 (1987); Schoofs et al., *J. Immunol.*, 140:611-616 (1988), Cwirla, S. E. et al. (1990) *Proc. Natl. Acad. Sci. USA*, 87:6378; Lowman, H. B. et al. (1991) *Biochemistry*, 30:10832; Clackson, T. et al. (1991) *Nature*, 352: 624; Marks, J. D. et al. (1991), *J. Mol. Biol.*, 222:581; Kang, A. S. et al. (1991) *Proc. Natl. Acad. Sci. USA*, 88:8363, and Smith, G. P. (1991) *Current Opin. Biotechnol.*, 2:668).

In this regard, bacteriophage (phage) display is one well known technique which allows one to screen large oligopeptide libraries to identify member(s) of those libraries which are capable of specifically binding to a polypeptide target. Phage display is a technique by which variant polypeptides are displayed as fusion proteins to the coat protein on the surface of bacteriophage particles (Scott, J. K. and Smith, G. P. (1990) *Science*, 249: 386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al. (1990) *Proc. Natl. Acad. Sci. USA*, 87:6378) or protein (Lowman, H. B. et al. (1991) *Biochemistry*, 30:10832; Clackson, T. et al. (1991) *Nature*, 352: 624; Marks, J. D. et al. (1991), *J. Mol. Biol.*, 222:581; Kang, A. S. et al. (1991) *Proc. Natl. Acad. Sci. USA*, 88:8363) libraries on phage have been used for screening millions of polypeptides or oligopeptides for ones with specific binding properties (Smith, G. P. (1991) *Current Opin. Biotechnol.*, 2:668). Sorting phage libraries of random mutants requires a strategy for constructing and propagating a large number of variants, a procedure for affinity purification using the target receptor, and a means of evaluating the results of binding enrichments. U.S. Pat. Nos. 5,223,409, 5,403,484, 5,571,689, and 5,663,143.

Although most phage display methods have used filamentous phage, lambdoid phage display systems (WO 95/34683; U.S. Pat. No. 5,627,024), T4 phage display systems (Ren et al., *Gene,* 215: 439 (1998); Zhu et al., *Cancer Research,* 58(15): 3209-3214 (1998); Jiang et al., *Infection & Immunity,* 65(11): 4770-4777 (1997); Ren et al., Gene, 195(2):303-311 (1997); Ren, *Protein Sci.,* 5: 1833 (1996); Efimov et al., *Virus Genes,* 10: 173 (1995)) and T7 phage display systems (Smith and Scott, *Methods in Enzymology,* 217: 228-257 (1993); U.S. Pat. No. 5,766,905) are also known.

Many other improvements and variations of the basic phage display concept have now been developed. These improvements enhance the ability of display systems to screen peptide libraries for binding to selected target molecules and to display functional proteins with the potential of screening these proteins for desired properties. Combinatorial reaction devices for phage display reactions have been developed (WO 98/14277) and phage display libraries have been used to analyze and control bimolecular interactions (WO 98/20169; WO 98/20159) and properties of constrained helical peptides (WO 98/20036). WO 97/35196 describes a method of isolating an affinity ligand in which a phage display library is contacted with one solution in which the ligand will bind to a target molecule and a second solution in which the affinity ligand will not bind to the target molecule, to selectively isolate binding ligands. WO 97/46251 describes a method of biopanning a random phage display library with an affinity purified antibody and then isolating binding phage, followed by a micropanning process using microplate wells to isolate high affinity binding phage. The use of *Staphlylococcus aureus* protein A as an affinity tag has also been reported (Li et al. (1998) Mol Biotech., 9:187). WO 97/47314 describes the use of substrate subtraction libraries to distinguish enzyme specificities using a combinatorial library which may be a phage display library. A method for selecting enzymes suitable for use in detergents using phage display is described in WO 97/09446. Additional methods of selecting specific binding proteins are described in U.S. Pat. Nos. 5,498,538, 5,432,018, and WO 98/15833.

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

C. TAHO Binding Organic Molecules

TAHO binding organic molecules are organic molecules other than oligopeptides or antibodies as defined herein that bind, preferably specifically, to a TAHO polypeptide as described herein. TAHO binding organic molecules may be identified and chemically synthesized using known methodology (see, e.g., PCT Publication Nos. WO00/00823 and WO00/39585). TAHO binding organic molecules are usually less than about 2000 daltons in size, alternatively less than about 1500, 750, 500, 250 or 200 daltons in size, wherein such organic molecules that are capable of binding, preferably specifically, to a TAHO polypeptide as described herein may be identified without undue experimentation using well known techniques. In this regard, it is noted that techniques for screening organic molecule libraries for molecules that are capable of binding to a polypeptide target are well known in the art (see, e.g., PCT Publication Nos. WO00/00823 and WO00/39585). TAHO binding organic molecules may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

D. Screening for Anti-TAHO Antibodies, TAHO Binding Oligopeptides and TAHO Binding Organic Molecules with the Desired Properties Techniques for generating antibodies, oligopeptides and organic molecules that bind to TAHO polypeptides have been described above. One may further select antibodies, oligopeptides or other organic molecules with certain biological characteristics, as desired.

The growth inhibitory effects of an anti-TAHO antibody, oligopeptide or other organic molecule of the invention may be assessed by methods known in the art, e.g., using cells which express a TAHO polypeptide either endogenously or following transfection with the TAHO gene. For example, appropriate tumor cell lines and TAHO-transfected cells may be treated with an anti-TAHO monoclonal antibody, oligopeptide or other organic molecule of the invention at various concentrations for a few days (e.g., 2-7) days and stained with crystal violet or MTT or analyzed by some other colorimetric assay. Another method of measuring proliferation would be by comparing $^3$H-thymidine uptake by the cells treated in the presence or absence an anti-TAHO antibody, TAHO binding oligopeptide or TAHO binding organic molecule of the invention. After treatment, the cells are harvested and the amount of radioactivity incorporated into the DNA quantitated in a scintillation counter. Appropriate positive controls include treatment of a selected cell line with a growth inhibitory antibody known to inhibit growth of that cell line. Growth inhibition of tumor cells in vivo can be determined in various ways known in the art. The tumor cell may be one that overexpresses a TAHO polypeptide. The anti-TAHO antibody, TAHO binding oligopeptide or TAHO binding organic molecule will inhibit cell proliferation of a TAHO-expressing tumor cell in vitro or in vivo by about 25-100% compared to the untreated tumor cell, more preferably, by about 30-100%, and even more preferably by about 50-100% or 70-100%, in one embodiment, at an antibody concentration of about 0.5 to 30 µg/ml. Growth inhibition can be measured at an antibody concentration of about 0.5 to 30 µg/ml or about 0.5 nM to 200 nM in cell culture, where the growth inhibition is determined 1-10 days after exposure of the tumor cells to the antibody. The antibody is growth inhibitory in vivo if administration of the anti-TAHO antibody at about 1 µg/kg to about 100 mg/kg body weight results in reduction in tumor size or reduction of tumor cell proliferation within about 5 days to 3 months from the first administration of the antibody, preferably within about 5 to 30 days.

To select for an anti-TAHO antibody, TAHO binding oligopeptide or TAHO binding organic molecule which induces cell death, loss of membrane integrity as indicated by, e.g., propidium iodide (PI), trypan blue or 7AAD uptake may be assessed relative to control. A PI uptake assay can be performed in the absence of complement and immune effector cells. TAHO polypeptide-expressing tumor cells are incubated with medium alone or medium containing the appropriate anti-TAHO antibody (e.g., at about 10 µg/ml), TAHO binding oligopeptide or TAHO binding organic molecule. The cells are incubated for a 3 day time period. Following each treatment, cells are washed and aliquoted into 35 mm strainer-capped 12×75 tubes (1 ml per tube, 3 tubes per treatment group) for removal of cell clumps. Tubes then receive PI (10 µg/ml). Samples may be analyzed using a FACSCAN® flow cytometer and FACSCONVERT® CellQuest software (Becton Dickinson). Those anti-TAHO antibodies, TAHO binding oligopeptides or TAHO binding organic molecules that induce statistically significant levels of cell death as determined by PI uptake may be selected as cell death-inducing anti-TAHO antibodies, TAHO binding oligopeptides or TAHO binding organic molecules.

To screen for antibodies, oligopeptides or other organic molecules which bind to an epitope on a TAHO polypeptide bound by an antibody of interest, a routine cross-blocking assay such as that described in *Antibodies, A Laboratory Manual*, Cold Spring Harbor Laboratory, Ed Harlow and David Lane (1988), can be performed. This assay can be used to determine if a test antibody, oligopeptide or other organic molecule binds the same site or epitope as a known anti-TAHO antibody. Alternatively, or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of a TAHO polypeptide can be used in competition assays with the test antibodies or with a test antibody and an antibody with a characterized or known epitope.

E. Antibody Dependent Enzyme Mediated Prodrug Therapy (ADEPT)

The antibodies of the present invention may also be used in ADEPT by conjugating the antibody to a prodrug-activating enzyme which converts a prodrug (e.g., a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuramimidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328:457-458 (1987)). Antibody-abzyme conjugates can be prepared as described herein for delivery of the abzyme to a tumor cell population.

The enzymes of this invention can be covalently bound to the anti-TAHO antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature* 312:604-608 (1984).

F. Full-Length TAHO Polypeptides

The present invention also provides newly identified and isolated nucleotide sequences encoding polypeptides referred to in the present application as TAHO polypeptides. In particular, cDNAs (partial and full-length) encoding various TAHO polypeptides have been identified and isolated, as disclosed in further detail in the Examples below.

As disclosed in the Examples below, various cDNA clones have been deposited with the ATCC. The actual nucleotide sequences of those clones can readily be determined by the skilled artisan by sequencing of the deposited clone using routine methods in the art. The predicted amino acid sequence can be determined from the nucleotide sequence using routine skill. For the TAHO polypeptides and encoding nucleic acids described herein, in some cases, Applicants have identified what is believed to be the reading frame best identifiable with the sequence information available at the time.

G. Anti-TAHO Antibody and TAHO Polypeptide Variants

In addition to the anti-TAHO antibodies and full-length native sequence TAHO polypeptides described herein, it is contemplated that anti-TAHO antibody and TAHO polypeptide variants can be prepared. Anti-TAHO antibody and TAHO polypeptide variants can be prepared by introducing appropriate nucleotide changes into the encoding DNA, and/or by synthesis of the desired antibody or polypeptide. Those skilled in the art will appreciate that amino acid changes may alter post-translational processes of the anti-TAHO antibody or TAHO polypeptide, such as changing the number or position of glycosylation sites or altering the membrane anchoring characteristics.

Variations in the anti-TAHO antibodies and TAHO polypeptides described herein, can be made, for example, using any of the techniques and guidelines for conservative and non-conservative mutations set forth, for instance, in U.S. Pat. No. 5,364,934. Variations may be a substitution, deletion or insertion of one or more codons encoding the antibody or polypeptide that results in a change in the amino acid sequence as compared with the native sequence antibody or polypeptide. Optionally the variation is by substitution of at least one amino acid with any other amino acid in one or more of the domains of the anti-TAHO antibody or TAHO polypeptide. Guidance in determining which amino acid residue may be inserted, substituted or deleted without adversely affecting the desired activity may be found by comparing the sequence of the anti-TAHO antibody or TAHO polypeptide with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

Anti-TAHO antibody and TAHO polypeptide fragments are provided herein. Such fragments may be truncated at the N-terminus or C-terminus, or may lack internal residues, for example, when compared with a full length native antibody or protein. Certain fragments lack amino acid residues that are not essential for a desired biological activity of the anti-TAHO antibody or TAHO polypeptide.

Anti-TAHO antibody and TAHO polypeptide fragments may be prepared by any of a number of conventional techniques. Desired peptide fragments may be chemically synthesized. An alternative approach involves generating antibody or polypeptide fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired antibody or polypeptide fragment, by polymerase chain reaction (PCR). Oligonucleotides that define the desired termini of the DNA fragment are employed at the 5' and 3' primers in the PCR. Preferably, anti-TAHO antibody and TAHO polypeptide fragments share at least one biological and/or immunological activity with the native anti-TAHO antibody or TAHO polypeptide disclosed herein.

In particular embodiments, conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are introduced and the products screened.

TABLE 6

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the anti-TAHO antibody or TAHO polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gln, his, lys, arg;

(5) residues that influence chain orientation: gly, pro; and (6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA,* 317:415 (1986)] or other known techniques can be performed on the cloned DNA to produce the anti-TAHO antibody or TAHO polypeptide variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science,* 244:1081-1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.,* 150:1 (1976)]. If alanine substitution does not yield adequate amounts of variant, an isoteric amino acid can be used.

Any cysteine residue not involved in maintaining the proper conformation of the anti-TAHO antibody or TAHO polypeptide also may be substituted, generally with serine, to improve the oxidative stability of the molecule and prevent aberrant crosslinking. Conversely, cysteine bond(s) may be added to the anti-TAHO antibody or TAHO polypeptide to improve its stability (particularly where the antibody is an antibody fragment such as an Fv fragment).

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human TAHO polypeptide. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the anti-TAHO antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-TAHO antibody.

H. Modifications of Anti-TAHO Antibodies and TAHO Polypeptides

Covalent modifications of anti-TAHO antibodies and TAHO polypeptides are included within the scope of this invention. One type of covalent modification includes reacting targeted amino acid residues of an anti-TAHO antibody or TAHO polypeptide with an organic derivatizing agent that is capable of reacting with selected side chains or the N- or C-terminal residues of the anti-TAHO antibody or TAHO polypeptide. Derivatization with bifunctional agents is useful, for instance, for crosslinking anti-TAHO antibody or TAHO polypeptide to a water-insoluble support matrix or surface for use in the method for purifying anti-TAHO antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the anti-TAHO antibody or TAHO polypeptide included within the scope of this invention comprises altering the native glycosylation pattern of the antibody or polypeptide. "Altering the native glycosylation pattern" is intended for purposes herein to mean deleting one or more carbohydrate moieties found in native sequence anti-TAHO antibody or TAHO polypeptide (either by removing the underlying glycosylation site or by deleting the glycosylation by chemical and/or enzymatic means), and/or adding one or more glycosylation sites that are not present in the native sequence anti-TAHO antibody or TAHO polypeptide. In addition, the phrase includes qualitative changes in the glycosylation of the native proteins, involving a change in the nature and proportions of the various carbohydrate moieties present.

Glycosylation of antibodies and other polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the anti-TAHO antibody or TAHO polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original anti-TAHO antibody or TAHO polypeptide (for O-linked glycosylation sites). The anti-TAHO antibody or TAHO polypeptide amino acid sequence may optionally be altered through changes at the DNA level, particularly by mutating the DNA encoding the anti-TAHO antibody or TAHO polypeptide at preselected bases such that codons are generated that will translate into the desired amino acids.

Another means of increasing the number of carbohydrate moieties on the anti-TAHO antibody or TAHO polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981).

Removal of carbohydrate moieties present on the anti-TAHO antibody or TAHO polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of anti-TAHO antibody or TAHO polypeptide comprises linking the antibody or polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337. The antibody or polypeptide also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, 16th edition, Oslo, A., Ed., (1980).

The anti-TAHO antibody or TAHO polypeptide of the present invention may also be modified in a way to form chimeric molecules comprising an anti-TAHO antibody or TAHO polypeptide fused to another, heterologous polypeptide or amino acid sequence.

In one embodiment, such a chimeric molecule comprises a fusion of the anti-TAHO antibody or TAHO polypeptide with a tag polypeptide which provides an epitope to which an anti-tag antibody can selectively bind. The epitope tag is generally placed at the amino- or carboxyl-terminus of the anti-TAHO antibody or TAHO polypeptide. The presence of such epitope-tagged forms of the anti-TAHO antibody or TAHO polypeptide can be detected using an antibody against the tag polypeptide. Also, provision of the epitope tag enables the anti-TAHO antibody or TAHO polypeptide to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology,* 5:3610-3616 (1985)]; and the Herpes Simplex virus glycoprotein D (gD) tag and its antibody [Paborsky et al., *Protein Engineering,* 3(6):547-553 (1990)]. Other tag polypeptides include the Flag-peptide [Hopp et al., *BioTechnology,* 6: 1204-1210 (1988)]; the KT3 epitope peptide [Martin et al., *Science,* 255:192-194 (1992)]; an α-tubulin epitope peptide [Skinner et al., *J. Biol. Chem.,* 266:15163-15166 (1991)]; and the T7 gene 10 protein peptide tag [Lutz-Freyermuth et al., *Proc. Natl. Acad. Sci. USA,* 87:6393-6397 (1990)].

In an alternative embodiment, the chimeric molecule may comprise a fusion of the anti-TAHO antibody or TAHO polypeptide with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of an anti-TAHO antibody or TAHO polypeptide in place of at least one variable region within an Ig molecule. In a particularly preferred embodiment, the immunoglobulin fusion includes the hinge, $CH_2$ and $CH_3$, or the hinge, $CH_1$, $CH_2$ and $CH_3$ regions of an IgG1 molecule. For the production of immunoglobulin fusions see also U.S. Pat. No. 5,428,130 issued Jun. 27, 1995.

I. Preparation of Anti-TAHO Antibodies and TAHO Polypeptides

The description below relates primarily to production of anti-TAHO antibodies and TAHO polypeptides by culturing cells transformed or transfected with a vector containing anti-TAHO antibody- and TAHO polypeptide-encoding nucleic acid. It is, of course, contemplated that alternative methods, which are well known in the art, may be employed to prepare anti-TAHO antibodies and TAHO polypeptides. For instance, the appropriate amino acid sequence, or portions thereof, may be produced by direct peptide synthesis using solid-phase techniques [see, e.g., Stewart et al., *Solid-Phase Peptide Synthesis,* W.H. Freeman Co., San Francisco, Calif. (1969); Merrifield, *J. Am. Chem. Soc.,* 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the anti-TAHO antibody or TAHO polypeptide may be chemically synthesized separately and combined using chemical or enzymatic methods to produce the desired anti-TAHO antibody or TAHO polypeptide.

1. Isolation of DNA Encoding Anti-TAHO Antibody or TAHO Polypeptide

DNA encoding anti-TAHO antibody or TAHO polypeptide may be obtained from a cDNA library prepared from tissue believed to possess the anti-TAHO antibody or TAHO polypeptide mRNA and to express it at a detectable level. Accordingly, human anti-TAHO antibody or TAHO polypeptide DNA can be conveniently obtained from a cDNA library prepared from human tissue. The anti-TAHO antibody- or TAHO polypeptide-encoding gene may also be obtained from a genomic library or by known synthetic procedures (e.g., automated nucleic acid synthesis).

Libraries can be screened with probes (such as oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding anti-TAHO antibody or TAHO polypeptide is to use PCR methodology [Sambrook et al., supra; Dieffenbach et al., *PCR Primer: A Laboratory Manual* (Cold Spring Harbor Laboratory Press, 1995)].

Techniques for screening a cDNA library are well known in the art. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}P$-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for anti-TAHO antibody or TAHO polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach,* M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene,* 23:315 (1983) and WO 89/05859 published 29 Jun. 1989. For mammalian cells without such cell walls, the calcium phosphate precipitation method of Graham and van der Eb, *Virology,* 52:456-457 (1978) can be employed. General aspects of mammalian cell host system transfections have been described in U.S. Pat. No. 4,399,216. Transformations into yeast are typically carried out according to the method of Van Solingen et al., *J. Bact.,* 130:946 (1977) and Hsiao et al., *Proc. Natl. Acad. Sci. (USA),* 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789, 199 (Joly et al.), and U.S. Pat. No. 5,840,523 (Simmons et al.) which describes translation initiation regio (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for anti-TAHO antibody- or TAHO polypeptide-encoding vectors. *Saccharomyces cerevisiae* is a commonly used lower eukaryotic host microorganism. Others include *Schizosaccharomyces pombe* (Beach and Nurse, *Nature*, 290: 140 [1981]; EP 139,383 published 2 May 1985); *Kluyveromyces* hosts (U.S. Pat. No. 4,943,529; Fleer et al., *Bio/Technology*, 9:968-975 (1991)) such as, e.g., *K. lactis* (MW98-8C, CBS683, CBS4574; Louvencourt et al., *J. Bacteriol.*, 154(2): 737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8:135 (1990)), *K. thermotolerans*, and *K. marxianus; yarrowia* (EP 402,226); *Pichia pastoris* (EP 183,070; Sreekrishna et al., *J. Basic Microbiol.*, 28:265-278 [1988]); *Candida; Trichoderma reesia* (EP 244, 234); *Neurospora crassa* (Case et al., *Proc. Natl. Acad. Sci. USA*, 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.*, 112:284-289 [1983]; Tilburn et al., *Gene*, 26:205-221 [1983]; Yelton et al., *Proc. Natl. Acad. Sci. USA*, 81: 1470-1474 [1984]) and *A. niger* (Kelly and Hynes, *EMBO J.* 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, *The Biochemistry of Methylotrophs*, 269 (1982).

Suitable host cells for the expression of glycosylated anti-TAHO antibody or TAHO polypeptide are derived from multicellular organisms. Examples of invertebrate cells include insect cells such as *Drosophila* S2 and *Spodoptera* Sf9, as well as plant cells, such as cell cultures of cotton, corn, potato, soybean, petunia, tomato, and tobacco. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for anti-TAHO antibody or TAHO polypeptide production and cultured in conventional nutrient media modified as appropriate for inducing promoters, selecting transformants, or amplifying the genes encoding the desired sequences.

3. Selection and Use of a Replicable Vector

The nucleic acid (e.g., cDNA or genomic DNA) encoding anti-TAHO antibody or TAHO polypeptide may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The TAHO may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the anti-TAHO antibody- or TAHO polypeptide-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the anti-TAHO antibody- or TAHO polypeptide-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the anti-TAHO antibody- or TAHO polypeptide-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21-25 (1983)]. Promoters for use in bacterial systems also will contain a Shine-Dalgarno (S. D.) sequence operably linked to the DNA encoding anti-TAHO antibody or TAHO polypeptide.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Anti-TAHO antibody or TAHO polypeptide transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the anti-TAHO antibody or TAHO polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the anti-TAHO antibody or TAHO polypeptide coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-TAHO antibody or TAHO polypeptide.

Still other methods, vectors, and host cells suitable for adaptation to the synthesis of anti-TAHO antibody or TAHO polypeptide in recombinant vertebrate cell culture are described in Gething et al., Nature, 293:620-625 (1981); Mantei et al., Nature, 281:40-46 (1979); EP 117,060; and EP 117,058.

4. Culturing the Host Cells

The host cells used to produce the anti-TAHO antibody or TAHO polypeptide of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

5. Detecting Gene Amplification/Expression

Gene amplification and/or expression may be measured in a sample directly, for example, by conventional Southern blotting, Northern blotting to quantitate the transcription of mRNA [Thomas, Proc. Natl. Acad. Sci. USA, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence TAHO polypeptide or against a synthetic peptide based on the DNA sequences provided herein or against exogenous sequence fused to TAHO DNA and encoding a specific antibody epitope.

6. Purification of Anti-TAHO Antibody and TAHO Polypeptide

Forms of anti-TAHO antibody and TAHO polypeptide may be recovered from culture medium or from host cell lysates. If membrane-bound, it can be released from the membrane using a suitable detergent solution (e.g. Triton-X 100) or by enzymatic cleavage. Cells employed in expression of anti-TAHO antibody and TAHO polypeptide can be disrupted by various physical or chemical means, such as freeze-thaw cycling, sonication, mechanical disruption, or cell lysing agents.

It may be desired to purify anti-TAHO antibody and TAHO polypeptide from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the anti-TAHO antibody and TAHO polypeptide. Various methods of protein purification may be employed and such methods are known in the art and described for example in Deutscher, Methods in Enzymology, 182 (1990); Scopes, Protein Purification: Principles and Practice, Springer-Verlag, New York (1982). The purification step(s) selected will depend, for example, on the nature of the production process used and the particular anti-TAHO antibody or TAHO polypeptide produced.

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., Bio/Technology 10: 163-167 (1992) describe a procedure for isolating antibodies which are secreted to the periplasmic space of E. coli. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2 or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

J. Pharmaceutical Formulations

Therapeutic formulations of the anti-TAHO antibodies, TAHO binding oligopeptides, TAHO binding organic molecules and/or TAHO polypeptides used in accordance with the present invention are prepared for storage by mixing the antibody, polypeptide, oligopeptide or organic molecule having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g., Zn-protein complexes); and/or non-ionic surfactants such as TWEEN®, PLURONICS® or polyethylene glycol (PEG). The antibody preferably comprises the antibody at a concentration of between 5-200 mg/ml, preferably between 10-100 mg/ml.

The formulations herein may also contain more than one active compound as necessary for the particular indication being treated, preferably those with complementary activities that do not adversely affect each other. For example, in addition to an anti-TAHO antibody, TAHO binding oligopeptide, or TAHO binding organic molecule, it may be desirable to include in the one formulation, an additional antibody, e.g., a second anti-TAHO antibody which binds a different epitope on the TAHO polypeptide, or an antibody to some other target such as a growth factor that affects the growth of the particular cancer. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences*, 16th edition, Osol, A. Ed. (1980).

Sustained-release preparations may be prepared. Suitable examples of sustained-release preparations include semi-permeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

K. Treatment with Anti-TAHO Antibodies, TAHO Binding Oligopeptides and TAHO Binding Organic Molecules To determine TAHO expression in the cancer, various detection assays are available. In one embodiment, TAHO polypeptide overexpression may be analyzed by immunohistochemistry (IHC). Parrafin embedded tissue sections from a tumor biopsy may be subjected to the IHC assay and accorded a TAHO protein staining intensity criteria as follows:

Score 0—no staining is observed or membrane staining is observed in less than 10% of tumor cells.

Score 1+—a faint/barely perceptible membrane staining is detected in more than 10% of the tumor cells. The cells are only stained in part of their membrane.

Score 2+—a weak to moderate complete membrane staining is observed in more than 10% of the tumor cells.

Score 3+—a moderate to strong complete membrane staining is observed in more than 10% of the tumor cells.

Those tumors with 0 or 1+ scores for TAHO polypeptide expression may be characterized as not overexpressing TAHO, whereas those tumors with 2+ or 3+ scores may be characterized as overexpressing TAHO.

Alternatively, or additionally, FISH assays such as the INFORM® (sold by Ventana, Arizona) or PATHVISION® (Vysis, Illinois) may be carried out on formalin-fixed, paraffin-embedded tumor tissue to determine the extent (if any) of TAHO overexpression in the tumor.

TAHO overexpression or amplification may be evaluated using an in vivo detection assay, e.g., by administering a molecule (such as an antibody, oligopeptide or organic molecule) which binds the molecule to be detected and is tagged with a detectable label (e.g., a radioactive isotope or a fluorescent label) and externally scanning the patient for localization of the label.

As described above, the anti-TAHO antibodies, oligopeptides and organic molecules of the invention have various non-therapeutic applications. The anti-TAHO antibodies, oligopeptides and organic molecules of the present invention can be useful for staging of TAHO polypeptide-expressing cancers (e.g., in radioimaging). The antibodies, oligopeptides and organic molecules are also useful for purification or immunoprecipitation of TAHO polypeptide from cells, for detection and quantitation of TAHO polypeptide in vitro, e.g., in an ELISA or a Western blot, to kill and eliminate TAHO-expressing cells from a population of mixed cells as a step in the purification of other cells.

Currently, depending on the stage of the cancer, cancer treatment involves one or a combination of the following therapies: surgery to remove the cancerous tissue, radiation therapy, and chemotherapy. Anti-TAHO antibody, oligopeptide or organic molecule therapy may be especially desirable in elderly patients who do not tolerate the toxicity and side effects of chemotherapy well and in metastatic disease where radiation therapy has limited usefulness. The tumor targeting anti-TAHO antibodies, oligopeptides and organic molecules of the invention are useful to alleviate TAHO-expressing cancers upon initial diagnosis of the disease or during relapse. For therapeutic applications, the anti-TAHO antibody, oligopeptide or organic molecule can be used alone, or in combination therapy with, e.g., hormones, antiangiogens, or radiolabelled compounds, or with surgery, cryotherapy, and/or radiotherapy. Anti-TAHO antibody, oligopeptide or organic molecule treatment can be administered in conjunction with other forms of conventional therapy, either consecutively with, pre- or post-conventional therapy. Chemotherapeutic drugs such as TAXOTERE® (docetaxel), TAXOL® (palictaxel), estramustine and mitoxantrone are used in treating cancer, in particular, in good risk patients. In the present method of the invention for treating or alleviating cancer, the cancer patient can be administered anti-TAHO antibody, oligopeptide or organic molecule in conjunction with treatment with the one or more of the preceding chemotherapeutic agents. In particular, combination therapy with palictaxel and modified derivatives (see, e.g., EP0600517) is contemplated. The anti-TAHO antibody, oligopeptide or organic molecule will be administered with a therapeutically effective dose of the chemotherapeutic agent. In another embodiment, the anti-TAHO antibody, oligopeptide or organic molecule is administered in conjunction with chemotherapy to enhance the activity and efficacy of the chemotherapeutic agent, e.g., paclitaxel. The Physicians' Desk Reference (PDR) discloses dosages of these agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician.

In one particular embodiment, a conjugate comprising an anti-TAHO antibody, oligopeptide or organic molecule conjugated with a cytotoxic agent is administered to the patient. Preferably, the immunoconjugate bound to the TAHO protein is internalized by the cell, resulting in increased therapeutic efficacy of the immunoconjugate in killing the cancer cell to which it binds. In a preferred embodiment, the cytotoxic agent targets or interferes with the nucleic acid in the cancer cell. Examples of such cytotoxic agents are described above and include maytansinoids, calicheamicins, ribonucleases and DNA endonucleases.

The anti-TAHO antibodies, oligopeptides, organic molecules or toxin conjugates thereof are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody, oligopeptide or organic molecule is preferred.

Other therapeutic regimens may be combined with the administration of the anti-TAHO antibody, oligopeptide or organic molecule. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

It may also be desirable to combine administration of the anti-TAHO antibody or antibodies, oligopeptides or organic molecules, with administration of an antibody directed against another tumor antigen associated with the particular cancer.

In another embodiment, the therapeutic treatment methods of the present invention involves the combined administration of an anti-TAHO antibody (or antibodies), oligopeptides or organic molecules and one or more chemotherapeutic agents or growth inhibitory agents, including co-administration of cocktails of different chemotherapeutic agents. Chemotherapeutic agents include estramustine phosphate, prednimustine, cisplatin, 5-fluorouracil, melphalan, cyclophosphamide, hydroxyurea and hydroxyureataxanes (such as paclitaxel and doxetaxel) and/or anthracycline antibiotics. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

The antibody, oligopeptide or organic molecule may be combined with an anti-hormonal compound; e.g., an anti-estrogen compound such as tamoxifen; an anti-progesterone such as onapristone (see, EP 616 812); or an anti-androgen such as flutamide, in dosages known for such molecules. Where the cancer to be treated is androgen independent cancer, the patient may previously have been subjected to anti-androgen therapy and, after the cancer becomes androgen independent, the anti-TAHO antibody, oligopeptide or organic molecule (and optionally other agents as described herein) may be administered to the patient.

Sometimes, it may be beneficial to also co-administer a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy, before, simultaneously with, or post antibody, oligopeptide or organic molecule therapy. Suitable dosages for any of the above co-administered agents are those presently used and may be lowered due to the combined action (synergy) of the agent and anti-TAHO antibody, oligopeptide or organic molecule.

For the prevention or treatment of disease, the dosage and mode of administration will be chosen by the physician according to known criteria. The appropriate dosage of antibody, oligopeptide or organic molecule will depend on the type of disease to be treated, as defined above, the severity and course of the disease, whether the antibody, oligopeptide or organic molecule is administered for preventive or therapeutic purposes, previous therapy, the patient's clinical history and response to the antibody, oligopeptide or organic molecule, and the discretion of the attending physician. The antibody, oligopeptide or organic molecule is suitably administered to the patient at one time or over a series of treatments. Preferably, the antibody, oligopeptide or organic molecule is administered by intravenous infusion or by subcutaneous injections. Depending on the type and severity of the disease, about 1 µg/kg to about 50 mg/kg body weight (e.g., about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the anti-TAHO antibody. However, other dosage regimens may be useful. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

Aside from administration of the antibody protein to the patient, the present application contemplates administration of the antibody by gene therapy. Such administration of nucleic acid encoding the antibody is encompassed by the expression "administering a therapeutically effective amount of an antibody". See, for example, WO96/07321 published Mar. 14, 1996 concerning the use of gene therapy to generate intracellular antibodies.

There are two major approaches to getting the nucleic acid (optionally contained in a vector) into the patient's cells; in vivo and ex vivo. For in vivo delivery the nucleic acid is injected directly into the patient, usually at the site where the antibody is required. For ex vivo treatment, the patient's cells are removed, the nucleic acid is introduced into these isolated cells and the modified cells are administered to the patient either directly or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retroviral vector.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of the currently known gene marking and gene therapy protocols see Anderson et al., Science 256:808-813 (1992). See also WO 93/25673 and the references cited therein.

The anti-TAHO antibodies of the invention can be in the different forms encompassed by the definition of "antibody" herein. Thus, the antibodies include full length or intact antibody, antibody fragments, native sequence antibody or amino acid variants, humanized, chimeric or fusion antibodies, immunoconjugates, and functional fragments thereof. In fusion antibodies an antibody sequence is fused to a heterologous polypeptide sequence. The antibodies can be modified in the Fc region to provide desired effector functions. As discussed in more detail in the sections herein, with the appropriate Fc regions, the naked antibody bound on the cell surface can induce cytotoxicity, e.g., via antibody-dependent cellular cytotoxicity (ADCC) or by recruiting complement in complement dependent cytotoxicity, or some other mechanism. Alternatively, where it is desirable to eliminate or reduce effector function, so as to minimize side effects or therapeutic complications, certain other Fc regions may be used.

In one embodiment, the antibody competes for binding or bind substantially to, the same epitope as the antibodies of the invention. Antibodies having the biological characteristics of the present anti-TAHO antibodies of the invention are also contemplated, specifically including the in vivo tumor targeting and any cell proliferation inhibition or cytotoxic characteristics.

Methods of producing the above antibodies are described in detail herein.

The present anti-TAHO antibodies, oligopeptides and organic molecules are useful for treating a TAHO-expressing cancer or alleviating one or more symptoms of the cancer in a mammal. Such a cancer includes, but is not limited to, hematopoietic cancers or blood-related cancers, such as lymphoma, leukemia, myeloma or lymphoid malignancies, but also cancers of the spleen and cancers of the lymph nodes. More particular examples of such B-cell associated cancers, including for example, high, intermediate and low grade lymphomas (including B cell lymphomas such as, for example, mucosa-associated-lymphoid tissue B cell lymphoma and non-Hodgkin's lymphoma, mantle cell lymphoma, Burkitt's lymphoma, small lymphocytic lymphoma, marginal zone lymphoma, diffuse large cell lymphoma, follicular lymphoma, and Hodgkin's lymphoma and T cell lymphomas) and leukemias (including secondary leukemia, chronic lymphocytic leukemia, such as B cell leukemia (CD5+ B lymphocytes), myeloid leukemia, such as acute myeloid leukemia, chronic myeloid leukemia, lymphoid leukemia, such as acute lymphoblastic leukemia and myelodysplasia), multiple myeloma, such as plasma cell malignancy, and other hematological and/or B cell- or T-cell-associated cancers. The cancers encompass metastatic cancers of any of the preceding. The antibody, oligopeptide or organic molecule is able to bind to at least a portion of the cancer cells that express TAHO polypeptide in the mammal. In a preferred embodiment, the antibody, oligopeptide or organic molecule is effective to destroy or kill TAHO-expressing tumor cells or inhibit the growth of such tumor cells, in vitro or in vivo, upon binding to TAHO polypeptide on the cell. Such an antibody includes a naked anti-TAHO antibody (not conjugated to any agent). Naked antibodies that have cytotoxic or cell growth inhibition properties can be further harnessed with a cytotoxic agent to render them even more potent in tumor cell destruction. Cytotoxic properties can be conferred to an anti-TAHO antibody by, e.g., conjugating the antibody with a cytotoxic agent, to form an immunoconjugate as described herein. The cytotoxic agent or a growth inhibitory agent is preferably a small molecule. Toxins such as calicheamicin or a maytansinoid and analogs or derivatives thereof, are preferable.

The invention provides a composition comprising an anti-TAHO antibody, oligopeptide or organic molecule of the invention, and a carrier. For the purposes of treating cancer, compositions can be administered to the patient in need of such treatment, wherein the composition can comprise one or more anti-TAHO antibodies present as an immunoconjugate or as the naked antibody. In a further embodiment, the compositions can comprise these antibodies, oligopeptides or organic molecules in combination with other therapeutic agents such as cytotoxic or growth inhibitory agents, including chemotherapeutic agents. The invention also provides formulations comprising an anti-TAHO antibody, oligopeptide or organic molecule of the invention, and a carrier. In one embodiment, the formulation is a therapeutic formulation comprising a pharmaceutically acceptable carrier.

Another aspect of the invention is isolated nucleic acids encoding the anti-TAHO antibodies. Nucleic acids encoding both the H and L chains and especially the hypervariable region residues, chains which encode the native sequence antibody as well as variants, modifications and humanized versions of the antibody, are encompassed.

The invention also provides methods useful for treating a TAHO polypeptide-expressing cancer or alleviating one or more symptoms of the cancer in a mammal, comprising administering a therapeutically effective amount of an anti-TAHO antibody, oligopeptide or organic molecule to the mammal. The antibody, oligopeptide or organic molecule therapeutic compositions can be administered short term (acute) or chronic, or intermittent as directed by physician. Also provided are methods of inhibiting the growth of, and killing a TAHO polypeptide-expressing cell.

The invention also provides kits and articles of manufacture comprising at least one anti-TAHO antibody, oligopeptide or organic molecule. Kits containing anti-TAHO antibodies, oligopeptides or organic molecules find use, e.g., for TAHO cell killing assays, for purification or immunoprecipitation of TAHO polypeptide from cells. For example, for isolation and purification of TAHO, the kit can contain an anti-TAHO antibody, oligopeptide or organic molecule coupled to beads (e.g., sepharose beads). Kits can be provided which contain the antibodies, oligopeptides or organic molecules for detection and quantitation of TAHO in vitro, e.g., in an ELISA or a Western blot. Such antibody, oligopeptide or organic molecule useful for detection may be provided with a label such as a fluorescent or radiolabel.

L. Articles of Manufacture and Kits

Another embodiment of the invention is an article of manufacture containing materials useful for the treatment of anti-TAHO expressing cancer. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the cancer condition and may have a sterile access port (for example the container may be an intravenous solution bag or a vial having a stopper pierceable by a hypodermic injection needle). At least one active agent in the composition is an anti-TAHO antibody, oligopeptide or organic molecule of the invention. The label or package insert indicates that the composition is used for treating cancer. The label or package insert will further comprise instructions for administering the antibody, oligopeptide or organic molecule composition to the cancer patient. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for TAHO-expressing cell killing assays, for purification or immunoprecipitation of TAHO polypeptide from cells. For isolation and purification of TAHO polypeptide, the kit can contain an anti-TAHO antibody, oligopeptide or organic molecule coupled to beads (e.g., sepharose beads). Kits can be provided which contain the antibodies, oligopeptides or organic molecules for detection and quantitation of TAHO polypeptide in vitro, e.g., in an ELISA or a Western blot. As with the article of manufacture, the kit comprises a container and a label or package insert on or associated with the container. The container holds a composition comprising at least one anti-TAHO antibody, oligopeptide or organic molecule of the invention. Additional containers may be included that contain, e.g., diluents and buffers, control antibodies. The label or package insert may provide a description of the composition as well as instructions for the intended in vitro or detection use.

M. Uses for TAHO Polypeptides and TAHO-Polypeptide Encoding Nucleic Acids

Nucleotide sequences (or their complement) encoding TAHO polypeptides have various applications in the art of molecular biology, including uses as hybridization probes, in chromosome and gene mapping and in the generation of anti-sense RNA and DNA probes. TAHO-encoding nucleic acid will also be useful for the preparation of TAHO polypeptides by the recombinant techniques described herein, wherein those TAHO polypeptides may find use, for example, in the preparation of anti-TAHO antibodies as described herein.

The full-length native sequence TAHO gene, or portions thereof, may be used as hybridization probes for a cDNA library to isolate the full-length TAHO cDNA or to isolate still other cDNAs (for instance, those encoding naturally-occurring variants of TAHO or TAHO from other species) which have a desired sequence identity to the native TAHO sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence TAHO. By way of example, a screening method will comprise isolating the coding region of the TAHO gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the TAHO gene of the present invention can be used to screen libraries of human cDNA, genomic DNA or mRNA to determine which members of such libraries the probe hybridizes to. Hybridization techniques are described in further detail in the Examples below. Any EST sequences disclosed in the present application may similarly be employed as probes, using the methods disclosed herein.

Other useful fragments of the TAHO-encoding nucleic acids include antisense or sense oligonucleotides comprising a singe-stranded nucleic acid sequence (either RNA or DNA) capable of binding to target TAHO mRNA (sense) or TAHO DNA (antisense) sequences. Antisense or sense oligonucleotides, according to the present invention, comprise a fragment of the coding region of TAHO DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. Such methods are encompassed by the present invention. The antisense oligonucleotides thus may be used to block expression of TAHO proteins, wherein those TAHO proteins may play a role in the induction of cancer in mammals. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Preferred intragenic sites for antisense binding include the region incorporating the translation initiation/start codon (5'-AUG/5'-ATG) or termination/stop codon (5'-UAA, 5'-UAG and 5-UGA/5'-TAA, 5'-TAG and 5'-TGA) of the open reading frame (ORF) of the gene. These regions refer to a portion of the mRNA or gene that encompasses from about 25 to about 50 contiguous nucleotides in either direction (i.e., 5' or 3') from a translation initiation or termination codon. Other preferred regions for antisense binding include: introns; exons; intron-exon junctions; the open reading frame (ORF) or "coding region," which is the region between the translation initiation codon and the translation termination codon; the 5' cap of an mRNA which comprises an N7-methylated guanosine residue joined to the 5'-most residue of the mRNA via a 5'-5' triphosphate linkage and includes 5' cap structure itself as well as the first 50 nucleotides adjacent to the cap; the 5' untranslated region (5'UTR), the portion of an mRNA in the 5' direction from the translation initiation codon, and thus including nucleotides between the 5' cap site and the translation initiation codon of an mRNA or corresponding nucleotides on the gene; and the 3' untranslated region (3'UTR), the portion of an mRNA in the 3' direction from the translation termination codon, and thus including nucleotides between the translation termination codon and 3' end of an mRNA or corresponding nucleotides on the gene.

Specific examples of preferred antisense compounds useful for inhibiting expression of TAHO proteins include oligonucleotides containing modified backbones or non-natural internucleoside linkages. Oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides. Preferred modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included. Representative United States patents that teach the preparation of phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative United States patents that teach the preparation of such oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

In other preferred antisense oligonucleotides, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Preferred antisense oligonucleotides incorporate phosphorothioate backbones and/or heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] described in the above referenced U.S. Pat. No. 5,489,677, and the amide backbones of the above referenced U.S. Pat. No. 5,602,240. Also preferred are antisense oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-alkyl, S-alkyl, or N-alkyl; O-alkenyl, S-alkeynyl, or N-alkenyl; O-alkynyl, S-alkynyl or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10. Other preferred antisense oligonucleotides comprise one of the following at the 2' position: C$_1$ to C$_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$ CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH$_2$CH$_2$OCH$_3$, also known as 2'-O-(2-methoxyethyl) or 2'-MOE) (Martin et al., Helv. Chim. Acta, 1995, 78, 486-504) i.e., an alkoxyalkoxy group. A further preferred modification includes 2'-dimethylaminooxyethoxy, i.e., a O(CH$_2$)$_2$ON(CH$_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$).

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—CH$_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—CH$_3$), 2'-aminopropoxy (2'-OCH$_2$CH$_2$CH$_2$ NH$_2$), 2'-allyl (2'-CH$_2$—CH=CH$_2$), 2'-O-allyl (2'-O—CH$_2$—CH—CH$_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$ or —CH$_2$—C≡CH) uracil and cytosine and other alkynyl derivatives of pyrimidine bases, 6-azo uracil, cytosine and thymine, 5-uracil (pseudoutacil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido [5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi et al, Antisense Research and Applications, CRC Press, Boca Raton, 1993, pp. 276-278) and are preferred base substitutions, even more particularly when combined with 2'-O-methoxyethyl sugar modifications. Representative United States patents that teach the preparation of modified nucleobases include, but are not limited to: U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,681,941 and 5,750,692, each of which is herein incorporated by reference.

Another modification of antisense oligonucleotides chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, cation lipids, phospholipids, cationic phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) and U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Chimeric antisense compounds of the invention may be formed as composite structures of two or more oligonucleotides, modified oligonucleotides, oligonucleosides and/or oligonucleotide mimetics as described above. Preferred chimeric antisense oligonucleotides incorporate at least one 2' modified sugar (preferably 2'-O—(CH$_2$)$_2$—O—CH$_3$) at the 3' terminal to confer nuclease resistance and a region with at least 4 contiguous 2'-H sugars to confer RNase H activity. Such compounds have also been referred to in the art as hybrids or gapmers. Preferred gapmers have a region of 2' modified sugars (preferably 2'-O—(CH$_2$)$_2$—O—CH$_3$) at the 3'-terminal and at the 5' terminal separated by at least one region having at least 4 contiguous 2'-H sugars and preferably incorporate phosphorothioate backbone linkages. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, CaPO$_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

The probes may also be employed in PCR techniques to generate a pool of sequences for identification of closely related TAHO coding sequences.

Nucleotide sequences encoding a TAHO can also be used to construct hybridization probes for mapping the gene which encodes that TAHO and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for TAHO encode a protein which binds to another protein (example, where the TAHO is a receptor), the TAHO can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor TAHO can be used to isolate correlative ligand(s). Screening assays can be designed to find lead compounds that mimic the biological activity of a native TAHO or a receptor for TAHO. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode TAHO or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding TAHO can be used to clone genomic DNA encoding TAHO in accordance with established techniques and the genomic sequences used to generate transgenic animals that contain cells which express DNA encoding TAHO. Methods for generating transgenic animals, particularly animals such as mice or rats, have become conventional in the art and are described, for example, in U.S. Pat. Nos. 4,736,866 and 4,870,009. Typically, particular cells would be targeted for TAHO transgene incorporation with tissue-specific enhancers. Transgenic animals that include a copy of a transgene encoding TAHO introduced into the germ line of the animal at an embryonic stage can be used to examine the effect of increased expression of DNA encoding TAHO. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of TAHO can be used to construct a TAHO "knock out" animal which has a defective or altered gene encoding TAHO as a result of homologous recombination between the endogenous gene encoding TAHO and altered genomic DNA encoding TAHO introduced into an embryonic stem cell of the animal. For example, cDNA encoding TAHO can be used to clone genomic DNA encoding TAHO in accordance with established techniques. A portion of the genomic DNA encoding TAHO can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell*, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the TAHO polypeptide.

Nucleic acid encoding the TAHO polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA.

Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83:4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429-4432 (1987); and Wagner et al., *Proc. Natl. Acad. Sci. USA* 87, 3410-3414 (1990). For review of gene marking and gene therapy protocols see Anderson et al., *Science* 256, 808-813 (1992).

The nucleic acid molecules encoding the TAHO polypeptides or fragments thereof described herein are useful for chromosome identification. In this regard, there exists an ongoing need to identify new chromosome markers, since relatively few chromosome marking reagents, based upon actual sequence data are presently available. Each TAHO nucleic acid molecule of the present invention can be used as a chromosome marker.

The TAHO polypeptides and nucleic acid molecules of the present invention may also be used diagnostically for tissue typing, wherein the TAHO polypeptides of the present invention may be differentially expressed in one tissue as compared to another, preferably in a diseased tissue as compared to a normal tissue of the same tissue type. TAHO nucleic acid molecules will find use for generating probes for PCR, Northern analysis, Southern analysis and Western analysis.

This invention encompasses methods of screening compounds to identify those that mimic the TAHO polypeptide (agonists) or prevent the effect of the TAHO polypeptide (antagonists). Screening assays for antagonist drug candidates are designed to identify compounds that bind or complex with the TAHO polypeptides encoded by the genes identified herein, or otherwise interfere with the interaction of the encoded polypeptides with other cellular proteins, including e.g., inhibiting the expression of TAHO polypeptide from cells. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a TAHO polypeptide encoded by a nucleic acid identified herein under conditions and for a time sufficient to allow these two components to interact.

In binding assays, the interaction is binding and the complex formed can be isolated or detected in the reaction mixture. In a particular embodiment, the TAHO polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the TAHO polypeptide and drying. Alternatively, an immobilized antibody, e.g., a monoclonal antibody, specific for the TAHO polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular TAHO polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature (London)*, 340:245-246 (1989); Chien et al., *Proc. Natl. Acad. Sci. USA*, 88:9578-9582 (1991)) as disclosed by Chevray and Nathans, *Proc. Natl. Acad. Sci. USA*, 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a TAHO polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the TAHO polypeptide may be added to a cell along with the compound to be screened for a particular activity and the ability of the compound to inhibit the activity of interest in the presence of the TAHO polypeptide indicates that the compound is an antagonist to the TAHO polypeptide. Alternatively, antagonists may be detected by combining the TAHO polypeptide and a potential antagonist with membrane-bound TAHO polypeptide receptors or recombinant receptors under appropriate conditions for a competitive inhibition assay. The TAHO polypeptide can be labeled, such as by radioactivity, such that the number of TAHO polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.*, 1(2): Chapter 5 (1991). Preferably, expression cloning is employed wherein polyadenylated RNA is prepared from a cell responsive to the TAHO polypeptide and a cDNA library created from this RNA is divided into pools and used to transfect COS cells or other cells that are not responsive to the TAHO polypeptide. Transfected cells that are grown on glass slides are exposed to labeled TAHO polypeptide. The TAHO polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled TAHO polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled TAHO polypeptide in the presence of the candidate compound. The ability of the compound to enhance or block this interaction could then be measured.

More specific examples of potential antagonists include an oligonucleotide that binds to the fusions of immunoglobulin with TAHO polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the TAHO polypeptide that recognizes the receptor but imparts no effect, thereby competitively inhibiting the action of the TAHO polypeptide.

Another potential TAHO polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature TAHO polypeptides herein, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.*, 6:3073 (1979); Cooney et al., *Science*, 241: 456 (1988); Dervan et al., *Science*, 251:1360 (1991)), thereby preventing transcription and the production of the TAHO polypeptide. The antisense RNA oligonucleotide hybridizes to the mRNA in vivo and blocks translation of the mRNA molecule into the TAHO polypeptide (antisense—Okano, *Neurochem.*, 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the TAHO polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the TAHO polypeptide, thereby blocking the normal biological activity of the TAHO polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology*, 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

Isolated TAHO polypeptide-encoding nucleic acid can be used herein for recombinantly producing TAHO polypeptide using techniques well known in the art and as described herein. In turn, the produced TAHO polypeptides can be employed for generating anti-TAHO antibodies using techniques well known in the art and as described herein.

Antibodies specifically binding a TAHO polypeptide identified herein, as well as other molecules identified by the screening assays disclosed hereinbefore, can be administered for the treatment of various disorders, including cancer, in the form of pharmaceutical compositions.

If the TAHO polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA*, 90: 7889-7893 (1993).

The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. Antibodies used in the examples are commercially available antibodies or antibodies described herein. The source of those cells identified in the following examples, and throughout the specification, by ATCC accession numbers is the American Type Culture Collection, Manassas, Va.

Example 1

Microarray Data Analysis of TAHO Expression

Microarray data involves the analysis of TAHO expression by the performance of DNA microarray analysis on a wide a variety of RNA samples from tissues and cultured cells. Samples include normal and cancerous human tissue and various kinds of purified immune cells both at rest and following external stimulation. These RNA samples may be analyzed according to regular microarray protocols on Agilent microarrays.

In this experiment, RNA was isolated from cells and cyanine-3 and cyanine-5 labeled cRNA probes were generated by in vitro transcription using the Agilent Low Input RNA Fluorescent Linear Amplification Kit (Agilent). Cyanine-5 was used to label the samples to be tested for expression of the PRO polypeptide, for example, the myeloma and plasma cells, and cyanine-3 was used to label the universal reference (the Stratagene cell line pool) with which the expression of the test samples were compared. 0.1 μg-0.2 mg of cyanine-3 and cyanine-5 labeled cRNA probe was hybridized to Agilent 60-mer oligonucleotide array chips using the In Situ Hybridization Kit Plus (Agilent). These probes were hybridized to microarrays. For multiple myeloma analysis, probes were hybridized to Agilent Whole Human Genome oligonucleotide microarrays using standard Agilent recommended conditions and buffers (Agilent).

The cRNA probes are hybridized to the microarrays at 60° C. for 17 hours on a hybridization rotator set at 4 RPM. After washing, the microarrays are scanned with the Agilent microarray scanner which is capable of exciting and detecting the fluorescence from the cyanine-3 and cyanine-5 fluorescent molecules (532 and 633 nm laser lines). The data for each gene on the 60-mer oligonucleotide array was extracted from the scanned microarray image using Agilent feature extraction software which accounts for feature recognition, background subtraction and normalization and the resulting data was loaded into the software package known as the Rosetta Resolver Gene Expression Data Analysis System (Rosetta Inpharmatics, Inc.). Rosetta Resolver includes a relational database and numerous analytical tools to store, retrieve and analyze large quantities of intensity or ratio gene expression data.

In this example, B cells and T cells (control) were obtained for microarray analysis. For isolation of naive and memory B cells and plasma cells, human peripheral blood mononuclear cells (PBMC) were separated from either leukopack provided by four healthy male donors or from whole blood of several normal donors. CD138+ plasma cells were isolated from PBMC using the MACS (Miltenyi Biotec) magnetic cell sorting system and anti-CD138 beads. Alternatively, total CD19+ B cells were selected with anti-CD19 beads and MACS sorting. After enrichment of CD19+ (purity around 90%), FACS (Moflo) sorting was performed to separate naive and memory B cells. Sorted cells were collected by subjecting the samples to centrifugation. The sorted cells were immediately lysed in LTR buffer and homogenized with QIAshredder (Qiagen) spin column and followed by RNeasy mini kit for RNA purification. RNA yield was variable from 0.4-10 μg and depended on the cell numbers.

As a control, T cells were isolated for microarray analysis. Peripheral blood CD8 cells were isolated from leukopacks by negative selection using the Stem Cell Technologies CD8 cell isolation kit (Rosette Separation) and further purified by the MACS magnetic cell sorting system using CD8 cell isolation kit and CD45RO microbeads were added to remove CD45RO cells (Miltenyi Biotec). CD8 T cells were divided into 3 samples with each sample subjected to the stimulation as follows: (1) anti-CD3 and anti-CD28, plus IL-12 and anti-IL4 antibody, (2) anti-CD3 and anti-CD29 without adding cytokines or neutralizing antibodies and (3) anti-CD3 and anti-CD28, plus IL-4, anti-IL12 antibody and anti-IFN-γ antibody. 48 hours after stimulation, RNA was collected. After 72 hours, cells were expanded by adding diluting 8-fold with fresh media. 7 days after the RNA was collected, CD8 cells were collected, washed and restimulated by anti-CD3 and anti-CD28. 16 hours later, a second collection of RNA was made. 48 hours after restimulation, a third collection of RNA was made. RNA was collected by using Qiagen Midi preps as per the instructions in the manual with the addition of an on-column DNAse I digestion after the first RW1 wash step. RNA was eluted in RNAse free water and subsequently concentrated by ethanol precipitation. Precipitated RNA was taken up in nuclease free water to a final minimum concentration of 0.5 µg/µl.

Additional control microarrays were performed on RNA isolated from CD4+ T helper T cells, natural killer (NK) cells, neutrophils (N'phil), CD14+, CD16+ and CD16− monocytes and dendritic cells (DC).

Additional microarrays were performed on RNA isolated from cancerous tissue, such as Non-Hodgkin's Lymphoma (NHL), follicular lymphoma (FL) and multiple myeloma (MM). Additional microarrays were performed on RNA isolated from normal cells, such as normal lymph node (NLN), normal B cells, such as B cells from centroblasts, centrocytes and follicular mantel, memory B cells, and normal plasma cells (PC), which are from the B cell lineage and are normal counterparts of the myeloma cell, such as tonsil plasma cells, bone marrow plasma cells (BM PC), CD19+ plasma cells (CD19+ PC), CD19− plasma cells (CD19− PC). Additional microarrays were performed on normal tissue, such as cerebellum, heart, prostate, adrenal, bladder, small intestine (s. intestine), colon, fetal liver, uterus, kidney, placenta, lung, pancreas, muscle, brain, salivary, bone marrow (marrow), blood, thymus, tonsil, spleen, testes, and mammary gland.

The molecules listed below have been identified as being significantly expressed in B cells as compared to non-B cells. Specifically, the molecules are differentially expressed in naive B cells, memory B cells that are either IgGA+ or IgM+ and plasma cells from either PBMC or bone marrow, in comparison to non-B cells, for example T cells. Accordingly, these molecules represent excellent targets for therapy of tumors in mammals.

| Molecule | specific expression in: | as compared to: |
| --- | --- | --- |
| DNA182432 (TAHO3) | B cells | non-B cells |
| DNA340394 (TAHO17) | B cells | non-B cells |
| DNA56041 (TAHO18) | B cells | non-B cells |
| DNA257955 (TAHO20) | B cells | non-B cells |
| DNA329863 (TAHO21) | B cells | non-B cells |
| DNA346528 (TAHO22) | B cells | non-B cells |
| DNA257845 (TAHO38) | B cells | non-B cells |

Summary

In FIGS. 15-19, significant mRNA expression was generally indicated as a ratio value of greater than 2 (vertical axis of FIGS. 15-19). In FIGS. 15-19, any apparent expression in non-B cells, such as in prostate, spleen, etc. may represent an artifact, infiltration of normal tissue by lymphocytes or loss of sample integrity by the vendor.

Figure 15B:
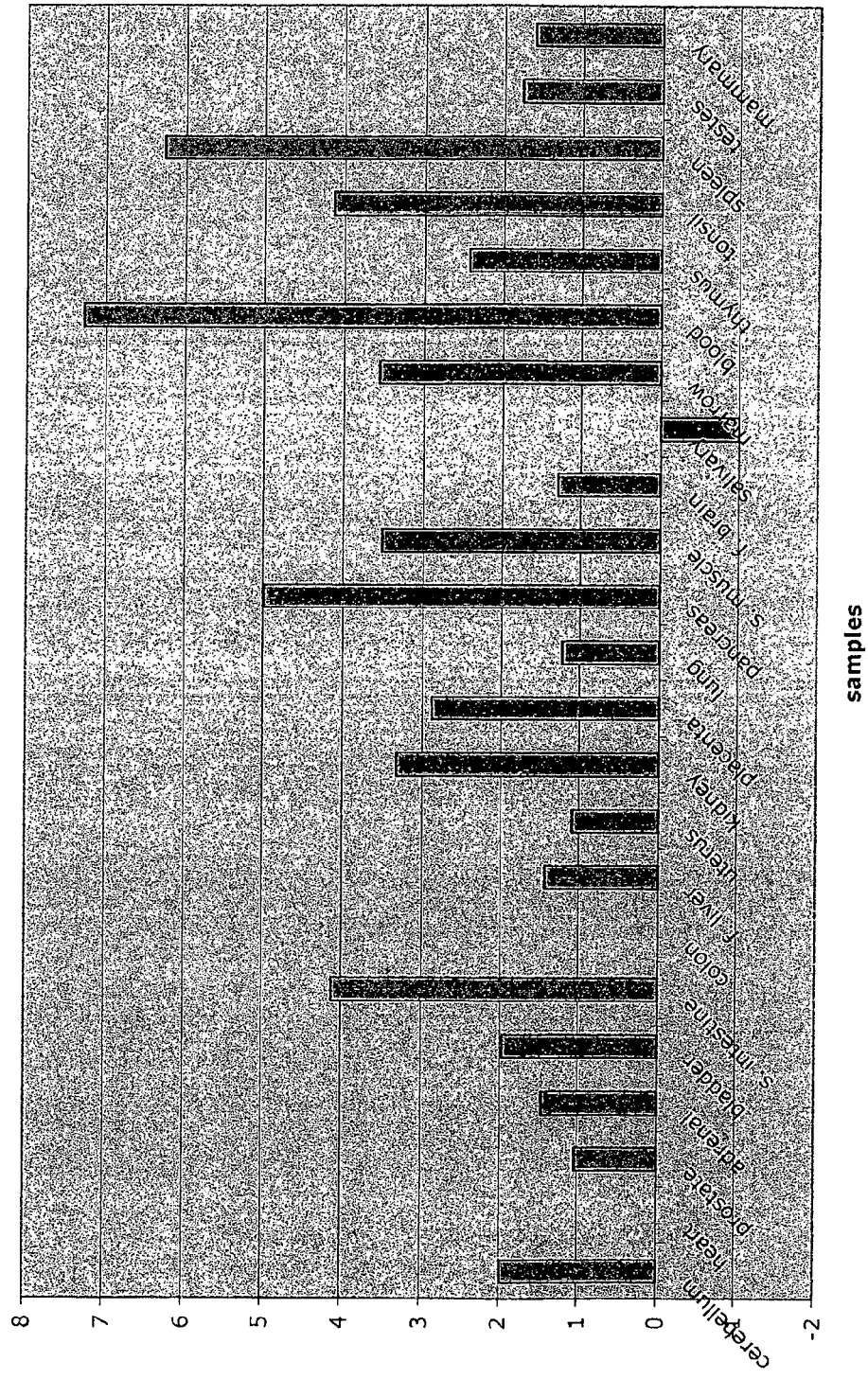
Figure 15D:
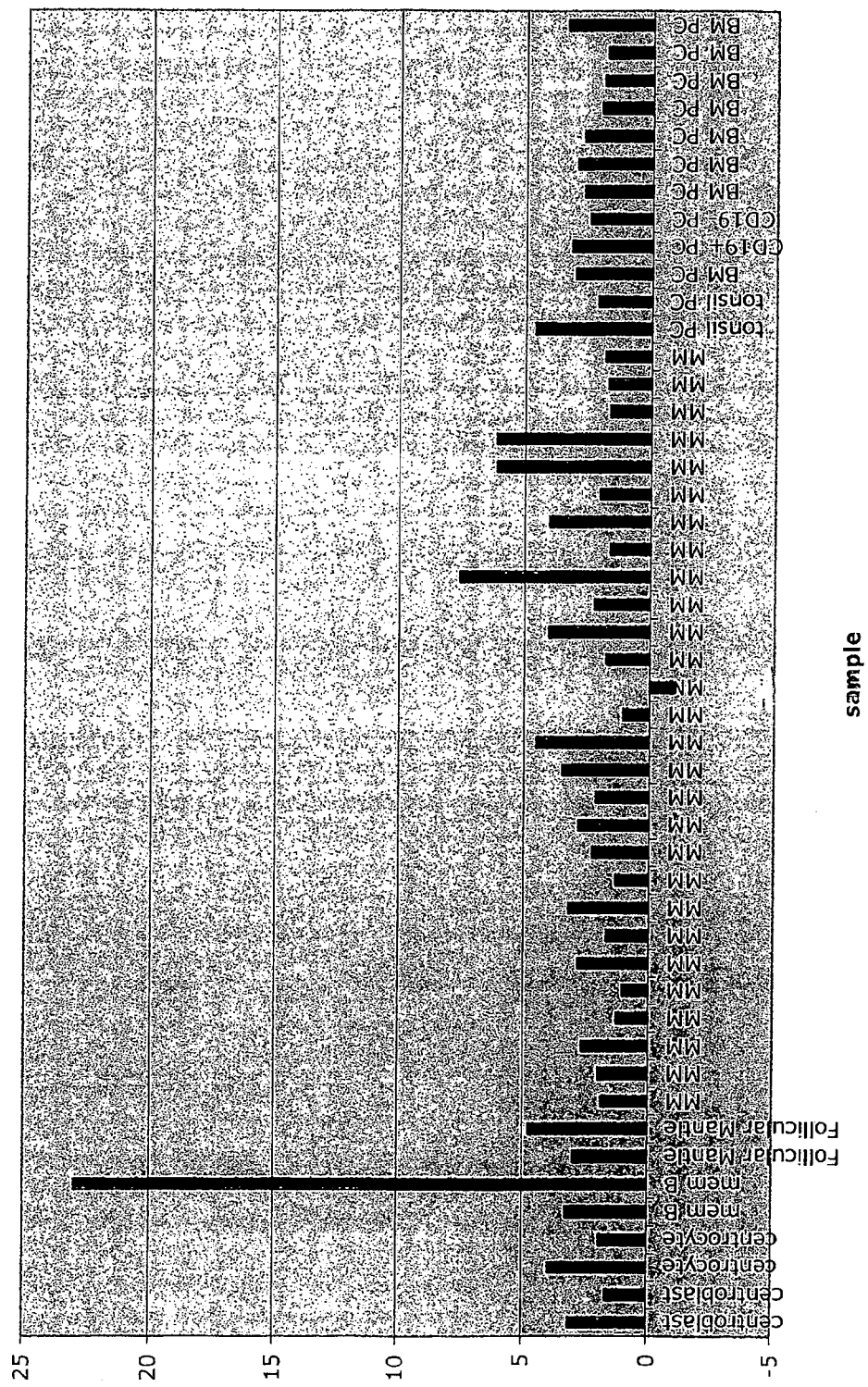
Figure 16A:
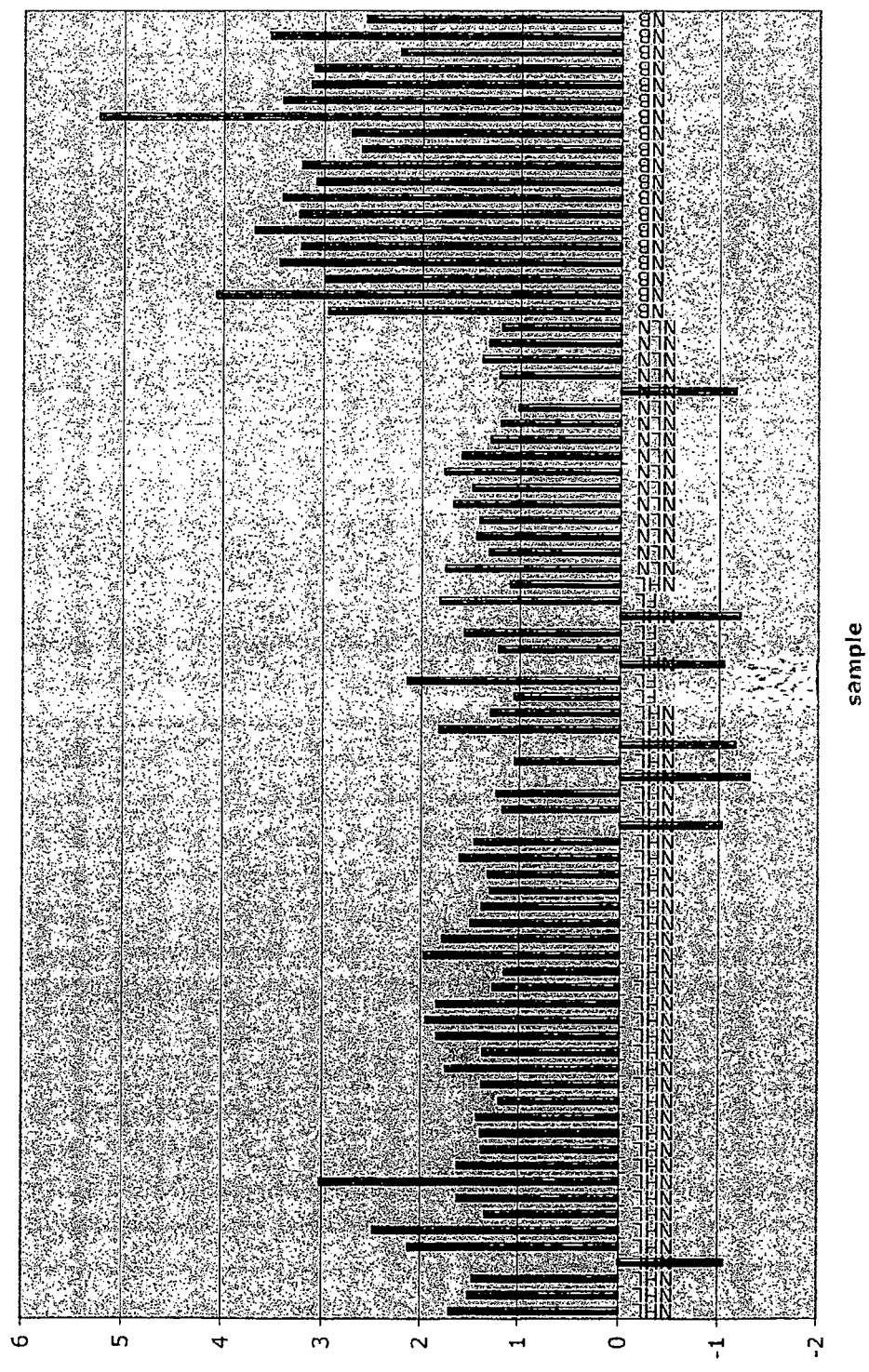
FIGS. 16A-16D show microarray data showing the expression of TAHO17 in normal samples and in diseased samples, such as significant expression in normal B cells (NB) and memory B cells (mem B). Abbreviations used in the Figures are designated as follows: Non-Hodgkin's Lymphoma (NHL), follicular lymphoma (FL), normal lymph node (NLN), normal B cells (NB), multiple myeloma cells (MM), small intestine (s. intestine), fetal liver (f. liver), smooth muscle (s. muscle), fetal brain (f. brain), natural killer cells (NK), neutrophils (N'phil), dendrocytes (DC), memory B cells (mem B), plasma cells (PC), bone marrow plasma cells (BM PC).
Figure 16B:
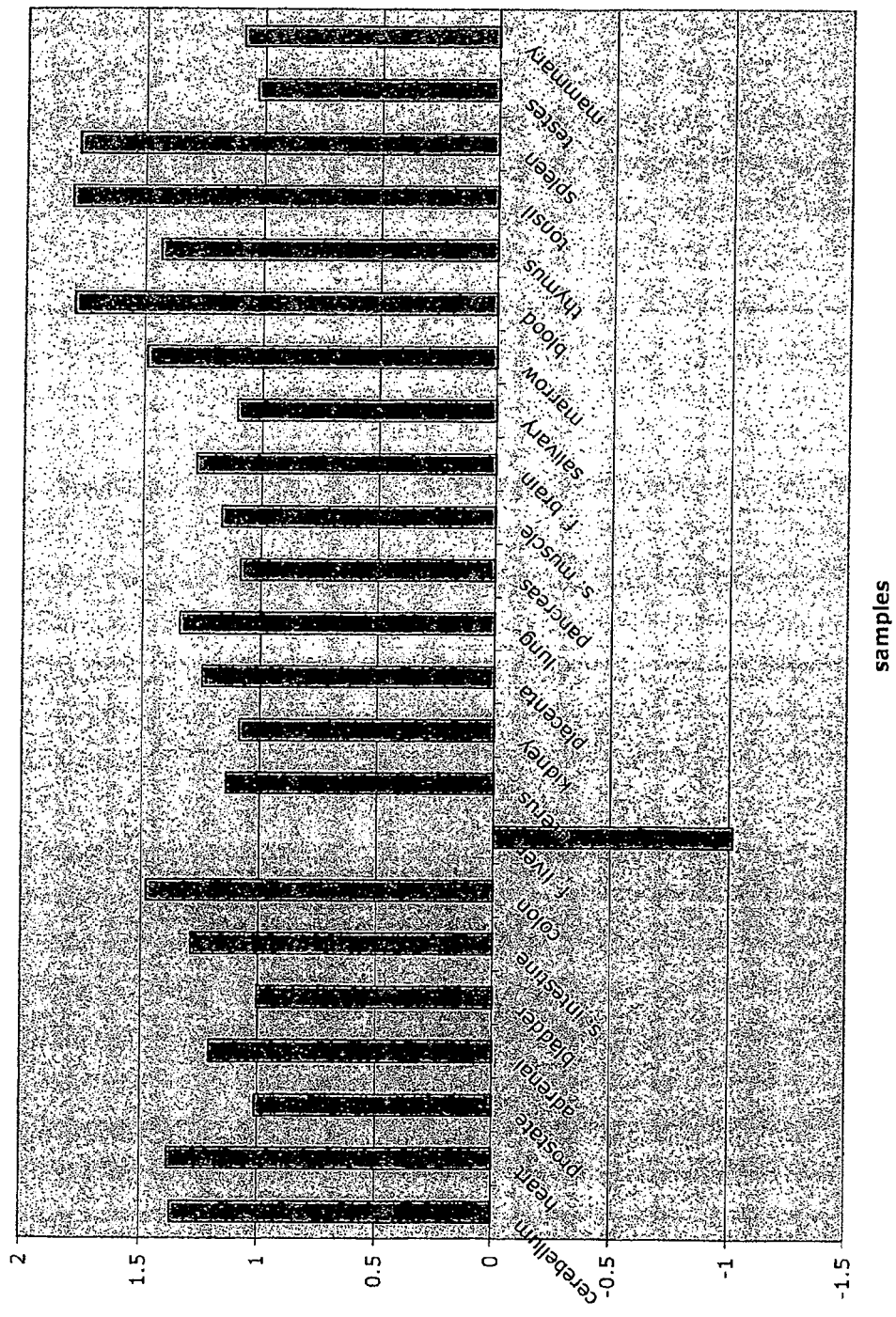
Figure 16C:
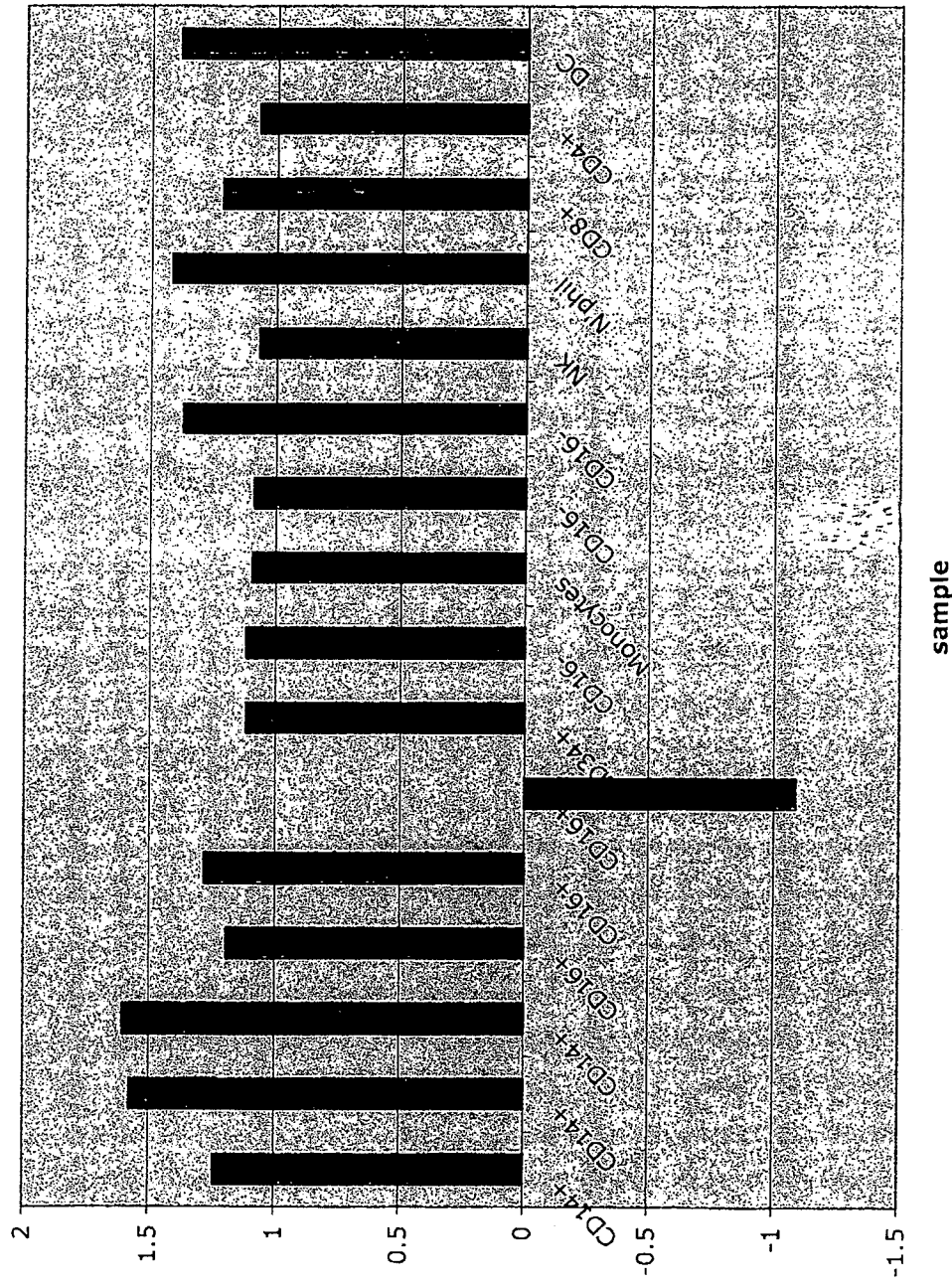
Figure 16D:
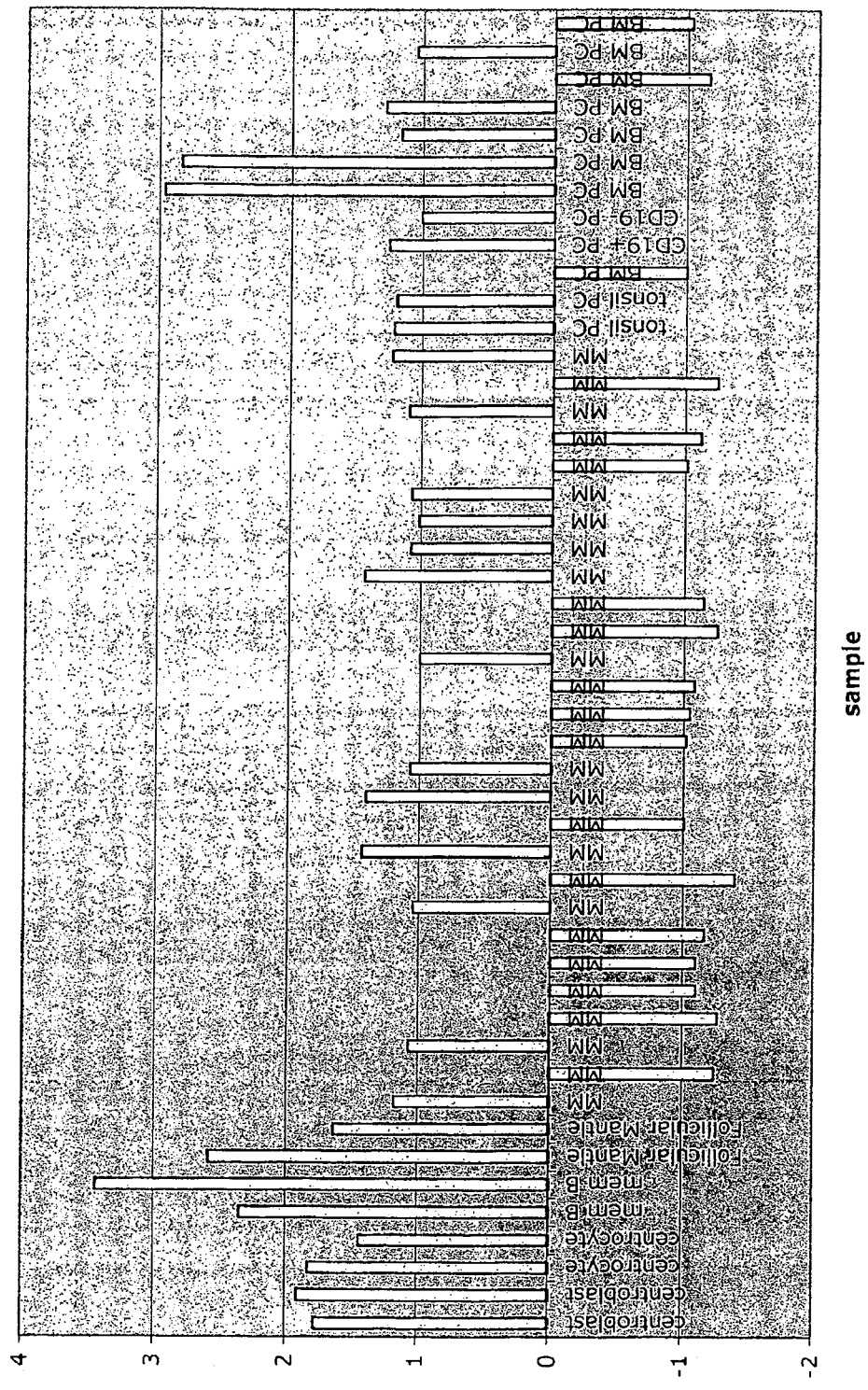
Figure 17A:
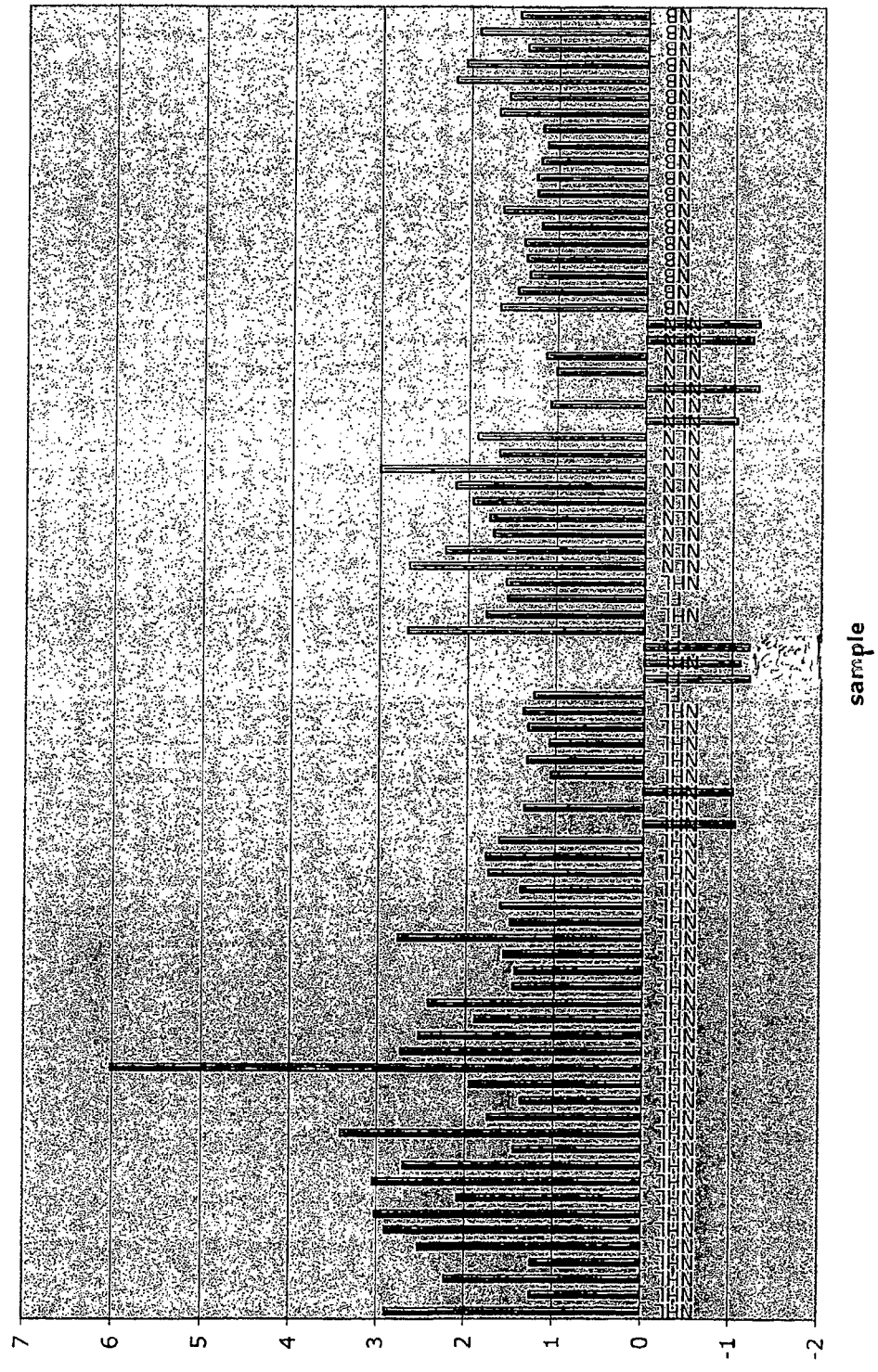
FIGS. 17A-17D show microarray data showing the expression of TAHO38 in normal samples and in diseased samples, such as significant expression in NHL samples. Abbreviations used in the Figures are designated as follows: Non-Hodgkin's Lymphoma (NHL), follicular lymphoma (FL), normal lymph node (NLN), normal B cells (NB), multiple myeloma cells (MM), small intestine (s. intestine), fetal liver (f. liver), smooth muscle (s. muscle), fetal brain (f. brain), natural killer cells (NK), neutrophils (N'phil), dendrocytes (DC), memory B cells (mem B), plasma cells (PC), bone marrow plasma cells (BM PC).
Figure 17B:
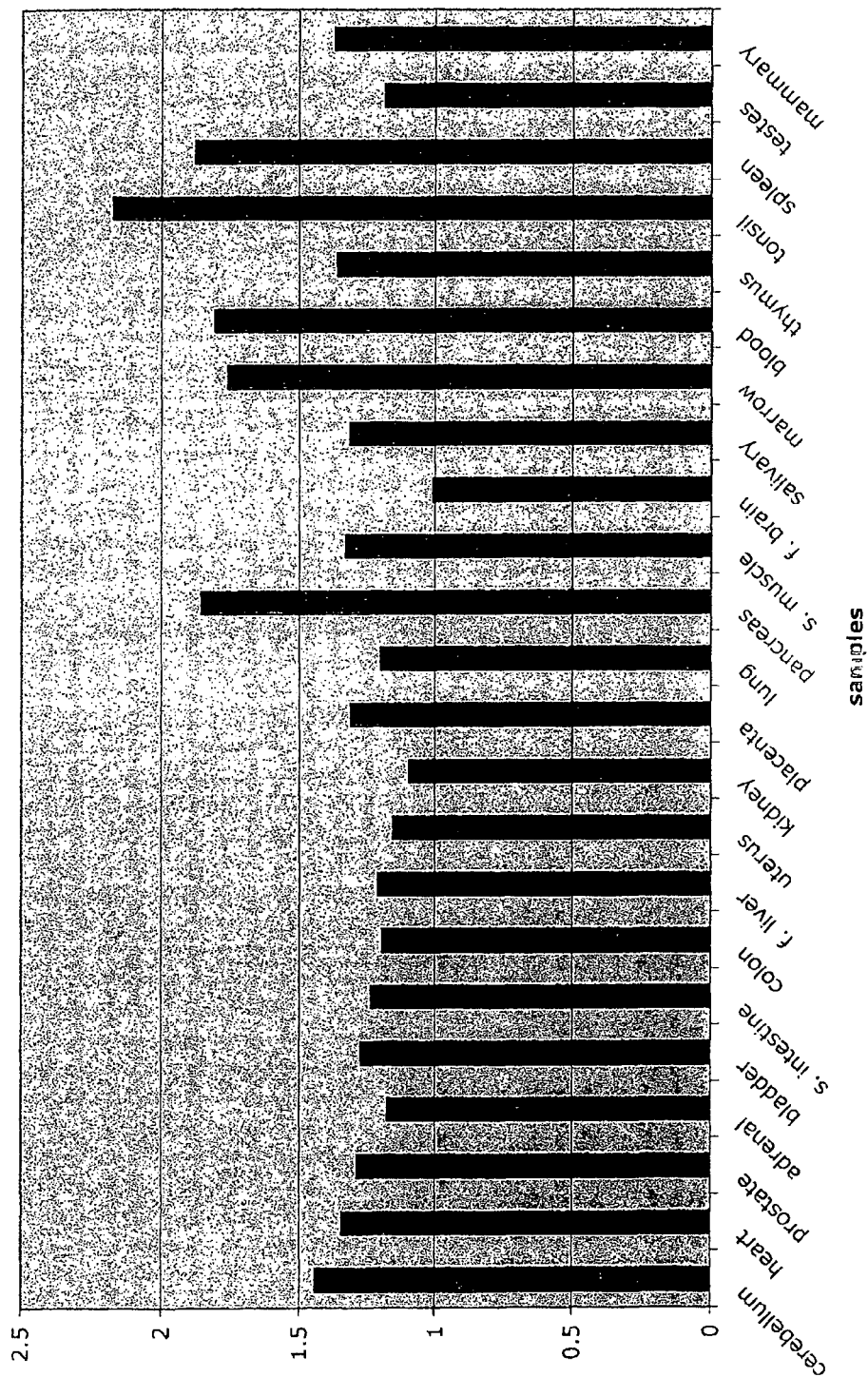
Figure 17C:
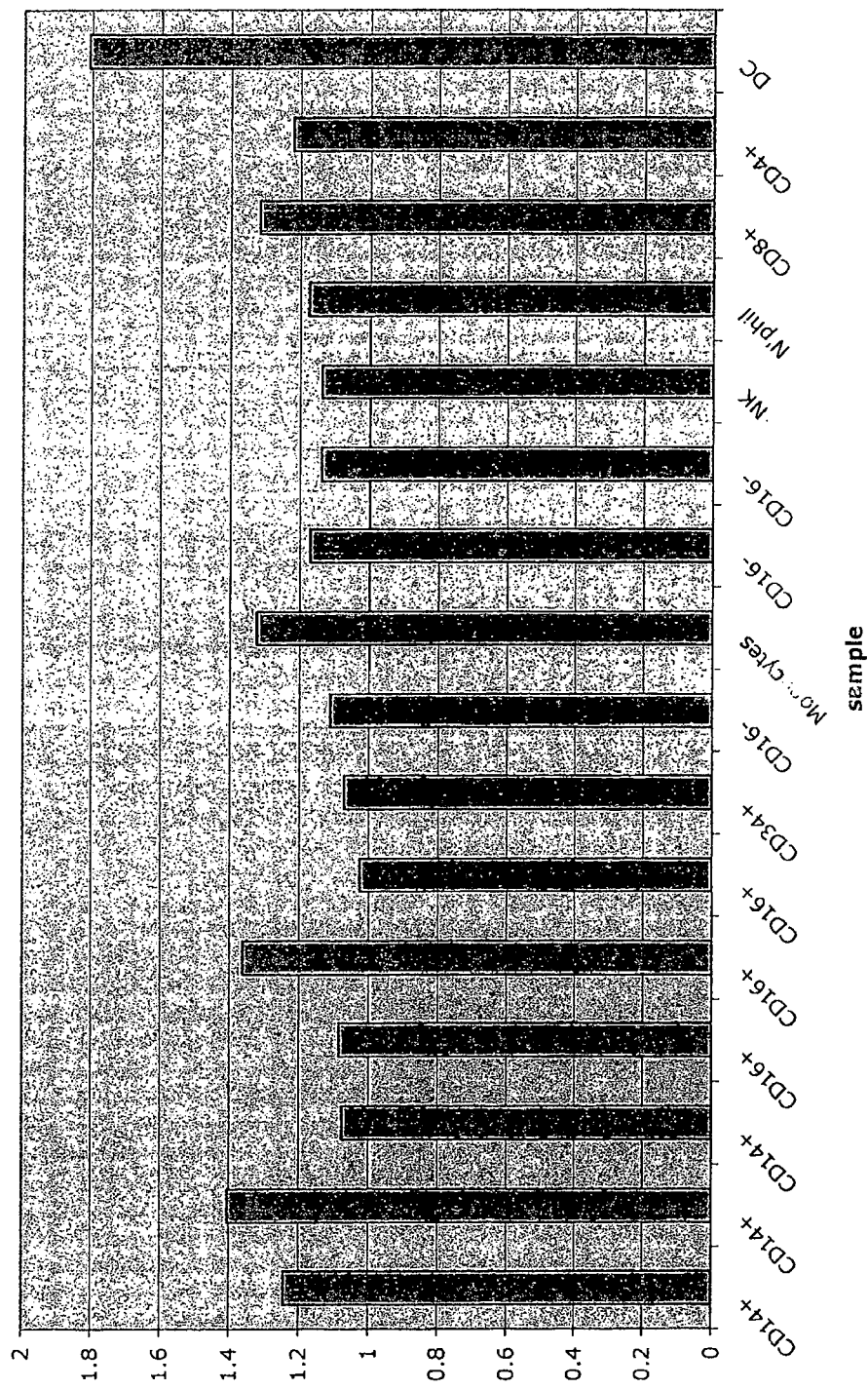
Figure 17D:
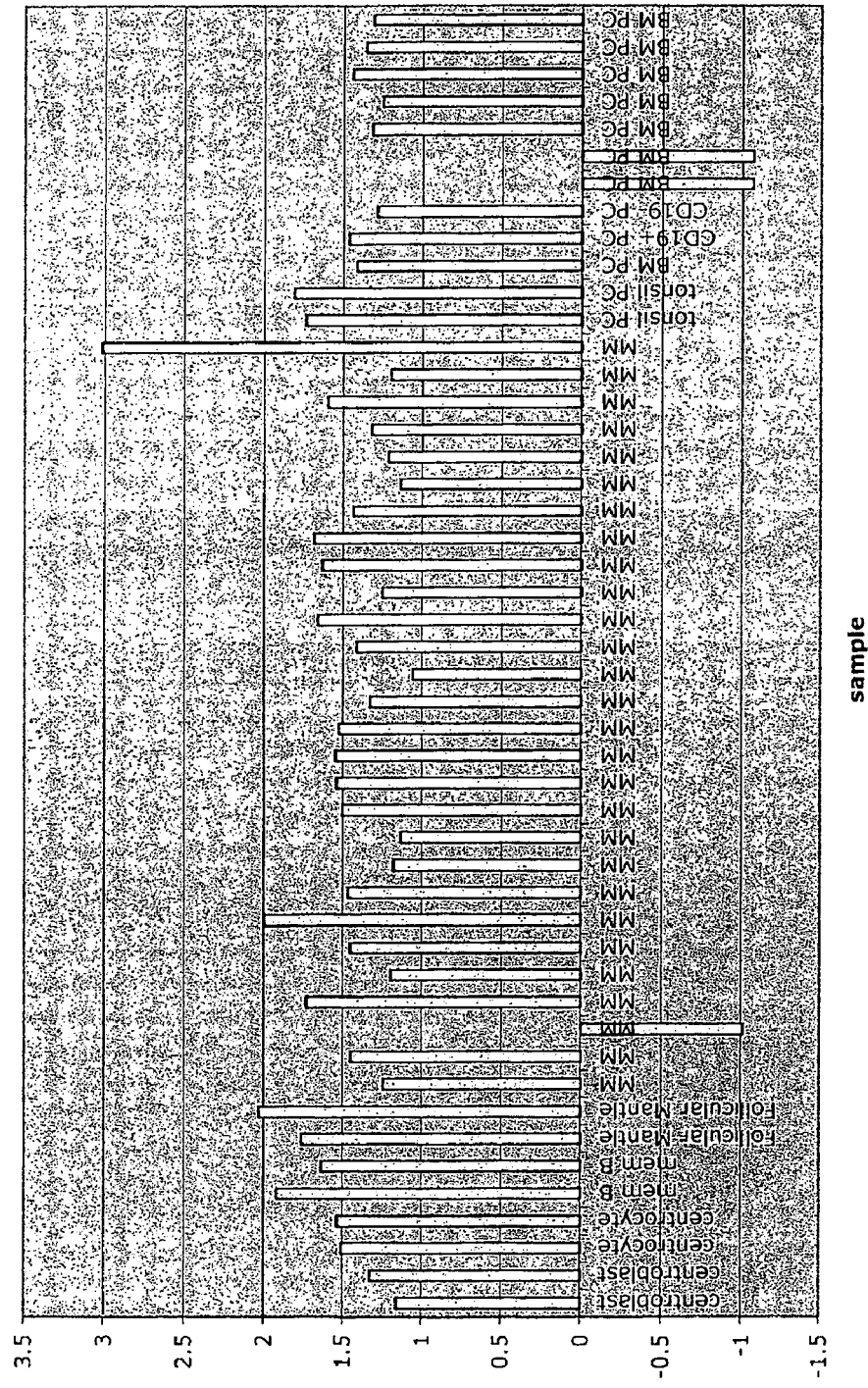
Figure 18A:
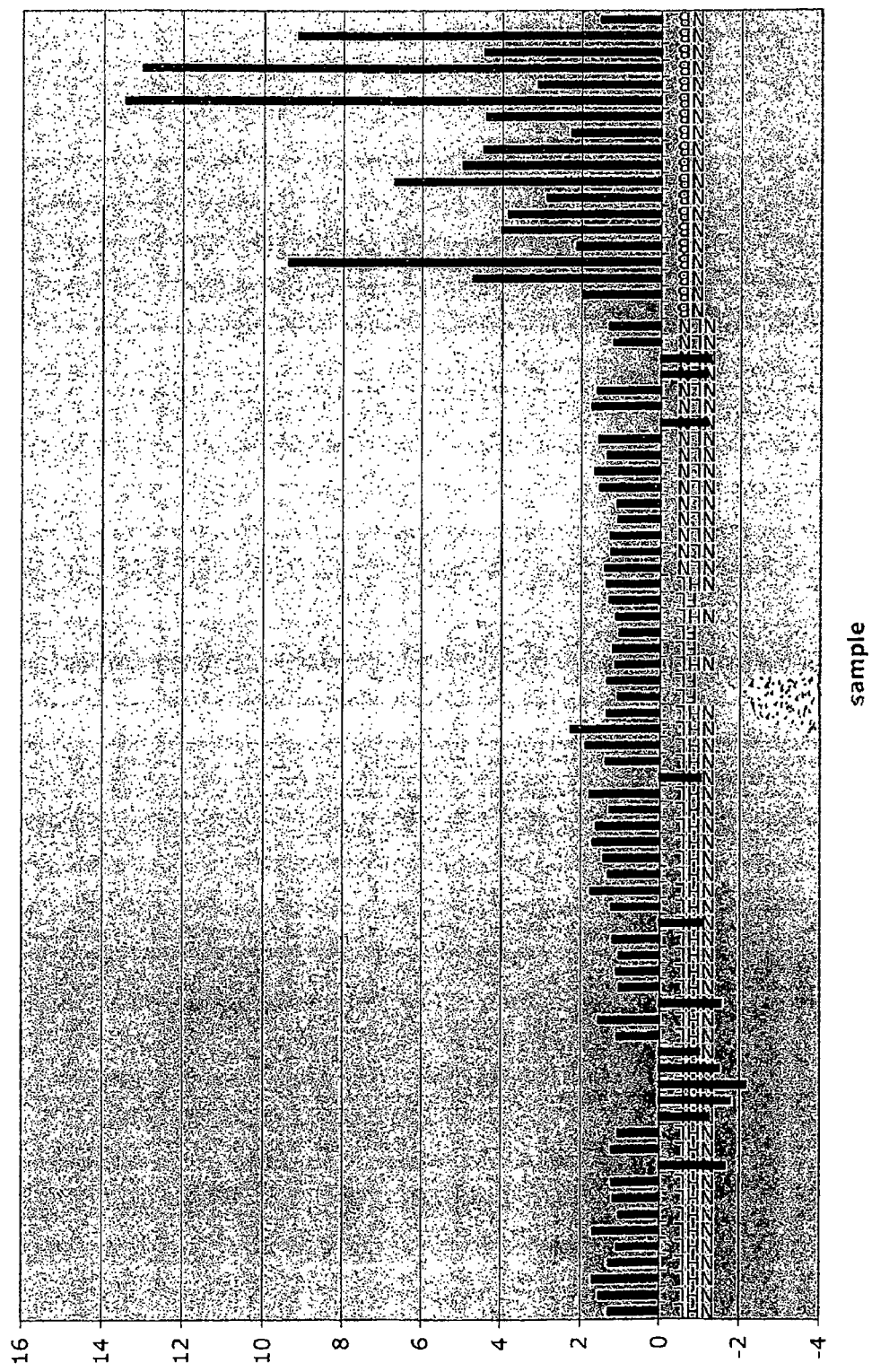
FIGS. 18A-18D show microarray data showing the expression of TAHO20 in normal samples and in diseased samples, such as significant expression in multiple myeloma (MM), normal B cells (NB) and normal colon, placenta, lung and spleen and bone marrow plasma cells (BM PC). Abbreviations used in the Figures are designated as follows: Non-Hodgkin's Lymphoma (NHL), follicular lymphoma (FL), normal lymph node (NLN), normal B cells (NB), multiple myeloma cells (MM), small intestine (s. intestine), fetal liver (f. liver), smooth muscle (s. muscle), fetal brain (f. brain), natural killer cells (NK), neutrophils (N'phil), dendrocytes (DC), memory B cells (mem B), plasma cells (PC), bone marrow plasma cells (BM PC).
Figure 18B:
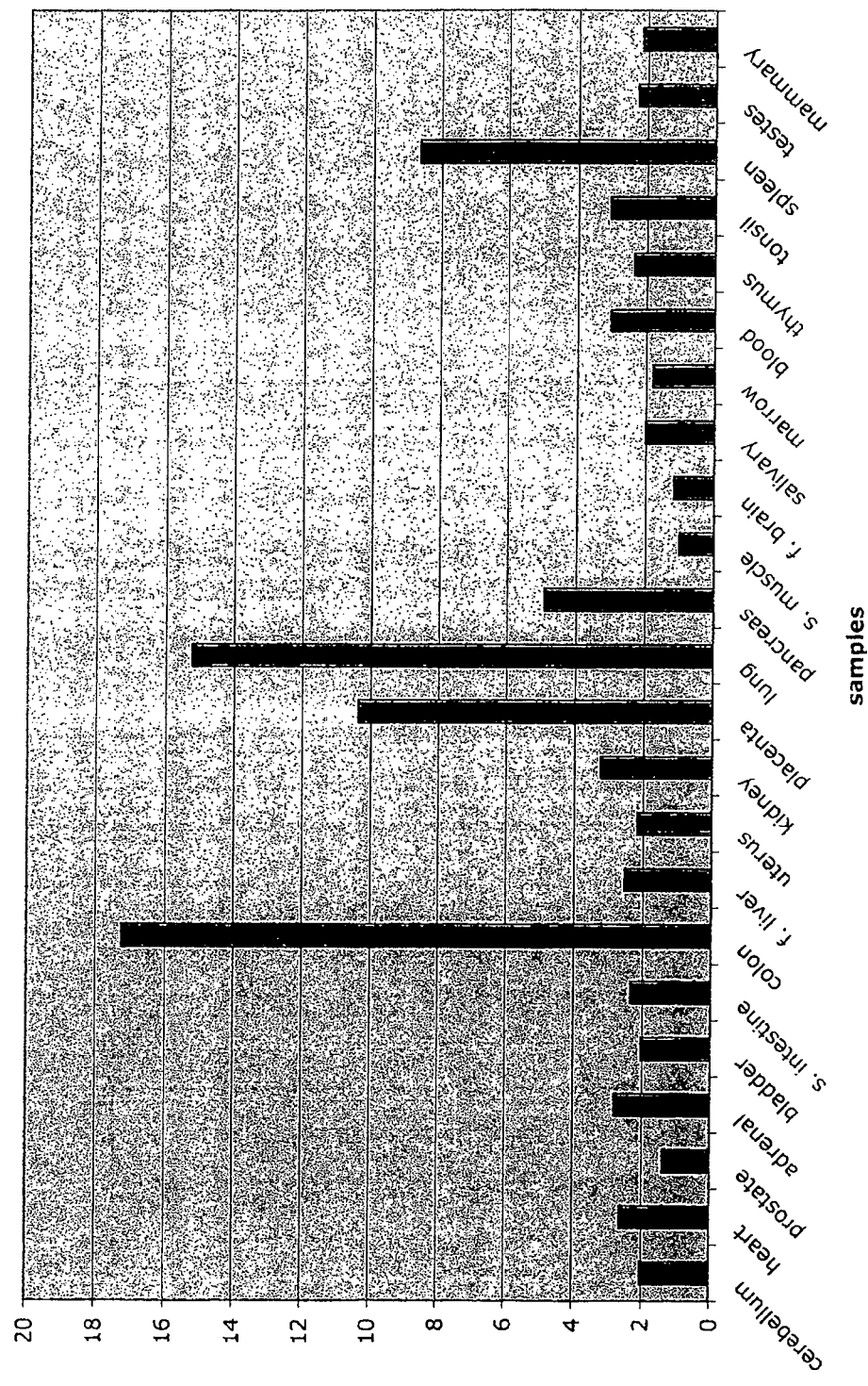
Figure 18C:
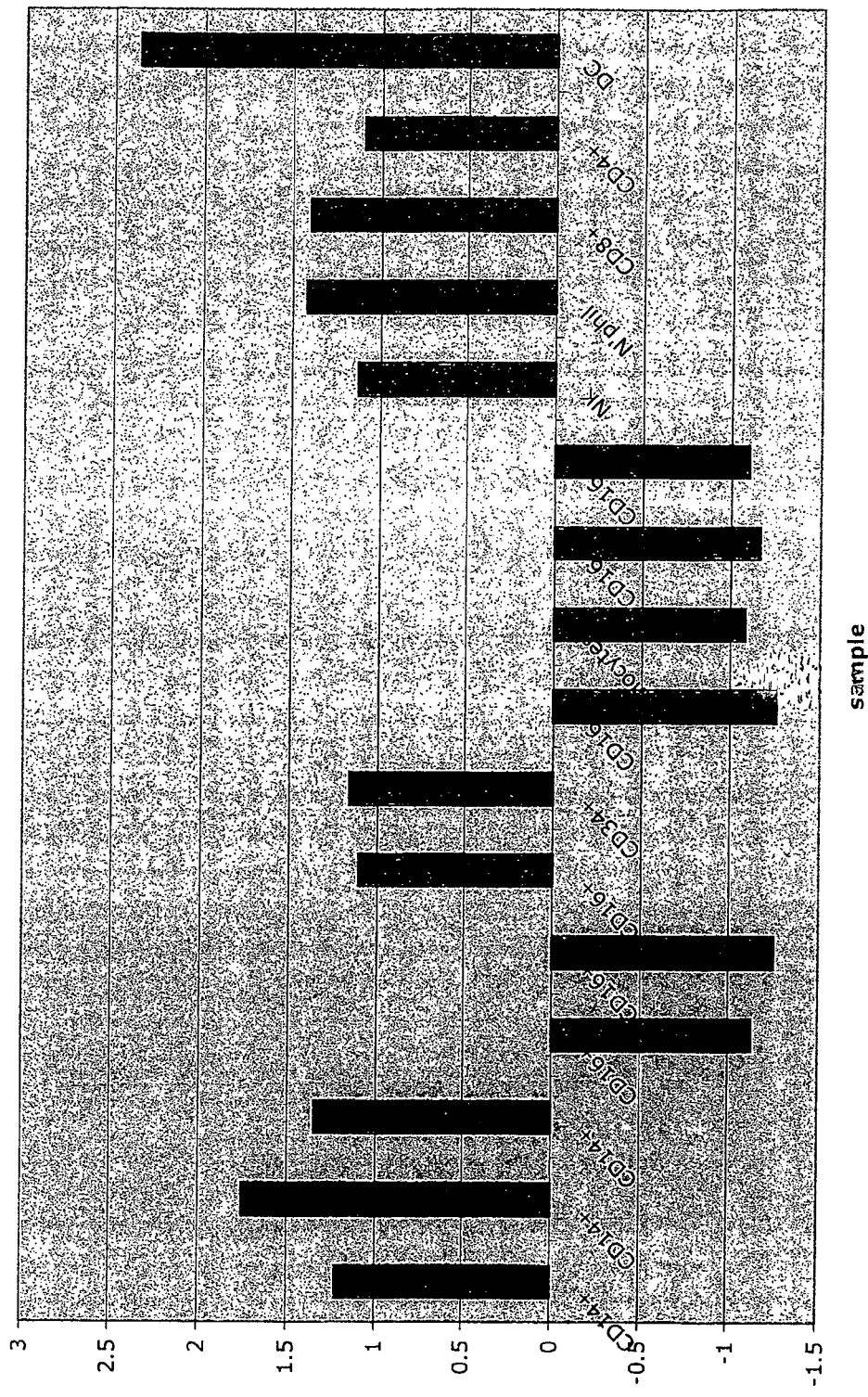
Figure 18D:
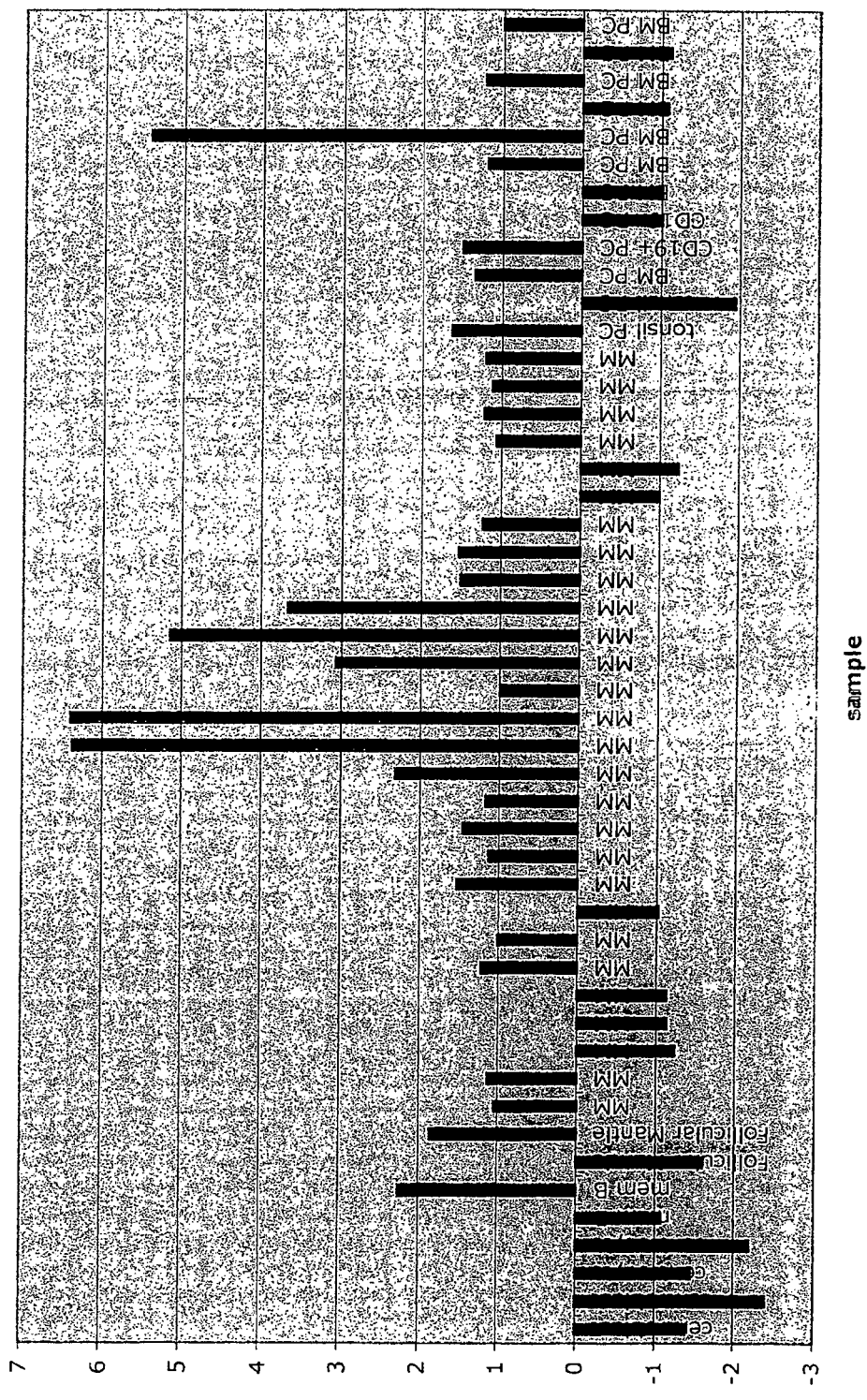

(1) TAHO3 (also referred herein as SPAP1 and FcRH2) was significantly expressed in non-hodgkin's lymphoma (NHL) and follicular lymphoma (FL) and memory B cells (mem B). Further TAHO3 was significantly expressed in blood and spleen (FIG. 15). However, as indicated above, any apparent expression in non-B cells, such as in prostate, spleen, blood etc. may represent an artifact, infiltration of normal tissue by lymphocytes or loss of sample integrity by the vendor.

(2) TAHO17 (also referred herein as FcRH1) was significantly expressed in normal B cells (NB), and memory B cells (FIG. 16).

(3) TAHO38 (also referred herein as IRTA2c) was significantly expressed in non-hodgkin's lymphoma (NHL) (FIG. 17). TAHO 18 (also referred herein as IRTA2, a portion of the extracellular region of TAHO38) was also significantly expressed in non-hodgkin's lymphoma (NHL) (data not shown).

(4) TAHO20 (also referred herein as FcRH3) was significantly expressed in normal B cells (NB) and multiple myeloma (MM). Further, TAHO20 was detected in expressed in colon, placenta, lung and spleen (FIG. 18). However, as indicated above, any apparent expression in non-B cells, such as in prostate, spleen, blood, tonsil, etc. may represent an artifact, infiltration of normal tissue by lymphocytes or loss of sample integrity by the vendor.

Figure 19A:
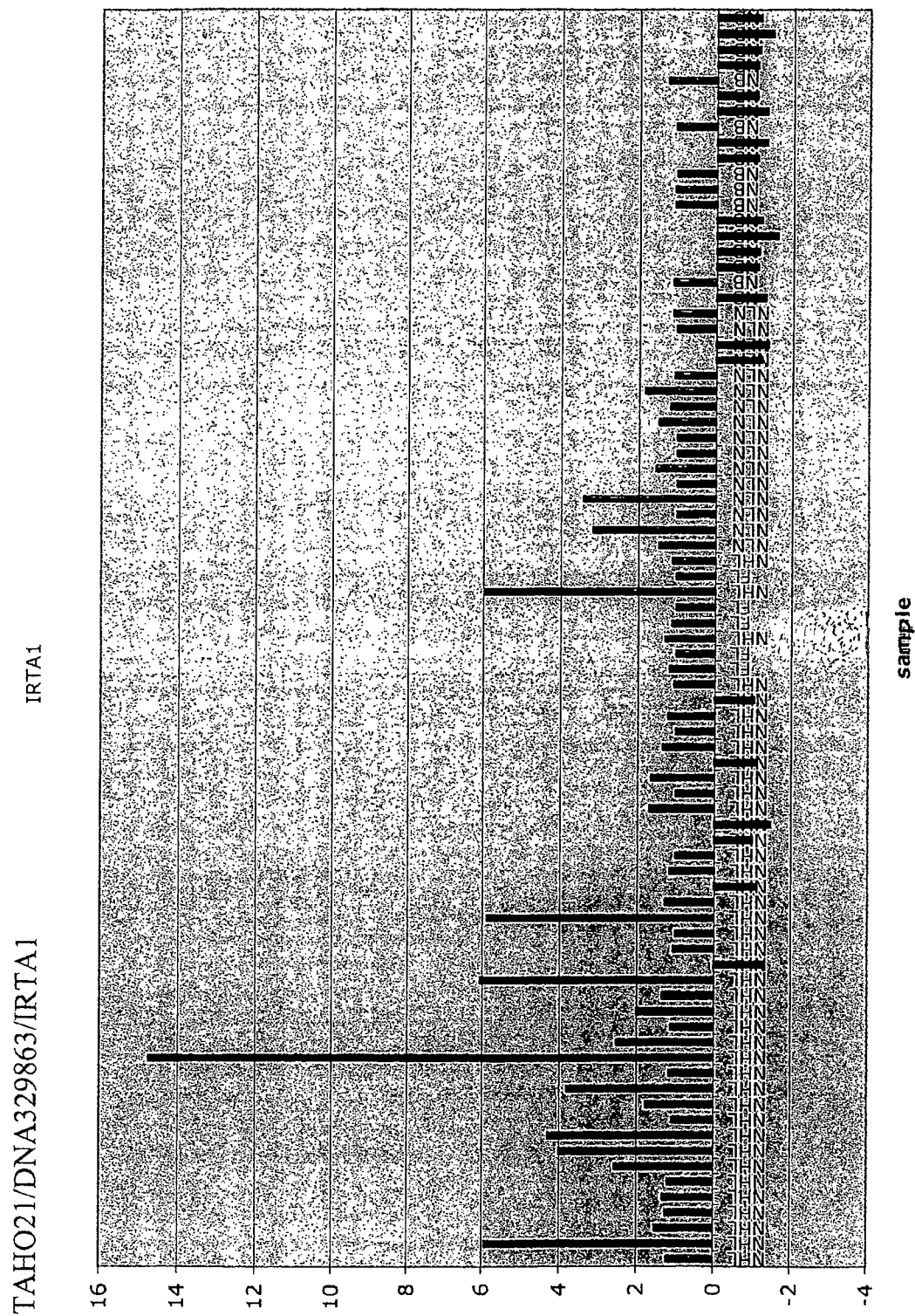
Figure 19C:
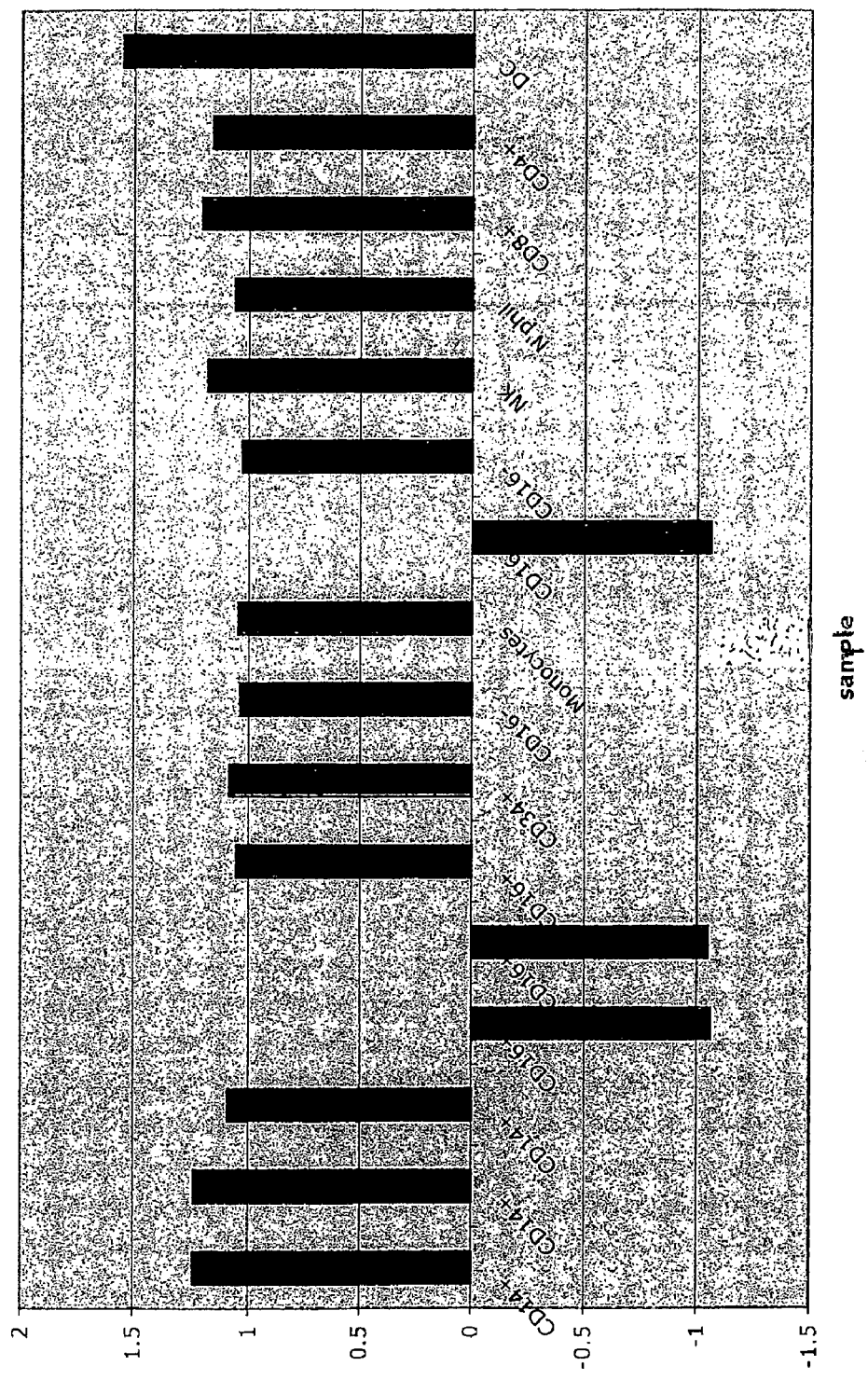
Figure 20:
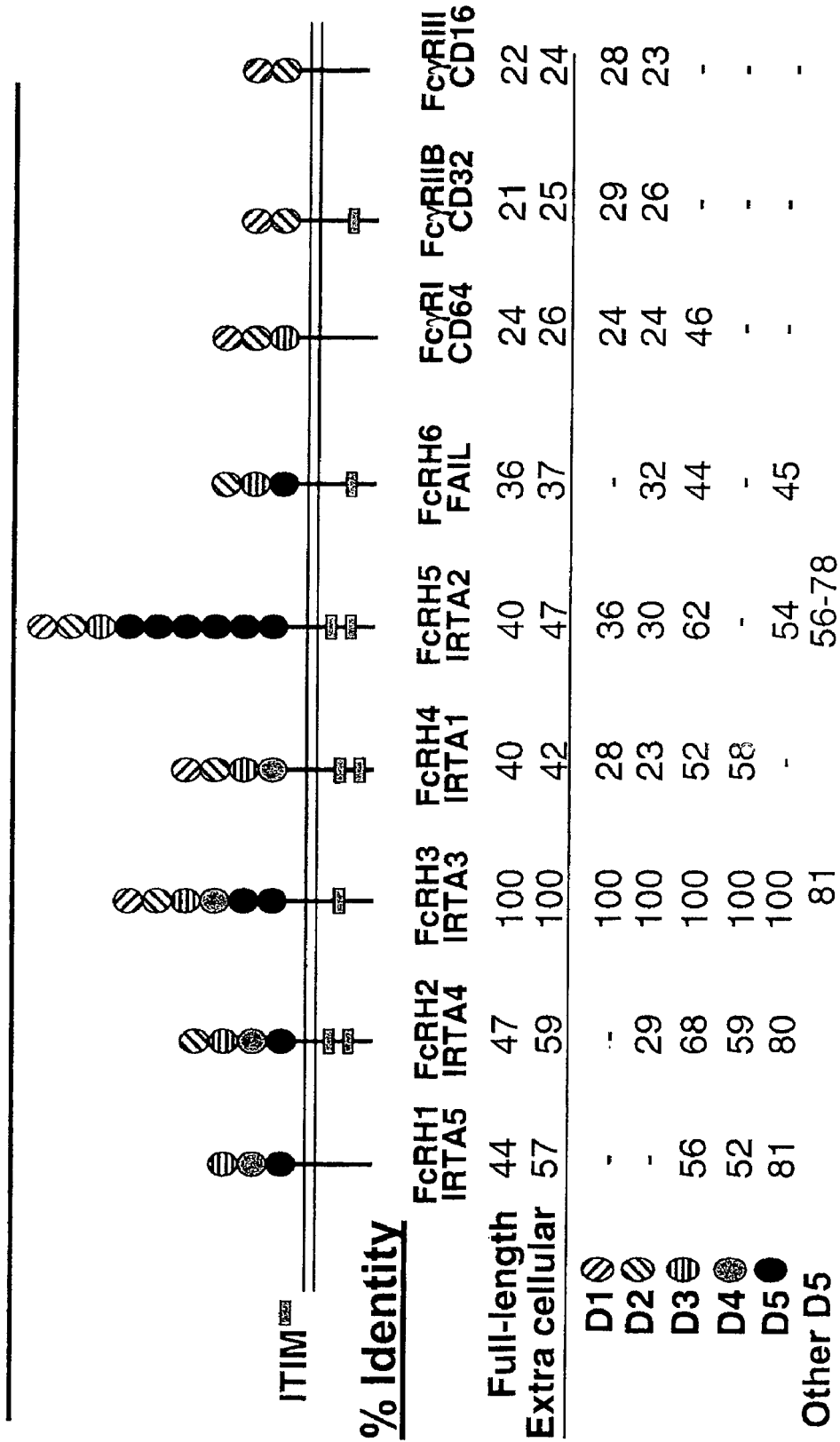
FIG. 20 shows the the homology and the percent identity between the immunoglobulin domains in the FcRHs (FcRH1, FcRH2, FcRH3, FcRH4, FcRH5c and FcRH6) and the Fcγ receptors (FcγRI, FcγRIIB, FcγRIII). The percent identity shown is identity of the respective domains with the domains of FcRH3.

(5) TAHO21 (also referred herein as IRTA1) was significantly expressed in non-hodgkin's lymphoma (NHL), centrocytes and memory B cells (FIG. 19).

Example 2

Quantitative Analysis of TAHO mRNA Expression

In this assay, a 5' nuclease assay (for example, TaqMan®) and real-time quantitative PCR (for example, Mx3000P™ Real-Time PCR System (Stratagene, La Jolla, Calif.)), were used to find genes that are significantly overexpressed in a specific tissue type, such as B cells, as compared to a different cell type, such as other primary white blood cell types, and which further may be overexpressed in cancerous cells of the specific tissue type as compared to non-cancerous cells of the specific tissue type. The 5' nuclease assay reaction is a fluorescent PCR-based technique which makes use of the 5' exonuclease activity of Taq DNA polymerase enzyme to monitor gene expression in real time. Two oligonucleotide primers (whose sequences are based upon the gene or EST sequence of interest) are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the PCR amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

The 5' nuclease procedure is run on a real-time quantitative PCR device such as the Mx3000™ Real-Time PCR System. The system consists of a thermocycler, a quartz-tungsten lamp, a photomultiplier tube (PMT) for detection and a computer. The system amplifies samples in a 96-well format on a thermocycler. During amplification, laser-induced fluorescent signal is collected in real-time through fiber optics cables for all 96 wells, and detected at the PMT. The system includes software for running the instrument and for analyzing the data. The starting material for the screen was mRNA (50 ng/well run in duplicate) isolated from a variety of different white blood cell types (Neturophil (Neutr), Natural Killer cells (NK), Dendritic cells (Dend.), Monocytes (Mono), T cells (CD4+ and CD8+ subsets), stem cells (CD34+) as well as 20 separate B cell donors (donor Ids 310, 330, 357, 362, 597, 635, 816, 1012, 1013, 1020, 1072, 1074, 1075, 1076, 1077, 1086, 1096, 1098, 1109, 1112) to test for donor variability. All RNA was purchased commercially (AllCells, LLC, Berkeley, Calif.) and the concentration of each was measured precisely upon receipt. The mRNA is quantitated precisely, e.g., fluorometrically.

5' nuclease assay data are initially expressed as Ct, or the threshold cycle. This is defined as the cycle at which the reporter signal accumulates above the background level of fluorescence. The ΔCt values are used as quantitative measurement of the relative number of starting copies of a particular target sequence in a nucleic acid sample. As one Ct unit corresponds to 1 PCR cycle or approximately a 2-fold relative increase relative to normal, two units corresponds to a 4-fold relative increase, 3 units corresponds to an 8-fold relative increase and so on, one can quantitatively measure the relative fold increase in mRNA expression between two or more different tissues. The lower the Ct value in a sample, the higher the starting copy number of that particular gene. If a standard curve is included in the assay, the relative amount of each target can be extrapolated and facilitates viewing of the data as higher copy numbers also have relative quantities (as opposed to higher copy numbers have lower Ct values) and also corrects for any variation of the generalized 1Ct equals a 2 fold increase rule. Using this technique, the molecules listed below have been identified as being significantly overexpressed (i.e., at least 2 fold) in a single (or limited number) of specific tissue or cell types as compared to a different tissue or cell type (from both the same and different tissue donors) with some also being identified as being significantly overexpressed (i.e., at least 2 fold) in cancerous cells when compared to normal cells of the particular tissue or cell type, and thus, represent excellent polypeptide targets for therapy of cancer in mammals.

| Molecule | specific expression in: | as compared to: |
|---|---|---|
| DNA182432 (TAHO3) | B cells | non-B cells |
| DNA340394 (TAHO17) | B cells | non-B cells |

Summary

TAHO3 and TAHO17 expression levels in total RNA isolated from purified B cells or from B cells from 20 B cell donors (310-1112) (AllCells) and averaged (Avg. B) was significantly higher than respective TAHO3 and TAHO17 expression levels in total RNA isolated from several white blood cell types, neutrophils (Neutr), natural killer cells (NK) (a T cell subset), dendritic cells (Dend), monocytes (Mono), CD4+ T cells, CD8+ T cells, CD34+ stem cells (data not shown).

Accordingly, as TAHO3 and TAH17 significantly expressed on B cells as compared to non-B cells as detected by TaqMan analysis, the molecules are excellent targets for therapy of tumors in mammals, including B-cell associated cancers, such as lymphomas (i.e. Non-Hodgkin's Lymphoma), leukemias (i.e. chronic lymphocytic leukemia), myelomas (i.e. multiple myeloma) and other cancers of hematopoietic cells.

Example 3

In Situ Hybridization

In situ hybridization is a powerful and versatile technique for the detection and localization of nucleic acid sequences within cell or tissue preparations. It may be useful, for example, to identify sites of gene expression, analyze the tissue distribution of transcription, identify and localize viral infection, follow changes in specific mRNA synthesis and aid in chromosome mapping.

In situ hybridization was performed following an optimized version of the protocol by Lu and Gillett, Cell Vision 1:169-176 (1994), using PCR-generated $^{33}$P-labeled riboprobes. Briefly, formalin-fixed, paraffin-embedded human tissues were sectioned, deparaffinized, deproteinated in proteinase K (20 g/ml) for 15 minutes at 37° C., and further processed for in situ hybridization as described by Lu and Gillett, supra. A [$^{33}$-P] UTP-labeled antisense riboprobe was generated from a PCR product and hybridized at 55° C. overnight. The slides were dipped in Kodak NTB2 nuclear track emulsion and exposed for 4 weeks.

$^{33}$P-Riboprobe Synthesis
   6.0 µl (125 mCi) of $^{33}$P-UTP (Amersham BF 1002, SA<2000 Ci/mmol) were speed vac dried. To each tube containing dried $^{33}$P-UTP, the following ingredients were added:
   2.0 µl 5× transcription buffer
   1.0 µl DTT (100 mM)
   2.0 µl NTP mix (2.5 mM: 10µ; each of 10 mM GTP, CTP & ATP+10 µl H$_2$O)
   1.0 µl UTP (50 µM)
   1.0 µl Rnasin
   1.0 µl DNA template (1 µg)
   1.0 µl H$_2$O
   1.0 µl RNA polymerase (for PCR products T3=AS, T7=S, usually)

The tubes were incubated at 37° C. for one hour. 1.0 µl RQ1 DNase were added, followed by incubation at 37° C. for 15 minutes. 90 µl TE (10 mM Tris pH 7.6/1 mM EDTA pH 8.0) were added, and the mixture was pipetted onto DE81 paper. The remaining solution was loaded in a Microcon-50 ultrafiltration unit, and spun using program 10 (6 minutes). The filtration unit was inverted over a second tube and spun using program 2 (3 minutes). After the final recovery spin, 100 µl TE were added. 1 µl of the final product was pipetted on DE81 paper and counted in 6 ml of Biofluor II.

The probe was run on a TBE/urea gel. 1-3 µl of the probe or 5 µl of RNA Mrk III were added to 3 µl of loading buffer. After heating on a 95° C. heat block for three minutes, the probe was immediately placed on ice. The wells of gel were flushed, the sample loaded, and run at 180-250 volts for 45 minutes. The gel was wrapped in saran wrap and exposed to XAR film with an intensifying screen in −70° C. freezer one hour to overnight.

$^{33}$P-Hybridization
   A. Pretreatment of Frozen Sections

The slides were removed from the freezer, placed on aluminium trays and thawed at room temperature for 5 minutes. The trays were placed in 55° C. incubator for five minutes to reduce condensation. The slides were fixed for 10 minutes in 4% paraformaldehyde on ice in the fume hood, and washed in 0.5×SSC for 5 minutes, at room temperature (25 ml 20×SSC+ 975 ml SQ H$_2$O). After deproteination in 0.5 µg/ml proteinase K for 10 minutes at 37° C. (12.5 µl of 10 mg/ml stock in 250 ml prewarmed RNase-free RNAse buffer), the sections were washed in 0.5×SSC for 10 minutes at room temperature. The sections were dehydrated in 70%, 95%, 100% ethanol, 2 minutes each.

B. Pretreatment of Paraffin-Embedded Sections

The slides were deparaffinized, placed in SQ H$_2$O, and rinsed twice in 2×SSC at room temperature, for 5 minutes each time. The sections were deproteinated in 20 µg/ml proteinase K (500 µl of 10 mg/ml in 250 ml RNase-free RNase buffer; 37° C., 15 minutes)—human embryo, or 8× proteinase K (100 μl in 250 ml Rnase buffer, 37° C., 30 minutes)—formalin tissues. Subsequent rinsing in 0.5×SSC and dehydration were performed as described above.

C. Prehybridization

The slides were laid out in a plastic box lined with Box buffer (4×SSC, 50% formamide)—saturated filter paper.

D. Hybridization $1.0 \times 10^6$ cpm probe and 1.0 μl tRNA (50 mg/ml stock) per slide were heated at 95° C. for 3 minutes.

The slides were cooled on ice, and 48 μl hybridization buffer were added per slide. After vortexing, 50 μl $^{33}$P mix were added to 50 μl prehybridization on slide. The slides were incubated overnight at 55° C.

E. Washes

Washing was done 2×10 minutes with 2×SSC, EDTA at room temperature (400 ml 20×SSC+16 ml 0.25M EDTA, $V_f$=4 L), followed by RNaseA treatment at 37° C. for 30 minutes (500 μl of 10 mg/ml in 250 ml Rnase buffer=20 μg/ml), The slides were washed 2×10 minutes with 2×SSC, EDTA at room temperature. The stringency wash conditions were as follows: 2 hours at 55° C., 0.1×SSC, EDTA (20 ml 20×SSC+16 ml EDTA, $V_f$=4 L).

F. Oligonucleotides

In situ analysis was performed on a variety of DNA sequences disclosed herein. The oligonucleotides employed for these analyses were obtained so as to be complementary to the nucleic acids (or the complements thereof) as shown in the accompanying figures.

(2) DNA257955 (TAHO20)

```
p1   5'-TCAGCACGTGGATTCGAGTCA-3'   (SEQ ID NO: 15)

p2   5'-GTGAGGACGGGGCGAGAC-3'      (SEQ ID NO: 16)
```

G. Results

In situ analysis was performed on a variety of DNA sequences disclosed herein. The results from these analyses are as follows.

(1) DNA257955 (TAHO20)

Expression was observed in benign and neoplastic lymphoid cells. Specifically, in normal tissues, expression was observed in B cell areas, such as germinal centers, mantle and marginal zones, and in white pulp tissue of the spleen. This data is consistent with the potential role of this molecule in hematopoietic tumors, specifically B-cell tumors.

Example 4

Use of TAHO as a Hybridization Probe

The following method describes use of a nucleotide sequence encoding TAHO as a hybridization probe for, i.e., detection of the presence of TAHO in a mammal.

DNA comprising the coding sequence of full-length or mature TAHO as disclosed herein can also be employed as a probe to screen for homologous DNAs (such as those encoding naturally-occurring variants of TAHO) in human tissue cDNA libraries or human tissue genomic libraries.

Hybridization and washing of filters containing either library DNAs is performed under the following high stringency conditions. Hybridization of radiolabeled TAHO-derived probe to the filters is performed in a solution of 50% form amide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence TAHO can then be identified using standard techniques known in the art.

Example 5

Expression of TAHO in E. coli

This example illustrates preparation of an unglycosylated form of TAHO by recombinant expression in E. coli.

The DNA sequence encoding TAHO is initially amplified using selected PCR primers. The primers should contain restriction enzyme sites which correspond to the restriction enzyme sites on the selected expression vector. A variety of expression vectors may be employed. An example of a suitable vector is pBR322 (derived from E. coli; see Bolivar et al., Gene, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the TAHO coding region, lambda transcriptional terminator, and an argU gene.

The ligation mixture is then used to transform a selected E. coli strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized TAHO protein can then be purified using a metal chelating column under conditions that allow tight binding of the protein.

TAHO may be expressed in E. coli in a poly-His tagged form, using the following procedure. The DNA encoding TAHO is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an E. coli host based on strain 52 (W3110 fuhA(tonA) lon galE rpoHts(htpRts) clpP(lacIq). Transformants are first grown in LB containing 50 mg/ml carbenicillin at 30° C. with shaking until an O.D.600 of 3-5 is reached. Cultures are then diluted 50-100 fold into CRAP media (prepared by mixing 3.57 g $(NH_4)_2SO_4$, 0.71 g sodium citrate.2H2O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

E. coli paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1 M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3-5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded TAHO polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Certain of the TAHO polypeptides disclosed herein have been successfully expressed and purified using this technique(s).

Example 6

Expression of TAHO in Mammalian Cells

This example illustrates preparation of a potentially glycosylated form of TAHO by recombinant expression in mammalian cells.

The vector, pRK5 (see EP 307,247, published Mar. 15, 1989), is employed as the expression vector. Optionally, the TAHO DNA is ligated into pRK5 with selected restriction enzymes to allow insertion of the TAHO DNA using ligation methods such as described in Sambrook et al., supra. The resulting vector is called pRK5-TAHO.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-TAHO DNA is mixed with about 1 μg DNA encoding the VA RNA gene [Thimmappaya et al., Cell, 31:543 (1982)] and dissolved in 500 μl of 1 mM Tris-HCl, 0.1 mM EDTA, 0.227 M CaCl$_2$. To this mixture is added, dropwise, 500 μl of 50 mM HEPES (pH 7.35), 280 mM NaCl, 1.5 mM NaPO$_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of TAHO polypeptide. The cultures containing transfected cells may undergo further incubation (in serum free medium) and the medium is tested in selected bioassays.

In an alternative technique, TAHO may be introduced into 293 cells transiently using the dextran sulfate method described by Somparyrac et al., Proc. Natl. Acad. Sci., 12:7575 (1981). 293 cells are grown to maximal density in a spinner flask and 700 μg pRK5-TAHO DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed TAHO can then be concentrated and purified by any selected method, such as dialysis and/or column chromatography.

In another embodiment, TAHO can be expressed in CHO cells. The pRK5-TAHO can be transfected into CHO cells using known reagents such as CaPO$_4$ or DEAE-dextran. As described above, the cell cultures can be incubated, and the medium replaced with culture medium (alone) or medium containing a radiolabel such as $^{35}$S-methionine. After determining the presence of TAHO polypeptide, the culture medium may be replaced with serum free medium. Preferably, the cultures are incubated for about 6 days, and then the conditioned medium is harvested. The medium containing the expressed TAHO can then be concentrated and purified by any selected method.

Epitope-tagged TAHO may also be expressed in host CHO cells. The TAHO may be subcloned out of the pRK5 vector. The subclone insert can undergo PCR to fuse in frame with a selected epitope tag such as a poly-his tag into a Baculovirus expression vector. The poly-his tagged TAHO insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged TAHO can then be concentrated and purified by any selected method, such as by $Ni^{2+}$-chelate affinity chromatography.

TAHO may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., *Nucl. Acids Res.* 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect® (Quiagen), Dosper® or Fugene® (Boehringer Mannheim). The cells are grown as described in Lucas et al., supra. Approximately $3 \times 10^7$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 µm filtered PS20 with 5% 0.2 µm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with $3 \times 10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3 L production spinner is seeded at $1.2 \times 10^6$ cells/mL. On day 0, the cell number pH ie determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 µm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 µL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Certain of the TAHO polypeptides disclosed herein have been successfully expressed and purified using this technique(s).

Example 7

Expression of TAHO in Yeast

The following method describes recombinant expression of TAHO in yeast.

First, yeast expression vectors are constructed for intracellular production or secretion of TAHO from the ADH2/GAPDH promoter. DNA encoding TAHO and the promoter is inserted into suitable restriction enzyme sites in the selected plasmid to direct intracellular expression of TAHO. For secretion, DNA encoding TAHO can be cloned into the selected plasmid, together with DNA encoding the ADH2/GAPDH promoter, a native TAHO signal peptide or other mammalian signal peptide, or, for example, a yeast alpha-factor or invertase secretory signal/leader sequence, and linker sequences (if needed) for expression of TAHO.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant TAHO can subsequently be isolated and purified by removing the yeast cells from the fermentation medium by centrifugation and then concentrating the medium using selected cartridge filters. The concentrate containing TAHO may further be purified using selected column chromatography resins.

Certain of the TAHO polypeptides disclosed herein have been successfully expressed and purified using this technique(s).

Example 8

Expression of TAHO in Baculovirus-Infected Insect Cells

The following method describes recombinant expression of TAHO in Baculovirus-infected insect cells.

The sequence coding for TAHO is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding TAHO or the desired portion of the coding sequence of TAHO such as the sequence encoding an extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated byco-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged TAHO can then be purified, for example, by $Ni^{2+}$-chelate affinity chromatography as follows. Extracts are prepared from recombinant virus-infected Sf9 cells as described by Rupert et al., *Nature*, 362:175-179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 µm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged TAHO are pooled and dialyzed against loading buffer.

Alternatively, purification of the IgG tagged (or Fc tagged) TAHO can be performed using known chromatography techniques, including for instance, Protein A or protein G column chromatography.

Certain of the TAHO polypeptides disclosed herein have been successfully expressed and purified using this technique(s).

Example 9

Preparation of Antibodies that Bind TAHO

This example illustrates preparation of monoclonal antibodies which can specifically bind TAHO.

Techniques for producing the monoclonal antibodies are known in the art and are described, for instance, in Goding, supra. Immunogens that may be employed include purified TAHO, fusion proteins containing TAHO, and cells expressing recombinant TAHO on the cell surface. Selection of the immunogen can be made by the skilled artisan without undue experimentation.

Mice, such as Balb/c, are immunized with the TAHO immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-TAHO antibodies.

After a suitable antibody titer has been detected, the animals "positive" for antibodies can be injected with a final intravenous injection of immunogen. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against immunogen. Determination of "positive" hybridoma cells secreting the desired monoclonal antibodies against immunogen is within the skill in the art.

The positive hybridoma cells can be injected intraperitoneally into syngeneic Balb/c mice to produce ascites containing the anti-immunogen monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Antibodies directed against certain of the TAHO polypeptides disclosed herein can be successfully produced using this technique(s). More specifically, functional monoclonal antibodies that are capable of recognizing and binding to TAHO protein (as measured by standard ELISA, FACS sorting analysis and/or immunohistochemistry analysis) can be successfully generated against the following TAHO proteins as disclosed herein: TAHO3 (DNA182432), TAHO17 (DNA340394), TAHO18 (DNA56041), TAHO20 (DNA257955), TAHO21 (DNA329863), TAHO22 (DNA346528), TAHO38 (DNA257845).

In addition to the preparation of monoclonal antibodies directed against the TAHO polypeptides as described herein, many of the monoclonal antibodies can be successfully conjugated to a cell toxin for use in directing the cellular toxin to a cell (or tissue) that expresses a TAHO polypeptide of interested (both in vitro and in vivo). For example, toxin (e.g., DM1) derivitized monoclonal antibodies can be successfully generated to the following TAHO polypeptides as described herein: TAHO3 (DNA182432), TAHO17 (DNA340394), TAHO18 (DNA56041), TAHO20 (DNA257955), TAHO21 (DNA329863), TAHO22 (DNA346528), TAHO38 (DNA257845).

Generation of FcRH/IRTA (TAHO3, TAHO17, TAHO18. TAHO20, TAHO21. TAHO38) Stable Cell Lines To make cell lines for screening the FcRH antibodies, SVT2 mouse fibroblast cell lines stably expressing the tagged and untagged FcRH/IRTAs were generated. The FcRH/IRTA cDNA were PCR amplified from a spleen cell library and TA cloned (Invitrogen) into pCR4. To make the untagged expression construct the open reading frames (ORFs) were cloned into the mammalian expression vector pCMV.PD.nbe by using PCR to add restriction sites, digestion of the PCR product and ligation into the vector. N-terminal tagged expression constructs were made by amplification of the FcRH/IRTA ORFs without the signal sequence and ligation of the PCR product into the pMSCVneo (Clontech) vector containing the gD tag and signal sequence (M G G T A A R L G A V I L F V V I V G H G V R G K Y A L A D A S L K M A D P N R F R G K D L P V L D Q L L)(SEQ ID NO: 17). For each FcRH/IRTA two stable cell lines were established for use in screening the monoclonal antibodies for FACS specific reactivity and crossreactivity between the FcRH/IRTAs. The gD-tagged and untagged expression vectors were transfected into SVT2 (grown in high glucose DMEM+10% FBS+2 mM L-glutamine cells) by the standard Lipofectamine 2000 (Invitrogen; Carlsbad, Calif.) protocol. The gD-tagged transfectants were put under 0.5 mg/ml Geneticin (Invitrogen; Carlsbad, Calif.) selection for one week and then single cell FACS sorted with gD-tag specific monoclonal antibody (gD:952, Genentech; South San Francisco) to acquire the highest expressing clone. The untagged transfectants were put under 5.0 ug/ml puromycin (Calbiochem; La Jolla, Calif.) selection until visible colonies grew out. RNA from each colony was isolated by the standard Trizolâ (Invitrogen; Carlsbad, Calif.) protocol and TaqManâ (ABI; Foster City, Calif.) run to determine the highest producing clone.

Generation of Monoclonal Antibodies to the FcRHs/IRTAs (TAHO3, TAHO17, TAHO18. TAHO20, TAHO21, TAHO38)

Protein for immunization of mice was generated by transient transfection of vectors that expresses the His-tagged extra-cellular domains (ECDs) of the FcRHs/IRTAs into CHO cells. The proteins were purified from the transfected cell supernatants on nickel columns and the identity of the protein confirmed by N-terminal sequencing.

Ten Balb/c mice (Charles River Laboratories, Hollister, Calif.) or twenty Xenomiceä (Abgenix, Fremont, Calif.) were hyperimmunized with recombinant polyhistidine-tagged (HIS6) protein, in Ribi adjuvant (Ribi Immunochem Research, Inc., Hamilton, Mo.). B-cells from mice demonstrating high antibody titers against the immunogen by direct ELISA, and specific binding to SVT2 mouse fibroblast cells stably expressing the FcRH of interest by FACS, were fused with mouse myeloma cells (X63.Ag8.653; American Type Culture Collection, Rockville, Md.) using a modified protocol analogous to one previously described (Kohler and Milstein, 1975; Hongo et al., 1995). After 10-12 days, the supernatants were harvested and screened for antibody production and binding by direct ELISA and FACS. Positive clones, showing the highest immunobinding after the second round of subcloning by limiting dilution, were expanded and cultured for further characterization, including FcRH1, -2, -3, -4, and -5 specificity and crossreactivity. The supernatants harvested from each hybridoma lineage were purified by affinity chromatography (Pharmacia fast protein liquid chromatography [FPLC]; Pharmacia, Uppsala, Sweden) using a modified protocol analogous to one previously described (Hongo et al., 1995). The purified antibody preparations were then sterile filtered (0.2-μm pore size; Nalgene, Rochester N.Y.) and stored at 4° C. in phosphate buffered saline (PBS).

Monoclonal antibodies that are capable of recognizing and binding to TAHO protein (as measured by standard ELISA, FACS sorting analysis and/or immunohistochemistry analysis) have been successfully generated against the TAHO3 (FcRH2/IRTA4), TAHO17 (FcRH1/IRTA5), TAHO38 (FcRH5c/IRTA2c), TAHO20 (FcRHA3/IRTA3) and TAHO21 (FcRH4/IRTA1) and have been designated as anti-FcRH2-7G7 (herein referred to as 7G7 or 7G7.7.8), anti-FcRH1-1F9 (herein referred to as 1F9 or 1F9.1.1) and anti-FcRH1-2A10 (herein referred to as 2A10 or 2A10.1.1), anti-FcRH5c-7D11 (herein referred to as 7D11 or 7D11.1.1), anti-FcRH3-6F2 (herein referred to as 6F2 or 6F2.1.1), anti-FcRH4-1A3 (herein referred to as 1A3 or 1A3.1.1), respectively, and deposited with the ATCC on Nov. 30, 2004 as PTA-6336 (7G7.7.8), PTA-6332 (1F9.1.1), PTA-6333 (2A10.1.1), PTA-6340 (7D11.1.1), PTA-6337 (6F2.1.1) and PTA-6339 (1A3.1.1).

Monoclonal antibodies that are capable of recognizing and binding to TAHO protein may also be generated against TAHO18 (FcRH5/IRTA2, a portion of the extracellular region of TAHO38).

Further, cross-reactive antibody, anti-FcRH1, 2-1D6 (herein referred to as 1D6 or 1D6.3.8), which was generated using FcRH2 antigen, but reacts with FcRH1 antigen as well as FcRH2 antigen and deposited with the ATCC as PTA-6334 on Nov. 30, 2004. 1D6 antibody was cloned and sequenced with the sequence of the heavy chain as shown in FIG. 13 (SEQ ID NO: 13) and the sequence of the light chain as shown in FIG. 14 (SEQ ID NO: 14). Cross-reactive antibody, anti-FcRH1, 2, 3-7A2 (herein referred to as 7A2.4.1), which was generated using FcRH2 antigen, but reacts with FcRH1, FcRH2, and FcRH3 antigen and deposited with the ATCC as PTA-6335 on Nov. 30, 2004. Cross-reactive antibody, anti-FcRH1, 2, 3, 5-7E4 (herein referred to as 7E4 or 7E4.1.1), which was generated using FcRH3 antigen, but reacts with FcRH1, FcRH2, FcRH3 and FcRH5c antigen and each deposited with the ATCC as PTA-6338 on Nov. 30, 2004.

Since TAHO18(FcRH5) is a portion of the extracellular domain of TAHO38 (FcRH5c), the cross-reactive antibody, anti-FcRH1, 2, 3, 5-7E4 (herein referred to as 7E4 or 7E4.1.1), may also react with TAHO18 (FcRH5).

Example 10

Purification of TAHO Polypeptides Using Specific Antibodies

Native or recombinant TAHO polypeptides may be purified by a variety of standard techniques in the art of protein purification. For example, pro-TAHO polypeptide, mature TAHO polypeptide, or pre-TAHO polypeptide is purified by immunoaffinity chromatography using antibodies specific for the TAHO polypeptide of interest. In general, an immunoaffinity column is constructed by covalently coupling the anti-TAHO polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of TAHO polypeptide by preparing a fraction from cells containing TAHO polypeptide in a soluble form. This preparation is derived by solubilization of the whole cell or of a subcellular fraction obtained via differential centrifugation by the addition of detergent or by other methods well known in the art. Alternatively, soluble TAHO polypeptide containing a signal sequence may be secreted in useful quantity into the medium in which the cells are grown.

A soluble TAHO polypeptide-containing preparation is passed over the immunoaffinity column, and the column is washed under conditions that allow the preferential absorbance of TAHO polypeptide (e.g., high ionic strength buffers in the presence of detergent). Then, the column is eluted under conditions that disrupt antibody/TAHO polypeptide binding (e.g., a low pH buffer such as approximately pH 2-3, or a high concentration of a chaotrope such as urea or thiocyanate ion), and TAHO polypeptide is collected.

Example 11

In Vitro Tumor Cell Killing Assay

Mammalian cells expressing the TAHO polypeptide of interest may be obtained using standard expression vector and cloning techniques. Alternatively, many tumor cell lines expressing TAHO polypeptides of interest are publicly available, for example, through the ATCC and can be routinely identified using standard ELISA or FACS analysis. Anti-TAHO polypeptide monoclonal antibodies (commercially available and toxin conjugated derivatives thereof) may then be employed in assays to determine the ability of the antibody to kill TAHO polypeptide expressing cells in vitro.

For example, cells expressing the TAHO polypeptide of interest are obtained as described above and plated into 96 well dishes. In one analysis, the antibody/toxin conjugate (or naked antibody) is included throughout the cell incubation for a period of 4 days. In a second independent analysis, the cells are incubated for 1 hour with the antibody/toxin conjugate (or naked antibody) and then washed and incubated in the absence of antibody/toxin conjugate for a period of 4 days. Cell viability is then measured using the CellTiter-Glo Luminescent Cell Viability Assay from Promega (Cat# G7571). Untreated cells serve as a negative control.

B cell lines (ARH-77, BJAB, Daudi, DOHH-2, Su-DHL-4, Raji and Ramos) are prepared at 5000 cells/well in separate sterile round bottom 96 well tissue culture treated plates (Cellstar 650 185). Cells are in assay media (RPMI 1460, 1% L-Glutamine, 10% fetal bovine serum (FBS; from Hyclone) and 10 mM HEPES). Cells are immediately placed in a 37° C. incubator overnight. Antibody drug conjugates are diluted at 2×10 µg/ml in assay medium. Conjugates may be linked with crosslinkers such as SMCC or disulfide linker SPP to DM1 toxin. Further, conjugates may be linked with Vc-PAB to MMAE toxin. Herceptin based conjugates (SMCC-DM1 or SPP-DM1) may be used as negative controls. Free L-DM1 equivalent to the conjugate loading dose may be used as a positive control. Samples are vortexed to ensure homogenous mixture prior to dilution. The antibody drug conjugates are further diluted serially 1:3. The cell lines are loaded 50 µl of each sample per row using a Rapidplate® 96/384 Zymark automation system. When the entire plate is loaded, the plates are reincubated for 3 days to permit the toxins to take effect. The reactions are stopped by applying 100 µl/well of Cell Glo (Promega, Cat. #G7571/2/3) to all the wells for 10 minutes. The 100 µl of the stopped well are transferred into 96 well white tissue culture treated plates, clear bottom (Costar 3610) and the luminescence is read and reported as relative light units (RLU).

Anti-TAHO polypeptide monoclonal antibodies are useful for reducing in vitro tumor growth of tumors, including B-cell associated cancers, such as lymphomas (i.e. Non-Hodgkin's Lyphoma), leukemias (i.e. chronic lymphocytic leukemia), myelomas (i.e. multiple myeloma) and other cancers of hematopoietic cells.

Example 12

In Vivo Tumor Cell Killing Assay

To test the efficacy of conjugated or unconjugated anti-TAHO polypeptide monoclonal antibodies, the effect of anti-TAHO antibody on tumors in mice is analyzed. Female CB17 ICR SCID mice (6-8 weeks of age from Charles Rivers Laboratories; Hollister, Calif.) are inoculated subcutaneously with $5×10^6$ RAJI cells or $2×10^7$ BJAB-luciferase cells. Tumor volume is calculated based on two dimensions, measured using calipers, and is expressed in $mm^3$ according to the formula: $V=0.5a×b^2$, where a and b are the long and the short diameters of the tumor, respectively. Data collected from each experimental group are expressed as mean±SE. Mice are separated into groups of 8-10 mice with a mean tumor volume between 100-200 $mm^3$, at which point intravenous (i.v.) treatment began at the antibody dose of 5 mg/kg weekly for two to three weeks. Tumors are measured either once or twice a week throughout the experiment. Mice are euthanized before tumor volumes reached 3000 $mm^3$ or when tumors showed signs of impending ulceration. All animal protocols are approved by an Institutional Animal Care and Use Committee (IACUC). Linkers between the antibody and the toxin that are used were SPP, SMCC or cys-MC-vc-PAB (a valine-citrulline (vc) dipeptide linker reagent having a maleimide component and a para-aminobenzylcarbamoyl (PAB) self-immolative component. Toxins used may be DM1 or MMAE.

Anti-TAHO polypeptide monoclonal antibodies are useful for reducing in vivo tumor growth of tumors in mammals, including B-cell associated cancers, such as lymphomas (i.e. Non-Hodgkin's Lyphoma), leukemias (i.e. chronic lymphocytic leukemia), myelomas (i.e. multiple myeloma) and other cancers of hematopoietic cells.

Example 13

Immunohistochemistry

To determine tissue expression of TAHO polypeptide and to confirm the microarray results from Example 1, immunohistochemical detection of TAHO polypeptide expression was examined in snap-frozen and formalin-fixed paraffin-embedded (FFPE) lymphoid tissues, including palatine tonsil, spleen, lymph node and Peyer's patches from the Genentech Human Tissue Bank.

Prevalence of TAHO target expression was evaluated on FFPE lymphoma tissue microarrays (Cybrdi) and a panel of 24 frozen human lymphoma specimens. Frozen tissue specimens were sectioned at 5 µm, air-dried and fixed in acetone for 5 minutes prior to immunostaining. Paraffin-embedded tissues were sectioned at 5 µm and mounted on SuperFrost Plus microscope slides (VWR).

For frozen sections, slides were placed in TBST, 1% BSA and 10% normal horse serum containing 0.05% sodium azide for 30 minutes, then incubated with Avidin/Biotin blocking kit (Vector) reagents before addition of primary antibody. Mouse monoclonal primary antibodies (commercially available) were detected with biotinylated horse anti-mouse IgG (Vector), followed by incubation in Avidin-Biotin peroxidase complex (ABC Elite, Vector) and metal-enhanced diaminobenzidine tetrahydrochloride (DAB, Pierce). Control sections were incubated with isotype-matched irrelevant mouse monoclonal antibody (Pharmingen) at equivalent concentration. Following application of the ABC-HRP reagent, sections were incubated with biotinyl-tyramide (Perkin Elmer) in amplification diluent for 5-10 minutes, washed, and again incubated with ABC-HRP reagent. Detection was using DAB as described above.

FFPE human tissue sections were dewaxed into distilled water, treated with Target Retrieval solution (Dako) in a boiling water bath for 20 minutes, followed by a 20 minute cooling period. Residual endogenous peroxidase activity was blocked using 1× Blocking Solution (KPL) for 4 minutes. Sections were incubated with Avidin/Biotin blocking reagents and Blocking Buffer containing 10% normal horse serum before addition of the monoclonal antibodies, diluted to 0.5-5.0 µg/ml in Blocking Buffer. Sections were then incubated sequentially with biotinylated anti-mouse secondary antibody, followed by ABC-HRP and chromogenic detection with DAB. Tyramide Signal Amplification, described above, was used to increase sensitivity of staining for a number of TAHO targets (TAHO17 and TAHO21). TAHO antibodies for this experiment included commercially available antibodies and the TAHO antibodies described herein, including anti-TAHO17 (1F9), anti-TAHO3 (2G7) and anti-TAHO21 (1A3).

Summary (1) TAHO17 (FcRH1 or IRTA5) showed strong labeling of mantle zone and weaker, but significant labeling in germinal centers as detected with clone 1F9, fully humanized monoclonal antibody produced in Xenomice (Abgenix) in frozen human tonsil tissue (data not shown). Bioitinylated IF9 was detected with avidin-biotin peroxidase complex (ABC-HRP). Biotinylated 1F9 was detected with avidin-biotin peroxidase complex (ABC-HRP) and signal amplification with tyramide-biotin was performed, followed by a second incubation with ABC-HRP and chromogenic development.

(2) TAHO3 (FcRH2) showed strong labeling of cells along the outer margin of B cell follicles and significant staining in the mantle zone, which maybe memory B cells, as detected with clone 2G7 in frozen human tonsil tissue (data not shown).

(3) TAHO21 (FcRH4 or IRTA1) showed strong labeling in mucosa-associated lymphoid tissues (MALT), including tonsil and Peyer's Patches in the small intestine as detected with clone 1A3 and using tryimide signal amplification (TSA) in FFPE human tonsil tissue and Peyer's Patch tissue (data not shown). The TAHO21 staining was concentrated along the margins of B cell follicles, which may be memory B cells.

Accordingly, in light of TAHO17, TAHO3 and TAHO21 expression pattern as assessed by immunohistochemistry in tonsil samples, a lymphoid organ where B cells develop, the molecules are excellent targets for therapy of tumors in mammals, including B-cell associated cancers, such as lymphomas (i.e. Non-Hodgkin's Lymphoma), leukemias (i.e. chronic lymphocytic leukemia), myelomas (i.e. multiple myeloma) and other cancers of hematopoietic cells.

Example 14

Flow Cytometry

To determine the expression of TAHO molecules, FACS analysis was performed using a variety of cells, including normal cells and diseased cells, such as chronic lymphocytic leukemia (CLL) cells.

A. Normal Cells: FcRHs (TAHO3, TAHO18. TAHO17. TAHO20, TAHO21, TAHO22, TAHO38)

The following purified or fluorochrome-conjugated mAbs were used for flow cytometry: CD16(clone: 3G8), CD32 (clone: 3D3), CD64(clone: 10.1), anti-human Ig, k(clone: G20-123) or l(clone: JDC-12) light chain-FITC, CD27 (clone: M-T271)-FITC, CD77(clone: 5B5)-FITC, IgD (clone: 1A6-2)-PE, CD34(clone: 581)-PE, CD138(clone: Mi15)-PE, CD38(clone: HIT2)-PerCp-Cy5.5, CD19(clone: SJ25C1)-PerCP-Cy5.5, IgM(clone: G20-127)-PECy5, CD3 (clone: UCHT1)-APC, CD15(clone: HI98)-APC, CD20 (clone: 2H7)-APC and CD56(clone: B159)-APC from BD Biosciences (San Jose, Calif.). CD14(clone: TüK4)-APC from Caltag Laboratories (Burlingame, Calif.). Biotin-conjugated antibodies either commercially available or described herein such as TAHO17/FcRH1 (1F9 or 2A10), TAHO3/FcRH2 (7G7, 1D6 or 7A2), TAHO20/FcRH3 (6F2 or 7E4), TAHO21/FcRH4 (1A3) and TAHO38/FcRH5c (7D11) were used in the flow cytometry.

Cells ($10^6$ cells in 100 m volume) were first incubated with 1 mg of each CD16, CD32, CD64 antibodies and 10 mg each of human and mouse gamma globulin (Jackson ImmunoResearch Laboratories, West Grove, Pa.) to block the nonspecific binding, then incubated with optimal concentrations of mAbs for 30 minutes in the dark at 4° C. When biotinylated antibodies were used, streptavidin-PE or streptavidin-APC (Jackson ImunoResearch Laboratories) were then added according to manufacture's instructions. Flow cytometry was performed on a FACS calibur (BD Biosciences, San Jose, Calif.). Forward scatter (FSC) and side scatter (SSC) signals were recorded in linear mode, fluorescence signals in logarithmic mode. Dead cells and debris were gated out using scatter properties of the cells. Data were analysed using CellQuest Pro software (BD Biosciences) and FlowJo (Tree Star Inc.).

For mononuclear cells (MNCs), human blood samples were collected from healthy individuals through Genentech in house Research Blood program, plasma bone marrow cells (PBMC) were prepared the standard density centrifugation over LSM medium (ICN/Cappel, Aurora, Ohio). Human bone marrow samples were obtained from AllCells (Berkeley, Calif.), BM-MNCs were prepared by the standard density centrifugation over LSM medium. Tonsils were obtained through Bio-Options (Fullerton, Calif.) from patients undergoing tonsillectomy, spleen biopsies were also obtained through Bio-Options. The tonsillar or spleen tissue was chopped into small pieces, digested with 1 mg/ml collagenase and 0.1 U/ml DNase (US Biological, Swampscott, Mass.) in RPMI-1640 at 37° C. for 20 minutes, and put through 30 mm cell strainer (BD Biosciences) to achieve the single cell suspension. The tonsil or spleen MNCs were then prepared by the standard density centrifugation over LSM medium. From PBMCs, B cells were first isolated with CD20 MicroBeads and LS MACS columns (Milteny Biotec, Auburn, Calif.) and then identified by gating on the CD20-APC positive populations; T cells, NK cells and monocytes were identified by gating on the CD3-APC, CD56-APC and CD14-APC positive populations, respectively, from the negative fraction of CD20 MACS isolation. Blood granulocytes were isolated by first treating human blood (1:1) with 3% (in PBS) Dextran 500 (Amersham Bioscience, Piscataway, N.J.) for 30 minutes at room temperature to remove the majority of the RBC, and then collecting the pellet from the standard density centrifugation over LSM medium. Granulocyte population was further identified by gating on the CD15-APC positive population.

From bone marrow mononuclear cells (BM-MNC), CD19+ B cells were first isolated with CD19 MicroBeads and MACS LS columns (Miltenyi Biotec) and then stained with either a marker combination of CD34-PE, CD19-PerCP-Cy5.5, CD27-FITC, anti-human Ig, k and l light chain-FITC, or a marker combination of IgD-PE, IgM-PECy5, anti-human Ig, k and l light chain-FITC. Pro-B cells were identified as CD34+/CD19+/CD27−, while pre-B cells were identified as CD34−/CD19+/CD27−/k and l light chain−. Immature-B cells were identified as IgD−/IgM+/CD27−, while mature-B cells were identified as IgD+/IgM+/CD27−. From tonsil or spleen MNC, from BM-MNC, CD19+ B cells were first isolated with CD19 MicroBeads and LS MACS columns and then stained with a marker combination of CD77-FITC, IgD-PE and CD38-PerCPCy5.5. Naïve B cells were identified as CD38−/IgD+, memory B cells were identified as CD38−/IgD−, mantle zone B cells were identified as CD38+/IgD−, and plasma cells were identified as CD38++/IgD−. Plasma cells were also isolated directly with CD138 MicroBeads and LS MACS column (Miltenyi Biotec) from tonsil or spleen mononuclear cells, and further identified by gating on the CD38-PerCPCy5.5 high and CD138-PE positive population.

Summary of FcRHs on Normal Cells

The expression pattern of the TAHO17 (FcRH1/IRTA5) using a monoclonal antibody specific for TAHO17 showed that TAHO17 expression is specific for the B-cell compartment. TAHO17 was expressed in pro-B and pre-B-cells, although at a much lower level than in naïve and memory B-cells but was not expressed in CD19−, CD34+stem cells. TAHO17 was highly expressed in mature B-cells and was expressed in most of the mature B-cell cell populations that was tested, including CD20+ CD27− peripheral blood naive B-cells, CD20+CD27+peripheral blood memory B-cells, IgD+, CD38− tonsil and spleen naive B-cells, IgD−, CD38− tonsil and spleen memory B-cells. However, TAHO17 had lower expression in IgD−, CD38+ germinal center cells and was not expressed in plasma cells (data not shown). Thus, TAHO17 is suggested to be a marker of B-cells, including pro-B-cells, pre-B-cells, mature B cells, germinal center B cells and memory B cells.

The expression pattern of TAHO3 (FcRH2/IRTA4) using a monoclonal antibody specific for TAHO3 showed that TAHO3 expression was specific for only memory B-cells. In peripheral blood, TAHO3 expression was confined to a subset of the CD20+ cells population, the CD20+ CD27+ population. In tonsil and spleen, TAHO3 was only expressed at high levels in the CD20+IgD− CD38− population which consists mostly of memory B-cells. Within the B-cell compartment, CD27 is a marker of memory B-cells as defined by hypermutated and class switched immunoglobulin genes. In peripheral blood and tonsil, TAHO3 was expressed only in CD20+ CD27+ cells. Further, all of the CD20+ CD27+ cells expressed TAHO3. TAHO3 was not expressed in pre-B-cells, pro-B-cells or in plasma cells from bone marrow. However, TAHO3 was expressed in some of the CD138+ CD38++ plasma cells from tonsil. Thus, TAHO3 is suggested to be a marker of memory B-cells.

The expression pattern of TAHO20 (FcRH3/IRTA3) using a monoclonal antibody specific for TAHO20 showed that TAHO20 expression was outside the B-cell compartment. TAHO20 was expressed outside the B-cell compartment. In blood, TAHO20 was expressed in CD56+ lymphocytes indicating that TAHO20 was expressed in NK cells. Further, TAHO20 was expressed at very low levels in naïve and memory cells from blood, tonsil and spleen, and was expressed at low levels in germinal center B-cells, pro-B-cells, pre-B-cells, and plasma cells from bone marrow. Thus, TAHO20 is suggested to be a marker of NK cells and of mature B cells, germinal center B-cells, and memory B cells.

The expression pattern of TAHO21 (FcRH4/IRTA1) using a monoclonal antibody specific for TAHO21 showed that TAHO21 expression was on memory B cells. TAHO21 was not significantly expressed in pre-B-cells, Pro-B-cells or plasma cells from bone marrow. However, in tonsil, a subset of the CD20+ IgD− CD38− memory B-cell population associated with the marginal zone of mucosal associated lymphoid tissue (MALT) showed strong expression of TAHO21. This population was much smaller in spleen. Thus, TAHO21 is suggested to be a marker of a subset of memory B-cells.

The expression pattern of TAHO38 (FcRH5c/IRTA2c) using a monoclonal antibody specific for TAHO38 showed expression in B cells, plasma cells and in multiple myeloma cells (see below). TAHO38 expression was detected in naïve and memory B-cells in the blood, tonsil, and spleen. TAHO38 was not expressed on the surface of pro-B-cells, pre-B-cells, or GC cells. TAHO38 was expressed in plasma cells from tonsil, spleen, and bone marrow. TAHO38 expression was detected in multiple meloma cells. Thus, TAHO38 is suggested to be a marker of mature B cells, memory B cells, plasma cells and in multiple myeloma cells. Since TAHO18 (FcRH5) is a portion of the extracellular domain of TAHO38 (FcRH5c), the expression pattern of TAHO 18 (FcHR5/IRTA2, a portion of the extracellular region) using a monoclonal antibody specific for TAHO 18 may show similar expression pattern as TAHO38 (as assessed by FACS) in B cells, plasma cells and in multiple myeloma cells.

Accordingly, in light of TAHO17, TAHO3, TAHO20, TAHO21 and TAHO38 expression pattern on tonsil-B subtypes as assessed by FACS, the molecules are excellent targets for therapy of tumors in mammals, including B-cell associated cancers, such as lymphomas (i.e. Non-Hodgkin's Lyphoma), leukemias (i.e. chronic lymphocytic leukemia), myelomas (i.e. multiple myeloma) and other cancers of hematopoietic cells. Since TAHO18 is expected to have a similar expression pattern to TAHO38, TAHO18 is also an excellent target for therapy of tumors in mammals, including B-cell associated cancers, such as lymphomas (i.e. Non-Hodgkin's Lyphoma), leukemias (i.e. chronic lymphocytic leukemia), myelomas (i.e. multiple myeloma) and other cancers of hematopoietic cells.

B. CLL Cells: FcRHs (TAHO3, TAHO38, TAHO17, TAHO 18, TAHO20)

The following purified or fluorochrome-conjugated mAbs were used for flow cytometry of CLL samples (peripheral blood samples obtained from CLL patients): CD5-PE, CD19-PerCP Cy5.5, CD20-FITC, CD20-APC. Further, biotinylated antibodies against CD79A, CD22, CD23, CD79A (ZL7-4), CD79B (SN8), CD180, CXCR5, FcRH1-2A10, FcRH2-7G7, FcRH2-1D6, FcRH2-7A2, FcRH3-6F2, FcRH4-1A3 or FcRH5c-7D11 were used for the flow cytometry. The CD5, CD19 and CD20 antibodies were used to gate on CLL cells and PI staining was performed to check the cell viability.

Peripheral blood mononuclear cells (PBMCs) from peripheral blood samples from CLL patients were isolated by gradient centrifugation over LSM medium (Lymphocyte Separation medium; ICN/Cappel, Aurora, Ohio). Cells ($10^6$ cells in 100 ml volume) were first incubated with 1 mg of each CD5, CD19 and CD20 antibodies and 10 mg each of human and mouse gamma globulin (Jackson ImmunoResearch Laboratories, West Grove, Pa.) to block the nonspecific binding, then incubated with optimal concentrations of mAbs for 30 minutes in the dark at 4° C. When biotinylated antibodies were used, streptavidin-PE or streptavidin-APC (Jackson ImunoResearch Laboratories) were then added according to manufacture's instructions. Flow cytometry was performed on a FACS calibur (BD Biosciences, San Jose, Calif.). Forward scatter (FSC) and side scatter (SSC) signals were recorded in linear mode, fluorescence signals in logarithmic mode. Dead cells and debris were gated out using scatter properties of the cells. Data were analysed using CellQuest Pro software (BD Biosciences) and FlowJo (Tree Star Inc.). Biotin-conjugated antibodies either commercially available or described herein such as TAHO17/FcRH1 (1F9 or 2A10), TAHO3/FcRH2 (7G7, 1D6 or 7A2), TAHO20/FcRH3 (6F2 or 7E4), TAHO21/FcRH4 (1A3) and TAHO38/FcRH5c (7D11) were used in the flow cytometry.

Summary of FcRHs on CLL Samples

The expression pattern on CLL samples was performed using monoclonal antibody specific to the TAHO polypeptide of interest. TAHO 17 (FcRH 1), TAHO3 (FcRH2), TAHO20 (FcRH3) and TAHO38 (FcRH5c) showed significant expression in CLL samples (data not shown). Since TAHO18 (FcRH5) is a portion of the extracellular domain of TAHO38 (FcRH5c), the expression pattern of TAHO18 (FcHR5/IRTA2, a portion of the extracellular region) using a monoclonal antibody specific for TAHO18 may show similar expression pattern as TAHO38 (as assessed by FACS) in CLL samples.

Accordingly, in light of TAHO17, TAHO3, TAHO20 and TAHO38 expression pattern on chronic lymphocytic leukemia (CLL) samples as assessed by FACS, the molecules are excellent targets for therapy of tumors in mammals, including B-cell associated cancers, such as lymphomas (i.e. Non-Hodgkin's Lyphoma), leukemias (i.e. chronic lymphocytic leukemia), myelomas (i.e. multiple myeloma) and other cancers of hematopoietic cells. Since TAHO18 is expected to have a similar expression pattern to TAHO38, TAHO18 is also an excellent target for therapy of tumors in mammals, including B-cell associated cancers, such as lymphomas (i.e. Non-Hodgkin's Lyphoma), leukemias (i.e. chronic lymphocytic leukemia), myelomas (i.e. multiple myeloma) and other cancers of hematopoietic cells.

C. Multiple Myeloma (MM) Cells: FcRH5c (TAHO38) and FcRH5 (TAHO18)

10 samples from newly diagnosed and untreated multiple myeloma patients (referred to as "untreated" samples), 7 samples from relapsed multiple myeloma patients that were treated and the tumor reappearing (referred to as "relapsed" samples) and 8 samples from multiple myeloma patients of unknown history (referred to as "unknown" samples) were examined. Mononuclear cells were isolated from the bone aspirates of the patients by gradient centrifugation. As a control, 6 samples of plasma cells from bone marrow, tonsil and spleen of normal individuals were examined. To determine the expression level of TAHO38/FcRH5c, isolates were then stained with biotinylated anti-FcRH5c antibody (7D11) followed by staining with CD38-FITC, CD138-PE, 7-AAD which is a dye that binds dead cells, and strepavidin-APC. Mean Fluorescent Intensity (MFI) of FL4 channel was calculated on CD38++/CD138+/7-AAD− live cells, adjusted by the MFI of isotype control. All the samples tested were positive for expression of TAHO38/FcRH5c.

The MFI measured for TAHO38/FcRH5c expression were as follows: 254 MFI for untreated samples, 192 MFI for relapsed samples, and 146 MFI for unknown samples from the multiple myeloma patients and 167 MFI for the plasma cells from the normal individuals.

Accordingly, in light of TAHO38 expression pattern in multiple myeloma samples as assessed by FACS, the molecules are excellent targets for therapy of tumors in mammals, including plasma-cell associated cancers, such as myelomas (i.e. multiple myeloma) and diseases associated with antibody-secretion, such as allergy or autoimmune diseases. Since TAHO18 is expected to have a similar expression pattern to TAHO38, TAHO18 is also an excellent target for therapy of tumors in mammals, including plasma-cell associated cancers, such as myelomas (i.e. multiple myeloma) and diseases associated with antibody-secretion, such as allergy or autoimmune diseases.

D. Combination of TAHO38/FcRH5c and CD38 as Improved Marker Pair for Identifying Plasma Cells and Multiple Myeloma Cells Expression from flow cytometry was examined as described above in bone marrow aspirates from either multiple myeloma patients or from healthy individuals.

In some of the multiple myeloma patient samples, the CD138 expression was weak but the TAHO38 expression was strong (data not shown). Specifically, the TAHO38/CD38 marker combination was more effective in identifying the plasma cell population than the CD38/CD138 marker combination (data not shown). In the bone marrow aspirate sample from healthy individuals, the TAHO38/CD38 marker combination performed as well as the CD38/CD138 marker combination in identifying the plasma cell population (data not shown).

This data indicates that the TAHO38 may be useful in combination with other plasma cell markers in identifying plasma cell populations. Specifically, the addition of TAHO38 as a marker to current plasma cell markers (CD38 and CD138) may improve the diagnostic sensitivity and accuracy for identifying plasma cells, including multiple myeloma cells or other plasma-cell associated diseased cells. TAHO38 as an additional marker may be useful for diagnosis for multiple myeloma, other plasma-cell associated diseases or diseases associated with antibody secretion such as allergy or autoimmune diseases, and for the identification of plasma cells, for example, when aberrant immunophenotypes interfere or when CD38 or CD138 expression is low.

Even further, the expression data for TAHO38 in multiple myeloma cells, plasma cells and normal B-cells indicates TAHO38 as an excellent improved target over CD38 and CD138 for immunotherapy. CD38 and CD138 are expressed in essential tissues in contrast to TAHO38 which is expressed primarily in the B-cell lineage and not in essential tissues. The expression of CD38 and CD138 in essential tissues poses a safety concern for their use as immunotherapy targets even though CD38 and CD138 have demonstrated some efficacy in in vitro assays (Ellis, J. H. et al., Engineered anti-CD38 monoclonal antibodies for immuontherapy of multiple myeloma, *J. Immunology,* 155(2): 925-937 (1995)) and xenograft mouse models (Tassone, P. et al., Cytotoxic Activity of the Maytansinoid Immunoconjugate B-B4-DM1 against CD138+multiple myeloma cells, *Blood,* 104(12): 3688-3696 (2004)).

Thus, TAHO38 and spliced isoforms of TAHO 38 (Hatzivassiliou, G., et al., IRTA1 and IRTA2, Novel Immunoglobulin Superfamily Receptors Expressed in B Cells and Involved in Chromosome 1q21 Abnormalities in B Cell Malignancy, *Immunity*, 14:277-289(2001); Miller, I. et al., IRTAs: a new family of immunoglobulinlike receptors differentially expressed in B cells, *Blood*, 99(8): 2662-2669 (2002)) may be an immunotherapy target and one that may be advantageous over CD38 and CD138 for the diagnosis and treatment of tumors in mammals, including plasma-cell associated diseases, such as multiple myeloma, or diseases associated with antibody-secretion such as allergy or autoimmune diseases. Since TAHO18 is expected to have a similar expression pattern to TAHO38, TAHO18 is also an excellent target for therapy of tumors in mammals, including plasma-cell associated cancers, such as myelomas (i.e. multiple myeloma) and diseases associated with antibody-secretion, such as allergy or autoimmune diseases.

Example 15

TAHO Internalization

Internalization of the TAHO antibodies into B-cell lines may be assessed in Raji, Ramos, Daudi and other B cell lines, including ARH77, SuDHL4, U698M, huB and BJAB cell lines.

One ready-to-split 15 cm dish of B-cells (~50×10$^6$ cells) with cells for use in up to 20 reactions is used. The cells are below passage 25 (less than 8 weeks old) and growing healthily without any mycoplasma.

In a loosely-capped 15 ml Falcon tube add 1 µg/ml mouse anti-TAHO antibody to 2.5×10$^6$ cells in 2 ml normal growth medium (e.g. RPMI/10% FBS/1% glutamine) containing 1:10 FcR block (MACS kit, dialyzed to remove azide), 1% pen/strep, 5 µM pepstatin A, 10 µg/ml leupeptin (lysosomal protease inhibitors) and 25 µg/ml Alexa488-transferrin (which labeled the recycling pathway and indicated which cells were alive; alternatively Ax488 dextran fluid phase marker may be used to mark all pathways) for 24 hours in a 37° C. 5% $CO_2$ incubator. For quickly-internalizing antibodies, time-points every 5 minutes are taken. For time-points taken less than 1 hour, 1 ml complete carbonate-free medium (Gibco 18045-088+10% FBS, 1% glutamine, 1% pen/strep, 10 mM Hepes pH 7.4) is used and the reactions are performed in a 37° C. waterbath instead of the $CO_2$ incubator.

After completion of the time course, the cells are collected by centrifugation (1500 rpm 4° C. for 5 minutes in G6-SR or 2500 rpm 3 minutes in 4° C. benchtop eppendorf centrifuge) and washed once in 1.5 ml carbonate free medium (in Eppendorfs) or 10 ml medium for 15 nm Falcon tubes. The cells are subjected to a second centrifugation and resuspended in 0.5 ml 3% paraformaldehyde (EMS) in PBS for 20 minutes at room temp to allow fixation of the cells.

All following steps are followed by a collection of the cells via centrifugation. Cells are washed in PBS and then quenched for 10 minutes in 0.5 ml 50 mM $NH_4Cl$ (Sigma) in PBS and permeablized with 0.5 ml 0.1% Triton-X-100 in PBS for 4 minutes during a 4 minute centrifugation spin. Cells are washed in PBS and subjected to centrifugation. 1 µg/ml Cy3-anti mouse (or anti-species 1° antibody was) is added to detect uptake of the antibody in 200 µl complete carbonate free medium for 20 minutes at room temperature. Cells are washed twice in carbonate free medium and resuspended in 25 µl carbonate free medium and the cells are allowed to settle as a drop onto one well of a polylysine-coated 8-well LabtekII slide for at least one hour (or overnight in fridge). Any non-bound cells are aspirated and the slides are mounted with one drop per well of DAPI-containing Vectashield under a 50×24 mm coverslip. The cells are examined under 100× objective for internalization of the antibodies.

Deposit of Material

The following materials have been deposited with the American Type Culture Collection, 10801 University Blvd., Manassas, Va. 20110-2209, USA (ATCC):

TABLE 7

| Material | ATCC Dep. No. | Deposit Date |
|---|---|---|
| anti-FcRH2-7G7 (7G7.7.8) | PTA-6336 | Nov. 30, 2004 |
| anti-FcRH1-1F9 (1F9.1.1) | PTA-6332 | Nov. 30, 2004 |
| anti-FcRH1-2A10 (2A10.1.1) | PTA-6333 | Nov. 30, 2004 |
| anti-FcRH5c-7D11 (7D11.1.1) | PTA-6340 | Nov. 30, 2004 |
| anti-FcRH3-6F2 (6F2.1.1) | PTA-6337 | Nov. 30, 2004 |
| anti-FcRH4-1A3 (1A3.1.1) | PTA-6339 | Nov. 30, 2004 |
| anti-FcRH1,2-1D6 (1D6.3.8) | PTA-6334 | Nov. 30, 2004 |
| anti-FcRH1,2,3-7A2 (7A2.4.1) | PTA-6335 | Nov. 30, 2004 |
| anti-FcRH1,2,3,5-7E4 (7E4.1.1) | PTA-6338 | Nov. 30, 2004 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposits will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. A method of diagnosing the presence of a multiple myeloma tumor in a mammal, said method comprising detecting the presence of cells expressing a polypeptide comprising an amino acid sequence having at least 95% amino acid sequence identity to:

(a) the polypeptide having the amino acid sequence shown in FIG. 22 (SEQ ID NO: 19);

(b) the polypeptide having the amino acid sequence shown in FIG. 22 (SEQ ID NO: 19), lacking its associated signal peptide;

(c) an extracellular domain of the polypeptide having the amino acid sequence shown in FIG. 22 (SEQ ID NO: 19), with its associated signal peptide;

(d) an extracellular domain of the polypeptide having the amino acid sequence shown in FIG. 22 (SEQ ID NO: 19), lacking its associated signal peptide;

(e) a polypeptide encoded by the nucleotide sequence shown in FIG. 21 (SEQ ID NO: 18); or (f) a polypeptide encoded by the full-length coding region of the nucleotide sequence shown in FIG. 21 (SEQ ID NO: 18), said method comprising contacting a test sample of tissue cells obtained from said mammal with an antibody that binds to said polypeptide or extracellular domain in combination with an antibody that binds to CD38, and detecting the formation of a complex between the antibody that binds the polypeptide or extracellular domain, and the polypeptide or extracellular domain, and a complex between an antibody that binds to CD38 and CD38, wherein an increased number of cells demonstrating said complex formations, as compared to a control sample, is indicative of the presence of a multiple myeloma tumor in said mammal.

2. The method of claim 1, wherein at least one of said antibodies is a monoclonal antibody.

3. The method of claim 1, wherein at least one of said antibodies is an antibody fragment.

4. The method of claim 1, wherein at least one of said antibodies is a chimeric or a humanized antibody.

5. The method of claim 1, wherein at least one of said antibodies is detectably labeled.

6. The method of claim 1, wherein said test sample of tissue cells is obtained from an individual suspected of having said tumor.

7. The method of claim 1, wherein at least one of said antibodies is produced in bacteria.

8. The method of claim 1, wherein at least one of said antibodies is produced in CHO cells.

9. The method of claim 1, wherein said polypeptide has:
(a) the amino acid sequence shown in FIG. 22 (SEQ ID NO: 19);
(b) the amino acid sequence shown in FIG. 22 (SEQ ID NO: 19), lacking its associated signal peptide sequence;
(c) an amino acid sequence of an extracellular domain of the polypeptide shown in FIG. 22 (SEQ ID NO: 19), with its associated signal peptide sequence;
(d) an amino acid sequence of an extracellular domain of the polypeptide shown in FIG. 22 (SEQ ID NO: 19), lacking its associated signal peptide sequence;
(e) an amino acid sequence encoded by the nucleotide sequence shown in FIG. 21 (SEQ ID NO: 18); or
(f) an amino acid sequence encoded by the full-length coding region of the nucleotide sequence shown in FIG. 21 (SEQ ID NO: 18).

10. A method of detecting the presence of multiple myeloma tumor cells in a sample suspected of containing said cells, said method comprising detecting said cells by detecting cells expressing a polypeptide comprising an amino acid sequence having at least 95% amino acid sequence identity to:
(a) the polypeptide having the amino acid sequence shown in FIG. 22 (SEQ ID NO: 19);
(b) the polypeptide having the amino acid sequence shown in FIG. 22 (SEQ ID NO: 19), lacking its associated signal peptide;
(c) an extracellular domain of the polypeptide having the amino acid sequence shown in FIG. 22 (SEQ ID NO: 19), with its associated signal peptide;
(d) an extracellular domain of the polypeptide having the amino acid sequence shown in FIG. 22 (SEQ ID NO: 19), lacking its associated signal peptide;
(e) a polypeptide encoded by the nucleotide sequence shown in FIG. 21 (SEQ ID NO: 18); or
(f) a polypeptide encoded by the full-length coding region of the nucleotide sequence shown in FIG. 21 (SEQ ID NO 18), said method comprising contacting said sample with an antibody that binds to said polypeptide or extracellular domain in combination with an antibody that binds to CD38, and detecting the formation of a complex between the antibody that binds the polypeptide or extracellular domain and the polypeptide or extracellular domain, and a complex between an antibody that binds to CD38 and CD38, wherein the formation of said complexes indicates the presence of said multiple myeloma tumor cells.

11. The method of claim 10, wherein at least one of said antibodies is a monoclonal antibody.

12. The method of claim 10, wherein at least one of said antibodies is an antibody fragment.

13. The method of claim 10, wherein at least one of said antibodies is a chimeric or a humanized antibody.

14. The method of claim 10, wherein at least one of said antibodies is detectably labeled.

15. The method of claim 10, wherein said test sample of tissue cells is obtained from an individual suspected of having a multiple myeloma tumor.

16. The method of claim 10, wherein at least one of said antibodies is produced in bacteria.

17. The method of claim 10, wherein at least one of said antibodies is produced in CHO cells.

18. The method of claim 10, wherein said polypeptide has:
(a) the amino acid sequence shown in FIG. 22 (SEQ ID NO: 19);
(b) the amino acid sequence shown in FIG. 22 (SEQ ID NO: 19), lacking its associated signal peptide sequence;
(c) an amino acid sequence of an extracellular domain of the polypeptide shown in FIG. 22 (SEQ ID NO: 19), with its associated signal peptide sequence;
(d) an amino acid sequence of an extracellular domain of the polypeptide shown in FIG. 22 (SEQ ID NO: 19), lacking its associated signal peptide sequence;
(e) an amino acid sequence encoded by the nucleotide sequence shown in FIG. 21 (SEQ ID NO: 18); or
(f) an amino acid sequence encoded by the full-length coding region of the nucleotide sequence shown in FIG. 21 (SEQ ID NO: 18).

19. The method of claim 1, further comprising contacting the test sample with an antibody that binds to CD138, and detecting the formation of a complex between the antibody that binds CD138 and CD138.

20. The method of claim 10, further comprising contacting the sample with an antibody that binds to CD138, and detecting the formation of a complex between the antibody that binds CD138 and CD138.

* * * * *